(12) United States Patent
Takahashi et al.

(10) Patent No.: US 9,018,134 B2
(45) Date of Patent: Apr. 28, 2015

(54) FUSED HETEROCYCLIC COMPOUND AND USE THEREOF FOR PEST CONTROL

(75) Inventors: Masaki Takahashi, Takarazuka (JP); Takamasa Tanabe, Takarazuka (JP); Mai Ito, Takarazuka (JP); Yoshihiko Nokura, Takarazuka (JP); Atsushi Iwata, Tokyo (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/234,717

(22) PCT Filed: Aug. 3, 2012

(86) PCT No.: PCT/JP2012/070409
§ 371 (c)(1),
(2), (4) Date: Jan. 24, 2014

(87) PCT Pub. No.: WO2013/018928
PCT Pub. Date: Feb. 7, 2013

(65) Prior Publication Data
US 2014/0194290 A1  Jul. 10, 2014

(30) Foreign Application Priority Data

Aug. 4, 2011 (JP) .................. 2011-170833
Mar. 30, 2012 (JP) .................. 2012-079323
May 30, 2012 (JP) .................. 2012-122837

(51) Int. Cl.

| A01N 43/90 | (2006.01) |
|---|---|
| A01N 43/52 | (2006.01) |
| A01N 43/76 | (2006.01) |
| A01N 43/78 | (2006.01) |
| C07D 471/04 | (2006.01) |
| C07D 495/04 | (2006.01) |
| C07D 498/04 | (2006.01) |

(52) U.S. Cl.
CPC ............ *A01N 43/90* (2013.01); *A01N 43/76* (2013.01); *A01N 43/78* (2013.01); *C07D 471/04* (2013.01); *C07D 495/04* (2013.01); *C07D 498/04* (2013.01); *A01N 43/52* (2013.01)

(58) Field of Classification Search
None
See application file for complete search history.

(56) References Cited

U.S. PATENT DOCUMENTS

| 4,581,297 A | 4/1986 | Delseth et al. |
| 8,071,701 B2 | 12/2011 | Klosin et al. |
| 2011/0039843 A1 | 2/2011 | Iwakoshi et al. |
| 2012/0015975 A1 | 1/2012 | Takahashi et al. |
| 2012/0196891 A1 | 8/2012 | Iwakoshi |
| 2013/0090353 A1 | 4/2013 | Iwakoshi et al. |
| 2013/0252981 A1 | 9/2013 | Takahashi et al. |

FOREIGN PATENT DOCUMENTS

| CN | 1067653 A | 1/1993 |
| CN | 102006776 A | 4/2011 |
| EP | 0508800 A1 | 10/1992 |
| EP | 1302466 A1 | 4/2003 |
| EP | 2274983 A1 | 1/2011 |
| JP | 2004-034438 A | 2/2004 |
| WO | 2011040629 A1 | 4/2011 |
| WO | 2011049221 A1 | 4/2011 |
| WO | 2012086848 A1 | 6/2012 |

OTHER PUBLICATIONS

Int'l Search Report and Written Opinion issued Nov. 26, 2012 in Int'l Application No. PCT/JP2012/070409.
Int'l Preliminary Report on Patentability issued Feb. 13, 2014 in Int'l Application No. PCT/JP2012/070409.
Office Action issued Feb. 4, 2015 in CN Application No. 201280037185.2.

*Primary Examiner* — Timothy R Rozof
(74) *Attorney, Agent, or Firm* — Panitch Schwarze Belisario & Nadel LLP

(57) ABSTRACT

There is provided a compound having an excellent controlling effect on pests represented by the formula (1):

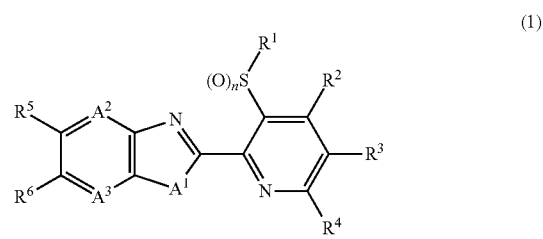

wherein, $A^1$ represents —$NR^7$—, etc., $A^2$ represents a nitrogen atom, etc., $A^3$ represents a nitrogen atom, etc., $R^1$ represents a C1-C6 chain hydrocarbon group optionally substituted by one or more atoms or groups selected from Group X, etc., $R^2$, $R^3$ and $R^4$ are the same or different and each represents a C1-C6 chain hydrocarbon group optionally substituted by one or more halogen atoms, etc., $R^5$ and $R^6$ are the same or different and each represents a C1-C6 chain hydrocarbon group optionally substituted by one or more atoms or groups selected from Group X, etc., $R^7$ represents a C1-C6 chain hydrocarbon group optionally substituted by one or more atoms or groups selected from Group W, etc., n represents 0, 1 or 2, or an N-oxide thereof.

20 Claims, No Drawings

FUSED HETEROCYCLIC COMPOUND AND USE THEREOF FOR PEST CONTROL

CROSS-REFERENCE TO RELATED APPLICATION

This application is a Section 371 of International Application No. PCT/JP2012/070409, filed Aug. 3, 2012, which was published in the English language on Feb. 7, 2013, under International Publication No. WO 2013/018928 A1, and the disclosure of which is incorporated herein by reference.

TECHNICAL FIELD

The present application is filed claiming the priority of the Japanese Patent Application Nos. 2011-170833, 2012-079323 and 2012-122837, the entire contents of which are herein incorporated by reference.

The present invention relates to a fused heterocyclic, compound and the use thereof for pest control.

BACKGROUND ART

For controlling pests, various compounds have been developed and used practically.

Further, some fused heterocyclic compounds are known (see, Patent Literature 1).

CITATION LIST

Patent Literature

Patent Literature 1: JP-A-2004-34438

SUMMARY OF INVENTION

Technical Problem

An object of the present invention is to provide a novel compound having an excellent controlling effect on pests and a method for controlling pests with said compound.

Solution to Problem

The inventors of the present invention have intensively studied, and as a result, they have found that a fused heterocyclic compound represented by the following formula (1) has an excellent controlling effect on pests. Thus, the present invention has been completed.

The present invention includes the followings:

[1] A fused heterocyclic compound represented by the formula (1):

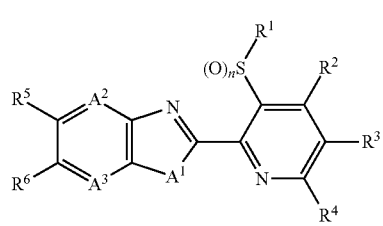

(1)

wherein
$A^1$ represents —$NR^7$—, an oxygen atom or a sulfur atom,
$A^2$ represents a nitrogen atom or =$CR^8$—,
$A^3$ represents a nitrogen atom or =$CR^9$—,
$R^1$ represents a C1-C6 chain hydrocarbon group optionally substituted by one or more atoms or groups selected from Group X or a C3-C6 alicyclic hydrocarbon group optionally substituted by one or more atoms or groups selected from Group Y,
$R^2$, $R^3$ and $R^4$ are the same or different and each represents a C1-C6 chain hydrocarbon group optionally substituted by one or more atoms or groups selected from Group X, a phenyl group optionally substituted by one or more atoms or groups selected from Group Z, a 5- or 6-membered heterocyclic group optionally substituted by one or more atoms or groups selected from Group Z, —$OR^{10}$, —$S(O)_m R^{10}$, —$S(O)_2 NR^{10} R^{11}$, —$NR^{10} R^{11}$, —$NR^{10} CO_2 R^{11}$, —$NR^{10} C(O)R^{11}$, $CO_2 R^{10}$, —$C(O)R^{10}$, —$C(O)NR^{10} R^{11}$, —$SF_5$, a cyano group, a nitro group, a halogen atom or a hydrogen atom,
$R^5$ and $R^6$ are the same or different and each represents a C1-C6 chain hydrocarbon group optionally substituted by one or more atoms or groups selected from Group X, a phenyl group optionally substituted by one or more atoms or groups selected from Group Z, a 5- or 6-membered heterocyclic group optionally substituted by one or more atoms or groups selected from Group Z, —$OR^{10}$, $S(O)_m R^{10}$, —$S(O)_2 NR^{10} R^{11}$, —$NR^{10} R^{11}$, —$NR^{10} CO_2 R^{11}$, $NR^{10} C(O)R^{11}$, $CO_2 R^{10}$, —$C(O)R^{10}$, —$C(O)NR^{10} R^{11}$, —$SF_5$, a cyano group, a nitro group, a halogen atom or a hydrogen atom (wherein $R^5$ and $R^6$ do not represents a hydrogen atom at the same time),
$R^7$ represents a C1-C6 chain hydrocarbon group optionally substituted by one or more atoms or groups selected from Group W, a C1-C6 chain hydrocarbon group substituted by one phenyl group (wherein the phenyl group is optionally substituted by one or more atoms or groups selected from Group Z), a C1-C6 chain hydrocarbon group substituted by one 5- or 6-membered heterocyclic group (wherein the 5- or 6-membered heterocyclic group is optionally substituted by one or more atoms or groups selected from Group Z), —$CO_2 R^{10}$, —$C(O)R^{10}$, a C3-C6 alicyclic hydrocarbon group optionally substituted by one or more atoms or groups selected from Group Y or a hydrogen atom,
$R^8$ and $R^9$ are the same or different and each represents a C1-C6 chain hydrocarbon group optionally substituted by one or more halogen atoms, —$OR^{10}$, —$S(O)_m R^{10}$, —$NR^{10} R^{11}$, —$CO_2 R^{10}$, —$C(O)R^{10}$, a cyano group, a nitro group, a halogen atom or a hydrogen atom,
$R^{10}$ and $R^{11}$ are the same or different and each represents a C1-C6 chain hydrocarbon group optionally substituted by one or more atoms or groups selected from Group X, a phenyl group optionally substituted by one or more atoms or groups selected from Group Z or a hydrogen atom,
each m independently represents 0, 1 or 2, and
n represents 0, 1 or 2,
wherein the —$S(O)_m R^{10}$, $R^{10}$ does not a hydrogen atom when m is 1 or 2,
Group X: the group consisting of a C1-C6 alkoxy group optionally substituted by one or more halogen atoms, a C2-C6 alkenyloxy group optionally substituted by one or more halogen atoms, a C2-C6 alkynyloxy group optionally substituted by one or more halogen atoms, a C1-C6 alkylsulfanyl group optionally substituted by one or more halogen atoms, a C1-C6 alkylsulfinyl group optionally substituted by one or more halogen atoms, a C1-C6 alkylsulfonyl group optionally substituted by one or more halogen atoms, a C2-C6 alkylcarbonyl group optionally substituted by one or more halogen atoms, a C2-C6 alkoxycarbonyl group optionally substituted by one or more halogen atoms, a C3-C6 cycloalkyl group optionally substituted by one or more halogen atoms or one or more C1-C3 alkyl groups, a cyano group, a hydroxy group and a halogen atom, Group Y: the group consisting of a C1-C6 chain hydrocarbon group optionally substituted by one or more halogen atoms, a C1-C6 alkoxy group optionally substituted by one or more halogen atoms, a C2-C6 alkenyloxy group optionally substituted by one or more halogen atoms, a C2-C6 alkynyloxy group optionally substituted by one or more halogen atoms and a halogen atom, Group Z: the group consisting of a C1-C6 chain hydrocarbon group optionally substituted by one or more halogen atoms, a C1-C6 alkoxy group optionally substituted by one or more halogen atoms, a C1-C6 alkylsulfanyl group optionally substituted by one or more halogen atoms, a C1-C6 alkylsulfinyl group optionally substituted by one or more halogen atoms, a C1-C6 alkylsulfonyl group optionally substituted by one or more halogen atoms, a C2-C6 alkylcarbonyl group optionally substituted by one or more halogen atoms, a C2-C6 alkoxycarbonyl group optionally substituted by one or more halogen atoms, a C1-C6 alkylamino group optionally substituted by one or more halogen atoms, a C2-C8 dialkylamino group optionally substituted by one or more halogen atoms, a halogen atom, a cyano group and a nitro group, Group W: the group consisting of a C1-C6 alkoxy group optionally substituted by one or more halogen atoms, a C2-C6 alkenyloxy group optionally substituted by one or more halogen atoms, a C2-C6 alkynyloxy group optionally substituted by one or more halogen atoms, a C1-C6 alkylsulfanyl group optionally substituted by one or more halogen atoms, a C2-C6 alkylcarbonyl group optionally substituted by one or more halogen atoms, a C2-C6 alkoxycarbonyl group optionally substituted by one or more halogen atoms, a C3-C6 cycloalkyl group optionally substituted by one or more halogen atoms, a C1-C6 alkylsulfinyl group optionally substituted by one or more halogen atoms, a C1-C6 alkylsulfonyl group optionally substituted by one or more halogen atoms, hydroxy group, a halogen atom and a cyano group, or an N-oxide thereof (hereinafter referred to as "the present compound").

[2] The compound according to the above [1], wherein
$A^1$ is —$NR^7$—, an oxygen atom or a sulfur atom,
$A^2$ is a nitrogen atom or =$CR^8$—,
$A^3$ is a nitrogen atom or =$CR^9$—,
$R^1$ is a C1-C6 chain hydrocarbon group optionally substituted by one or more atoms or groups selected from Group X,
$R^2$, $R^3$ and $R^4$ are the same or different and each represents a C1-C6 chain hydrocarbon group optionally substituted by one or more atoms or groups selected from Group X, a phenyl group optionally substituted by one or more atoms or groups selected from Group Z, a 5- or 6-membered heterocyclic group optionally substituted by one or more atoms or groups selected from Group Z, —$OR^{10}$, —$S(O)_mR^{10}$, —$SF_5$, a cyano group, a nitro group, a halogen atom or a hydrogen atom,
$R^5$ and $R^6$ are the same or different and each represents a C1-C6 chain hydrocarbon group optionally substituted by one or more atoms or groups selected from Group X, —$OR^{10}$, —$S(O)_mR^{10}$, —$SF_5$, a halogen atom or a hydrogen atom,
$R^7$ is a C1-C6 chain hydrocarbon group optionally substituted by one or more atoms or groups selected from Group W, a C1-C6 chain hydrocarbon group substituted by one phenyl group (wherein the phenyl group is optionally substituted by one or more atoms or groups selected from Group Z), a C1-C6 chain hydrocarbon group substituted by one 5- or 6-membered heterocyclic group (wherein the 5- or 6-membered heterocyclic group is optionally substituted by one or more atoms or groups selected from Group Z), or a hydrogen atom,
$R^8$ is a C1-C6 chain hydrocarbon group optionally substituted by one or more halogen atoms, —$OR^{10}$, —$S(O)_mR^{10}$, a halogen atom or a hydrogen atom, and
$R^9$ is a C1-C6 chain hydrocarbon group optionally substituted by one or more halogen atoms, —$OR^{10}$, —$S(O)_mR^{10}$, a halogen atom or a hydrogen atom.

[3] The compound according to the above [1], wherein
$A^1$ is —$NR^7$—, an oxygen atom or a sulfur atom,
$A^2$ is a nitrogen atom or =$CR^8$—,
$A^3$ is a nitrogen atom or =$CR^9$—,
$R^1$ is a C1-C6 alkyl group optionally substituted by one or more atoms or groups selected from the group consisting of a halogen atom and cyclopropyl group (wherein the cyclopropyl group is optionally substituted by one or more halogen atoms or one or more C1-C3 alkyl group), a C2-C6 alkenyl group optionally substituted by one or more halogen atoms or a C2-C6 alkynyl group optionally substituted by one or more halogen atoms,
$R^2$ and $R^4$ are the same or different each other and each represents a halogen atom or a hydrogen atom,
$R^3$ is a C1-C6 alkyl group optionally substituted by one or more halogen atoms, a C2-C6 alkenyl group optionally substituted by one or more halogen atoms, a C2-C6 alkynyl group optionally substituted by one or more halogen atoms, 5- or 6-membered aromatic heterocyclic group (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), —$OR^{10}$, —$S(O)_mR^{10}$, a cyano group, a nitro group, a halogen atom or a hydrogen atom,
$R^5$ is a C1-C6 alkyl group optionally substituted by one or more halogen atoms, —$OR^{10}$, —$S(O)_mR^{10}$—$SF_5$ or a halogen atom,
$R^6$ is a C1-C6 alkyl group optionally substituted by one or more halogen atoms, —$OR^{10}$, —$S(O)_mR^{10}$, a halogen atom or a hydrogen atom,
$R^{10}$ is a C1-C6 alkyl group optionally substituted by one or more halogen atoms,
$R^7$ is a C1-C6 alkyl group optionally substituted by one or more halogen atoms, a C3-C6 alkenyl group optionally substituted by one or more halogen atoms, a C3-C6 alkynyl group optionally substituted by one or more halogen atoms, a C1-C6 alkyl group substituted by one 5- or 6-membered aromatic heterocyclic group (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), a hydrogen atom or a C2-C6 alkoxyalkyl group optionally substituted by one or more halogen atoms,
$R^8$ is a C1-C6 alkyl group optionally substituted by one or more halogen atoms, —$OR^{10}$, —$S(O)_mR^{10}$, a halogen atom or a hydrogen atom, and
$R^9$ is a C1-C6 alkyl group optionally substituted by one or more halogen atoms, —$OR^{10}$, —$S(O)_mR^{10}$, a halogen atom or a hydrogen atom.

[4] The compound according to any one of the above [1] to [3], wherein $A^1$ is —$NR^7$—.
[5] The compound according to any one of the above [1] to [3], wherein $A^1$ is an oxygen atom.
[6] The compound according to any one of the above [1] to [3], wherein $A^1$ is a sulfur atom.

[7] The compound according to any one of the above [1] to [6], wherein $A^2$ is =$CR^8$—.

[8] The compound according to any one of the above [1] to [6], wherein $A^2$ is =$CR^8$—, and $A^3$ is a nitrogen atom.

[9] The compound according to any one of the above [1] to [6], wherein $A^2$ is =$CR^8$—, and $A^3$ is =$CR^9$—.

[10] A compound represented by the formula (1-1):

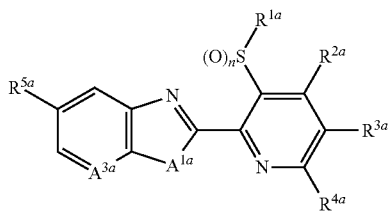

(1-1)

wherein
$A^{1a}$ represents —$NR^{7a}$—, an oxygen atom or a sulfur atom,
$A^{3a}$ represents a nitrogen atom or =$CR^{9a}$—,
$R^{1a}$ represents a C1-C6 alkyl group optionally substituted by one or more atoms or groups selected from the group consisting of a halogen atom and a cyclopropyl group (wherein the cyclopropyl group is optionally substituted by one or more halogen atoms or one or more C1-C3 alkyl groups), a C2-C6 alkenyl group optionally substituted by one or more halogen atoms or a C2-C6 alkynyl group optionally substituted by one or more halogen atoms, $R^{2a}$ and $R^{4a}$ are the same or different and each represents a halogen atom or a hydrogen atom,
$R^{3a}$ represents a C1-C6 alkyl group optionally substituted by one or more halogen atoms, a C2-C6 alkenyl group optionally substituted by one or more halogen atoms, a C2-C6 alkynyl group optionally substituted by one or more halogen atoms, 5- or 6-membered aromatic heterocyclic group (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), —$OR^{20a}$ (wherein $R^{20a}$ represents a C1-C6 alkyl group optionally substituted by one or more halogen atoms), —$S(O)_mR^{21a}$ (wherein $R^{21a}$ represents a C1-C6 alkyl group optionally substituted by one or more halogen atoms, m represents 0, 1 or 2), a cyano group, a nitro group, a halogen atom or a hydrogen atom, $R^{5a}$ represents a C1-C6 alkyl group optionally substituted by one or more halogen atoms, —$OR^{22a}$ (wherein $R^{22a}$ represents a C1-C6 alkyl group optionally substituted by one or more halogen atoms), —$S(O)_m R^{23a}$ (wherein $R^{23a}$ represents a C1-C6 alkyl group optionally substituted by one or more halogen atoms, m represents 0, 1 or 2), —$SF_5$ or a halogen atom,
$R^{7a}$ represents a C1-C6 alkyl group optionally substituted by one or more halogen atoms, a C3-C6 alkenyl group optionally substituted by one or more halogen atoms, a C3-C6 alkynyl group optionally substituted by one or more halogen atoms or a C1-C6 alkyl group substituted by one 5- or 6-membered aromatic heterocyclic group, (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms),
$R^{9a}$ represents a C1-C6 alkyl group optionally substituted by one or more halogen atoms, —$OR^{24a}$ (wherein $R^{24a}$ represents a C1-C6 alkyl group optionally substituted by one or more halogen atoms), —$S(O)_mR^{25a}$ (wherein $R^{25a}$ represents a C1-C6 alkyl group optionally substituted by one or more halogen atoms, m represents 0, 1 or 2), a halogen atom or a hydrogen atom, and n represents 0, 1 or 2, or an N-oxide thereof.

[11] The compound according to the above [10], wherein
$A^{1a}$ is —$NR^{7a}$—, an oxygen atom or a sulfur atom,
$A^{3a}$ is a nitrogen atom or =$CR^{9a}$—,
$R^{1a}$ is a C2-C6 alkyl group, a C1-C6 haloalkyl group or C4-C9 cyclopropylalkyl group (wherein the cyclopropyl group is optionally substituted by one or more halogen atoms or one or more C1-C3 alkyl groups),
$R^{2a}$ and $R^{4a}$ both are a hydrogen atom,
$R^{3a}$ is a C1-C6 alkyl group optionally substituted by one or more halogen atoms, a C2-C6 alkenyl group optionally substituted by one or more halogen atoms, a C2-C6 alkynyl group optionally substituted by one or more halogen atoms, pyridyl group (wherein the pyridyl group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), a pyrimidinyl group (wherein the pyrimidinyl group is optionally substituted by one or more atoms or groups selected from the group consisting of halogen atom, a C1-C3 alkyl group optionally substituted by one or more halogen atoms, and a C1-C3 alkoxy group optionally substituted by one or more halogen atoms), —$OR^{20a}$ (wherein $R^{20a}$ is a C1-C6 alkyl group optionally substituted by one or more halogen atoms), —$S(O)_mR^{21a}$ (wherein $R^{21a}$ is a C1-C6 alkyl group optionally substituted by one or more halogen atoms, and m is 0, 1 or 2), a halogen atom or a hydrogen atom,
$R^{5a}$ is a C1-C6 haloalkyl group, —$OR^{22a}$ (wherein $R^{22a}$ is a C1-C6 haloalkyl group), —$S(O)_mR^{23a}$ (wherein $R^{23a}$ is a C1-C6 haloalkyl group, and m is 0, 1 or 2), —$SF_5$ or a halogen atom, and
$R^{7a}$ is C1-C6 alkyl group optionally substituted by one or more halogen atoms, a C3-C6 alkenyl group optionally substituted by one or more halogen atoms, a C3-C6 alkynyl group optionally substituted by one or more halogen atoms, a C1-C6 alkyl group substituted by one thiazolyl group (wherein the thiazolyl group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms) or a C1-C6 alkyl group substituted by one pyridyl group (wherein the pyridyl group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms).

[12] The compound according to the above [10] or [11], wherein $A^{1a}$ is —$NR^{7a}$—.

[13] The compound according to the above [10] or [11], wherein is an oxygen atom.

[14] The compound according to the above [10] or [11], wherein $A^{1a}$ is a sulfur atom.

[15] A compound represented by the formula (1-2):

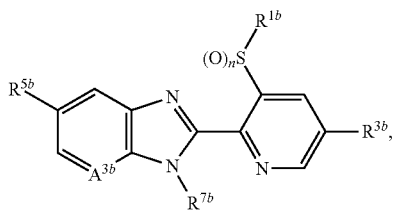

(1-2)

wherein
$A^{3b}$ represents a nitrogen atom or $=CR^{9b}-$ (wherein $R^{9b}$ represents a hydrogen atom or a halogen atom), $R^{1b}$ represents an ethyl group or a cyclopropylmethyl group, $R^{7b}$ represents methyl group or a propargyl group, $R^{3b}$ represents a C1-C6 alkyl group optionally substituted by one or more halogen atoms, $-OR^{20b}$ (wherein $R^{20b}$ represents a C1-C6 alkyl group optionally substituted by one or more halogen atoms), $-S(O)_m R^{21b}$ (wherein $R^{21b}$ represents a C1-C6 alkyl group optionally substituted by one or more halogen atoms, m represents 0, 1 or 2), a halogen atom or a hydrogen atom, $R^{5b}$ represents a C1-C6 haloalkyl group, $-OR^{22b}$ (wherein $R^{22b}$ represents a C1-C6 haloalkyl group), $-S(O)_m R^{23b}$ (wherein $R^{23b}$ represents a C1-C6 haloalkyl group, m represents 0, 1 or 2), $-SF_5$ or a halogen atom, and n represents 0, 1 or 2, or an N-oxide thereof.

[16] A compound represented by the formula (1-3):

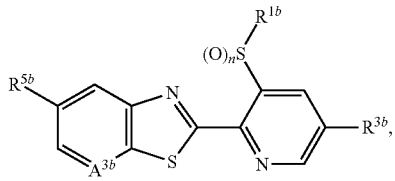

(1-3)

wherein
$A^{3b}$ represents a nitrogen atom or $=CR^{9b}-$ (wherein $R^{9b}$ represents a hydrogen atom or a halogen atom), $R^{1b}$ represents an ethyl group or a cyclopropylmethyl group, $R^{3b}$ represents a C1-C6 alkyl group optionally substituted by one or more halogen atoms, $-OR^{20b}$ (wherein $R^{20b}$ represents a C1-C6 alkyl group optionally substituted by one or more halogen atoms), $-S(O)_m R^{21b}$ (wherein $R^{21b}$ represents a C1-C6 alkyl group optionally substituted by one or more halogen atoms, m represents 0, 1 or 2), a halogen atom or a hydrogen atom, $R^{5b}$ represents a C1-C6 haloalkyl group, $-OR^{22b}$ (wherein $R^{22b}$ represents a C1-C6 haloalkyl group), $-S(O)_m R^{23b}$ (wherein $R^{23b}$ represents a C1-C6 haloalkyl group, m represents 0, 1 or 2), $-SF_5$ or a halogen atom, and n represents 0, 1 or 2, or an N-oxide thereof.

[17] A compound represented by the formula (1-4):

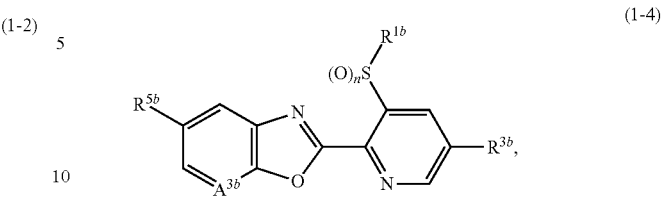

(1-4)

wherein
$A^{3b}$ represents a nitrogen atom or $=CR^{9b}-$ (wherein $R^{9b}$ represents a hydrogen atom or a halogen atom), $R^{1b}$ represents an ethyl group or a cyclopropylmethyl group, $R^{3b}$ represents a C1-C6 alkyl group optionally substituted by one or more halogen atoms, $-OR^{20b}$ (wherein $R^{20b}$ represents a C1-C6 alkyl group optionally substituted by one or more halogen atoms), $-S(O)_m R^{21b}$ (wherein $R^{21b}$ represents a C1-C6 alkyl group optionally substituted by one or more halogen atoms, m represents 0, 1 or 2), a halogen atom or a hydrogen atom, $R^{5b}$ represents a C1-C6 haloalkyl group, $-OR^{22b}$ (wherein $R^{22b}$ represents a C1-C6 haloalkyl group), $-S(O)_m R^{23b}$ (wherein $R^{23b}$ represents a C1-C6 haloalkyl group, m represents 0, 1 or 2), $-SF_5$ or a halogen atom, and n represents 0, 1 or 2, or an N-oxide thereof.

[18] A compound represented by the formula (1-5):

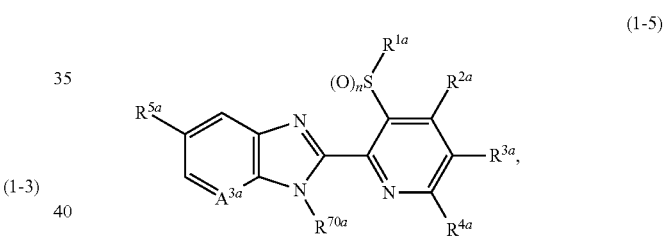

(1-5)

wherein
$R^{70a}$ represents a hydrogen atom or a C2-C6 alkoxyalkyl group optionally substituted by one or more halogen atoms, $A^{3a}$ represents a nitrogen atom or $=CR^{9a}-$, $R^{1a}$ represents a C1-C6 alkyl group optionally substituted by one or more atoms or groups selected from the group consisting of a halogen atom and a cyclopropyl group (wherein the cyclopropyl group is optionally substituted by one or more halogen atoms or one or more C1-C3 alkyl groups), a C2-C6 alkenyl group optionally substituted by one or more halogen atoms or a C2-C6 alkynyl group optionally substituted by one or more halogen atoms, $R^{2a}$ and $R^{4a}$ are the same or different and each represents a halogen atom or a hydrogen atom, $R^{3a}$ represents a C1-C6 alkyl group optionally substituted by one or more halogen atoms, a C2-C6 alkenyl group optionally substituted by one or more halogen atoms, a C2-C6 alkynyl group optionally substituted by one or more halogen atoms, 5- or 6-membered aromatic heterocyclic group (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), $-OR^{20a}$ (wherein $R^{20a}$ represents a C1-C6 alkyl group optionally substituted by one or more halogen atoms), —S(O)$_m$R$^{21a}$ (wherein R$^{21a}$ represents a C1-C6 alkyl group optionally substituted by one or more halogen atoms, m represents 0, 1 or 2), a cyano group, a nitro group, a halogen atom or a hydrogen atom, R$^{5a}$ represents a C1-C6 alkyl group optionally substituted by one or more halogen atoms, —OR$^{22a}$ (wherein R$^{22a}$ represents a C1-C6 alkyl group optionally substituted by one or more halogen atoms), —S(O)$_m$R$^{23a}$ (wherein R$^{23a}$ represents a C1-C6 alkyl group optionally substituted by one or more halogen atoms, m represents 0, 1 or 2), —SF$_5$ or a halogen atom, R$^{9a}$ represents a C1-C6 alkyl group optionally substituted by one or more halogen atoms, —OR$^{24a}$ (wherein R$^{24a}$ represents a C1-C6 alkyl group optionally substituted by one or more halogen atoms), —S(O)$_m$R$^{25a}$ (wherein R$^{25a}$ represents a C1-C6 alkyl group optionally substituted by one or more halogen atoms, m represents 0, 1 or 2), a halogen atom or a hydrogen atom, and n represents 0, 1 or 2,
or an N-oxide thereof.

[19] A pest control composition comprising a compound according to any one of the above [1] to [18] and an inert carrier.

[20] A method for controlling a pest, which comprises applying an effective amount of the compound according to any one of the above [1] to [18] to the pest or a habitat of the pest.

[21] A compound represented by the formula (M3-1):

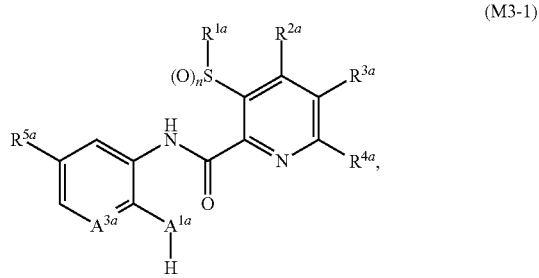

wherein
A$^{1a}$ represents —NR$^{7a}$—, an oxygen atom or a sulfur atom,
A$^{3a}$ represents a nitrogen atom or =CR$^{9a}$—,
R$^{1a}$ represents a C1-C6 alkyl group optionally substituted by one or more atoms or groups selected from the group consisting of a halogen atom and a cyclopropyl group (wherein the cyclopropyl group is optionally substituted by one or more halogen atoms or one or more C1-C3 alkyl groups), a C2-C6 alkenyl group optionally substituted by one or more halogen atoms or a C2-C6 alkynyl group optionally substituted by one or more halogen atoms,
R$^{2a}$ and R$^{4a}$ are the same or different and each represents a halogen atom or a hydrogen atom,
R$^{3a}$ represents a C1-C6 alkyl group optionally substituted by one or more halogen atoms, a C2-C6 alkenyl group optionally substituted by one or more halogen atoms, a C2-C6 alkynyl group optionally substituted by one or more halogen atoms, 5- or 6-membered aromatic heterocyclic group (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), —OR$^{20a}$ (wherein R$^{20a}$ represents a C1-C6 alkyl group optionally substituted by one or more halogen atoms), —S(O)$_m$R$^{21a}$ (wherein R$^{21a}$ represents a C1-C6 alkyl group optionally substituted by one or more halogen atoms, m represents 0, 1 or 2), a cyano group, a nitro group, a halogen atom or a hydrogen atom, R$^{5a}$ represents a C1-C6 alkyl group optionally substituted by one or more halogen atoms, —OR$^{22a}$ (wherein R$^{22a}$ represents a C1-C6 alkyl group optionally substituted by one or more halogen atoms), —S(O)$_m$R$^{23a}$ (wherein R$^{23a}$ represents a C1-C6 alkyl group optionally substituted by one or more halogen atoms, m represents 0, 1 or 2), —SF$_5$ or a halogen atom, R$^{7a}$ represents a C1-C6 alkyl group optionally substituted by one or more halogen atoms, a C3-C6 alkenyl group optionally substituted by one or more halogen atoms, a C3-C6 alkynyl group optionally substituted by one or more halogen atoms, or a C1-C6 alkyl group substituted by one 5- or 6-membered aromatic heterocyclic group, (wherein the 5- or 6-membered aromatic heterocyclic group is optionally substituted by one-or more atoms or groups selected from the group consisting of a halogen atom, a C1-C3 alkyl group optionally substituted by one or more halogen atoms, and a C1-C3 alkoxy group optionally substituted by one or more halogen atoms), R$^{9a}$ represents a C1-C6 alkyl group optionally substituted by one or more halogen atoms, —OR$^{24a}$ (wherein R$^{24a}$ represents a C1-C6 alkyl group optionally substituted by one or more halogen atoms), —S(O)$_m$R$^{25a}$ (wherein R$^{25a}$ represents a C1-C6 alkyl group optionally substituted by one or more halogen atoms, m represents 0, 1 or 2), a halogen atom or a hydrogen atom, n represents 0, 1 or 2, and
or an N-oxide thereof.

[22] A compound represented by the formula (M6-1):

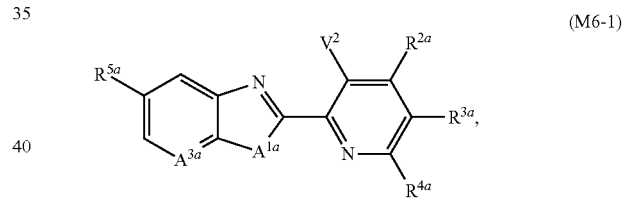

wherein
V$^2$ represents a halogen atom,
A$^{1a}$ represents —NR$^{7a}$—, an oxygen atom or a sulfur atom,
A$^{3a}$ represents a nitrogen atom or =CR$^{9a}$—,
R$^{2a}$ and R$^{4a}$ are the same or different and each represents a halogen atom or a hydrogen atom,
R$^{3a}$ represents a C1-C6 alkyl group optionally substituted by one or more halogen atoms, a C2-C6 alkenyl group optionally substituted by one or more halogen atoms, a C2-C6 alkynyl group optionally substituted by one or more halogen atoms, 5- or 6-membered aromatic heterocyclic group (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), —OR$^{20a}$ (wherein R$^{20a}$ represents a C1-C6 alkyl group optionally substituted by one or more halogen atoms), —S(O)$_m$R$^{21a}$ (wherein R$^{21a}$ represents a C1-C6 alkyl group optionally substituted by one or more halogen atoms, m represents 0, 1 or 2), a cyano group, a nitro group, a halogen atom or a hydrogen atom, R$^{5a}$ represents a C1-C6 alkyl group optionally substituted by one or more halogen atoms, —OR$^{22a}$ (wherein R$^{22a}$ represents a C1-C6 alkyl group optionally substituted by one or more halogen atoms), —S(O)$_m$R$^{23a}$ (wherein R$^{23a}$ represents a C1-C6 alkyl group optionally substituted by one or more halogen atoms, m represents 0, 1 or 2), —SF$_5$ or a halogen atom, R$^{7a}$ represents a C1-C6 alkyl group optionally substituted by one or more halogen atoms, a C3-C6 alkenyl group optionally substituted by one or more halogen atoms, a C3-C6 alkynyl group optionally substituted by one or more halogen atoms, or a C1-C6 alkyl group substituted by one 5- or 6-membered aromatic heterocyclic group, (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), and R$^{9a}$ represents a C1-C6 alkyl group optionally substituted by one or more halogen atoms, —OR$^{24a}$ (wherein R$^{24a}$ represents a C1-C6 alkyl group optionally substituted by one or more halogen atoms), —S(O)$_m$R$^{25a}$ (wherein R$^{25a}$ represents a C1-C6 alkyl group optionally substituted by one or more halogen atoms, m represents 0, 1 or 2), a halogen atom or a hydrogen atom, or an N-oxide thereof.

[23] A compound represented by the formula (M20-1):

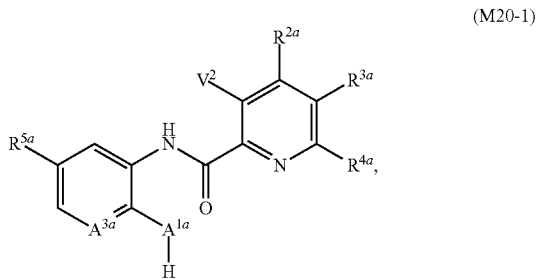

(M20-1)

wherein

V$^2$ represents a halogen atom,

A$^{1a}$ represents —NR$^{7a}$—, an oxygen atom or a sulfur atom,

A$^{3a}$ represents a nitrogen atom or ═CR$^{9a}$—,

R$^{2a}$ and R$^{4a}$ are the same or different and each represents a halogen atom or a hydrogen atom, R$^{3a}$ represents a C1-C6 alkyl group optionally substituted by one or more halogen atoms, a C2-C6 alkenyl group optionally substituted by one or more halogen atoms, a C2-C6 alkynyl group optionally substituted by one or more halogen atoms, 5- or 6-membered aromatic heterocyclic group (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), —OR$^{20a}$ (wherein R$^{20a}$ represents a C1-C6 alkyl group optionally substituted by one or more halogen atoms), —S(O)$_m$R$^{21a}$ (wherein R$^{21a}$ represents a C1-C6 alkyl group optionally substituted by one or more halogen atoms, m represents 0, 1 or 2), a cyano group, a nitro group, a halogen atom or a hydrogen atom, R$^{5a}$ represents a C1-C6 alkyl group optionally substituted by one or more halogen atoms, —OR$^{22a}$ (wherein R$^{22a}$ represents a C1-C6 alkyl group optionally substituted by one or more halogen atoms), —S(O)$_m$R$^{23a}$ (wherein R$^{23a}$ represents a C1-C6 alkyl group optionally substituted by one or more halogen atoms, m represents 0, 1 or 2), —SF$_5$ or a halogen atom, R$^{7a}$ represents a C1-C6 alkyl group optionally substituted by one or more halogen atoms, a C3-C6 alkenyl group optionally substituted by one or more halogen atoms, a C3-C6 alkynyl group optionally substituted by one or more halogen atoms, or a C1-C6 alkyl group substituted by one 5- or 6-membered aromatic heterocyclic group, (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), and R$^{9a}$ represents a C1-C6 alkyl group optionally substituted by one or more halogen atoms, —OR$^{24a}$ (wherein R$^{24a}$ represents a C1-C6 alkyl group optionally substituted by one or more halogen atoms), —S(O)$_m$R$^{25a}$ (wherein R$^{25a}$ represents a C1-C6 alkyl group optionally substituted by one or more halogen atoms, m represents 0, 1 or 2), a halogen atom or a hydrogen atom, or an N-oxide thereof.

Effect of Invention

The present compound has an excellent controlling effect on pests and is useful as an active ingredient of a pest control agent.

DESCRIPTION OF EMBODIMENTS

The "N-oxide" in the present compound means a compound wherein a nitrogen atom constituting a ring in heterocyclic group is oxidized. Examples of the "heterocyclic group" which can form the N-oxide in the present compound include a pyridine ring.

The groups used herein will be illustrated in detail by way of examples.

In the present application, the "Ca-Cb chain hydrocarbon group" means a linear or branched, saturated or unsaturated hydrocarbon group having a to b carbon atoms;

the "Ca-Cb alkyl group" means a linear or branched hydrocarbon group having a to b carbon atoms;

the "Ca-Cb alkenyl group" means a linear or branched, unsaturated hydrocarbon group having a to b carbon atoms and one or more double bonds within the molecule;

the "Ca-Cb alkynyl group" means a linear or branched, unsaturated hydrocarbon group having a to b carbon atoms and one or more triple bonds within the molecule;

the "Ca-Cb haloalkyl group" means a linear or branched alkyl group having a to b carbon atoms, wherein the hydrogen atom(s) bound to the carbon atom(s) is/are substituted by one or more halogen atoms, and when the group is substituted by two or more halogen atoms, these halogen atoms are the same or different from each other;

the Ca-Cb alkoxy group" means a linear or branched alkyl-O-group having a to b carbon atoms;

the "Ca-Cb alkenyloxy group" means a linear or branched alkenyl-O-group having a to b carbon atoms and one or more double bonds within the molecule;

the "Ca-Cb" alkynyloxy group" means a linear or branched alkynyl-O-group having a to b carbon atoms and one or more triple bonds within the molecule;

the "Ca-Cb alkylsulfanyl group" means a linear or branched alkyl-S-group having a to b carbon atoms;

the "Ca-Cb alkylsulfinyl group" means a linear or branched alkyl-S(O)-group having a to b carbon atoms;

the "Ca-Cb alkylsulfonyl group" means a linear or branched alkyl-S(O)$_2$-group having a to b carbon atoms;

the "Ca-Cb alkyl carbonyl group" means a linear or branched alkyl-C(O)-group having a to b carbon atoms;

the "Ca-Cb alkoxycarbonyl group" means a linear or branched alkyl-O—C(O)-group having a to b carbon atoms;

the "Ca-Cb alicyclic hydrocarbon group" means a cyclic nonaromatic hydrocarbon group having a to b carbon atoms;

the "Ca-Cb cycloalkyl group" means a cyclic alkyl group having a to b carbon atoms;

the "Ca-Cb alkylamino group" means a linear or branched alkyl-NH-group having a to b carbon atoms;

the "Ca-Cb dialkylamino group" means a linear or branched dialkylamino group, wherein the alkyl groups have the same or different carbon atoms and the total number of carbon atoms is a to b;

the "Ca-Cb alkoxyalkyl group" means a linear or branched alkyl-O-alkyl group, wherein the alkyl groups have the same or different carbon atoms and the total number of carbon atoms is a to b.

In the "optionally substituted by one or more atoms or groups selected from Group X" used herein, when two or more atoms or groups selected from Group X are present, these atoms or groups selected from Group X are the same or different from each other.

In the "optionally substituted by one or more atoms or groups selected from Group Y" used herein, when two or more atoms or groups selected from Group Y are present, these atoms or groups selected from Group Y are the same or different from each other.

In the "optionally substituted by one or more atoms or groups selected from Group Z" used herein, when two or more atoms or groups selected from Group Z are present, these atoms or groups selected from Group Z are the same or different from each other.

In the "optionally substituted by one or more atoms or groups selected from Group W" used herein, when two or more atoms or groups selected from Group W are present, these atoms or groups selected from Group W are the same or different from each other.

In the "optionally substituted by one or more halogen atoms" used herein, when two or more halogen atoms are present, these halogen atoms are the same or different from each other.

The "halogen atom" in the present compound includes a fluorine atom, a chlorine atom, a bromine atom and an iodine atom.

The "C1-C6 chain hydrocarbon group optionally substituted by one or more atoms or groups selected from Group X" in the present compound means a linear or branched hydrocarbon group having 1 to 6 carbon atoms, wherein the hydrogen atom(s) bound to the carbon atom(s) is/are optionally substituted by one or more atoms or groups selected from Group X, and when the group is substituted by two or more atoms or groups selected from Group X, these atoms or groups are the same or different from each other.

Examples of the "C1-C6 chain hydrocarbon group optionally substituted by one or more atoms or groups selected from Group X" in the present compound include C1-C6 alkyl groups optionally substituted by one or more atoms or groups selected from Group X, such as a methyl group, an ethyl group, a propyl group, an isopropyl group, a butyl group, an isobutyl group, a sec-butyl group, a tert-butyl group, a pentyl group, a neopentyl group, a hexyl group, methoxymethyl group, an ethoxymethyl group, a propyloxymethyl group, an isopropyloxymethyl group, a butyloxymethyl group, a sec-butyloxymethyl group, a tert-butyloxymethyl group, a 2-methoxyethyl group, a 2-ethoxyethyl group, a 2-propyloxyethyl group, a 2-isopropyloxyethyl group, a 2-butyloxy-ethyl group, a 2-sec-butyloxyethyl group, a 2-tert-butyloxyethyl group, a trifluoromethyl group, a trichloromethyl group, a 2-fluoroethyl group, a 2,2-difluoroethyl group, a 2,2,2-trifluoroethyl group and a pentafluoroethyl group, a methylsulfanylethyl group, a ethylsulfanylethyl group, a methylsulfinylethyl group, a methylsulfonylethyl group, a 2-hydroxy ethyl group, a cyclopropylmethyl group, a 1-methylcyclopropylmethyl group, a 2,2-difluorocyclopropylmethyl group, and the like;

C2-C6 alkenyl groups optionally substituted by one or more atoms or groups selected from Group X, such as a vinyl group, a 1-propenyl group, a 2-propenyl group, a 1-methyl vinyl group, a 2-methyl-1-propenyl group, a 1-butenyl group, a 2-butenyl group, a 3-butenyl group, a 1-pentenyl group, a 1-hexenyl group, a 1,1-difluoroallyl group, a pentafluoroallyl group, and the like; and C2-C6 alkynyl groups optionally substituted by one or more atoms or groups selected from Group X, such as an ethynyl group, a propargyl group, a 2-butynyl group, a 3-butynyl group, a 1-pentynyl group, a 1-hexynyl group and a 4,4,4-trifluoro-2-butynyl group, and the like; which is selected depending on a given range of carbon atoms.

The "C3-C6 alicyclic hydrocarbon group optionally substituted by one or more atoms or groups selected from Group Y" in the present compound means a cyclic non-aromatic hydrocarbon group having 3 to 6 carbon atoms, wherein the hydrogen atom(s) bound to the carbon atom(s) is/are optionally substituted by one or more atoms or groups selected from Group Y, and when the group is substituted by two or more atoms or groups selected from Group Y, these atoms or groups are the same or different from each other.

Examples of the "C3-C6 alicyclic hydrocarbon group optionally substituted by one or more atoms or groups selected from Group Y" in the present compound include a cyclopropyl group, a cyclobutyl group, a cyclopentyl group, a cyclohexyl group, a 1-cyclohexenyl group, a 2-cyclohexenyl group, a 3-cyclohexenyl group, a 1-methylcyclohexyl group, a 2-methylcyclohexyl group, a 3-methylcyclohexyl group, a 4-methylcyclohexyl group, a 2-methoxycyclohexyl group, a 3-methoxycyclohexyl group, a 4-methoxycyclohexyl group, a 1-fluorocyclohexyl group, a 2-fluorocyclohexyl group, a 3-fluorocyclohexyl group, and a 4-fluorocyclohexyl group.

The "C1-C6 chain hydrocarbon group optionally substituted by one or more halogen atoms" in the present compound means a linear or branched hydrocarbon group having 1 to 6 carbon atoms, wherein the hydrogen atom(s) bound to the carbon atom(s) is/are optionally substituted by one or more halogen atoms, and when the group is substituted by two or more halogen atoms, these halogen atoms are the same or different from each other.

Examples of the "C1-C6 chain hydrocarbon group optionally substituted by one or more halogen atoms" in the present compound include C1-C6 alkyl groups optionally substituted by one or more halogen atoms such as a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2-trifluoroethyl group, a pentafluoroethyl group, a heptafluoroisopropyl group, and the like;

C2-C6 alkenyl groups optionally substituted by one or more halogen atoms such as a vinyl group, a 1-propenyl group, 2-propenyl group, a 1-methylvinyl group, a 2-methyl-1-propenyl group, a 1-butenyl group, a 2-butenyl group, a 3-butenyl group, a 1-pentenyl group, a 1-hexenyl group, 1,1-difluoroallyl group, a pentafluoroallyl group, and the like;

C2-C6 alkynyl groups optionally substituted by one or more halogen atoms such as an ethynyl group, a propargyl group, a 2-butynyl group, a 3-butynyl group, a 1-pentynyl group, a 1-hexynyl group, a 4,4,4-trifluoro-2-butynyl group, and the like; which is selected depending on a given range of carbon atoms.

The "phenyl group optionally substituted by one or more atoms or groups selected from Group Z" in the present compound means a phenyl group, wherein the hydrogen atom(s) bound to the carbon atom(s) is/are optionally substituted by one or more atoms or groups selected from Group Z, and when the group is substituted by two or more atoms or groups selected from Group Z, these atoms or groups are the same or different from each other.

Examples of the "phenyl group optionally substituted by one or more atoms or groups selected from Group Z" in the present compound include a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4,5,6-pentafluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-trifluoromethyl phenyl group, a 3-trifluoromethylphenyl group, a 4-trifluoromethylphenyl group, a 2-trifluoromethoxyphenyl group, a 3-trifluoromethoxyphenyl group, a 4-trifluoromethoxyphenyl group, a 2-trifluoromethylsulfanylphenyl group, a 3-trifluoromethylsulfanylphenyl group, a 4-trifluoromethylsulfanylphenyl group, a 4-methoxycarbonylphenyl group, a 4-nitrophenyl group, a 4-cyanophenyl group, a 4-methylaminophenyl group, a 4-dimethylaminophenyl group, a 4-methylsulfinylphenyl group, a 4-methylsulfonylphenyl group, a 4-acetylphenyl group and a 4-methoxycarbonylphenyl group.

The "heterocyclic group" in the present compound means a residue of a heterocyclic compound having one or more nitrogen atoms, oxygen atoms or sulfur atoms in addition to carbon atoms in the ring structure.

The "5-membered heterocyclic group" in the present compound means a 5-membered aromatic heterocyclic group or 5-membered non-aromatic heterocyclic group, and the "6-membered heterocyclic group" means a 6-membered aromatic heterocyclic group or a 6-membered non-aromatic heterocyclic group.

The "heterocyclic group" in the "5- or 6-membered heterocyclic group optionally substituted by one or more atoms or groups selected from Group Z" in the present compound means a residue of a heterocyclic compound having one or more nitrogen atoms, oxygen atoms or sulfur atoms in addition to carbon atoms in the ring structure, wherein the group has two or more atoms or groups selected from Group Z, these atoms or groups are the same or different from each other.

The "5- or 6-membered heterocyclic group" in the present compound means a 5- or 6-membered aromatic heterocyclic group, or a or 6-membered non-aromatic heterocyclic group.

Examples of the "5- or 6-membered heterocyclic group optionally substituted by one or more atoms or groups selected from Group Z" in the present compound include 5 or 6-membered non-aromatic heterocyclic groups optionally substituted by one or more atoms or groups selected from Group Z, such as a pyrrolidin-1-yl group, a 3,3,4,4-tetrafluoropyrrolidin-1-yl group, a tetrahydrofuran-2-yl group, a piperidyl group, a morpholyl group, a thiomorpholyl group, and the like;

5- or 6-membered aromatic heterocyclic groups optionally substituted by one or more atoms or groups selected from Group Z, such as a 2-pyrroly group, a 2-furyl group, a 3-furyl group, a 5-pyrazolyl group, a 4-pyrazolyl group, a 1-pyrroly group, a 1-methyl-2-pyrroly group, a 2-methylsulfanyl-1-pyrroly group, a 2-methylsulfinyl-1-pyrroly group, a 2-methylsulfonyl-1-pyrroly group, a 2-methylamino-1-pyrroly group, a 2-dimethylamino-1-pyrroly group, a 5-bromo-2-furyl group, a 5-nitro-2-furyl group, a 5-cyano-2-furyl group, a 5-methoxy-2-furyl group, a acetyl-2-furyl group, a 5-methoxycarbonyl-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazole-1-yl group, a 1,2,4-triazol-1-yl group, a 3-chloro-1,2,4-triazol-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluotomethylpyrazol-1-yl group, pyrazinyl group, 4-pyrimidinyl group, a 5-pyrimidinyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group, a 5-trifluoromethylpyridin-2-yl group, and the like.

Examples of the "C1-C6 chain hydrocarbon group substituted by one phenyl group (wherein the phenyl group is optionally substituted by one or more atoms or groups selected from Group Z)" in the present compound include a phenylmethyl group, a 4-chlorophenylmethyl group and a 4-trifluoromethyl phenylmethyl group, and the like. When the group has two or more atoms or groups selected from Group Z, these atoms or groups are the same or different from each other.

Examples of the "C1-C6 chain hydrocarbon group substituted by one 5- or 6-membered heterocyclic group (wherein the 5- or 6-membered heterocyclic group is optionally substituted by one or more atoms or groups selected from Group Z)" in the present compound include 5 or 6-membered non-aromatic heterocyclic groups such as a tetrahydrofuran-2-ylmethyl group, a tetrahydropyran-2-ylmethyl group, a tetrahydropyran-3-ylmethyl group, and the like;
5- or 6-membered aromatic heterocyclic groups such as a thiazol-5-ylmethyl group, a 2-chlorothiazol-5-ylmethyl group, a pyridin-3-ylmethyl group, a 6-chloropyridin-3-ylmethyl group, a 6-trifluoromethylpyridin-3-ylmethyl group, and the like. When the group has two or more atoms or groups selected from Group Z, these atoms or groups are the same or different from each other.

Examples of the "C1-C6 alkyl group substituted by one 5- or 6-membered aromatic heterocyclic group (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms)" in the present compound include a thiazol-5-ylmethyl group, a 2-chlorothiazol-5-ylmethyl group, a pyridin-3-ylmethyl group, a 6-chloropyridin-3-ylmethyl group, a 6-trifluoromethylpyridin-3-ylmethyl group, and the like.

Examples of the "5- or 6-membered aromatic heterocyclic group (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms)" in the present compound include a 2-pyrroly group, a 2-furyl group, a 3-furyl group, a 5-pyrazolyl group, a 4-pyrazolyl group, a 1-pyrroly group, a 1-methyl-2-pyrroly group, a 5-bromo-2-furyl group, a 5-methoxy-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazole-1-yl group, a 1,2,4-triazol-1-yl group, a 3-chloro-1,2,4-triazol-1-yl group, 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluoromethylpyrazol-1-yl group, a pyrazinyl group, a 4-pyrimidinyl group, a 5-pyrimidinyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group, a 5-trifluoromethylpyridin-2-yl group, and the like.

Examples of the "C1-C6 alkyl group optionally substituted by one or more atoms or groups selected from the group consisting of a halogen atom and a cyclopropyl group (wherein the cyclopropyl group is optionally substituted by one or more halogen atoms or one or more C1-C3 alkyl groups)" in the present compound include a methyl group, an ethyl group, a propyl group, an isopropyl group, butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2-trifluoroethyl group, a pentafluoroethyl group, a heptafluoroisopropyl group, a cyclopropylmethyl group, a 2-cyclopropylethyl group, a 1-cyclopropylethyl group, a 1-methylcyclopropylmethyl group, and the like.

Examples of the "C1-C6 chain hydrocarbon group optionally substituted by one or more atoms or groups selected from Group W" in the present compound include C1-C6 alkyl groups optionally substituted by one or more atoms or groups selected from Group W, such as a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2-trifluoroethyl group, a pentafluoroethyl group, a methoxymethyl group, an ethoxymethyl group, a propyloxymethyl group, an isopropyloxymethyl group, a butyloxymethyl group, a sec-butyloxymethyl group, an isobutyloxymethyl group, a tert-butyloxymethyl group, a methoxyethyl group, an ethoxyethyl group, a propyloxyethyl group, an isopropyloxyethyl group, a butyloxyethyl group, a sec-butyloxyethyl group, an isobutyloxyethyl group, a tert-butyloxyethyl group, a methylsulfanylethyl group, an ethylsulfanylethyl group, a methylsulfinylethyl group, methylsulfonylethyl group, a methoxycarbonylmethyl group, a methoxycarbonylethyl group, a 2-cyanoethyl group, a 2-oxopropyl, a cyclopropylmethyl group, a cyclohexylmethyl group, and the like;

C2-C6 alkenyl groups optionally substituted by one or more atoms or groups selected from Group W, such as a vinyl group, 1-propenyl group, a 2-propenyl group, a 1-methylvinyl group, a 2-methyl-1-propenyl group, a 1-butenyl group, a 2-butenyl group, a 3-butenyl group, a 1-pentenyl, group, a 1-hexenyl group, a 1,1-difluoroallyl group, pentafluoroallyl group, and the like;

C2-C6 alkynyl groups optionally substituted by one or more atoms or groups selected from Group W, such as an ethynyl group, a propargyl group, a 2-butynyl group, a 3-butynyl group, a 1-pentynyl group, a 1-hexynyl group, a 4,4,4-trifluoro-2-butynyl group, and the like. When the group has two or more atoms or groups selected from Group W, these atoms or groups are the same or different from each other.

Examples of the "C1-C6 alkoxy group optionally substituted by one or more halogen atoms" in the present compound include a methoxy group, a trifluoromethoxy group, an ethoxy group, a 2,2,2-trifluoroethoxy group, a propyloxy group, an isopropyloxy group, a butyloxy group, an isobutyloxy group, a sec-butyloxy group, a tert-butyloxy group, a pentyloxy group, a hexyloxy group, and the like.

Examples of the "C2-C6 alkenyloxy group substituted by one or more halogen atoms" in the present compound include a 2-propenyloxy group, a 2-methyl-2-propenyloxy group, a 2-butenyloxy group, a 3-butenyloxy group, a 2-pentenyloxy group, a 2-hexenyloxy group, a 3,3-difluoroallyloxy group, a 3,3-dichloro allyloxy group, and the like.

Examples of the "C2-C6 alkynyloxy group optionally substituted by one or more halogen atoms" in the present compound include a propargyloxy group, a 2-butynyloxy group, a 3-butynyloxy group, a 2-pentynyloxy group, a 2-hexynyloxy group, a 4,4,4-trifluoro-2-butynyl oxy group, and the like.

Examples of the "C1-C6 alkylsulfanyl group optionally substituted by one or more halogen atoms" in the present compound include a methylsulfanyl group, an ethylsulfanyl group, a propylsulfanyl group, an isopropylsulfanyl group, a butylsulfanyl group, a pentylsulfanyl group, hexylsulfanyl group, a trifluoromethylsulfanyl group, 2,2,2-trifluoroethylsulfanyl group, a pentafluoroethylsulfanyl group, and the like.

Examples of the "C1-C6 alkylsulfinyl group optionally substituted by one or more halogen atoms" in the present compound include a methylsulfinyl group, an ethylsulfinyl group, a propylsulfinyl group, an isopropylsulfinyl group, butylsulfinyl group, pentylsulfinyl group, a hexylsulfinyl group, a trifluoromethylsulfinyl group, a 2,2,2-trifluoroethylsulfinyl group, a pentafluoroethylsulfinyl group, and the like.

Examples of the "C1-C6 alkylsulfonyl group optionally substituted by one or more halogen atoms" in the present compound include a methylsulfonyl group, an ethylsulfonyl group, a propylsulfonyl group, an isopropylsulfonyl group, a butylsulfonyl group, a pentylsulfonyl group, a hexylsulfonyl group, a trifluoromethylsulfonyl group, a 2,2,2-trifluoroethylsulfonyl group, a pentafluoroethylsulfonyl group, and the like.

Examples of the "C2-C6 alkylcarbonyl group optionally substituted by one or more halogen atoms" in the present compound include an acetyl group, a propionyl group, a butyryl group, a pentanoyl group, a hexanoyl group, trifluoroacetyl group, and the like.

Examples of the "C2-C6 alkoxycarbonyl group optionally substituted by one or more halogen atoms" in the present compound include a methoxycarbonyl group, an ethoxycarbonyl group, a propyloxycarbonyl group, a butyloxycarbonyl group, a pentyloxycarbonyl group, a tert-butyloxycarbonyl group, a 2,2,2-trifluoroethyloxycarbonyl group, and the like.

Examples of the "C1-C6 alkylamino group optionally substituted by one or more halogen atoms" in the present compound include a methylamino group, an ethylamino group, a 2,2,2-trifluoroethylamino group, a propylamino group, an isopropylamino group, a butylamino group, and the like.

Examples of the "C2-C8 dialkylamino group optionally substituted by one or more halogen atoms" in the present compound include a dimethylamino group, a diethylamino group, a bis(2,2,2-trifluoroethyl)amino group, a dipropylamino group, and the like.

Examples of the "C3-C6 cycloalkyl group optionally substituted by one or more halogen atoms" in the present compound include a cyclopropyl group, a 2,2-difluorocyclopropyl group, a 2,2-dichlorocyclopropyl group, a 2,2-dibromocyclopropyl group, a cyclobutyl group, a cyclopentyl group, a cyclohexyl group, and the like.

Examples of the "C3-C6 cycloalkyl group optionally substituted by one or more halogen atoms or one or more C1-C3 alkyl groups" in the present compound include a cyclopropyl group, a 1-methylcyclopropyl group, a 2 methylcyclopropyl group, a 1-fluorocyclopropyl group, a 2,2-difluorocyclopropyl group, a 2,2-dichlorocyclopropyl group, a 2,2-dibromocyclopropyl group, a cyclobutyl group, a cyclopentyl group, a cyclohexyl group, and the like.

Examples of the "C2-C6 alkyl group" in the present compound include an ethyl group, a propyl group, an isopropyl group, a butyl group, an isobutyl group, a sec-butyl group, a tert-butyl group, a pentyl group, a neopentyl group, a hexyl group, and the like.

The "C1-C6 haloalkyl group" in the present compound means a linear or branched hydrocarbon group having 1 to 6 carbon atoms, wherein the hydrogen atom(s) bound to the carbon atom(s) is/are substituted by one or more halogen atoms, and when the group is substituted by two or more halogen atoms, these halogen atoms are the same or different from each other.

Examples of the "C1-C6 haloalkyl group" in the present compound include a fluoro methyl group, a chloromethyl group, a bromomethyl group, an iodomethyl group, a difluoromethyl group, a dichloromethyl group, a trifluoromethyl group, a chlorodifluoromethyl group; bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, a heptafluoroisopropyl group, and the like.

Examples of the "C4-C9 cyclopropylalkyl group (wherein the cyclopropyl group is optionally substituted by one or more halogen atoms or one or more C1-C3 alkyl groups)" in the present compound include a cyclopropylmethyl group, a 2-cyclopropylethyl group, a 1-cyclopropylethyl group, a 1-methylcyclopropyl group, and the like.

Examples of the "C1-C6 perfluoroalkyl group" in the present compound include a trifluoromethyl group, a pentafluoroethyl group, a heptafluoropropyl group, a heptafluoroisopropyl group, and the like.

Examples of the "C1-C6 alkyl group optionally substituted by one or more halogen atoms" in the present compound include a methyl group, an ethyl group, a propyl group, an isopropyl group, butyl group, an isobutyl group, a sec-butyl group, a tert-butyl group, a pentyl group, a neopentyl group, a hexyl group, a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, a heptafluoroisopropyl group, and the like.

Examples of the "C2-C6 alkenyl group optionally substituted by one or more halogen atoms" in the present compound include a vinyl group, a 1-propenyl group, a 2-propenyl group, a 1-methyl vinyl group, a 2-methyl-1-propenyl group, a 1-butenyl group, a 2-butenyl group, a 3-butenyl group, a 1-pentenyl group, a 1-hexenyl group, a 1,1-difluoroallyl group, a pentafluoroallyl group, and the like.

Examples of the "C2-C6 alkynyl group optionally substituted by one or more halogen atoms" in the present compound include an ethynyl group, a propargyl group, a 2-butynyl group, a 3-butynyl group, a 1-pentynyl group, a 1-hexynyl group, a 4,4,4-trifluoro-2-butynyl group, and the like.

Examples of the "C3-C6 alkenyl group optionally substituted by one or more halogen atoms" in the present compound include a 1-propenyl group, a 2-propenyl group, a 1-methyl vinyl group, a 2-methyl-1-propenyl group, a 1-butenyl group, a 2-butenyl group, a 3-butenyl group, a 1-pentenyl group, a 1-hexenyl group, a 1,1-difluoroallyl group, a pentafluoroallyl group, and the like.

Examples of the "C3-C6 alkynyl group optionally substituted by one or more halogen atoms" in the present compound include a propargyl group, a 2-butynyl group, a 3-butynyl group, a 1-pentynyl group, a 1-hexynyl group, a 4,4,4-trifluoro-2-butynyl group, and the like.

Examples of the "C2-C6 alkoxyalkyl group optionally substituted by one or more halogen atoms" in the present compound include a methoxymethyl group, an ethoxymethyl group, a 1-(methoxy)ethyl group, a 2-(methoxy)ethyl group, a 1-(ethoxy)ethyl group, a 2-(ethoxy)ethyl group, a 2,2,2-trifluoroethoxymethyl group, and the like.

Examples of the "pyridyl group (wherein the pyridyl group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms)" in the present compound include a 2-pyridyl group, a 3-pyridyl group, a 4-pyridyl group, a 5-trifluoromethyl-2-pyridyl group, a 3-chloro-5-trifluoromethyl-2-pyridyl group, and the like.

Examples of the "pyrimidinyl group (wherein the pyrimidinyl group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms)" in the present compound include a 2-pyrimidinyl group, a 4-pyrimidinyl group, a 5-pyrimidinyl group, a 2-chloro-4-pyrimidinyl group, and the like.

Examples of the "C1-C6 alkyl group substituted by one thiazolyl group (wherein the thiazolyl group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms)" in the present compound include a (thiazol-5-yl)methyl group, a (2-chlorothiazol-5-yl)methyl group, a 1-(2-chlorothiazol-5-yl)ethyl group, and the like.

Examples of the "C1-C6 alkyl group substituted by one pyridyl group (wherein the pyridyl group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms)" in the present compound include a (pyridin-5-yl)methyl group, a (2-chloropyridin-5-yl)methyl group, a 1-(2-chloropyridin-5-yl)ethyl group, a (2-trifluoromethylpyridin-5-yl)methyl group, and the like.

Examples of the present compound include the following compounds:

A compound represented by the formula (1-1):

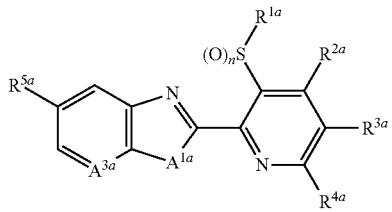

(1-1)

wherein $A^{1a}$ represents —$NR^{7a}$—, an oxygen atom or a sulfur atom, $A^{3a}$ represents a nitrogen atom or =$CR^{9a}$—, $R^{1a}$ represents a C1-C6 alkyl group optionally substituted by one or more atoms or groups selected from the group consisting of a halogen atom and a cyclopropyl group (wherein the cyclopropyl group is optionally substituted by one or more halogen atoms or one or more C1-C3 alkyl groups), a C2-C6 alkenyl group optionally substituted by one or more halogen atoms or a C2-C6 alkynyl group optionally substituted by one or more halogen atoms, $R^{2a}$ and $R^{4a}$ are the same or different and each represents a halogen atom or a hydrogen atom, $R^{3a}$ represents a C1-C6 alkyl group optionally substituted by one or more halogen atoms, a C2-C6 alkenyl group optionally substituted by one or more halogen atoms, a C2-C6 alkynyl group optionally substituted by one or more halogen atoms, 5- or 6-membered aromatic heterocyclic group (wherein the 5- or 6-membered aromatic heterocyclic group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), —$OR^{20a}$ (wherein $R^{20a}$ represents a C1-C6 alkyl group optionally substituted by one or more halogen atoms), —$S(O)_m R^{21a}$ (wherein $R^{21a}$ represents a C1-C6 alkyl group optionally substituted by one or more halogen atoms, m represents 0, 1 or 2), a cyano group, a nitro group, a halogen atom or a hydrogen atom, $R^{5a}$ represents a C1-C6 alkyl group optionally substituted by one or more halogen atoms, —$OR^{22a}$ (wherein $R^{22a}$ represents a C1-C6 alkyl group optionally substituted by one or more halogen atoms), —$S(O)_m R^{23a}$ (wherein $R^{23a}$ represents a C1-C6 alkyl group optionally substituted by one or more halogen atoms, m represents 0, 1 or 2), —$SF_5$ or a halogen atom, $R^{7a}$ represents a C1-C6 alkyl group optionally substituted by one or more halogen atoms, a C3-C6 alkenyl group optionally substituted by one or more halogen atoms, a C3-C6 alkynyl group optionally substituted by one or more halogen atoms or a C1-C6 alkyl group substituted by one 5- or 6-membered aromatic heterocyclic group (wherein the 5- or 6-membered aromatic heterocyclic group is optionally substituted by one or more atoms or substituents selected from the group consisting of a halogen atom, a C1-C3 alkyl group optionally substituted by one or more halogen atom, and a C1-C3 alkoxy group optionally substituted by one or more halogen atoms), $R^{9a}$ represents a C1-C6 alkyl group optionally substituted by one or more halogen atoms, —$OR^{24a}$ (wherein $R^{24a}$ represents a C1-C6 alkyl group optionally substituted by one or more halogen atoms), —$S(O)_m R^{25a}$ (wherein $R^{25a}$ represents a C1-C6 alkyl group optionally substituted by one or more halogen atoms, m represents 0, 1 or 2), a halogen atom or hydrogen atom, and n represents 0, 1 or 2, or an N-oxide thereof.

A compound represented by the formula (1-2):

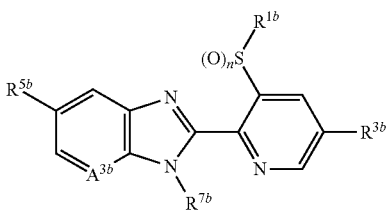

(1-2)

wherein $A^{3b}$ represents a nitrogen atom or =$CR^{9b}$— (wherein $R^{9b}$ represents a hydrogen atom or a halogen atom), $R^{1b}$ represents an ethyl group or a cyclopropylmethyl group, $R^{7b}$ represents methyl group or a propargyl group, $R^{3b}$ represents a C1-C6 alkyl group optionally substituted by one or more halogen atoms, —$OR^{20b}$ (wherein $R^{20b}$ represents a C1-C6 alkyl group optionally substituted by one or more halogen atoms), —$S(O)_m R^{21b}$ (wherein $R^{21b}$ represents a C1-C6 alkyl group optionally substituted by one or more halogen atoms, m represents 0, 1 or 2), a halogen atom or a hydrogen atom, $R^{5b}$ represents a C1-C6 haloalkyl group, —$OR^{22b}$ (wherein $R^{22b}$ represents a C1-C6 haloalkyl group), —$S(O)_m R^{23b}$ (wherein $R^{23b}$ represents a C1-C6 haloalkyl group, m represents 0, 1 or 2), —$SF_5$ or a halogen atom, and n represents 0, 1 or 2, or an N-oxide thereof.

A compound represented by the formula (1-3):

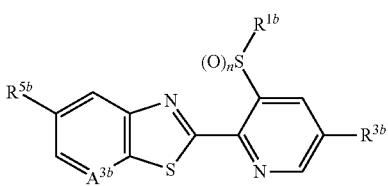

(1-3)

wherein $A^{3b}$ represents a nitrogen atom or =$CR^{9b}$— (wherein $R^{9b}$ represents a hydrogen atom or a halogen atom), $R^{1b}$ represents an ethyl group or a cyclopropylmethyl group, $R^{3b}$ represents a C1-C6 alkyl group optionally substituted by one or more halogen atoms, —$OR^{20b}$ (wherein $R^{20b}$ represents a C1-C6 alkyl group optionally substituted by one or more halogen atoms), —$S(O)_m R^{21b}$ (wherein $R^{21b}$ represents a C1-C6 alkyl group optionally substituted by one or more halogen atoms, m represents 0, 1 or 2), a halogen atom or a hydrogen atom, $R^{5b}$ represents a C1-C6 haloalkyl group, —$OR^{22b}$ (wherein $R^{22b}$ represents a C1-C6 haloalkyl group), —$S(O)_m R^{23b}$ (wherein $R^{23b}$ represents a C1-C6 haloalkyl group, m represents 0, 1 or 2), —$SF_5$ or a halogen atom, and n represents 0, 1 or 2, or an N-oxide thereof.

A compound represented by the formula (1-4):

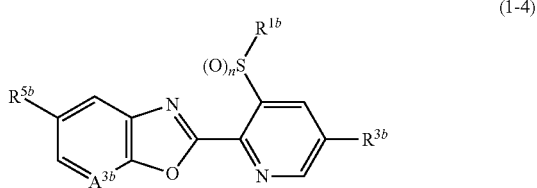

wherein
$A^{3b}$ represents a nitrogen atom or $=CR^{9b}$— (wherein $R^{9b}$ represents a hydrogen atom or a halogen atom),
$R^{1b}$ represents an ethyl group or a cyclopropylmethyl group,
$R^{3b}$ represents a C1-C6 alkyl group optionally substituted by one or more halogen atoms, —$OR^{20b}$ (wherein $R^{20b}$ represents a C1-C6 alkyl group optionally substituted by one or more halogen atoms), —$S(O)_m R^{21b}$ (wherein $R^{21b}$ represents a C1-C6 alkyl group optionally. Substituted by one or more halogen atoms, m represents 0, 1 or 2), a halogen atom or a hydrogen atom,
$R^{5b}$ represents a C1-C6 haloalkyl group, —$OR^{22b}$ (wherein $R^{22b}$ represents a C1-C6 haloalkyl group), —$S(O)_m R^{23b}$ (wherein $R^{23b}$ represents a C1-C6 haloalkyl group, m represents 0, 1 or 2), —$SF_5$ or a halogen atom, and
n represents 0, 1 or 2,
or an N-oxide thereof.

A compound represented by the formula (1-5):

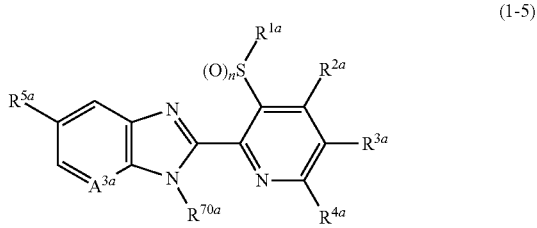

wherein
$R^{70a}$ represents a hydrogen atom or a C2-C6 alkoxyalkyl group optionally substituted by one or more halogen atoms,
$A^{3a}$ represents a nitrogen atom or $=CR^{9a}$—,
$R^{1a}$ represents a C1-C6 alkyl group optionally substituted by one or more atoms or groups selected from the group consisting of a halogen atom and a cyclopropyl group (wherein the cyclopropyl group is optionally substituted by one or more halogen atoms or one or more C1-C3 alkyl groups), a C2-C6 alkenyl group optionally substituted by one or more halogen atoms or a C2-C6 alkynyl group optionally substituted by one or more halogen atoms,
$R^{2a}$ and $R^{4a}$ are the same or different and each represents a halogen atom or a hydrogen atom,
$R^{3a}$ represents a C1-C6 alkyl group optionally substituted by one or more halogen atoms, a C2-C6 alkenyl group optionally substituted by one or more halogen atoms, a C2-C6 alkynyl group optionally substituted by one or more halogen atoms, 5- or 6-membered aromatic heterocyclic group (wherein the 5- or 6-membered aromatic heterocyclic group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), —$OR^{20a}$ (wherein $R^{20a}$ represents a C1-C6 alkyl group optionally substituted by one or more halogen atoms), —$S(O)_m R^{21a}$ (wherein $R^{22a}$ represents a C1-C6 alkyl group optionally substituted by one or more halogen atoms, m represents 0, 1 or 2), a cyano group, a nitro group, a halogen atom or a hydrogen atom,
$R^{5a}$ represents a C1-C6 alkyl group optionally substituted by one or more halogen atoms, —$OR^{22a}$ (wherein $R^{22a}$ represents a C1-C6 alkyl group optionally substituted by one or more halogen atoms), —$S(O)_m R^{23a}$ (wherein $R^{23a}$ represents a C1-C6 alkyl group optionally substituted by one or more halogen atoms, m represents 0, 1 or 2), —$SF_5$ or a halogen atom,
$R^{9a}$ represents a C1-C6 alkyl group optionally substituted by one or more halogen atoms, —$OR^{24a}$ (wherein $R^{24a}$ represents a C1-C6 alkyl group optionally substituted by one or more halogen atoms), —$S(O)_m R^{25a}$ (wherein $R^{25a}$ represents a C1-C6 alkyl group optionally substituted by one or more halogen atoms, m represents 0, 1 or 2), a halogen atom or hydrogen atom, and
n represents 0, 1 or 2,
or an N-oxide thereof.

A compound represented by the formula (1-5) wherein
$R^{70a}$ is a hydrogen atom or a C2-C6 alkoxyalkyl group,
$A^{3a}$ is a nitrogen atom or $=CR^{9a}$—,
$R^{1a}$ is a C1-C6 alkyl group optionally substituted by one or more atoms or groups selected from the group consisting of a halogen atom and a cyclopropyl group (wherein the cyclopropyl group is optionally substituted by one or more halogen atoms or one or more C1-C3 alkyl groups), a C2-C6 alkenyl group optionally substituted by one or more halogen atoms or a C2-C6 alkynyl group optionally substituted by one or more halogen atoms,
$R^{2a}$ and $R^{4a}$ are the same or different and each represents a halogen atom or a hydrogen atom,
$R^{3a}$ is a C1-C6 alkyl group optionally substituted by one or more halogen atoms, a C2-C6 alkenyl group optionally substituted by one or more halogen atoms, a C2-C6 alkynyl group optionally substituted by one or more halogen atoms, 5- or 6-membered aromatic heterocyclic group (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), —$OR^{20a}$ (wherein $R^{20a}$ represents a C1-C6 alkyl group optionally substituted by one or more halogen atoms), —$S(O)_m R^{21a}$ (wherein $R^{21a}$ represents a C1-C6 alkyl group optionally substituted by one or more halogen atoms, m represents 0, 1 or 2), a cyano group, a nitro group, a halogen atom or a hydrogen atom,
$R^{5a}$ is a C1-C6 alkyl group optionally substituted by one or more halogen atoms, —$OR^{22a}$ (wherein $R^{22a}$ represents a C1-C6 alkyl group optionally substituted by one or more halogen atoms), —$S(O)_m R^{23a}$ (wherein $R^{23a}$ represents a C1-C6 alkyl group optionally substituted by one or more halogen atoms, m represents 0, 1 or 2), —$SF_5$ or a halogen atom,
$R^{9a}$ is a C1-C6 alkyl group optionally substituted by one or more halogen atoms, —$OR^{24a}$ (wherein $R^{24a}$ represents a C1-C6 alkyl group optionally substituted by one or more halogen atoms), —$S(O)_m R^{25a}$ (wherein $R^{25a}$ represents a C1-C6 alkyl group optionally substituted by one or more halogen atoms, m represents 0, 1 or 2), a halogen atom or a hydrogen atom, and
n is 0, 1 or 2,
or an N-oxide thereof.

A compound represented by the formula (1-6):

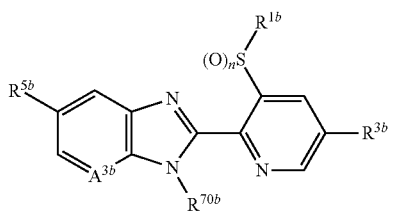

wherein
$R^{70b}$ represents a hydrogen atom or a C2-C6 alkoxyalkyl group optionally substituted by one or more halogen atoms,
$A^{3b}$ represents a nitrogen atom or $=CR^{9b}$— (wherein $R^{9b}$ represents a hydrogen atom or a halogen atom),
$R^{1b}$ represents an ethyl group or a cyclopropylmethyl group,
$R^{3b}$ represents a C1-C6 alkyl group optionally substituted by one or more halogen atoms, $-OR^{20b}$ (wherein $R^{20b}$ represents a C1-C6 alkyl group optionally substituted by one or more halogen atoms), $-S(O)_m R^{21b}$ (wherein $R^{21b}$ represents a C1-C6 alkyl group optionally substituted by one or more halogen atoms, m represents 0, 1 or 2), a halogen atom or a hydrogen atom,
$R^{5b}$ represents a C1-C6 haloalkyl group, $-OR^{22b}$ (wherein $R^{22b}$ represents a C1-C6 haloalkyl group), $-S(O)_m R^{23b}$ (wherein $R^{23b}$ represents a C1-C6 haloalkyl group, m represents 0, 1 or 2), $-SF_5$ or a halogen atom, and
n represents 0, 1 or 2,
or an N-oxide thereof.

A compound represented by the formula (1):

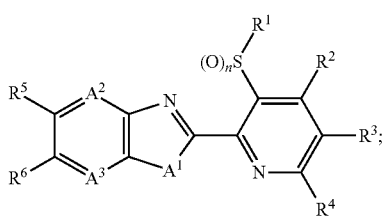

A compound represented by the formula (1) wherein $A^1$ is $-NR^7-$;
A compound represented by the formula (1) wherein $A^1$ is an oxygen atom;
A compound represented by the formula (1) wherein $A^1$ is a sulfur atom;
A compound represented by the formula (1) wherein $A^2$ is $=CR^8-$;
A compound represented by the formula (1) wherein $A^2$ is $=CR^8-$, and $A^3$ is a nitrogen atom;
A compound represented by the formula (1) wherein $A^2$ is $=CR^8-$, and $A^3$ is $=CR^9-$;
A compound represented by the formula (1) wherein $A^1$ is $-NR^7-$, and $A^2$ is $=CR^8-$;
A compound represented by the formula (1) wherein $A^1$ is $-NR^7-$, $A^2$ is $=CR^8-$, and $A^3$ is a nitrogen atom;
A compound represented by the formula (1) wherein $A^1$ is $-NR^7-$, $A^2$ is $=CR^8-$, and $A^3$ is $=CR^9-$;
A compound represented by the formula (1) wherein $A^1$ is an oxygen atom, and $A^2$ is $=CR^8-$;
A compound represented by the formula (1) wherein $A^1$ is an oxygen atom, $A^2$ is $=CR^8-$, and $A^3$ is a nitrogen atom;
A compound represented by the formula (1) wherein $A^1$ is an oxygen atom, $A^2$ is $=CR^8-$, and $A^3$ is $=CR^9-$;
A compound represented by the formula (1) wherein $A^1$ is a sulfur atom, and $A^2$ is $=CR^8-$;
A compound represented by the formula (1) wherein $A^1$ is a sulfur atom, $A^2$ is $=CR^8-$, and $A^3$ is a nitrogen atom;
A compound represented by the formula (1) wherein $A^1$ is a sulfur atom, $A^2$ is $=CR^8-$, and $A^3$ is $=CR^9-$;
A compound represented by the formula (1) wherein $R^1$ is a C1-C6 chain hydrocarbon group optionally substituted by one or more atoms or groups selected from Group X;
A compound represented by the formula (1) wherein is a C1-C6 alkyl group optionally substituted by one or more atoms or groups selected from the group consisting of a halogen atom and a cyclopropyl group (wherein the cyclopropyl group is optionally substituted by one or more halogen atoms or one or more C1-C3 alkyl groups), a C2-C6 alkenyl group optionally substituted by one or more halogen atoms or a C2-C6 alkynyl group optionally substituted by one or more halogen atoms;
A compound represented by the formula (1) wherein $R^3$ is a C1-C6 chain hydrocarbon group optionally substituted by one or more atoms or groups selected from Group X, a phenyl group optionally substituted by one or more atoms or groups selected from Group Z, a 5-membered heterocyclic group optionally substituted by one or more atoms or groups selected from Group. Z, a 6-membered heterocyclic group optionally substituted by one or more atoms or groups selected from Group Z, $-OR^{10}$, $-S(O)_m R^{10}$, $-SF_5$, a cyano group, a nitro group, a halogen atom or a hydrogen atom;
A compound represented by the formula (1) wherein $R^3$ is a C1-C6 alkyl group optionally substituted by one or more halogen atoms, a C2-C6 alkenyl group optionally substituted by one or more halogen atoms, a C2-C6 alkynyl group optionally substituted by one or more halogen atoms, 5-membered aromatic heterocyclic group (wherein the aromatic heterocyclic group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), 6-membered aromatic heterocyclic group (wherein the aromatic heterocyclic group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), $-OR^{10}$ (wherein $R^{10}$ is a C1-C6 alkyl group optionally substituted by one or more halogen atoms), $-S(O)_m R^{10}$ (wherein $R^{10}$ is a C1-C6 alkyl group optionally substituted by one or more halogen atoms), a cyano group, a nitro group, a halogen atom or a hydrogen atom;
A compound represented by the formula (1) wherein $R^2$ and $R^4$ are the same or different each other and each represents a C1-C6 chain hydrocarbon group optionally substituted by one or more atoms or groups selected from Group X, a phenyl group optionally substituted by one or more atoms or groups selected from Group Z, a 5-membered heterocyclic group optionally substituted by one or more atoms or groups selected from Group Z, a 6-membered heterocyclic group optionally substituted by one or more atoms or groups selected from Group Z, $-OR^{10}$, $-S(O)_m R^{10}$, $-SF_5$, a cyano group, a nitro group, a halogen atom or a hydrogen atom;
A compound represented by the formula (1) wherein $R^2$ and $R^4$ are the same or different each other and each represents a halogen atom or a hydrogen atom;

A compound represented by the formula (1) wherein $R^5$ is a C1-C6 chain hydrocarbon group optionally substituted by one or more atoms or groups selected from Group X, $-OR^{10}$, $-S(O)_m R^{10}$, $-SF_5$, a halogen atom or a hydrogen atom;

A compound represented by the formula (1) wherein $R^5$ is a C1-C6 chain hydrocarbon group optionally substituted by one or more atoms or groups selected from Group X, $-OR^{10}$, $-S(O)_m R^{10}$, $-SF_5$ or a halogen atom;

A compound represented by the formula (1) wherein $R^5$ is a C1-C6 alkyl group optionally substituted by one or more halogen atoms, $-OR^{10}$ (wherein $R^{10}$ is a C1-C6 alkyl group optionally substituted by one or more halogen atoms), $-S(O)_m R^{10}$ (wherein $R^{10}$ is a C1-C6 alkyl group optionally substituted by one or more halogen atoms), $-SF_5$ or a halogen atom;

A compound represented by the formula (1) wherein when $A^1$ is $-NR^7-$, $R^7$ is a C1-C6 chain hydrocarbon group optionally substituted by one or more atoms or groups selected from Group W, a C1-C6 chain hydrocarbon group substituted by one phenyl group (wherein the phenyl group is optionally substituted by one or more atoms or groups selected from Group Z), a C1-C6 chain hydrocarbon group substituted by one 5-membered heterocyclic group (wherein the 5-membered heterocyclic group is optionally substituted by one or more atoms or groups selected from Group Z), a C1-C6 chain hydrocarbon group substituted by one 6-membered heterocyclic group (wherein the 6-membered heterocyclic group is optionally substituted by one or more atoms or groups selected from Group Z) or a hydrogen atom;

A compound represented by the formula (1) wherein when $A^1$ is $-NR^7-$, $R^7$ is a C1-C6 alkyl group optionally substituted by one or more halogen atoms, a C3-C6 alkenyl group optionally substituted by one or more halogen atoms, a C3-C6 alkynyl group optionally substituted by one or more halogen atoms, a C1-C6 alkyl group substituted by one 5-membered aromatic heterocyclic group (wherein the 5-membered aromatic heterocyclic group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), a C1-C6 alkyl group substituted by one 6-membered aromatic heterocyclic group (wherein the 6-membered aromatic heterocyclic group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), a hydrogen atom or a C2-C6 alkoxyalkyl group;

A compound represented by the formula (1) wherein when $A^1$ is $-NR^7-$, $R^7$ is a C1-C6 alkyl group optionally substituted by one or more halogen atoms, a C3-C6 alkenyl group optionally substituted by one or more halogen atoms, a C3-C6 alkynyl group optionally substituted by one or more halogen atoms; a C1-C6 alkyl group substituted by one 5-membered aromatic heterocyclic group (wherein the 5-membered aromatic heterocyclic group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms) or a C1-C6 alkyl group substituted by one 6-membered aromatic heterocyclic group (wherein the 6-membered aromatic heterocyclic group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms);

A compound represented by the formula (1) wherein when $A^1$ is $-NR^7-$, $R^7$ is a C1-C6 alkyl group optionally substituted by one or more halogen atoms, a C3-C6 alkenyl group optionally substituted by one or more halogen atoms, a C3-C6 alkynyl group optionally substituted by one or more halogen atoms, a C1-C6 alkyl group substituted by one thiazolyl group (wherein the thiazolyl group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), a C1-C6 alkyl group substituted by one pyridyl group (wherein the pyridyl group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), a hydrogen atom or a C2-C6 alkoxyalkyl group;

A compound represented by the formula (1) wherein when $A^1$ is $-NR^7-$, $R^7$ is a methyl group, an ethyl group, a propyl group, an allyl group, a propargyl group, a (2-chlorothiazol-5-yl)methyl group, a (2-chloropyridin-5-yl)methyl group, a hydrogen atom, a methoxymethyl group, an ethoxymethyl group, a 1-(methoxy)ethyl group or a 1-(ethoxy)ethyl group;

A compound represented by the formula (1) wherein $A^1$ is $-NR^7-$, and $R^7$ is a hydrogen atom or a C2-C6 alkoxyalkyl group;

A compound represented by the formula (1) wherein $A^1$ is $-NR^7-$, and $R^7$ is a hydrogen atom, a methoxymethyl group, an ethoxymethyl group, a 1-(methoxy)ethyl group or a 1-(ethoxy)ethyl group;

A compound represented by the formula (1) wherein $A^2$ is $=CR^8-$, $R^8$ is a C1-C6 chain hydrocarbon group optionally substituted by one or more halogen atoms, $-OR^{10}$, $-S(O)_m R^{10}$, a halogen atom or a hydrogen atom;

A compound represented by the formula (1) wherein $A^2$ is $=CR^8-$, $R^8$ is a C1-C6 alkyl group optionally substituted by one or more halogen atoms, $-OR^{10}$ (wherein $R^{10}$ is a C1-C6 alkyl group optionally substituted by one or more halogen atoms), $-S(O)_m R^{10}$ (wherein $R^{10}$ is a C1-C6 alkyl group optionally substituted by one or more halogen atoms), a halogen atom or a hydrogen atom;

A compound represented by the formula (1) wherein is $=CR^8-$, $R^8$ is a halogen atom or a hydrogen atom;

A compound represented by the formula (1) wherein is $=CR^8-$, $R^8$ is a hydrogen atom;

A compound represented by the formula (1) wherein $A^3$ is $=CR^9-$, $R^9$ is a C1-C6 chain hydrocarbon group optionally substituted by one or more halogen atoms, a halogen atom or a hydrogen atom;

A compound represented by the formula (1) wherein $A^3$ is $=CR^9-$, $R^9$ is a C1-C6 alkyl group optionally substituted by one or more halogen atoms, $-OR^{10}$ (wherein $R^{10}$ is a C1-C6 alkyl group optionally substituted by one or more halogen atoms), $-S(O)_m R^{10}$ (wherein $R^{10}$ is a C1-C6 alkyl group optionally substituted by one or more halogen atoms), a halogen atom or a hydrogen atom;

A compound represented by the formula (1) wherein $R^1$ is a C1-C6 alkyl group optionally substituted by one or more atoms or groups selected from the group consisting of a halogen atom and a cyclopropyl group (wherein the cyclopropyl group is optionally substituted by one or more halogen atoms or one or more C1-C3 alkyl groups);

A compound represented by the formula (1) wherein $R^1$ is a C1-C6 alkyl group, a C1-C6 haloalkyl group, or a C4-C9 cyclopropylalkyl group (wherein the cyclopropyl group is optionally substituted by one or more halogen atoms or one or more C1-C3 alkyl groups);

A compound represented by the formula (1) wherein $R^1$ is a C2-C6 alkyl group, a C1-C6 haloalkyl group or C4-C9 cyclopropylalkyl group (wherein the cyclopropyl group is optionally substituted by one or more halogen atoms or one or more C1-C3 alkyl groups);

A compound represented by the formula (1) wherein $R^1$ is a methyl group, an ethyl group, a propyl group, an isopropyl group, a trifluoromethyl group, a 2,2,2-trifluoroethyl group or a cyclopropylmethyl group;

A compound represented by the formula (1) wherein $R^1$ is an ethyl group or a cyclopropylmethyl group;

A compound represented by the formula (1) wherein $R^1$ is an ethyl group;

A compound represented by the formula (1) wherein $R^3$ is a C1-C6 alkyl group optionally substituted by one or more halogen atoms, a C2-C6 alkenyl group optionally substituted by one or more halogen atoms, a C2-C6 alkynyl group optionally substituted by one or more halogen atoms, pyridyl group (wherein the pyridyl group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), a pyrimidinyl group (wherein the pyrimidinyl group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), —$OR^{20a}$ (wherein $R^{20a}$ is a C1-C6 alkyl group optionally substituted by one or more halogen atoms), —$S(O)_mR^{21a}$ (wherein $R^{21a}$ is a C1-C6 alkyl group optionally substituted by one or more halogen atoms, and m is 0, 1 or 2), a halogen atom or a hydrogen atom;

A compound represented by the formula (1) wherein $R^3$ is a C1-C6 alkyl group optionally substituted by one or more halogen atoms, —$OR^{20b}$ (wherein $R^{20b}$ represents a C1-C6 alkyl group optionally substituted by one or more halogen atoms), —$S(O)_mR^{21b}$ (wherein $R^{21b}$ represents a C1-C6 alkyl group optionally substituted by one or more halogen atoms, m represents 0, 1 or 2), a halogen atom or a hydrogen atom;

A compound represented by the formula (1) wherein $R^3$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, —$CF_2CF_3$, —$CF_2CF_2CF_3$, —$CF(CF_3)_2$, —$CF_2CF_2CF_2CF_3$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, a 2-pyridyl group, a 5-trifluoromethyl-2-pyridyl group, a 2-pyrimidinyl group, a fluorine atom, a chlorine atom, a bromine atom, an iodine atom or a hydrogen atom;

A compound represented by the formula (1) wherein $R^3$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, —$CF_2CF_3$, —$CF_2CF_2CF_3$, —$CF(CF_3)_2$, —$CF_2CF_2CF_2CF_3$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, a fluorine atom, a chlorine atom, a bromine atom, an iodine atom or a hydrogen atom;

A compound represented by the formula (1) wherein $R^2$ and $R^4$ both are a hydrogen atom;

A compound represented by the formula (1) wherein $R^5$ is a C1-C6 haloalkyl group, —$OR^{22b}$ (wherein $R^{22b}$ is a C1-C6 haloalkyl group), —$S(O)_mR^{23b}$ (wherein $R^{23b}$ is a C1-C6 haloalkyl group, and m is 0, 1 or 2), —$SF_5$ or a halogen atom;

A compound represented by the formula (1) wherein $R^5$ is a C1-C6 haloalkyl group, —$OR^{22b}$ (wherein $R^{22b}$ is a C1-C6 haloalkyl group), —$S(O)_mR^{23b}$ (wherein $R^{23b}$ is a C1-C6 haloalkyl group, and m is 0, 1 or 2) or —$SF_5$;

A compound represented by the formula (1) wherein $R^5$ is a C1-C6 haloalkyl group, —$OR^{22b}$ (wherein $R^{22b}$ is a C1-C6 haloalkyl group), —$S(O)_mR^{23b}$ (wherein $R^{23b}$ is a C1-C6 haloalkyl group, and m is 0, 1 or 2) or a halogen atom;

A compound represented by the formula (1) wherein $R^5$ is a C1-C6 haloalkyl group, —$OR^{22b}$ (wherein $R^{22b}$ is a C1-C6 haloalkyl group) or —$S(O)_mR^{23b}$ (wherein $R^{23b}$ is a C1-C6 haloalkyl group, and m is 0, 1 or 2);

A compound represented by the formula (1) wherein $R^5$ is a C1-C6 perfluoroalkyl group, —$OR^{10}$ (wherein $R^{10}$ is a C1-C6 perfluoroalkyl group) or —$S(O)_mR^{10}$ (wherein $R^{10}$ is a C1-C6 perfluoroalkyl group);

A compound represented by the formula (1) wherein $R^5$ is a trifluoromethyl group, —$CF_2CF_3$, —$CF_2CF_2CF_3$, —$CF(CF_3)_2$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, $SF_5$, a fluorine atom, a chlorine atom, a bromine atom or an iodine atom;

A compound represented by the formula (1) wherein when $A^1$ is —$NR^7$—, $R^7$ is a C1-C6 alkyl group optionally substituted by one or more halogen atoms, a C3-C6 alkenyl group optionally substituted by one or more halogen atoms, a C3-C6 alkynyl group optionally substituted by one or more halogen atoms, a C1-C6 alkyl group substituted by one thiazolyl group (wherein the thiazolyl group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms) or a C1-C6 alkyl group substituted by one pyridyl group (wherein the pyridyl group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms);

A compound represented by the formula (1) wherein when $A^1$ is —$NR^7$—, $R^7$ is a methyl group, an ethyl group, a propyl group, an allyl group, a propargyl group, (2-chlorothiazol-5-yl)methyl group, or, (2-chloropyridin-5-yl)methyl group;

A compound represented by the formula (1) wherein when $A^1$ is —$NR^7$—, $R^7$ is a methyl group or a propargyl group;

A compound represented by the formula (1) wherein when $A^3$ is =$CR^9$—, $R^9$ is a halogen atom or a hydrogen atom;

A compound represented by the formula (1) wherein when $A^3$ is =$CR^9$—, $R^9$ is a fluorine atom, a chlorine atom, bromine atom, an iodine atom or a hydrogen atom;

A compound represented by the formula (1) wherein when $A^3$ is =$CR^9$—, $R^9$ is a fluorine atom or a hydrogen atom;

A compound represented by the formula (1) wherein $R^1$ is a C1-C6 chain hydrocarbon group optionally substituted by one or more atoms or groups selected from Group X, $R^2$, $R^3$ and $R^4$ are the same or different each other and each represents a C1-C6 chain hydrocarbon group optionally substituted by one or more atoms or groups selected from Group X, a phenyl group optionally substituted by one or more atoms or groups selected from Group Z, a 5-membered heterocyclic group optionally substituted by one or more atoms or groups selected from Group Z, a 6-membered heterocyclic group optionally substituted by one or more atoms or groups selected, from Group Z, —OR$^{10}$, —S(O)$_m$R$^{10}$, —SF$_5$, a cyano group, a nitro group, a halogen atom or a hydrogen atom, R$^5$ and R$^6$ are the same or different each other and each represents a C1-C6 chain hydrocarbon group optionally substituted by one or more atoms or groups selected from Group X, —OR$^{10}$, —S(O)$_m$R$^{10}$, —SF$_5$, a halogen atom or a hydrogen atom, when A$^1$ is —NR$^7$—, R$^7$ is a C1-C6 chain hydrocarbon group optionally substituted by one or more atoms or groups selected from Group W, a C1-C6 chain hydrocarbon group substituted by one phenyl group (wherein the phenyl group is optionally substituted by one or more atoms or groups selected from Group Z), a C1-C6 chain hydrocarbon group substituted by one 5-membered heterocyclic group (wherein the 5-membered heterocyclic group is optionally substituted by one or more atoms or groups selected from Group Z), a C1-C6 chain hydrocarbon group substituted by one 6-membered heterocyclic group (wherein the 6-membered heterocyclic group is optionally substituted by one or more atoms or groups selected from Group Z) or a hydrogen atom, when A$^2$ is =CR$^8$—, R$^8$ is a C1-C6 chain hydrocarbon group optionally substituted by one or more halogen atoms, —OR$^{10}$, —S(O)$_m$R$^{10}$, a halogen atom or a hydrogen atom, when A$^3$ is =CR$^9$—, R$^9$ is a C1-C6 chain hydrocarbon group optionally substituted by one or more halogen atoms, —OR$^{10}$, —S(O)$_m$R$^{10}$, a halogen atom or a hydrogen atom.

A compound represented by the formula (1) wherein, R$^1$ is a C1-C6 alkyl group optionally substituted by one or more atoms or groups selected from the group consisting of a halogen atom and a cyclopropyl group (wherein the cyclopropyl group is optionally substituted by one or more halogen atoms or one or more C1-C3 alkyl groups), a C2-C6 alkenyl group optionally substituted by one or more halogen atoms or a C2-C6 alkynyl group optionally substituted by one or more halogen atoms, R$^2$ and R$^4$ are the same or different each other and each represents a halogen atom or a hydrogen atom, R$^3$ is a C1-C6 alkyl group optionally substituted by one or more halogen atoms, a C2-C6 alkenyl group optionally substituted by one or more halogen atoms, a C2-C6 alkynyl group optionally substituted by one or more halogen atoms, 5-membered aromatic heterocyclic group (wherein the aromatic heterocyclic group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), 6-membered aromatic heterocyclic group (wherein the aromatic heterocyclic group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), —OR$^{10}$, —S(O)$_m$R$^{10}$, a cyano group, a nitro group, a halogen atom or a hydrogen atom, R$^5$ is a C1-C6 alkyl group optionally substituted by one or more halogen atoms, —OR$^{10}$, —S(O)$_m$R$^{10}$, —SF$_5$ or a halogen atom, R$^6$ is a C1-C6 alkyl group optionally substituted by one or more halogen atoms, —OR$^{10}$, —S(O)$_m$R$^{10}$, a halogen atom or a hydrogen atom, R$^{10}$ is a C1-C6 alkyl group optionally substituted by one or more halogen atoms, when A$^1$ is —NR$^7$—, R$^7$ is a C1-C6 alkyl group optionally substituted by one or more halogen atoms, a C3-C6 alkenyl group optionally substituted by one or more halogen atoms, a C3-C6 alkynyl group optionally substituted by one or more halogen atoms, a C1-C6 alkyl group substituted by one 5-membered aromatic heterocyclic group (wherein the 5-membered aromatic heterocyclic group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), a C1-C6 alkyl group substituted by one 6-membered aromatic heterocyclic group (wherein the 6-membered aromatic heterocyclic group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), a hydrogen atom or a C2-C6 alkoxyalkyl group, when A$^2$ is =CR$^8$—, R$^8$ is a C1-C6 alkyl group optionally substituted by one or more halogen atoms, —OR$^{10}$, —S(O)$_m$R$^{10}$, a halogen atom or a hydrogen atom, when A$^3$ is =CR$^9$—, R$^9$ is a C1-C6 alkyl group optionally) substituted by one or more halogen atoms, —OR$^{10}$, —S(O)$_m$R$^{10}$, a halogen atom or a hydrogen atom.

A compound represented by the formula (1-1) wherein A$^{1a}$ is —NR$^{7a}$—;

A compound represented by the formula (1-1) wherein A$^{1a}$ is an oxygen atom;

A compound represented by the formula (1-1) wherein A$^{1a}$ is a sulfur atom;

A compound represented by the formula (1-1) wherein A$^{1a}$ is —NR$^{7a}$—, and A$^{3a}$ is a nitrogen atom;

A compound represented by the formula (1-1) wherein A$^{1a}$ is —NR$^{7a}$—, and A$^{3a}$ is =CR$^{9a}$— compound;

A compound represented by the formula (1-1) wherein A$^{1a}$ is an oxygen atom, and A$^{3a}$ is a nitrogen atom;

A compound represented by the formula (1-1) wherein A$^{1a}$ is an oxygen atom, and A$^{3a}$ is =CR$^{9a}$— compound;

A compound represented by the formula (1-1) wherein A$^{1a}$ is a sulfur atom, and A$^{3a}$ is a nitrogen atom;

A compound represented by the formula (1-1) wherein A$^{1a}$ is a sulfur atom, and A$^{3a}$ is =CR$^{9a}$— compound;

A compound represented by the formula (1-1) wherein R$^{1a}$ is a C1-C6 alkyl group optionally substituted by one or more atoms or groups selected from the group consisting of a halogen atom and a cyclopropyl group (wherein the cyclopropyl group is optionally substituted by one or more halogen atoms or one or more C1-C3 alkyl groups);

A compound represented by the formula (1-1) wherein R$^{1a}$ is a C1-C6 alkyl group, a C1-C6 haloalkyl group, or a C4-C9 cyclopropylalkyl group (wherein the cyclopropyl group is optionally substituted by one or more halogen atoms or one or more C1-C3 alkyl groups);

A compound represented by the formula (1-1) wherein R$^{1a}$ is a C2-C6 alkyl group, a C1-C6 haloalkyl group or C4-C9 cyclopropylalkyl group (wherein the cyclopropyl group is optionally substituted by one or more halogen atoms or one or more C1-C3 alkyl groups);

A compound represented by the formula (1-1) wherein R$^{1a}$ is a methyl group, an ethyl group, a propyl group, an isopropyl group, a trifluoromethyl group, a 2,2,2-trifluoroethyl group or a cyclopropylmethyl group;

A compound represented by the formula (1-1) wherein R$^{1a}$ is an ethyl group or a cyclopropylmethyl group;

A compound represented by the formula (1-1) wherein R$^{1a}$ is an ethyl group;

A compound represented by the formula (1-1) wherein $R^{3a}$ is a C1-C6 alkyl group optionally substituted by one or more halogen atoms, a C2-C6 alkenyl group optionally substituted by one or more halogen atoms, a C2-C6 alkynyl group optionally substituted by one or more halogen atoms, pyridyl group (wherein the pyridyl group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), a pyrimidinyl group (wherein the pyrimidinyl group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), —$OR^{20a}$ (wherein $R^{20a}$ is a C1-C6 alkyl group optionally substituted by one or more halogen atoms), —$S(O)_mR^{21a}$ (wherein $R^{21a}$ is a C1-C6 alkyl group optionally substituted by one or more halogen atoms, and m is 0, 1 or 2), a halogen atom or a hydrogen atom;

A compound represented by the formula (1-1) wherein $R^{3a}$ is a C1-C6 alkyl group optionally substituted by one or more halogen atoms, —$OR^{20a}$ (wherein $R^{20a}$ represents a C1-C6 alkyl group optionally substituted by one or more halogen atoms), —$S(O)_mR^{21a}$ (wherein $R^{21a}$ represents a C1-C6 alkyl group optionally substituted by one or more halogen atoms, m represents 0, 1 or 2), a halogen atom or a hydrogen atom;

A compound represented by the formula (1-1) wherein $R^{3a}$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, —$CF_2CF_3$, —$CF_2CF_2CF_3$, —$CF(CF_3)_2$, —$CF_2CF_2CF_2CF_3$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, a 2-pyridyl group, a 5-trifluoromethyl-2-pyridyl group, a 2-pyrimidinyl group, a fluorine atom, a chlorine atom, a bromine atom, an iodine atom or a hydrogen atom;

A compound represented by the formula (1-1) wherein $R^{3a}$ is methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, —$CF_2CF_3$, —$CF_2CF_2CF_3$, —$CF(CF_3)_2$, —$CF_2CF_2CF_2CF_3$, —$OCF_3$, —$OCF_2CF_3$—, —$SCF_3$, —$S(O)CF_3$, —$S(O)_2CF_3$, —$SCF_2CF_3$, —$S(O)CF_2CF_3$, —$S(O)_2CF_2CF_3$, a fluorine atom, a chlorine atom, a bromine atom, an iodine atom or a hydrogen atom;

A compound represented by the formula (1-1) wherein $R^{2a}$ and $R^{4a}$ both are a hydrogen atom;

A compound represented by the formula (1-1) wherein $R^{5a}$ is a C1-C6 haloalkyl group, —$OR^{22a}$ (wherein $R^{22a}$ is a C1-C6 haloalkyl group), —$S(O)_mR^{23a}$ (wherein $R^{23a}$ is a C1-C6 haloalkyl group, and m is 0, 1 or 2), —$SF_5$ or a halogen atom;

A compound represented by the formula (1-1) wherein $R^{5a}$ is a C1-C6 haloalkyl group, —$OR^{22a}$ (wherein $R^{22a}$ is a C1-C6 haloalkyl group), —$S(O)_mR^{23a}$ (wherein $R^{23a}$ is a C1-C6 haloalkyl group, and m is 0, 1 or 2) or —$SF_5$;

A compound represented by the formula (1-1) wherein $R^{5a}$ is a C1-C6 haloalkyl group, —$OR^{22a}$ (wherein $R^{22a}$ is a C1-C6 haloalkyl group), —$S(O)_mR^{23a}$ (wherein $R^{23a}$ is a C1-C6 haloalkyl group, and m is 0, 1 or 2) or a halogen atom;

A compound represented by the formula (1-1) wherein $R^{5a}$ is a C1-C6 haloalkyl group, —$OR^{22a}$ (wherein $R^{22a}$ is a C1-C6 haloalkyl group) or —$S(O)_mR^{23a}$ (wherein $R^{23a}$ is a C1-C6 haloalkyl group, and m is 0, 1 or 2);

A compound represented by the formula (1-1) wherein $R^{5a}$ is a C1-C6 perfluoroalkyl group, —$OR^{22a}$ (wherein $R^{22a}$ is a C1-C6 perfluoroalkyl group) or —$S(O)_mR^{23a}$ (wherein $R^{23a}$ is a C1-C6 perfluoroalkyl group);

A compound represented by the formula (1-1) wherein $R^{5a}$ is a trifluoromethyl group, —$CF_2CF_3$, —$CF_2CF_2CF_3$, —$CF(CF_3)_2$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, $SF_5$, a fluorine atom, a chlorine atom, a bromine atom or an iodine atom;

A compound represented by the formula (1-1) wherein when $A^{1a}$ is —$NR^{7a}$—, $R^{7a}$ is a C1-C6 alkyl group optionally substituted by one or more halogen atoms, a C3-C6 alkenyl group optionally substituted by one or more halogen atoms, a C3-C6 alkynyl group optionally substituted by one or more halogen atoms, a C1-C6 alkyl group substituted by one thiazolyl group (wherein the thiazolyl group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms) or a C1-C6 alkyl group substituted by one pyridyl group (wherein the pyridyl group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms);

A compound represented by the formula (1-1) wherein when $A^{1a}$ is —$NR^{7a}$—, $R^{7a}$ is a methyl group, an ethyl group, a propyl group, an allyl group, a propargyl group, (2-chlorothiazol-5-yl)methyl group, or, (2-chloropyridin-5-yl)methyl group;

A compound represented by the formula (1-1) wherein when $A^{1a}$ is —$NR^{7a}$—, $R^{7a}$ is a methyl group or a propargyl group;

A compound represented by the formula (1-1) wherein when $A^{3a}$ is =$CR^{9a}$—, $R^{9a}$ is a halogen atom or a hydrogen atom;

A compound represented by the formula (1-1) wherein when $A^{3a}$ is =$CR^{9a}$—, $R^{9a}$ is a fluorine atom, a chlorine atom, a bromine atom, an iodine atom or a hydrogen atom;

A compound represented by the formula (1-1) wherein when $A^{3a}$ is =$CR^{9a}$—, $R^{9a}$ is a fluorine atom or a hydrogen atom;

A compound represented by the formula (1-2) wherein $A^{3b}$ is a nitrogen atom;

A compound represented by the formula (1-2) wherein $A^{3b}$ is =$CR^{9b}$— compound;

A compound represented by the formula (1-2) wherein $R^{1b}$ is an ethyl group;

A compound represented by the formula (1-2) wherein $R^{3b}$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, —$CF_2CF_3$, —$CF_2CF_2CF_3$, —$CF(CF_3)_2$, —$CF_2CF_2CF_2CF_3$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, a fluorine atom, a chlorine atom, a bromine atom, an iodine atom or a hydrogen atom;

A compound represented by the formula (1-2) wherein $R^{5b}$ is a C1-C6 haloalkyl group, —$OR^{22b}$ (wherein $R^{22b}$ is a C1-C6 haloalkyl group), —$S(O)_mR^{23b}$ (wherein $R^{23b}$ is a C1-C6 haloalkyl group, and m is 0, 1 or 2), —$SF_5$ or a halogen atom;

A compound represented by the formula (1-2) wherein $R^{5b}$ is a C1-C6 haloalkyl group, —$OR^{22b}$ (wherein $R^{22b}$ is a C1-C6 haloalkyl group), —$S(O)_m R^{23b}$ (wherein $R^{23b}$ is a C1-C6 haloalkyl group, and m is 0, 1 or 2) or —$SF_5$;

A compound represented by the formula (1-2) wherein $R^{5b}$ is a C1-C6 haloalkyl group, —$OR^{22b}$ (wherein $R^{22b}$ is a C1-C6 haloalkyl group), —$S(O)_m R^{23b}$ (wherein $R^{23b}$ is a C1-C6 haloalkyl group, and m is 0, 1 or 2) or a halogen atom;

A compound represented by the formula (1-2) wherein $R^{5b}$ is a C1-C6 haloalkyl group, —$OR^{22b}$ (wherein $R^{22b}$ is a C1-C6 haloalkyl group) or —$S(O)_m R^{23b}$ (wherein $R^{23b}$ is a C1-C6 haloalkyl group, and m is 0, 1 or 2);

A compound represented by the formula (1-2) wherein $R^{5b}$ is a C1-C6 perfluoroalkyl group, —$OR^{22b}$ (wherein $R^{22b}$ is a C1-C6 perfluoroalkyl group) or —$S(O)_m R^{23b}$ (wherein $R^{23b}$ is a C1-C6 perfluoroalkyl group);

A compound represented by the formula (1-2) wherein $R^{5b}$ is a trifluoromethyl group, —$CF_2CF_3$, —$CF_2CF_2CF_3$, —$CF(CF_3)_2$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, $SF_5$, a fluorine atom, a chlorine atom, a bromine atom or an iodine atom;

A compound represented by the formula (1-2) wherein when $A^{3b}$ is =$CR^{9b}$—, $R^{9b}$ is a fluorine atom, a chlorine atom, a bromine atom, an iodine atom or a hydrogen atom;

A compound represented, by the formula (1-2) wherein when $A^{3b}$ is =$CR^{9b}$—, $R^{9b}$ is a fluorine atom or a hydrogen atom;

A compound represented by the formula (1-3) wherein $A^{3b}$ is a nitrogen atom;

A compound represented by the formula (1-3) wherein $A^{3b}$ is =$CR^{9b}$— compound;

A compound represented by the formula (1-3) wherein $R^{1b}$ is an ethyl group;

A compound represented by the formula (1-3) wherein $R^{3b}$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, —$CF_2CF_3$, —$CF_2CF_2CF_3$, —$CF(CF_3)_2$, —$CF_2CF_2CF_2CF_3$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, a fluorine atom, a chlorine atom, a bromine atom, an iodine atom or a hydrogen atom;

A compound represented by the formula (1-3) wherein $R^{5b}$ is a C1-C6 haloalkyl group, —$OR^{22b}$ (wherein $R^{22b}$ is a C1-C6 haloalkyl group), —$S(O)_m R^{23b}$ (wherein $R^{23b}$ is a C1-C6 haloalkyl group, and m is 0, 1 or 2), —$SF_5$ or a halogen atom;

A compound represented by the formula (1-3) wherein $R^{5b}$ is a C1-C6 haloalkyl group, —$OR^{22b}$ (wherein $R^{22b}$ is a C1-C6 haloalkyl group), —$S(O)_m R^{23b}$ (wherein $R^{23b}$ is a C1-C6 haloalkyl group, and m is 0, 1 or 2) or —$SF_5$;

A compound represented by the formula (1-3) wherein $R^{5b}$ is a C1-C6 haloalkyl group, —$OR^{22b}$ (wherein $R^{22b}$ is a C1-C6 haloalkyl group), —$S(O)_m R^{23b}$ (wherein $R^{23b}$ is a C1-C6 haloalkyl group, and m is 0, 1 or 2) or a halogen atom;

A compound represented by the formula (1-3) wherein $R^{5b}$ is a C1-C6 haloalkyl group, —$OR^{22b}$ (wherein $R^{22b}$ is a C1-C6 haloalkyl group) or —$S(O)_m R^{23b}$ (wherein $R^{23b}$ is a C1-C6 haloalkyl group, and m is 0, 1 or 2);

A compound represented by the formula (1-3) wherein $R^{5b}$ is a C1-C6 perfluoroalkyl group, —$OR^{22b}$ (wherein $R^{22b}$ is a C1-C6 perfluoroalkyl group) or —$S(O)_m R^{23b}$ (wherein $R^{23b}$ is a C1-C6 perfluoroalkyl group);

A compound represented by the formula (1-3) wherein $R^{5b}$ is a trifluoromethyl group, —$CF_2CF_3$, —$CF_2CF_2CF_3$, —$CF(CF_3)_2$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, $SF_5$, a fluorine atom, a chlorine atom, a bromine atom or an iodine atom;

A compound represented by the formula (1-3) wherein when $A^{3b}$ is =$CR^{9b}$—, $R^{9b}$ is a fluorine atom, a chlorine atom, a bromine atom, an iodine atom or a hydrogen atom;

A compound represented by the formula (1-3) wherein when $A^{3b}$ is =$CR^{9b}$—, $R^{9b}$ is a fluorine atom or a hydrogen atom;

A compound represented by the formula (1-4) wherein $A^{3b}$ is a nitrogen atom;

A compound represented by the formula (1-4) wherein $A^{3b}$ is =$CR^{9b}$— compound;

A compound represented by the formula (1-4) wherein $R^{1b}$ is an ethyl group;

A compound represented by the formula (1-4) wherein $R^{3b}$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, —$CF_2CF_3$, —$CF_2CF_2CF_3$, —$CF(CF_3)_2$, —$CF_2CF_2CF_2CF_3$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, a fluorine atom, a chlorine atom, a bromine atom, an iodine atom or a hydrogen atom;

A compound represented by the formula (1-4) wherein $R^{5b}$ is a C1-C6 haloalkyl group, —$OR^{22b}$ (wherein $R^{22b}$ is a C1-C6 haloalkyl group), —$S(O)_m R^{23b}$ (wherein $R^{23b}$ is a C1-C6 haloalkyl group, and m is 0, 1 or 2), —$SF_5$ or a halogen atom;

A compound represented by the formula (1-4) wherein $R^{5b}$ is a C1-C6 haloalkyl group, —$OR^{22b}$ (wherein $R^{22b}$ is a C1-C6 haloalkyl group), —$S(O)_m R^{23b}$ (wherein $R^{23b}$ is a C1-C6 haloalkyl group, and m is 0, 1 or 2) or —$SF_5$;

A compound represented by the formula (1-4) wherein $R^{5b}$ is a C1-C6 haloalkyl group, —$OR^{22b}$ (wherein $R^{22b}$ is a C1-C6 haloalkyl group), —$S(O)_m R^{23b}$ (wherein $R^{23b}$ is a C1-C6 haloalkyl group, and m is 0, 1 or 2) or a halogen atom;

A compound represented by the formula (1-4) wherein $R^{5b}$ is a C1-C6 haloalkyl group, —$OR^{22b}$ (wherein $R^{22b}$ is a C1-C6 haloalkyl group) or —$S(O)_m R^{23b}$ (wherein $R^{23b}$ is a C1-C6 haloalkyl group, and m is 0, 1 or 2);

A compound represented by the formula (1-4) wherein $R^{5b}$ is a C1-C6 perfluoroalkyl group, —$OR^{22b}$ (wherein $R^{22b}$ is a C1-C6 perfluoroalkyl group) or —$S(O)_m R^{23b}$ (wherein $R^{23b}$ is a C1-C6 perfluoroalkyl group);

A compound represented by the formula (1-4) wherein $R^{5b}$ is a trifluoromethyl group, —$CF_2CF_3$, —$CF_2CF_2CF_3$, —$CF(CF_3)_2$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, $SF_5$, a fluorine atom, a chlorine atom, a bromine atom or an iodine atom;

A compound represented by the formula (1-4) wherein when $A^{3b}$ is =$CR^{9b}$—, $R^{9b}$ is a fluorine atom, a chlorine atom, a bromine atom, an iodine atom or a hydrogen atom;

A compound represented by the formula (1-4) wherein when $A^{3b}$ is =$CR^{9b}$—, $R^{9b}$ is a fluorine atom or a hydrogen atom;

A compound represented by the formula (1-5) wherein $A^{3a}$ is a nitrogen atom;

A compound represented by the formula (1-5) wherein $A^{3a}$ is =$CR^{9a}$— compound;

A compound represented by the formula (1-5) wherein $R^{1a}$ is a C1-C6 alkyl group optionally substituted by one or more atoms or groups selected from the group consisting of a halogen atom and a cyclopropyl group (wherein the cyclopropyl group is optionally substituted by one or more halogen atoms or one or more C1-C3 alkyl groups);

A compound represented by the formula (1-5) wherein $R^{1a}$ is a C1-C6 alkyl group, a C1-C6 haloalkyl group, or a C4-C9 cyclopropylalkyl group (wherein the cyclopropyl group is optionally substituted by one or more halogen atoms or one or more C1-C3 alkyl groups);

A compound represented by the formula (1-5) wherein $R^{1a}$ is a C2-C6 alkyl group, a C1-C6 haloalkyl group or C4-C9 cyclopropylalkyl group (wherein the cyclopropyl group is optionally substituted by one or more halogen atoms or one or more C1-C3 alkyl groups);

A compound represented by the formula (1-5) wherein $R^{1a}$ is a methyl group, an ethyl group, a propyl group, an isopropyl group, a trifluoromethyl group, a 2,2,2-trifluoroethyl group or a cyclopropylmethyl group;

A compound represented by the formula (1-5) wherein $R^{1a}$ is an ethyl group or a cyclopropylmethyl group;

A compound represented by the formula (1-5) wherein $R^{1a}$ is an ethyl group;

A compound represented by the formula (1-5) wherein $R^{3a}$ is a C1-C6 alkyl group optionally substituted by one or more halogen atoms, a C2-C6 alkenyl group optionally substituted by one or more halogen atoms, a C2-C6 alkynyl group optionally substituted by one or more halogen atoms, pyridyl group (wherein the pyridyl group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), a pyrimidinyl group (wherein the pyrimidinyl group is optionally substituted by one or more atoms or substituents selected from the group consisting of a halogen atom, a C1-C3 alkyl group optionally substituted by one or more halogen atoms, and a C1-C3 alkoxy group optionally substituted by one or more halogen atoms), —$OR^{20a}$ (wherein $R^{20a}$ is a C1-C6 alkyl group optionally substituted by one or more halogen atoms), —$S(O)_m R^{21a}$ (wherein $R^{21a}$ is a C1-C6 alkyl group optionally substituted by one or more halogen atoms, and m is 0, 1 or 2), a halogen atom or a hydrogen atom;

A compound represented by the formula (1-5) wherein $R^{3a}$ is a C1-C6 alkyl group optionally substituted by one or more halogen atoms, —$OR^{20a}$ (wherein $R^{20a}$ represents a C1-C6 alkyl group optionally substituted by one or more halogen atoms), —$S(O)_m R^{21a}$ (wherein $R^{21a}$ represents a C1-C6 alkyl group optionally substituted by one or more halogen atoms, m represents 0, 1 or 2), a halogen atom or a hydrogen atom;

A compound represented by the formula (1-5) wherein $R^{3a}$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, —$CF_2CF_3$, —$CF_2CF_2CF_3$, —$CF(CF_3)_2$, —$CF_2CF_2CF_2CF_3$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, a 2-pyridyl group, a 5-trifluoromethyl-2-pyridyl group, a 2-pyrimidinyl group, a fluorine atom, a chlorine atom, a bromine atom, an iodine atom or a hydrogen atom;

A compound represented by the formula (1-5) wherein $R^{3a}$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, —$CF_2CF_3$, —$CF_2CF_2CF_3$, —$CF(CF_3)_2$, —$CF_2CF_2CF_2CF_3$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, a fluorine atom, a chlorine atom, a bromine atom, an iodine atom or a hydrogen atom;

A compound represented by the formula (1-5) wherein $R^{2a}$ and $R^{4a}$ both are a hydrogen atom;

A compound represented by the formula (1-5) wherein $R^{5a}$ is a C1-C6 haloalkyl group, —$OR^{22a}$ (wherein $R^{22a}$ is a C1-C6 haloalkyl group), —$S(O)_m R^{23a}$ (wherein $R^{23a}$ is a C1-C6 haloalkyl group, and m is 0, 1 or 2), —$SF_5$ or a halogen atom;

A compound represented by the formula (1-5) wherein $R^{5a}$ is a C1-C6 haloalkyl group, —$OR^{22a}$ (wherein $R^{22a}$ is a C1-C6 haloalkyl group), —$S(O)_m R^{23a}$ (wherein $R^{23a}$ is a C1-C6 haloalkyl group, and m is 0, 1 or 2) or —$SF_5$;

A compound represented by the formula (1-5) wherein $R^{5a}$ is a C1-C6 haloalkyl group, —$OR^{22a}$ (wherein $R^{22a}$ is a C1-C6 haloalkyl group), —$S(O)_m R^{23a}$ (wherein $R^{23a}$ is a C1-C6 haloalkyl group, and m is 0, 1 or 2) or a halogen atom;

A compound represented by the formula (1-5) wherein $R^{5a}$ is a C1-C6 haloalkyl group, —$OR^{22a}$ (wherein $R^{22a}$ is a C1-C6 haloalkyl group) or —$S(O)_m R^{23a}$ (wherein $R^{23a}$ is a C1-C6 haloalkyl group, and m is 0, 1 or 2);

A compound represented by the formula (1-5) wherein $R^{5a}$ is a C1-C6 perfluoroalkyl group, —$OR^{22a}$ (wherein $R^{22a}$ is a C1-C6 perfluoroalkyl group) or —$S(O)_m R^{23a}$ (wherein $R^{23a}$ is a C1-C6 perfluoroalkyl group);

A compound represented by the formula (1-5) wherein $R^{5a}$ is a trifluoromethyl group, —$CF_2CF_3$, —$CF_2CF_2CF_3$, —$CF(CF_3)_2$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, $SF_5$, a fluorine atom, a chlorine atom, a bromine atom or an iodine atom;

A compound represented by the formula (1-5) wherein $R^{70a}$ is a hydrogen atom, methoxymethyl group, an ethoxymethyl group, a 1-(methoxy)ethyl group or a 1-(ethoxy)ethyl group;

A compound represented by the formula (1-5) wherein when $A^{3a}$ is =$CR^{9a}$—, $R^{9a}$ is a halogen atom or a hydrogen atom;

A compound represented by the formula (1-5) wherein when $A^{3a}$ is =$CR^{9a}$—, $R^{9a}$ is a fluorine atom, a chlorine atom, a bromine atom, an iodine atom or a hydrogen atom;

A compound represented by the formula (1-5) wherein when $A^{3a}$ is =$CR^{9a}$—, $R^{9a}$ is a fluorine atom or a hydrogen atom;

A compound represented by the formula (1-6) wherein $A^{3b}$ is a nitrogen atom;

A compound represented by the formula (1-6) wherein $A^{3b}$ is =$CR^{9b}$— compound;

A compound represented by the formula (1-6) wherein $R^{1b}$ is an ethyl group;

A compound represented by the formula (1-6) wherein $R^{3b}$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, —$CF_2CF_3$, —$CF_2CF_2CF_3$, —$CF(CF_3)_2$, —$CF_2CF_2CF_2CF_3$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, a fluorine atom, a chlorine atom, a bromine atom, an iodine atom or a hydrogen atom;

A compound represented by the formula (1-6) wherein $R^{5b}$ is a C1-C6 haloalkyl group, —$OR^{22b}$ (wherein $R^{22b}$ is a C1-C6 haloalkyl group), —$S(O)_m R^{23b}$ (wherein $R^{23b}$ is a C1-C6 haloalkyl group, and m is 0, 1 or 2), —$SF_5$ or a halogen atom;

A compound represented by the formula (1-6) wherein $R^{5b}$ is a C1-C6 haloalkyl group, —$OR^{22b}$ (wherein $R^{22b}$ is a C1-C6 haloalkyl group), —$S(O)_mR^{23b}$ (wherein $R^{23b}$ is a C1-C6 haloalkyl group, and m is 0, 1 or 2) or —$SF_5$;

A compound represented by the formula (1-6) wherein $R^{5b}$ is a C1-C6 haloalkyl group, —$OR^{22b}$ (wherein $R^{22b}$ is a C1-C6 haloalkyl group), —$S(O)_mR^{23b}$ (wherein $R^{23b}$ is a C1-C6 haloalkyl group, and m is 0, 1 or 2) or a halogen atom;

A compound represented by the formula (1-6) wherein $R^{5b}$ is a C1-C6 haloalkyl group, —$OR^{22b}$ (wherein $R^{22b}$ is a C1-C6 haloalkyl group) or —$S(O)_mR^{23b}$ (wherein $R^{23b}$ is a C1-C6 haloalkyl group, and m is 0, 1 or 2);

A compound represented by the formula (1-6) wherein $R^{5b}$ is a C1-C6 perfluoroalkyl group, —$OR^{22b}$ (wherein $R^{22b}$ is a C1-C6 perfluoroalkyl group) or —$S(O)_mR^{23b}$ (wherein $R^{23b}$ is a C1-C6 perfluoroalkyl group);

A compound represented by the formula (1-6) wherein $R^{5b}$ is a trifluoromethyl group, —$CF_2CF_3$, —$CF_2CF_2CF_3$, —$CF(CF_3)_2$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, $SF_5$, a fluorine atom, a chlorine atom, a bromine atom or an iodine atom;

A compound represented by the formula (1-6) wherein $R^{70b}$ is a hydrogen atom, a methoxymethyl group, an ethoxymethyl group, a 1-(methoxy)ethyl group or a 1-(ethoxy)ethyl group;

A compound represented by the formula (1-6) wherein when $A^{3b}$ is =$CR^{9b}$—, $R^{9b}$ is a fluorine atom, a chlorine atom, a bromine atom, an iodine atom or a hydrogen atom;

A compound represented by the formula (1-6) wherein when $A^{3b}$ is =$CR^{9b}$—, $R^{9b}$ is a fluorine atom or a hydrogen atom;

A fused heterocyclic compound represented by the formula (1-7):

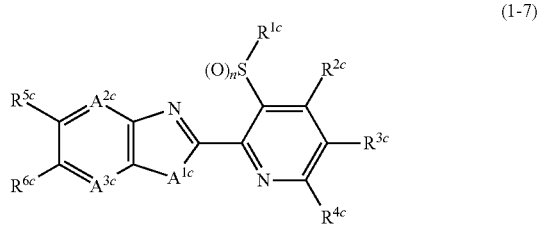

(1-7)

wherein
$A^{1c}$ represents —$NR^{7c}$—, an oxygen atom or a sulfur atom,
$A^{2c}$ represents a nitrogen atom or =$CR^{8c}$—,
$A^{3c}$ represents a nitrogen atom or =$CR^{9c}$—,
$R^{1c}$ represents a C1-C6 chain hydrocarbon group optionally substituted by one or more atoms or groups selected from Group $X^c$ or a C3-C6 alicyclic hydrocarbon group optionally substituted by one or more atoms or groups selected from Group $Y^c$,
$R^{2c}$ and $R^{4c}$ are the same or different and each represents a C1-C6 chain hydrocarbon group optionally substituted by one or more halogen atoms, —$OR^{10c}$, —$S(O)_mR^{10c}$, —$NR^{10c}R^{11c}$, —$CO_2R^{10c}$, —$C(O)R^{10c}$, a cyano group, a nitro group, a halogen atom or a hydrogen atom,
$R^{3c}$ represents a C1-C6 chain hydrocarbon group optionally substituted by one or more halogen atoms, a phenyl group optionally substituted by one or more atoms or groups selected from Group $Z^c$, a 5-membered heterocyclic group optionally substituted by one or more atoms or groups selected from Group $Z^c$, a 6-membered heterocyclic group optionally substituted by one or more atoms or groups selected from Group $Z^c$, —$OR^{10c}$, —$S(O)_mR^{10c}$, —$NR^{10c}R^{11c}$, —$CO_2R^{10c}$, —$C(O)R^{10c}$, a cyano group, a nitro group, a halogen atom or a hydrogen atom,
$R^{5c}$ and $R^{6c}$ are the same or different and each represents a C1-C6 chain hydrocarbon group optionally substituted by one or more atoms or groups selected from Group $X^c$, a phenyl group optionally substituted by one or more atoms or groups selected from Group $Z^c$, a 5-membered heterocyclic group optionally substituted by one or more atoms or groups selected from Group $Z^c$, a 6-membered heterocyclic group optionally substituted by one or more atoms or groups selected from Group $Z^c$, —$OR^{10c}$, —$S(O)_mR^{10c}$, —$S(O)_2NR^{10c}R^{11c}$, —$NR^{10c}R^{11c}$, —$CO_2R^{10c}$, —$C(O)R^{10c}$, —$SF_5$, a cyano group, a nitro group, a halogen atom or a hydrogen atom,
$R^{7c}$ represents a C1-C6 chain hydrocarbon group optionally substituted by one or more atoms or groups selected from Group $W^c$, —$CO_2R^{10c}$, —$C(O)R^{10c}$, or a C3-C6 alicyclic hydrocarbon group optionally substituted by one or more atoms or groups selected from Group $Y^c$,
$R^{8c}$ and $R^{9c}$ are the same or different and each represents a C1-C6 chain hydrocarbon group optionally substituted by one or more halogen atoms, —$OR^{10c}$, —$S(O)_mR^{10c}$, —$NR^{10c}R^{11c}$, —$CO_2R^{10c}$, —$C(O)R^{10c}$, a cyano group, a nitro group, a halogen atom or a hydrogen atom,
$R^{10c}$ and $R^{11c}$ are the same or different and each represents a C1-C6 chain hydrocarbon group optionally substituted by one or more halogen atoms or a hydrogen atom,
m represents 0, 1 or 2, and
n represents 0, 1 or 2.
wherein $R^{5c}$ and $R^{6c}$ do not represents a hydrogen atom at the same time, and in the —$S(O)_mR^{10c}$, $R^{10c}$ does not a hydrogen atom when m is 1 or 2, Group $X^c$: the group consisting of a C1-C6 alkoxy group optionally substituted by one or more halogen atoms, a C2-C6 alkenyloxy group optionally substituted by one or more halogen atoms, a C2-C6 alkynyloxy group optionally substituted by one or more halogen atoms, a C1-C6 alkylsulfanyl group optionally substituted by one or more halogen atoms, a C1-C6 alkylsulfinyl group optionally substituted by one or more halogen atoms, a C1-C6 alkylsulfonyl group optionally substituted by one or more halogen atoms, a hydroxy group and a halogen atom, Group $Y^c$: the group consisting of a C1-C6 chain hydrocarbon group optionally substituted by one or more halogen atoms, a C1-C6 alkoxy group optionally substituted by one or more halogen atoms and a halogen atom, Group $Z^c$: the group consisting of a C1-C6 chain hydrocarbon group optionally substituted by one or more halogen atoms, a C1-C6 alkoxy group optionally substituted by one or more halogen atoms, a C1-C6 alkylsulfanyl group optionally substituted by one or more halogen atoms, a C1-C6 alkylsulfinyl group optionally substituted by one or more halogen atoms, a C1-C6 alkylsulfonyl group optionally substituted by one or more halogen atoms, a C2-C6 alkylcarbonyl group optionally substituted by one or more halogen atoms, a C2-C6 alkoxycarbonyl group optionally substituted by one or more halogen atoms, a C1-C6 alkylamino group optionally substituted by one or more halogen atoms, a C2-C8 dialkylamino group optionally substituted by one or more halogen atoms, a halogen atom, a cyano group and a nitro group, Group $W^c$: the group consisting of a C1-C6 alkoxy group optionally substituted by one or more halogen atoms, a C2-C6 alkenyloxy group optionally substituted by one or more halogen atoms, a C2-C6 alkynyloxy group optionally substituted by one or more halogen atoms, a C1-C6 alkylsulfanyl group optionally substituted by one or more halogen atoms, a C2-C6 alkylcarbonyl group optionally substituted by one or more halogen atoms, a C2-C6 alkoxycarbonyl group optionally substituted by one or more halogen atoms, a C3-C6 cycloalkyl group optionally substituted by one or more halogen atoms, a C1-C6 alkylsulfinyl group optionally substituted by one or more halogen atoms, a C1-C6 alkylsulfonyl group optionally substituted by one or more halogen atoms, hydroxy group, a halogen atom and a cyano group.

A compound represented by the formula (1-7) wherein $A^{1c}$ is $-NR^{7c}-$;

A compound represented by the formula (1-7) wherein $A^{1c}$ is an oxygen atom;

A compound represented by the formula (1-7) wherein $A^{1c}$ is a sulfur atom;

A compound represented by the formula (1-7) wherein $A^{1c}$ is $-NR^{7c}-$, $R^{7c}$ is a C1-C6 chain hydrocarbon group optionally substituted by one or more halogen atoms, a C1-C6 chain hydrocarbon group substituted by one C1-C6 alkoxy group optionally substituted by one or more halogen atoms, or a cyclopropyl group;

A compound represented by the formula (1-7) wherein $A^{1c}$ is $-NR^{7c}-$, $R^{7c}$ is a methyl group, an ethyl group, methoxymethyl group or an ethoxymethyl group;

A compound represented by the formula (1-7) wherein $A^{2c}$ is a nitrogen atom;

A compound represented by the formula (1-7) wherein $A^{2c}$ is $=CR^{8c}-$;

A compound represented by the formula (1-7) wherein $A^{2c}$ is $=CH-$;

A compound represented by the formula (1-7) wherein $A^{3c}$ is a nitrogen atom;

A compound represented by the formula (1-7) wherein $A^{3c}$ is $=CR^{9c}-$;

A compound represented by the formula (1-7) wherein $A^{3c}$ is a nitrogen atom or $=CR^{9c}-$, and $R^{9c}$ is a halogen atom or a hydrogen atom;

A compound represented by the formula (1-7) wherein $A^{2c}$ is $=CR^{8c}-$, $A^{3c}$ is $=CR^{9c}-$;

A compound represented by the formula (1-7) wherein $A^{2c}$ is a nitrogen atom, $A^{3c}$ is $=CR^{9c}-$;

A compound represented by the formula (1-7) wherein $A^{2c}$ is $=CR^{8c}-$, $A^{3c}$ is a nitrogen atom;

A compound represented by the formula (1-7) wherein $A^{2c}$ is a nitrogen atom, $A^{3c}$ is a nitrogen atom;

A compound represented by the formula (1-7) wherein $A^{2c}$ is $=CR^{8c}-$, $R^{8c}$ is a hydrogen atom, $A^{3c}$ is a nitrogen atom;

A compound represented by the formula (1-7) wherein $A^{1c}$ is $-NR^{7c}-$, $A^{2c}$ is $=CR^{8c}-$, $A^{3c}$ is $=CR^{9c}-$;

A compound represented by the formula (1-7) wherein $A^{1c}$ is $-NR^{7c}-$, $A^{2c}$ is a nitrogen atom, $A^{3c}$ is $=CR^{9c}-$;

A compound represented by the formula (1-7) wherein $A^{1c}$ is $-NR^{7c}-$, $A^{2c}$ is $=CR^{8c}-$, $A^{3c}$ is a nitrogen atom;

A compound represented by the formula (1-7) wherein $A^{1c}$ is $-NR^{7c}-$, $A^{2c}$ is $=CR^{8c}-$, $R^{8c}$ is a hydrogen atom, $A^{3c}$ is a nitrogen atom;

A compound represented by the formula (1-7) wherein $A^{1c}$ is $-NR^{7c}-$, $R^{7c}$ is a methyl group, and $A^{2c}$ is $=CR^{8c}-$, $R^{8c}$ is hydrogen atom, $A^{3c}$ is a nitrogen atom;

A compound represented by the formula (1-7) wherein $A^{1c}$ is $-NR^{7c}-$, $A^{2c}$ is a nitrogen atom, $A^{3c}$ is a nitrogen atom;

A compound represented by the formula (1-7) wherein $A^{1c}$ is an oxygen atom, and $A^{2c}$ is $=CR^{8c}-$, $A^{3c}$ is $=CR^{9c}-$;

A compound represented by the formula (1-7) wherein $A^{1c}$ is an oxygen atom, and $A^{2C}$ is a nitrogen atom, $A^{3c}$ is $=CR^{9c}-$;

A compound represented by the formula (1-7) wherein $A^{1C}$ is an oxygen atom, and $A^{2C}$ is $=CR^{8c}-$, $A^{3c}$ is a nitrogen atom;

A compound represented by the formula (1-7) wherein $A^{1c}$ is an oxygen atom, and $A^{2c}$ is $=CR^{8c}-$, $R^{8c}$ is a hydrogen atom, $A^{3c}$ is a nitrogen atom;

A compound represented by the formula (1-7) wherein $A^{1c}$ is an oxygen atom, and $A^{2C}$ is a nitrogen atom, $A^{3c}$ is a nitrogen atom;

A compound represented by the formula (1-7) wherein $A^{1c}$ is a sulfur atom, and $A^{2c}$ is $=CR^{8c}-$, $A^{3c}$ is $=CR^{9c}-$;

A compound represented by the formula (1-7) wherein $A^{1c}$ is a sulfur atom, and $A^{2c}$ is a nitrogen atom, $A^{3c}$ is $=CR^{9c}-$;

A compound represented by the formula (1-7) wherein $A^{1c}$ is a sulfur atom, and $A^{2c}$ is $=CR^{8c}-$, $A^{3c}$ is a nitrogen atom;

A compound represented by the formula (1-7) wherein $A^{1c}$ is a sulfur atom, and $A^{2c}$ is $=CR^{8c}-$, $A^{8c}$ is a hydrogen atom, $A^{3c}$ is a nitrogen atom;

A compound represented by the formula (1-7) wherein $A^{1c}$ is a sulfur atom, and $A^{2c}$ is a nitrogen atom, $A^{3c}$ is a nitrogen atom;

A compound represented by the formula (1-7) wherein $R^{1c}$ is a C1-C6 chain hydrocarbon group optionally substituted by one or more halogen atoms;

A compound represented by the formula (1-7) wherein $R^{1c}$ is a C1-C6 alkyl group optionally substituted by one or more halogen atoms;

A compound represented by the formula (1-7) wherein $R^2$ and $R^{4c}$ are the same or different and each represents a hydrogen atom or a halogen atom, $R^{3c}$ is a C1-C6 chain hydrocarbon group optionally substituted by one or more halogen atoms, $-OR^{10c}$, a halogen atom or a hydrogen atom;

A compound represented by the formula (1-7) wherein $R^{2c}$ and $R^{4c}$ both are a hydrogen atom
, $R^{3c}$ is a C1-C6 chain hydrocarbon group optionally substituted by one or more halogen atoms, a halogen atom or a hydrogen atom;

A compound represented by the formula (1-7) wherein $R^{2c}$ and $R^{4c}$ both are a hydrogen atom, $R^{3c}$ is a phenyl group optionally substituted by one or more halogen atoms or a C1-C3 alkyl group optionally substituted by one or more halogen atoms, a 5-membered heterocyclic group optionally substituted by one or more halogen atoms or a C1-C3 alkyl group optionally substituted by one or more halogen atoms or a 6-membered heterocyclic group optionally substituted by one or more halogen atoms or a C1-C3 alkyl group optionally substituted by one or more halogen atoms;

A compound represented by the formula (1-7) wherein $R^{2c}$, $R^{3c}$ and $R^{4c}$ is a hydrogen atom;

A compound represented by the formula (1-7) wherein $R^{5c}$ and $R^{6c}$ are the same or different and each represents a C1-C6 chain hydrocarbon group optionally substituted by one or more halogen atoms, $-OR^{10c}$, $-S(O)_mR^{10c}$, a halogen atom or a hydrogen atom;

A compound represented by the formula (1-7) wherein $R^{5c}$ is a C1-C6 chain hydrocarbon group optionally substituted by one or more halogen atoms, $-OR^{10c}$, $-S(O)_mR^{10c}$ or a halogen atom, $R^{6c}$ is a hydrogen atom;

A compound represented by the formula (1-7) wherein $R^{5c}$ is a C1-C3 alkyl group substituted by one or more fluorine atoms, a C1-C3 alkoxy group substituted by one or more fluorine atoms, a C1-C3 alkylsulfanyl group substituted by one or more fluorine atoms, a C1-C3 alkylsulfinyl group substituted by one or more fluorine atoms, a C1-C3 alkylsulfonyl group substituted by one or more fluorine atoms or a halogen atom, $R^{6c}$ is a hydrogen atom;

A compound represented by the formula (1-7) wherein $R^{1c}$ is a C1-C6 chain hydrocarbon group optionally substituted by one or more halogen atoms, $R^{2c}$ and $R^{4c}$ are the same or different and each represents a hydrogen atom or a halogen atom, $R^{3c}$ is a C1-C6 chain hydrocarbon group optionally substituted by one or more halogen atoms, $-OR^{10c}$, a halogen atom or a hydrogen atom, $R^{5c}$ and $R^{6c}$ are the same or different and each represents a C1-C6 chain hydrocarbon group optionally substituted by one or more halogen atoms, $-OR^{10c}$, $-S(O)_m R^{10c}$, a halogen atom or a hydrogen atom, $A^{1c}$ is $-NR^{7c}-$, $R^{7c}$ is a C1-C6 chain hydrocarbon group optionally substituted by one or more halogen atoms, a C1-C6 chain hydrocarbon group substituted by one C1-C6 alkoxy group optionally substituted by one or more halogen atoms, or a cyclopropyl group, and $A^{2c}$ is $-CH-$, and $A^{3c}$ is a nitrogen atom or $=CR^{9c}-$, and $R^{9c}$ is a halogen atom or a hydrogen atom;

A compound represented by the formula (1-7) wherein $A^{1c}$ is $-NR^{7c}-$, an oxygen atom or a sulfur atom, $R^{7c}$ is a C1-C6 chain hydrocarbon group optionally substituted by one or more halogen atoms, a C1-C6 chain hydrocarbon group substituted by one C1-C6 alkoxy group optionally substituted by one or more halogen atoms or a C1-C6 chain hydrocarbon group, $A^{2c}$ is $=R^{8c}-$, $A^{3c}$ is a nitrogen atom or $=CR^{9c}-$, and $R^{9c}$ is a halogen atom or a hydrogen atom, $R^{1c}$ is a C1-C6 chain hydrocarbon group optionally substituted by one or more halogen atoms, $R^{2c}$ and $R^{4c}$ are the same or different and each represents a halogen atom or a hydrogen atom, $R^{3c}$ is a C1-C6 chain hydrocarbon group optionally substituted by one or more halogen atoms, $-OR^{10c}$, $-S(O)_m R^{10c}$, a halogen atom or a hydrogen atom, $R^{5c}$ is a C1-C6 chain hydrocarbon group optionally substituted by one or more halogen atoms, $-OR^{10c}$, $-S(O)_m R^{10c}$ or a halogen atom, $R^{6c}$ is a hydrogen atom, $R^{10c}$ is a C1-C6 alkyl group optionally substituted by one or more halogen atoms;

A compound represented by the formula (1-7) wherein $A^{1c}$ is $-NR^{7c}-$, $R^{7c}$ is a C1-C6 alkyl group, $A^{2c}$ is $=CR^{8c}-$, $A^{3c}$ is $=CR^{9c}-$, and $R^{1c}$ is a C1-C3 alkyl group optionally substituted by one or more fluorine atoms, $R^{2c}$ and $R^{4c}$ both are a hydrogen atom, $R^{3c}$ is a C1-C3 alkyl group optionally substituted by one or more fluorine atoms, a halogen atom or a hydrogen atom, $R^{5c}$ is a C1-C3 alkyl group substituted by one or more fluorine atoms, a C1-C3 alkoxy group substituted by one or more fluorine atoms, a C1-C3 alkylsulfanyl group substituted by one or more fluorine atoms, a C1-C3 alkylsulfinyl group substituted by one or more fluorine atoms, a C1-C3 alkylsulfonyl group substituted by one or more fluorine atoms or a halogen atom, $R^{6c}$ is a hydrogen atom;

A compound represented by the formula (1-7) wherein $A^{1c}$ is $-NR^{7c}-$, $R^{7c}$ is a C1-C6 alkyl group, $A^{2c}$ is $=CR^8-$, $R^{8c}$ is a hydrogen atom, $A^{3c}$ is a nitrogen atom, $R^{1c}$ is a C1-C3 alkyl group optionally substituted by one or more fluorine atoms, $R^{2c}$ and $R^{4C}$ both are a hydrogen atom, $R^{3c}$ is a C1-C3 alkyl group optionally substituted by one or more fluorine atoms, a halogen atom or a hydrogen atom, $R^{5c}$ is a C1-C3 alkyl group substituted by one or more fluorine atoms, a C1-C3 alkoxy group substituted by one or more fluorine atoms, a C1-C3 alkylsulfanyl group substituted by one or more fluorine atoms, a C1-C3 alkylsulfinyl group substituted by one or more fluorine atoms, a C1-C3 alkylsulfonyl group substituted by one or more fluorine atoms or a halogen atom, $R^{6c}$ is a hydrogen atom;

A compound represented by the formula (1-7) wherein $A^{1c}$ is a sulfur atom, and $A^{2c}$ is $=CR^{8c}-$, $A^{3c}$ is $=CR^{9c}-$, and $R^{1c}$ is a C1-C3 alkyl group optionally substituted by one or more fluorine atoms, $R^{2c}$ and $R^{4C}$ both are a hydrogen atom, $R^3$ is a C1-C3 alkyl group optionally substituted by one or more fluorine atoms, a halogen atom or a hydrogen atom, $R^5$ is a C1-C3 alkyl group substituted by one or more fluorine atoms, a C1-C3 alkoxy group substituted by one or more fluorine atoms, a C1-C3 alkylsulfanyl group substituted by one or more fluorine atoms, a C1-C3 alkylsulfinyl group substituted by one or more fluorine atoms, a C1-C3 alkylsulfonyl group substituted by one or more fluorine atoms or a halogen atom, $R^{6c}$ is a hydrogen atom;

A compound represented by the formula (1-7) wherein $A^{1c}$ is a sulfur atom, and $A^{2c}$ is $=CR^{8c}-$, $R^{8c}$ is a hydrogen atom, $A^{3c}$ is a nitrogen atom, $R^{1c}$ is a C1-C3 alkyl group optionally substituted by one or more fluorine atoms, $R^{2c}$ and $R^{4c}$ both are a hydrogen atom
, $R^{3c}$ is a C1-C3 alkyl group optionally substituted by one or more fluorine atoms, a halogen atom or a hydrogen atom, $R^{5C}$ is a C1-C3 alkyl group substituted by one or more fluorine atoms, a C1-C3 alkoxy group substituted by one or more fluorine atoms, a C1-C3 alkylsulfanyl group substituted by one or more fluorine atoms, a C1-C3 alkylsulfinyl group substituted by one or more fluorine atoms, a C1-C3 alkylsulfonyl group substituted by one or more fluorine atoms or a halogen atom, $R^{6c}$ is a hydrogen atom;

A compound represented by the formula (1-7) wherein $A^{1c}$ is $-NR^{7c}-$, $R^{7c}$ is a methyl group, an ethyl group, a methoxymethyl group or an ethoxymethyl group, $R^{1c}$ is a methyl group, an ethyl group, a propyl group, an isopropyl group, butyl group, sec-butyl group, an isobutyl group, tert-butyl group, cyclopropyl group, a trifluoromethyl group, 2,2,2-trifluoroethyl group, $R^{2c}$ and $R^{4c}$ both are a hydrogen atom
, $R^{3c}$ is a methyl group, a trifluoromethyl group, trifluoromethoxy group, a chlorine atom, a bromine atom, an iodine atom or a hydrogen atom, $R^{5c}$ is a trifluoromethyl group, a difluoromethyl group, a fluoromethyl group, a pentafluoroethyl group, a heptafluoroisopropyl group, a trifluoromethoxy group, a trifluoromethylsulfanyl group, a trifluoromethylsulfinyl group, trifluoromethylsulfonyl group, a bromine atom or an iodine atom, $R^{6c}$ is a hydrogen atom;

A fused heterocyclic compound represented by the formula (1-8):

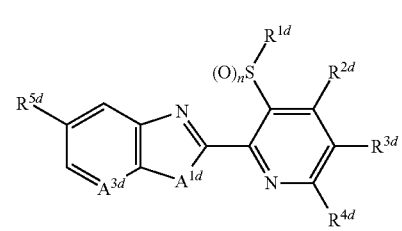

(1-8)

wherein
$A^{1d}$ represents $-NR^{7d}-$ or a sulfur atom,
$A^{3d}$ represents a nitrogen atom or $=CR^{9d}-$,
$R^{1d}$ represents a C1-C6 chain hydrocarbon group optionally substituted by one or more halogen atoms,
$R^{2d}$ and $R^{4d}$ are the same or different and each represents a C1-C6 chain hydrocarbon group optionally substituted by one or more halogen atoms, a halogen atom or a hydrogen atom,
$R^{3d}$ represents a C1-C6 chain hydrocarbon group optionally substituted by one or more halogen atoms, $-OR^{10d}$, a halogen atom or a hydrogen atom,
$R^{5d}$ represents a C1-C6 chain hydrocarbon group optionally substituted by one or more halogen atoms, $-OR^{10d}$, $-S(O)_m R^{10d}$, a bromine atom or an iodine atom, $R^{7d}$ represents a C1-C6 chain hydrocarbon group optionally substituted by one or more halogen atoms, $R^{9d}$ represents a halogen atom or a hydrogen atom, $R^{10d}$ represents a C1-C6 chain hydrocarbon group optionally substituted by one or more halogen atoms, m represents 0, 1 or 2, and n represents 0, 1 or 2;

A compound represented by the formula (1-8) wherein $A^{1d}$ is —$NR^{7d}$—;

A compound represented by the formula (1-8) wherein $A^{1d}$ is a sulfur atom;

A compound represented by the formula (1-8) wherein $A^{3d}$ is a nitrogen atom;

A compound represented by the formula (1-8) wherein $A^{3d}$ is $=CR^{9d}$—;

A compound represented by the formula (1-8) wherein $A^{1d}$ is —$NR^{7d}$— or a sulfur atom, $R^{7d}$ is a methyl group, and $A^{3d}$ is a nitrogen atom;

A compound represented by the formula (1-8) wherein $A^{1d}$ is —$NR^{7d}$—, and $A^{3d}$ is $=CR^{9d}$—;

A compound represented by the formula (1-8) wherein $A^{1d}$ is a sulfur atom, and $A^{3d}$ is $=CR^{9d}$—;

A compound represented by the formula (1-8) wherein $A^{1d}$ is —$NR^{7d}$—, and $A^{3d}$ is a nitrogen atom;

A compound represented by the formula (1-8) wherein $A^{1d}$ is a sulfur atom, and $A^{3d}$ is a nitrogen atom;

A compound represented by the formula (1-8) wherein $R^{1d}$ is a C1-C3 alkyl group;

A compound represented by the formula (1-8) wherein $R^{2d}$ and $R^{4d}$ is a hydrogen atom, $R^{3d}$ is a chlorine atom, a bromine atom, a trifluoromethyl group or a hydrogen atom;

A compound represented by the formula (1-8) wherein $R^{2d}$, $R^{3d}$ and $R^{4d}$ is a hydrogen atom;

A compound represented by the formula (1-8) wherein $R^{5d}$ is a C1-C3 chain hydrocarbon group substituted by one or more fluorine atoms, a C1-C3 alkoxy group substituted by one or more fluorine atoms, a C1-C3 alkylsulfanyl group substituted by one or more fluorine atoms, a C1-C3 alkylsulfinyl group substituted by one or more fluorine atoms or a C1-C3 alkylsulfonyl group substituted by one or more fluorine atoms;

A compound represented by the formula (1-8) wherein $R^{5d}$ is a trifluoromethyl group, a pentafluoroethyl group, a heptafluoroisopropyl group, a trifluoromethoxy group, a trifluoromethylsulfanyl group, a trifluoromethylsulfinyl group or a trifluoromethylsulfonyl group;

A compound represented by the formula (1-8) wherein $A^{1d}$ is —$NR^{7d}$— or a sulfur atom, $R^{7d}$ is a methyl group, and $A^{3d}$ is a nitrogen atom, $R^{1d}$ is an ethyl group, $R^{2d}$ and $R^{4d}$ are the same or different and each represents a halogen atom or a hydrogen atom, $R^{3d}$ is a trifluoromethyl group, a halogen atom or a hydrogen atom, $R^{5d}$ is a C1-C3 chain hydrocarbon group substituted by one or more fluorine atoms, a C1-C3 alkoxy group substituted by one or more fluorine atoms, a C1-C3 alkylsulfanyl group substituted by one or more fluorine atoms, a C1-C3 alkylsulfinyl group substituted by one or more fluorine atoms or a C1-C3 alkylsulfonyl group substituted by one or more fluorine atoms;

A compound represented by the formula (1-8) wherein $A^{1d}$ is —$NR^{7d}$—, and $R^{7d}$ is a methyl group, and $A^{3d}$ is $=CR^{9d}$—, and $R^{1d}$ is an ethyl group, $R^{2d}$ and $R^{4d}$ are the same or different and each represents a halogen atom or a hydrogen atom, $R^{3d}$ is a trifluoromethyl group, a halogen atom or a hydrogen atom, $R^{5d}$ is a C1-C3 chain hydrocarbon group substituted by one or more fluorine atoms, a C1-C3 alkoxy group substituted by one or more fluorine atoms, a C1-C3 alkylsulfanyl group substituted by one or more fluorine atoms, a C1-C3 alkylsulfinyl group substituted by one or more fluorine atoms or a C1-C3 alkylsulfonyl group substituted by one or more fluorine atoms;

A compound represented by the formula (1-8) wherein $A^{1d}$ is —$NR^{7d}$—, and $R^{7d}$ is a methyl group or a hydrogen atom, $A^{3d}$ is a nitrogen atom, $R^{1d}$ is an ethyl group, $R^{2d}$ and $R^{4d}$ are the same or different and each represents a halogen atom or a hydrogen atom, $R^{3d}$ is a trifluoromethyl group, a halogen atom or a hydrogen atom, $R^{5d}$ is a C1-C3 chain hydrocarbon group substituted by one or more fluorine atoms, a C1-C3 alkoxy group substituted by one or more fluorine atoms, a C1-C3 alkylsulfanyl group substituted by one or more fluorine atoms, a C1-C3 alkylsulfinyl group substituted by one or more fluorine atoms or a C1-C3 alkylsulfonyl group substituted by one or more fluorine atoms;

A compound represented by the formula (1-8) wherein $A^{1d}$ is —$NR^{7d}$— or a sulfur atom, $R^{7d}$ is a methyl group, and $A^{3d}$ is $=CR^{9d}$—, and $R^{1d}$ is an ethyl group, $R^{2d}$ and $R^{4d}$ is a hydrogen atom, $R^{3d}$ is a chlorine atom, a bromine atom, a trifluoromethyl group or a hydrogen atom, $R^{5d}$ is a trifluoromethyl group, a pentafluoroethyl group, a heptafluoroisopropyl group, a trifluoromethoxy group, a trifluoromethylsulfanyl group, a trifluoromethylsulfinyl group or a trifluoromethylsulfonyl group;

A compound represented by the formula (1-8) wherein $A^{1d}$ is —$NR^{7d}$— or a sulfur atom, $R^{7d}$ is a methyl group, and $A^{3d}$ is a nitrogen atom, $R^{1d}$ is an ethyl group, $R^{2d}$ and $R^{4d}$ is a hydrogen atom, $R^{3d}$ is a chlorine atom, a bromine atom, a trifluoromethyl group or a hydrogen atom, $R^{5d}$ is a trifluoromethyl group, a pentafluoroethyl group, a heptafluoroisopropyl group, a trifluoromethoxy group, a trifluoromethylsulfanyl group, a trifluoromethylsulfinyl group or a trifluoromethylsulfonyl group;

A compound represented by the formula (1) wherein $A^1$ is —$NR^7$—, an oxygen atom or a sulfur atom, $A^2$ is $=CR^8$—, $A^3$ is a nitrogen atom or $=CR^{9}$-, $R^1$ is a C1-C6 chain hydrocarbon group optionally substituted by one or more atoms or groups selected from Group X or a C3-C6 alicyclic hydrocarbon group optionally substituted by one or more atoms or groups selected from Group Y, $R^2$, $R^3$ and $R^4$ are the same or different and each represents a C1-C6 chain hydrocarbon group optionally substituted by one or more atoms or groups selected from Group X or a hydrogen atom, $R^5$ and $R^6$ are the same or different and each represents a C1-C6 chain hydrocarbon group optionally substituted by one or more atoms or groups selected from Group X, —$OR^{10}$, —$S(O)_mR^{10}$, —$NR^{10}R^{11}$, $CO_2R^{10}$, —$C(O)NR^{10}R^{11}$, —$SF_5$, a cyano group, a halogen atom or a hydrogen atom, $R^7$ is a C1-C6 chain hydrocarbon group optionally substituted by one or more atoms or groups selected from Group W, a C1-C6 chain hydrocarbon group substituted by one 5- or 6-membered heterocyclic group (wherein the 5- or 6-membered heterocyclic group is optionally substituted by one or more atoms or groups selected from Group Z) or a hydrogen atom, $R^8$ and $R^9$ are the same or different and each represents a C1-C6 chain hydrocarbon group optionally substituted by one or more halogen atoms, —$OR^{10}$, —$S(O)_mR^{10}$, —$NR^{10}R^{11}$, a cyano group, a halogen atom or a hydrogen atom, $R^{10}$ and $R^{11}$ are the same or different and each represents a C1-C6 chain hydrocarbon group optionally substituted by one or more atoms or groups selected from Group X, a phenyl group optionally substituted by one or more atoms or groups selected from Group Z or a hydrogen atom, each m independently represents 0, 1 or 2, and
n represents 0, 1 or 2;

The production processes of the present compound are described below.

The present compound and the intermediate compound thereof can be produced by, for example, the following (Production process 1) to (Production process 24).

(Production Process 1)

The present compound represented by the formula (1) wherein n is 1 or 2 can be produced by oxidizing the present compound wherein n is 0.

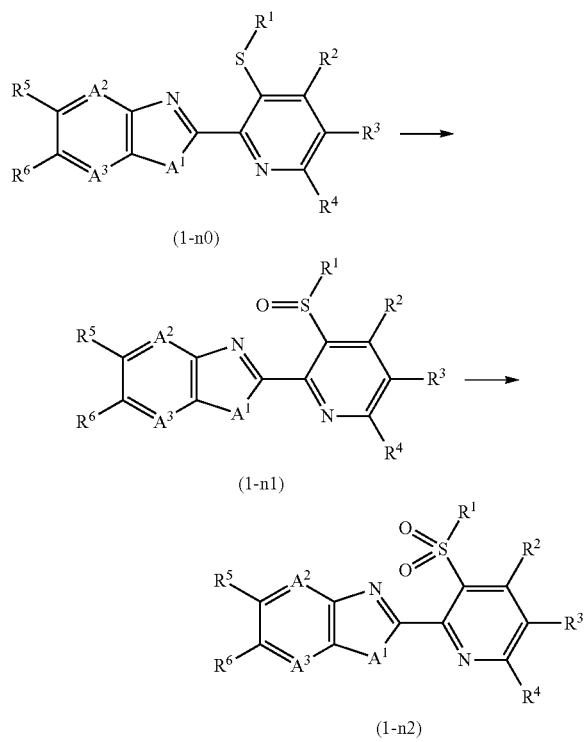

(1-n0)

(1-n1)

(1-n2)

wherein the symbols are as defined in the formula (1).

The present compound represented by the formula (1-n1) wherein n is 1 can be produced by oxidizing the present compound (1-n0) wherein n is 0.

The oxidation reaction is generally conducted in the presence of a solvent.

Examples of the solvent to be used in the reaction include aliphatic halogenated hydrocarbons such as dichloromethane and chloroform; alcohols such as methanol and ethanol; acetic acid; water; and mixtures thereof.

Examples of the oxidant to be used in the reaction include sodium periodate and m-chloroperbenzoic acid.

The amount of the oxidant to be used in the reaction is generally 1 to 3 moles, preferably 1 to 1.2 moles, relative to 1 mole of the present compound (1-n0).

The reaction temperature of the reaction is generally within a range of −20° C. to 80° C. The reaction time of the reaction is generally within a range of 0.1 to 12 hours.

After the completion of the reaction, the present compound (1-n1) can be isolated by post-treatments, for example, extracting the reaction mixture with an organic solvent, washing the organic layer with, optionally an aqueous solution of a reduction agent (e.g., sodium sulfite and sodium thiosulfate), followed by an aqueous solution of a base (e.g., sodium hydrogen carbonate), and then drying and concentrating the organic layer. The isolated present compound (1-n1) can be further purified by chromatography, recrystallization, and the like.

The present compound represented by the formula (1-n2) wherein n is 2 can be produced by reacting the present compound (1-n1) wherein n is 1 in the presence of an oxidant.

The reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof.

Examples of the oxidant to be used in the reaction include m-chloroperbenzoic acid and a hydrogen peroxide solution.

The amount of the oxidant to be used in the reaction is generally 1 to 4 moles, preferably 1 to 2 moles, relative to 1 mole of the present compound (1-n1).

The reaction temperature of the reaction is generally within a range of −20° C. to 120° C. The reaction time of the reaction is generally within a range of 0.1 to 12 hours.

After the completion of the reaction, the present compound (1-n2) can be isolated by post-treatments, for example, extracting the reaction mixture with an organic solvent, washing the organic layer with, optionally an aqueous solution of a reduction agent (e.g., sodium sulfite and sodium thiosulfate), followed by an aqueous solution of a base (e.g., sodium hydrogen carbonate), and then drying and concentrating the organic layer. The isolated present compound (1-n1) can be further purified by chromatography, recrystallization, and the like. The isolated present compound (1-n2) can be further purified by chromatography, recrystallization, and the like.

The present compound represented by the formula (1-n2) wherein n is 2 can be also produced in one step (one pot) by reacting the present compound (1-n0) wherein n is 0 in the presence of an oxidant.

The reaction is generally conducted in the presence of a solvent.

Examples of the solvent to be used in the reaction include aliphatic halogenated hydrocarbons such as dichloromethane and chloroform; alcohols such as methanol and ethanol; acetic acid; water; and mixtures thereof.

Examples of the oxidant to be used in the reaction include m-chloroperbenzoic acid and a hydrogen peroxide solution.

The reaction may be conducted in the presence of a catalyst. Examples of the catalyst to be used in the reaction include sodium tungstate.

The amount of the oxidant to be used in the reaction is generally 2 to 5 moles, preferably 2 to 3 moles, relative to 1 mole of the present compound (1-n0).

The amount of the catalyst to be used in the reaction is generally 0.01-0.5 moles relative to 1 mole of the present compound (1-n0).

The reaction temperature of the reaction is generally within a range of 0° C. to 120° C. The reaction time of the reaction is generally within a range of 0.1 to 12 hours.

After the completion of the reaction, the present compound (1-n2) can be isolated by post-treatments, for example, extracting the reaction mixture with an organic solvent, washing the organic layer with, optionally an aqueous solution of a reduction agent (e.g., sodium sulfite and sodium thiosulfate), followed by an aqueous solution of a base (e.g., sodium hydrogen carbonate), and then drying and concentrating the organic layer. The isolated present compound (1-n2) can be further purified by chromatography, recrystallization, and the like.

(Production Process 2)

The present compound (1) can be produced by reacting the intermediate compound (M1) with the intermediate compound (M2) or the intermediate compound (M18) to give the intermediate compound (M3), and then condensing the resulting intermediate compound (M3) within the molecule.

The reaction temperature of the reaction is generally within a range of 0° C. to 120° C. The reaction time of the reaction is generally within a range of 0.1 to 24 hours.

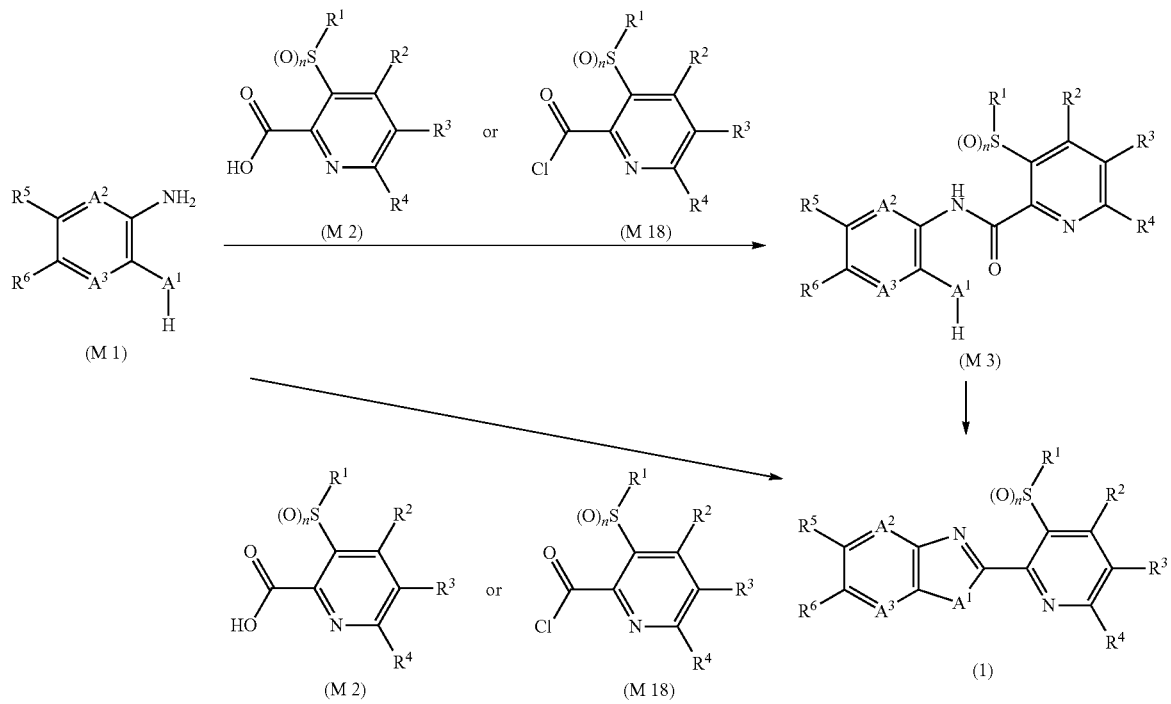

wherein the symbols are as defined in the formula (1).

The intermediate compound (M3) can be produced by reacting the intermediate compound (M1) with the intermediate compound (M2) in the presence of a condensing agent.

The reaction is generally conducted in the presence of a solvent. Examples of the solvent to be used in the reaction include ethers such as 1,4-dioxane, diethyl ether, tetrahydrofuran (hereinafter referred to as "THF"), and tert-butylmethyl ether; halogenated hydrocarbons such as dichloromethane, chloroform, carbon tetrachloride, 1,2-dichloroethane, and chlorobenzene; aromatic hydrocarbons such as toluene, benzene, and xylene; esters such as ethyl acetate, and butyl acetate; nitriles such as acetonitrile; aprotic polar solvents such as N,N-dimethylformamide (hereinafter referred to as "DMF"), N-methylpyrrolidone (hereinafter referred as "NMP"), 1,3-dimethyl-2-imidazolidinone, and dimethylsulfoxide (hereinafter referred to as "DMSO"); nitrogen-containing aromatic compounds such as pyridine and quinoline; and mixtures thereof.

Examples of the "condensing agent" to be used in the reaction include carbodiimides such as 1-ethyl-3-(3-dimethylaminopropyl)carbodiimide hydrochloride (hereinafter referred to as "WSC") and 1,3-dicyclohexyl carbodiimide.

The reaction may be conducted in the presence of a catalyst. Examples of the "catalyst" used in the reaction include 1-hydroxybenzotriazol (hereinafter referred to as "HOBt").

The amount of the intermediate compound (M2) to be used in the reaction is generally 0.5 to 2 moles relative to 1 mole of the intermediate compound (M1).

The amount of the condensing agent to be used in the reaction is generally 1 to 5 moles relative to 1 mole of the intermediate compound (M1).

The amount of the catalyst to be used in the reaction is generally 0.01 to 1 moles relative to 1 mole of the intermediate compound (M1).

After the completion of the reaction, the intermediate compound (M3) can be isolated by post-treatments, for example, pouring water to the reaction mixture, extracting the reaction mixture with an organic solvent, and concentrating the organic layer; pouring water to the reaction mixture, and collecting a solid by filtration; or collecting a solid formed in the reaction mixture by filtration. The isolated intermediate compound (M3) can be further purified by recrystallization, chromatography, and the like.

The intermediate compound (M3) can be also produced by reacting the intermediate compound (M1) with the intermediate compound (M18).

The reaction is generally conducted in the presence of a solvent. Examples of the solvent to be used in the reaction include ethers such as THF, ethylene glycol dimethyl ether, tert-butylmethyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; aprotic polar solvents such as DMF, NMP, and DMSO; and mixtures thereof.

The reaction can be optionally conducted in the presence of a base. Examples of the base include alkali metal carbonates such as sodium carbonate and potassium carbonate; tertiary amines such as triethylamine and N,N-diisopropylethylamine; and nitrogen-containing aromatic compounds such as pyridine and 4-dimethylaminopyridine.

The amount of the intermediate compound (M18) to be used in the reaction is generally 1 to 3 moles relative to 1 mole of the intermediate compound (M1).

The reaction temperature of the reaction is generally within a range of −20° C. to 100° C. The reaction time of the reaction is generally within a range of 0.1 to 24 hours.

After the completion of the reaction, the intermediate compound (M3) can be isolated by post-treatments, for example, pouring water to the reaction mixture, extracting the reaction mixture with an organic solvent, and drying and concentrating the organic layer. The isolated intermediate compound (M3) can be further purified by chromatography, recrystallization, and the like.

The present compound (1) can be produced by condensing the intermediate compound (M3) within the molecule.

The reaction is generally conducted in the presence of a solvent. Examples of the solvent to be used in the reaction include ethers such as 1,4-dioxane, diethyl ether, THF, and tert-butylmethyl ether; halogenated hydrocarbons such as dichloromethane, chloroform, carbon tetrachloride, 1,2-dichloroethane, and chlorobenzene; aromatic hydrocarbons such as toluene, benzene, and xylene; esters such as ethyl acetate, and butyl acetate; nitriles such as acetonitrile; aprotic polar solvents such as DMF, NMP, 1,3-dimethyl-2-imidazolidinone, and DMSO; nitrogen-containing aromatic compounds such as pyridine and quinoline; and mixtures thereof.

The reaction may be conducted in the presence of a condensing agent, an acid, a base or a chlorinating agent.

Examples of the condensing agent to be used in the reaction include acetic acid anhydride, trifluoroacetic acid anhydride, WSC, a mixture of triphenyl phosphine, a base, and carbon tetrachloride or carbon tetrabromide, a mixture of triphenyl phosphine and azodiesters such as diethyl azodicarboxylate.

Examples of the acid to be used in the reaction include sulfonic acids such as para-toluenesulfonic acid; carboxylic acids such as acetic acid; polyphosphoric acid; and the like.

Examples of the base to be used in the reaction include nitrogen-containing heterocyclic compounds such as pyridine, picoline, 2,6-lutidine, 1,8-diazabicyclo[5.4.0]-7-undecene (hereinafter referred to as "DBU"), and 1,5-diazabicyclo[4.3.0]-5-nonene; tertiary amines such as triethylamine and N,N-diisopropylethylamine; inorganic bases such as tripotassium phosphate, potassium carbonate, and sodium hydride.

Examples of the chlorinating agent to be used in the reaction include phosphorous oxychloride; and the like.

When a condensing agent is used in the reaction, the amount of the condensing agent is generally 1 to 5 moles relative to 1-mole of the intermediate compound (M3).

When an acid is used in the reaction, the amount of the acid is generally 0.1 to 5 moles relative to 1 mole of the intermediate compound (M3).

When a base is used in the reaction, the amount of the base is generally 1 to 5 moles relative to 1 mole of the intermediate compound (M3).

When a chlorinating agent is used in the reaction, the amount of the chlorinating agent is generally 1 to 5 moles relative to 1 mole of the intermediate compound (M3).

The reaction temperature of the reaction is generally within a range of 0° C. to 200° C. The reaction time of the reaction is generally within a range of 0.1 to 24 hours.

After the completion of the reaction, the present compound (1) can be isolated by post-treatments, for example, pouring water to the reaction mixture, extracting the reaction mixture with an organic solvent, and concentrating the organic layer; pouring water to the reaction mixture, and collecting a solid by filtration; or collecting a solid formed in the reaction mixture by filtration. The isolated present compound (1) can be further purified by recrystallization, chromatography, and the like.

The present compound (1) can be also produced in one step (one pot) by reacting the intermediate compound (M1) with the intermediate compound (M2) in the presence of a condensing agent.

The reaction is generally conducted in the presence of a solvent. Examples of the solvent to be used in the reaction include ethers such as 1,4-dioxane, diethyl ether, THF, and tert-butylmethyl ether; halogenated hydrocarbons such as dichloromethane, chloroform, carbon tetrachloride, 1,2-dichloro ethane, and chlorobenzene; aromatic hydrocarbons such as toluene, benzene, and xylene; esters such as ethyl acetate and butyl acetate; nitriles such as acetonitrile; aprotic polar solvents such as DMF, NMP, 1,3-dimethyl-2-imidazolidinone, and DMSO; nitrogen-containing aromatic compounds such as pyridine and quinoline; and mixtures thereof.

Examples of the condensing agent to be used in the reaction include carbodiimides such as WSC and 1,3-dicyclohexyl carbodiimide.

The reaction may be conducted in the presence of a catalyst. Examples of the catalyst to be used in the reaction include 1-hydroxybenzotriazol.

The amount of the intermediate compound (M2) to be used in the reaction is generally 0.5 to 2 moles relative to 1 mole of the intermediate compound (M1).

The amount of the condensing agent to be used in the reaction is generally 1 to 5 moles relative to 1 mole of the intermediate compound (M1).

The amount of the catalyst to be used in the reaction is generally 0.01 to 1 moles relative to 1 mole of the intermediate compound (M1).

The reaction temperature of the reaction is generally within a range of 0° C. to 200° C. The reaction time of the reaction is generally within a range of 0.1 to 24 hours.

After the completion of the reaction, the present compound (1) can be isolated by post-treatments, for example, pouring water to the reaction mixture, extracting the reaction mixture with an organic solvent, and concentrating the organic layer; pouring water to the reaction mixture, and collecting a solid by filtration; or collecting a solid formed in the reaction mixture by filtration. The isolated present compound (1) can be further purified by recrystallization, chromatography, and the like.

The present compound (1) can be also produced in one step (one pot) by reacting the intermediate compound (M1) with the intermediate compound (M18).

The reaction is generally conducted in the presence or absence of a solvent.

Examples of the solvent to be used in the reaction include ethers such as THF, ethylene glycol dimethyl ether, tert-butylmethyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; aprotic polar solvents such as DMF, NMP, and DMSO; and mixtures thereof.

The reaction may be conducted in the presence of a base. Examples of the base to be used in the reaction include alkali metal carbonates such as sodium carbonate and potassium carbonate; tertiary amines such as triethylamine and N,N-diisopropylethylamine; nitrogen-containing aromatic compounds such as pyridine and 4-dimethylaminopyridine; and the like.

The amount of the intermediate compound (M18) to be used in the reaction is generally 1 to 3 moles relative to 1 mole of the intermediate compound (M1).

The amount of the base to be used in the reaction is generally 1 to 10 moles relative to 1 mole of the intermediate compound (M1).

The reaction temperature of the reaction is generally within a range of 20° C. to 200° C. The reaction time of the reaction is generally within a range of 0.1 to 24 hours.

After the completion of the reaction, the present compound (1) can be isolated by post-treatments, for example, pouring water to the reaction mixture, extracting the reaction mixture with an organic solvent, and drying and concentrating the organic layer. The isolated present compound (1) can be further purified by chromatography, recrystallization, and the like.

(Production Process 3)

The present compound (P20) represented by the formula (1) wherein $A^1$ is a sulfur atom, and $A^3$ is a nitrogen atom can be produced by reacting the intermediate compound (M9) with the intermediate compound (M2) or the intermediate compound (M18) to give the intermediate compound (M14), and then reacting the resulting intermediate compound (M14) with a sulfating agent.

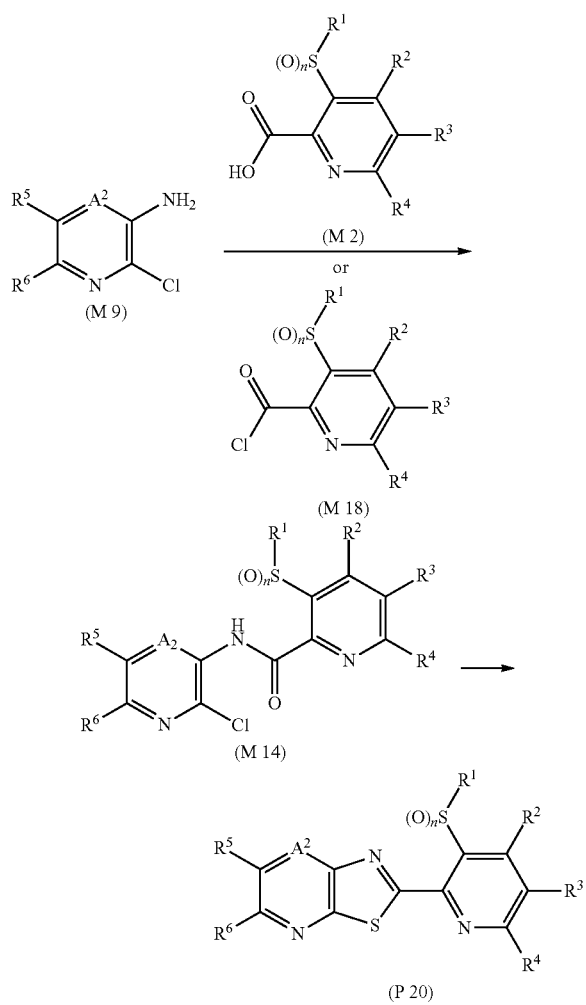

wherein the symbols are as defined in the formula (1).

The intermediate compound (M14) can be produced by reacting the intermediate compound (M9) with the intermediate compound (M2).

The reaction is generally conducted in the presence or absence of a solvent.

Examples of the solvent to be used in the reaction include ethers such as THF, ethylene glycol dimethyl ether, tert-butylmethyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; aprotic polar solvents such as DMF, NMP, and DMSO; nitrogen-containing aromatic compounds such as pyridine and quinoline; and mixtures thereof.

Examples of the dehydrating condensing agent to be used in the reaction include carbodiimides such as WSC, 1,3-dicyclohexylcarbodiimide, and BOP agents.

The amount of the intermediate compound (M2) to be used in the reaction is generally 1 to 3 moles relative to 1 mole of the intermediate compound (M9).

The amount of the dehydrating condensing agent to be used in the reaction is generally 1 to 5 moles relative to 1 mole of the intermediate compound (M9).

The reaction temperature of the reaction is generally within a range of 0° C. to 200° C. The reaction time of the reaction is generally within a range of 0.1 to 24 hours.

After the completion of the reaction, the intermediate compound (M14) can be isolated by post-treatments, for example, pouring water to the reaction mixture, extracting the reaction mixture with an organic solvent, and drying and concentrating the organic layer. The isolated intermediate compound (M14) can be further purified by chromatography, recrystallization, and the like.

The intermediate compound (M14) can be also produced by reacting the intermediate compound (M9) with the intermediate compound (M18).

The reaction is generally conducted in the presence or absence of a solvent, and may be conducted in the presence of a base.

Examples of the solvent to be used in the reaction include ethers such as THF, ethylene glycol dimethyl ether, tert-butylmethyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; aprotic polar solvents such as DMF, NMP, and DMSO; nitrogen-containing aromatic compounds such as pyridine and quinoline; and mixtures thereof.

Examples of the base to be used in the reaction include alkali metal carbonates such as sodium carbonate and potassium carbonate; tertiary amines such as triethylamine and N,N-diisopropylethylamine; nitrogen-containing aromatic compounds such as pyridine and 4-dimethylaminopyridine; and the like.

The amount of the intermediate compound (M18) to be used in the reaction is generally 1 to 3 moles relative to 1 mole of the intermediate compound (M9).

The amount of the base to be used in the reaction is generally 1 to 5 moles relative to 1 mole of the intermediate compound (M9).

The reaction temperature of the reaction is generally within a range of 0° C. to 200° C. The reaction time of the reaction is generally within a range of 0.1 to 24 hours.

After the completion of the reaction, the intermediate compound (M14) can be isolated by post-treatments, for example, pouring water to the reaction mixture, extracting the reaction mixture with an organic solvent, and drying and concentrating the organic layer. The isolated intermediate compound (M14) can be further purified by chromatography, recrystallization, and the like.

The present compound (P20) can be produced by reacting the intermediate compound (M14) with a sulfating agent.

The reaction is generally conducted in the presence or absence of a solvent. Examples of the solvent to be used in the reaction include ethers such as 1,4-dioxane, diethyl ether, tetrahydrofuran, tert-butylmethyl ether, and, diglyme; halogenated hydrocarbons such as dichloromethane, chloroform, carbon tetrachloride, 1,2-dichloroethane, and chlorobenzene; aromatic hydrocarbons such as toluene, benzene, and xylene; nitriles such as acetonitrile; nitrogen-containing aromatic compounds such as pyridine, picoline, lutidine, and quinoline; and mixtures thereof.

Examples of the sulfating agent to be used in the reaction include phosphorus pentasulfide, Lawesson's reagent (2,4-bis-(4-methoxyphenyl)-1,3-dithia-2,4-diphosphetane-2,4-disulfide; and the like.

The amount of the sulfating agent to be used in the reaction is generally 1 to 3 moles relative to 1 mole of the intermediate compound (M14).

The reaction temperature of the reaction is generally within a range of 0° C. to 200° C. The reaction time of the reaction is generally within a range of 1 to 24 hours.

After the completion of the reaction, the present compound (P20) can be isolated by post-treatments, for example, pouring water to the reaction mixture, extracting the reaction mixture with an organic solvent, and concentrating the organic layer; pouring water to the reaction mixture, and collecting a solid by filtration; or collecting a solid formed in the reaction mixture by filtration. The isolated present compound (P20) can be further purified by recrystallization, chromatography, and the like.

(Production Process 4)

The present compound (1) can be produced by reacting the intermediate compound (M1) with the intermediate compound (M4) in the presence of an oxidant.

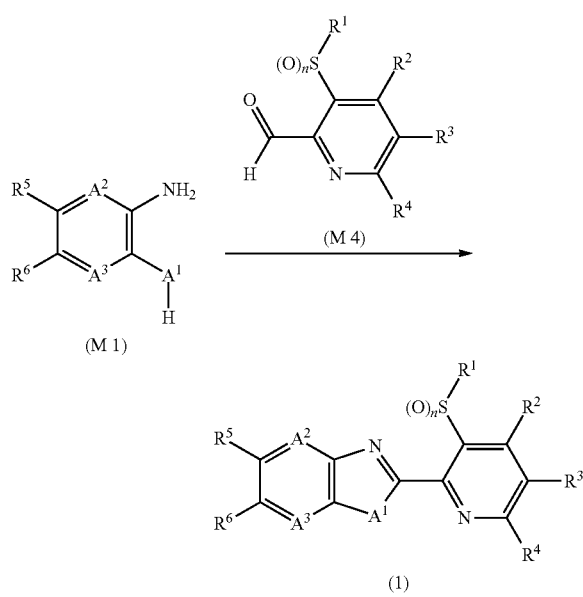

wherein the symbols are as defined in the formula (1).

The reaction is generally conducted in the presence of a solvent. Examples of the solvent to be used in the reaction include alcohols such as methanol and ethanol; ethers such as 1,4-dioxane, diethyl ether, THF, and tert-butylmethyl ether; halogenated hydrocarbons such as dichloromethane, chloroform, carbon tetrachloride, 1,2-dichloroethane, and chlorobenzene; aromatic hydrocarbons such as toluene, benzene, and xylene; esters such as ethyl acetate and butyl acetate; nitriles such as acetonitrile; aprotic polar solvents such as DMF, NMP, 1,3-dimethyl-2-imidazolidinone, and DMSO; nitrogen-containing aromatic compounds such as pyridine and quinoline; and mixtures thereof.

The reaction may be conducted in the presence of an acid. Examples of the acid to be used in the reaction include sulfonic acids such as para-toluenesulfonic acid; carboxylic acids such as acetic acid; polyphosphoric acid; and the like.

The reaction may be conducted in the presence of a sulfite. Examples of the sulfite to be used in the reaction include sodium hydrogen sulfite, and disodium sulfite.

Examples of the oxidant to be used in the reaction include oxygen, copper (II) chloride, DDQ; and the like.

The amount of the intermediate compound (M4) to be used in the reaction is generally 1 to 2 moles relative to 1 mole of the intermediate compound (M1).

The amount of the acid to be used in the reaction is generally 0.1 to 2 moles relative to 1 mole of the intermediate compound (M1).

The amount of the sulfite to be used in the reaction is generally 1 to 5 moles relative to 1 mole of the intermediate compound (M1).

The amount of the oxidant to be used in the reaction is generally 1 to 5 moles relative to 1 mole of the intermediate compound (M1).

The reaction temperature of the reaction is generally within a range of 0° C. to 200° C. The reaction time of the reaction is generally within a range of 0.1 to 24 hours.

After the completion of the reaction, the present compound (1) can be isolated by post-treatments, for example, pouring water to the reaction mixture, extracting the reaction mixture with an organic solvent, and concentrating the organic layer; pouring water to the reaction mixture, and collecting a solid by filtration; or collecting a solid formed in the reaction mixture by filtration. The isolated present compound (I) can be further purified by recrystallization, chromatography, and the like.

(Production Process 5)

The present compound represented by the formula (1) wherein n is 0 can be produced by reacting the intermediate compound (M6) with the intermediate compound (M7) in the presence of a base.

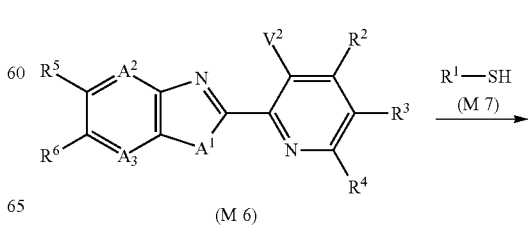

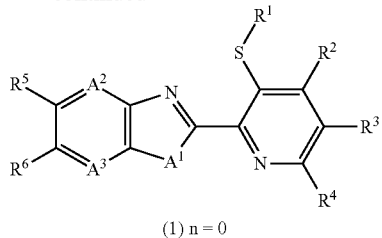

(1) n = 0 wherein $V^2$ represents a halogen atom, and the other symbols are as defined in the formula (1).

The reaction is generally conducted in the presence of a solvent.

Examples of the solvent to be used in the reaction include ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; water; and mixtures thereof.

Examples of the base to be used in the reaction include alkali metal carbonates such as sodium carbonate and potassium carbonate; and alkali metal hydrides such as sodium hydride.

The amount of the intermediate compound (M7) to be used in the reaction is generally 1 to 10 moles relative to 1 mole of the intermediate compound (M6).

The amount of the base to be used in the reaction is generally 1 to 10 moles relative to 1 mole of the intermediate compound (M6).

The reaction temperature of the reaction is generally within a range of 0° C. to 150° C. The reaction time of the reaction is generally within a range of 0.5 to 24 hours.

After the completion of the reaction, the present compound (1) wherein n is 0 can be isolated by post-treatments, for example, extracting the reaction mixture with an organic solvent, and drying and concentrating the organic layer. The isolated present compound (I) wherein n is 0 can be further purified by chromatography, recrystallization, and the like.

In reaction, $V^2$ is preferably a fluorine atom or a chlorine atom.

(Production Process 6)

The intermediate compound (M6) can be produced by reacting the intermediate compound (M1) with the intermediate compound (M19) or the intermediate compound (M39) to give the intermediate compound (M20), and then condensing the resulting intermediate compound (M20) within the molecule.

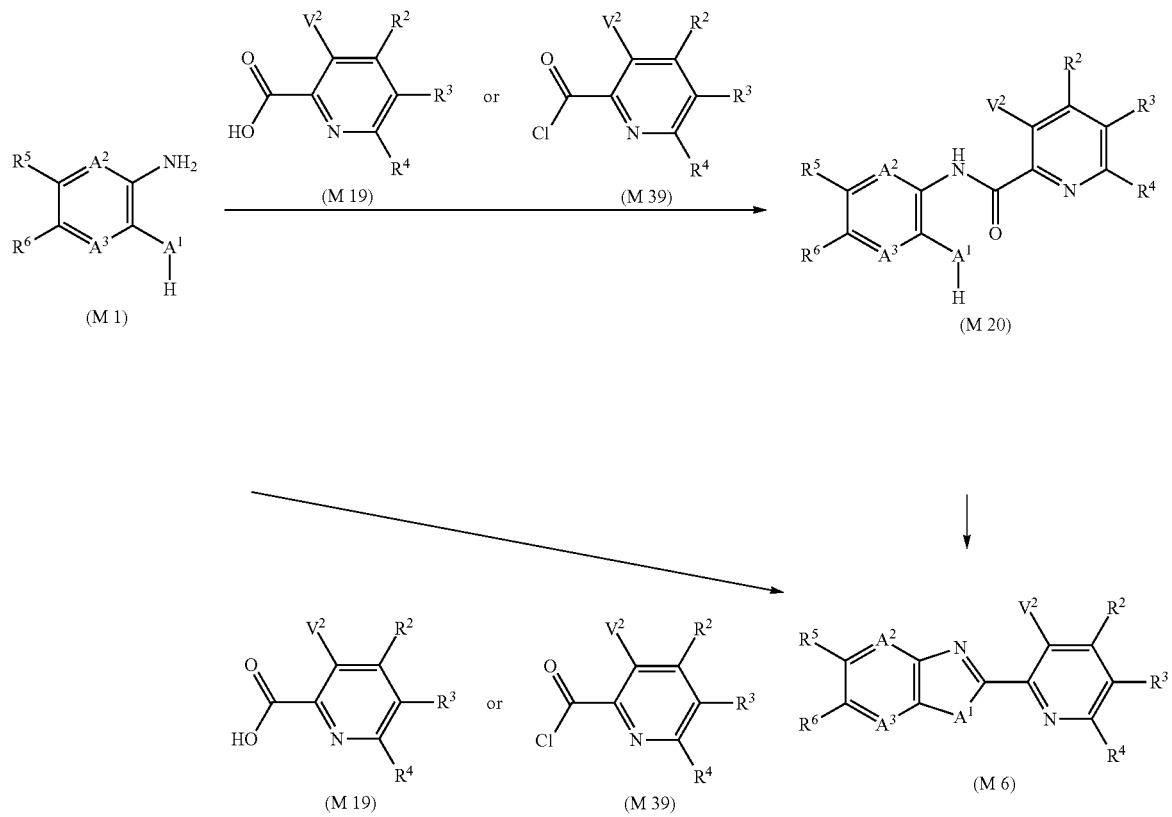

wherein $V^2$ represents a halogen atom, and the other symbols are as defined in the formula (1).

The intermediate compound (M20) can be produced in the same manner as in Production process 2 except for using the intermediate compound (M19) instead of the intermediate compound (M2).

The intermediate compound (M20) can be produced in the same manner as in Production process 2 except for using the intermediate compound (M39) instead of the intermediate compound (M18).

The intermediate compound (M6) can be produced in the same manner as in Production process 2 except for using the intermediate compound (M20) instead of the intermediate compound (M3).

The intermediate compound (M6) can be produced in one step (one pot) in the same manner as in Production process 2 except for using the intermediate compound (M19) instead of the intermediate compound (M6).

The intermediate compound (M6) can be produced in one step (one pot) in the same manner as in Production process 2 except for using the intermediate compound (M39) instead of the intermediate compound (M2).

In reaction, $V^2$ is preferably a fluorine atom or a chlorine atom.

(Production Process 7)

The intermediate compound represented by the formula (M3) wherein n is 0 can be produced by reacting the intermediate compound (M20) with the intermediate compound (M7).

The present compound represented by the formula (1) wherein n is 0 can be produced by condensing the resulting intermediate compound (M3) within the molecule.

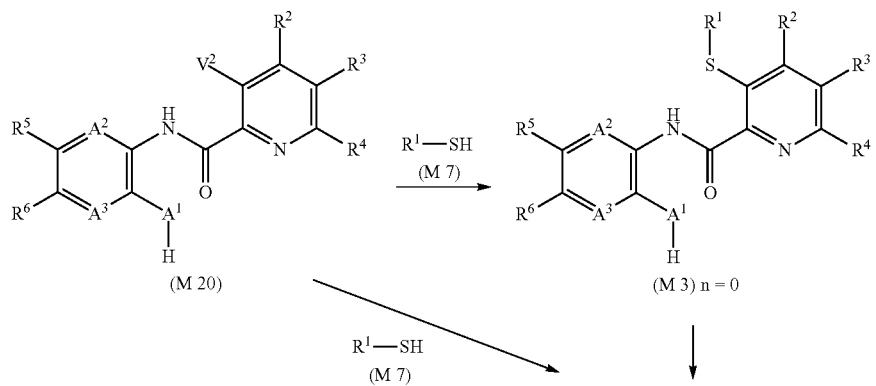

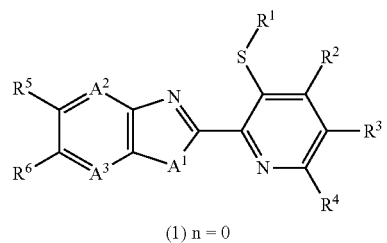

wherein $V^2$ represents a halogen atom, and the other symbols are as defined in the formula (1).

The intermediate compound represented by the formula (M3) wherein n is 0 can be produced in the same manner as in Production process 5 except for using the intermediate compound (M20) instead of the intermediate compound (M6).

The present compound represented by the formula (1) wherein n is 0 can be produced in the same manner as in Production process 2 except for using the intermediate compound represented by the formula (M3) wherein n is 0 instead of the intermediate compound (M3).

The present compound represented by the formula (1) wherein n is 0 can be produced in one step (one pot) in the same manner as in Production process 5 except for using the intermediate compound (M20) instead of the intermediate compound (M6).

In reaction, $V^2$ is preferably a fluorine atom or a chlorine atom.

(Production Process 8)

The present compound represented by the formula (1) wherein n is 0 can be produced by reacting the intermediate compound (M8) or a disulfide thereof, the intermediate compound (M8'), with the intermediate compound (M17) in the presence of a base.

When the intermediate compound (M8'), which is a sulfide, is used, the reaction is generally conducted in the presence of a reductant.

Examples of the reductant to be used in the reaction include sodium hydroxymethanesulfinate (trade name: Rongalite).

The amount of the intermediate compound (M17) to be used in the reaction is generally 1 to 10 moles relative to 1 mole of the intermediate compound (M8).

The amount of the base to be used in the reaction is generally 1 to 10 moles relative to 1 mole of the intermediate compound (M8).

When the intermediate compound (M8'), which is a disulfide, is used, the amount of the intermediate compound (M17) to be used in the reaction is generally 2 to 10 moles relative to 1 mole of the intermediate compound (M8'). The amount of the base to be used in the reaction is generally 2 to 10 moles relative to 1 mole of the intermediate compound (M8'). The amount of the reductant to be used in the reaction is generally 1 to 5 moles relative to 1 mole of the intermediate compound (M8').

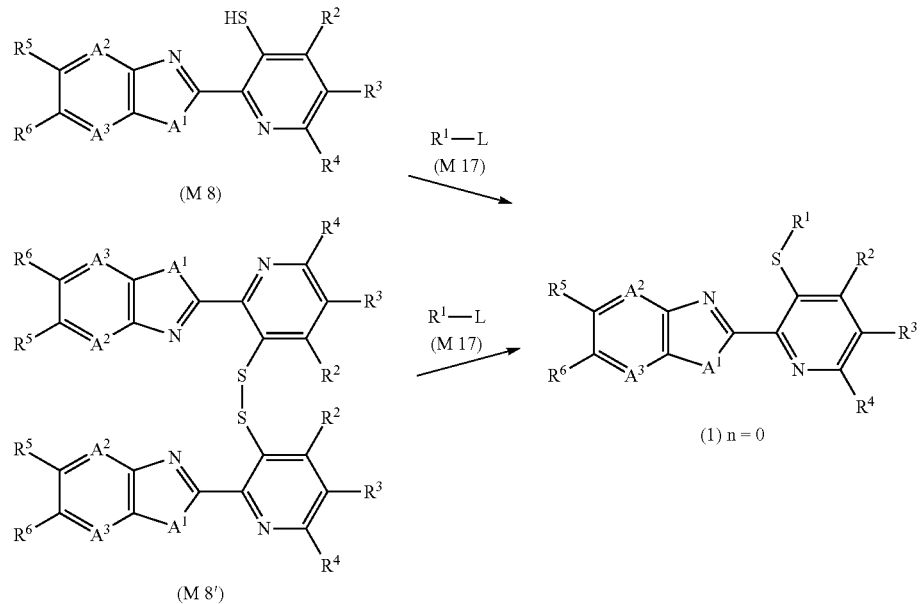

wherein L is a leaving group such as a chlorine atom, a bromine atom, an iodine atom, a trifluoromethanesulfonyloxy group and a methanesulfonyloxy group, and the other symbols are as defined in the formula (1).

The reaction is generally conducted in the presence of a solvent.

Examples of the solvent to be used in the reaction include ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; and mixtures thereof.

Examples of the base to be used in the reaction include inorganic bases such as alkali metal or alkaline earth metal hydrides, e.g., sodium hydride, potassium hydride, and calcium hydride; sodium carbonate; and potassium carbonate; and organic base such as triethylamine.

The reaction temperature of the reaction is generally within a range of 0° C. to 100° C. The reaction time of the reaction is generally within a range of 0.1 to 24 hours.

After the completion of the reaction, the present compound (1) wherein n is 0 can be isolated by post-treatments, for example, extracting the reaction mixture with an organic solvent, and drying and concentrating the organic layer. The isolated present compound (1) wherein n is 0 can be further purified by chromatography, recrystallization, and the like.

(Production Process 9)

The present compound represented by the formula (1) wherein n is 0 can be produced by reacting the intermediate compound (M8') with the intermediate compound (M17'-1) or the intermediate compound (M17'-2).

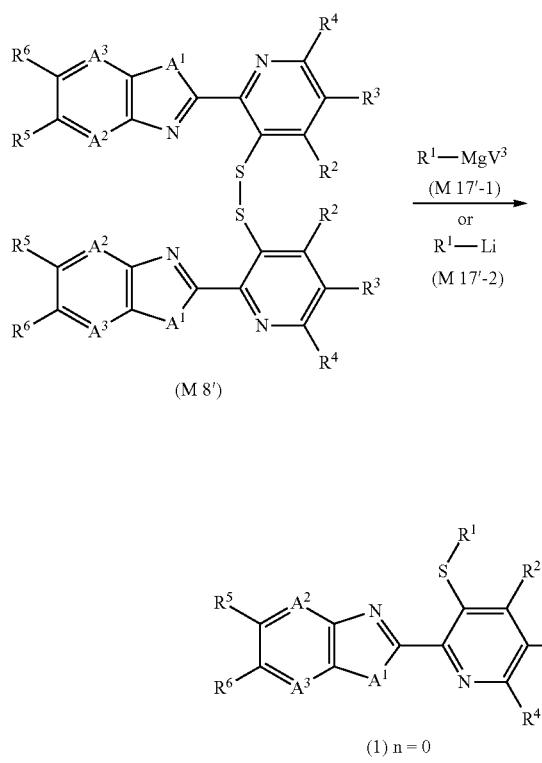

(M 8')

(1) n = 0

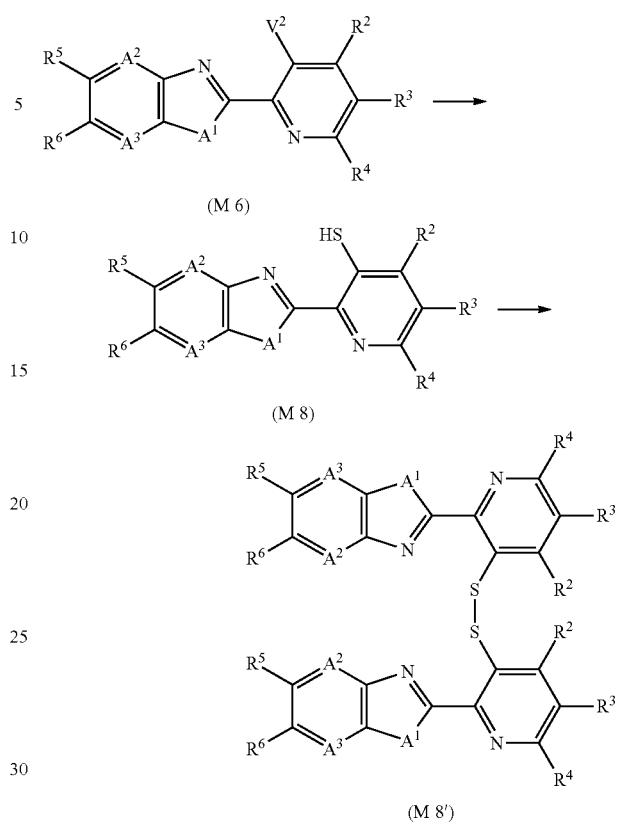

(M 6)

(M 8)

(M 8')

wherein $V^3$ is a chlorine atom, a bromine atom or an iodine atom, and the other symbols are as defined in the formula (1).

The reaction is generally conducted in the presence of a solvent.

Examples of the solvent to be used in the reaction include ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; and mixtures thereof.

The amount of the intermediate compound (M17'-1) to be used in the reaction is generally 1 to 2 moles relative to 1 mole of the intermediate compound (M8').

When the intermediate compound (M17'-2) is used, the intermediate compound (M17'-2) is generally used in an amount of 1 to 2 moles relative to 1 mole of the intermediate compound (M8').

The reaction temperature of the reaction is generally within a range of $-80°$ C. to $100°$ C. The reaction time of the reaction is generally within a range of 0.1 to 24 hours.

After the completion of the reaction, the present, compound (I) wherein n is 0 can be isolated by post-treatments, for example, extracting the reaction mixture with an organic solvent, and drying and concentrating the organic layer. The isolated present compound (I) wherein n is 0 can be further purified by chromatography, recrystallization, and the like.

(Production Process 10)

The intermediate compound (M8) can be produced by reacting the intermediate compound (M6) with a sulfating agent. The intermediate compound (M8'), which is a disulfide of the intermediate compound (M8), can be produced by oxidizing the intermediate compound (M8).

wherein $V^2$ represents a halogen atom, and the other symbols are as defined in the formula (1).

The intermediate compound (M8) can be produced in the same manner as in Production process 5 except for using sodium sulfide, sodium hydrogen sulfide, hydrogen sulfide or the like instead of the intermediate compound (M7).

In this case, the reaction from the intermediate compound (M8) to the intermediate compound (M8') is easily progressed, and thus the intermediate compound (M8') may be produced in the synthesis of the intermediate compound (M8).

In reaction, $V^2$ is preferably a fluorine atom or a chlorine atom.

The intermediate compound (M8') can be produced by reacting the intermediate compound (M8) with an oxidant.

The reaction is generally conducted in the presence of a solvent.

Examples of the solvent to be used in the reaction include water; alcohols such as methanol and ethanol; ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO;

carboxylic acids such as acetic acid; and mixtures thereof.

Examples of the oxidant to be used in the reaction include oxygen, iodine, hydrogen peroxide solution, potassium ferricyanide; and the like.

The amount of the oxidant to be used in the reaction is generally 0.5 to 10 moles relative to 1 mole of the intermediate compound (M8).

The reaction temperature of the reaction is generally within a range of $0°$ C. to $100°$ C. The reaction time of the reaction is generally within a range of 0.1 to 24 hours.

After the completion of the reaction, the intermediate compound (M8') can be isolated by post-treatments, for example, extracting the reaction mixture with an organic solvent, and drying and concentrating the organic layer. The isolated intermediate compound (M8') can be further purified by chromatography, recrystallization, and the like.

(Production Process 11)

The present compound (P3) represented by the formula (1) wherein $A^1$ is —$NR^{7'}$— can be produced by reacting the present compound (P2) represented by the formula (1) wherein $A^1$ is —NH— with the intermediate compound (M10) in the presence of a base.

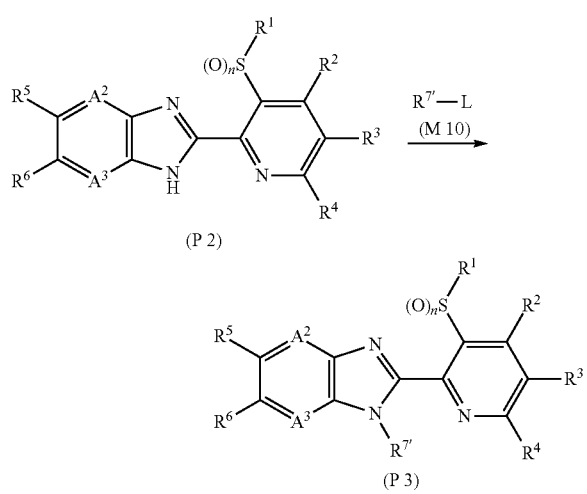

wherein $R^{7'}$ is any of the groups for $R^7$ other than a hydrogen atom in the formula (1), L is an leaving group such as a chlorine atom, a bromine atom, an iodine atom, a trifluoromethanesulfonyloxy group and a methanesulfonyloxy group, and the other symbols are as defined in the formula (1).

The reaction is generally conducted in the presence of a solvent.

Examples of the solvent to be used in the reaction include ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; and mixtures thereof.

Examples of the base to be used in the reaction include alkali metal or alkaline earth metal hydride such as sodium hydride, potassium hydride, and calcium hydride; inorganic bases such as sodium carbonate, and potassium carbonate; organic bases such as triethylamine; and the like.

The amount of the intermediate compound (M10) to be used in the reaction is generally 1 to 5 moles relative to 1 mole of the present compound (P2).

The amount of the base to be used in the reaction is generally 1 to 3 moles relative to 1 mole of the present compound (P2).

The reaction temperature of the reaction is generally within a range of 0° C. to 100° C. The reaction time of the reaction is generally within a range of 0.1 to 24 hours.

After the completion of the reaction, the present compound (P3) can be isolated by post-treatments, for example, extracting the reaction mixture with an organic solvent, and drying and concentrating the organic layer.

The isolated present compound (P3) can be further purified by chromatography, recrystallization, and the like.

(Production Process 12)

The intermediate compound (M2) can be produced by hydrolyzing the intermediate compound (M37).

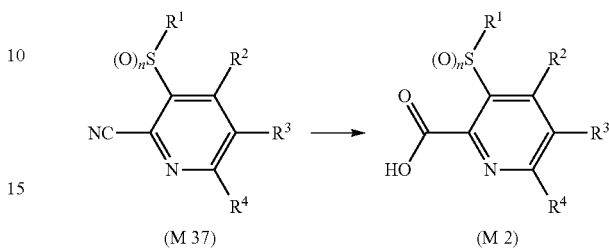

wherein the symbols are as defined in the formula (1).

When the hydrolysis is conducted by using an acid, an aqueous solution of the acid is generally used as a solvent in the reaction.

Examples of the acid to be used in the reaction include mineral acids such as hydrochloric acid, nitric acid, phosphoric acid, and sulfuric acid; and carboxylic acids such as acetic acid and trifluoroacetic acid.

The reaction temperature of the reaction is generally within a range of 0° C. to 100° C. The reaction time of the reaction is generally within a range of 0.1 to 24 hours.

After the completion of the reaction, the intermediate compound (M2) can be isolated by post-treatments, for example, extracting the reaction mixture with an organic solvent, and drying and concentrating the organic layer.

The isolated intermediate compound (M2) can be further purified by chromatography, recrystallization, and the like.

When the hydrolysis is conducted by using a base, the reaction is generally conducted in the presence of a solvent.

Examples of the solvent to be used in the reaction include ethers such as THF, ethylene glycol dimethyl ether, tert-butylmethyl ether, and 1,4-dioxane; alcohols such as methanol and ethanol; water; and mixtures thereof.

Examples of the base to be used in the reaction include alkali metal hydroxides such as sodium hydroxide and potassium hydroxide.

The amount of the base to be used in the reaction is generally 1 to 10 moles relative to 1 mole of the intermediate compound (M37).

The reaction temperature of the reaction is generally within a range of 0° C. to 120° C. The reaction time of the reaction is generally within a range of 0.1 to 24 hours. After the completion of the reaction, the intermediate compound (M2) can be isolated by post-treatments, for example, acidifying the reaction solution, extracting the reaction mixture with an organic solvent, and drying and concentrating the organic layer. The isolated intermediate compound (M2) can be further purified by chromatography, recrystallization, and the like.

(Production Process 13)

The intermediate compound (M18) can be produced by reacting the intermediate compound (M2) with a chlorinating agent.

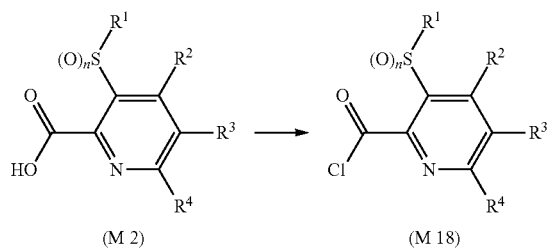

(M 2) → (M 18)

wherein the symbols are as defined in the formula (1).

The reaction is generally conducted in the presence of a solvent.

Examples of the solvent to be used in the reaction include ethers such as THF, ethylene glycol dimethyl ether, tert-butylmethyl ether, and 1,4-dioxane; aromatic hydrocarbons such as toluene and xylene; aliphatic halogenated hydrocarbons such as dichloromethane and chloroform; and mixtures thereof.

Examples of the chlorinating agent to be used in the reaction include thionyl chloride, oxalyl dichloride, phosphorous oxychloride; and the like.

The amount of the chlorinating agent to be used in the reaction is generally 1 to 5 moles relative to 1 mole of the intermediate compound (M2).

The reaction temperature of the reaction is generally within a range of 0° C. to 100° C. The reaction time of the reaction is generally within a range of 0.1 to 24 hours.

After the completion of the reaction, the intermediate compound (M18) can be isolated by removing the solvent from the reaction mixture.

(Production Process 14)

The intermediate compound (M2), the intermediate compound (M4) or the intermediate compound (M37) can be produced by reacting the intermediate compound (M7) with the intermediate compound (M19), the intermediate compound (M22) or the intermediate compound (M36), respectively, and optionally oxidizing the resulting compound.

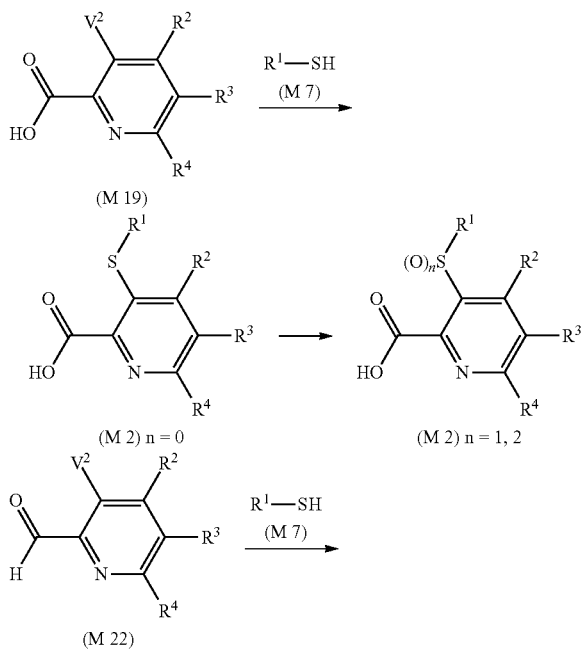

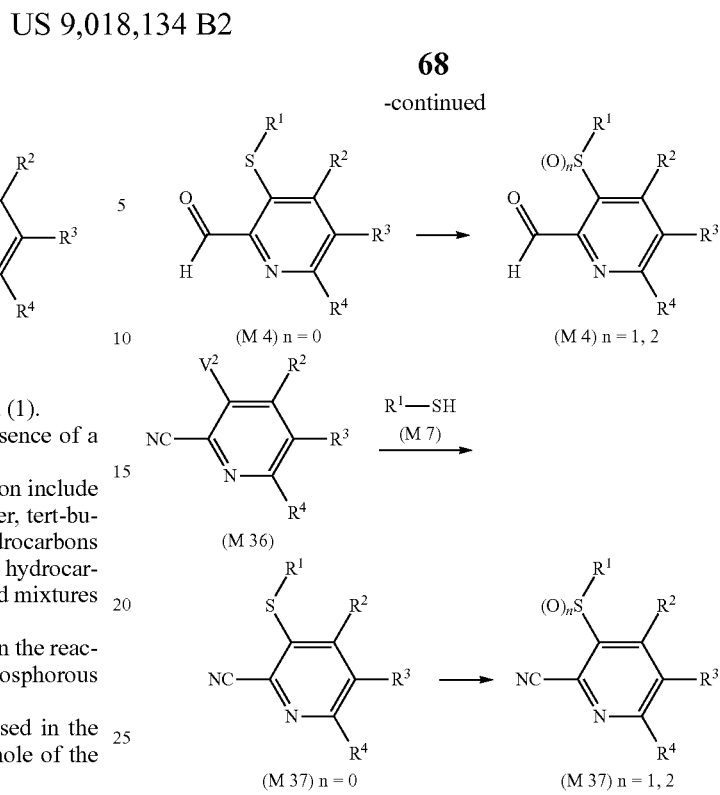

wherein $V^2$ represents a halogen atom, and the other symbols are as defined in the formula (1).

The intermediate compound (M2) wherein n is 0 can be produced in the same manner as in Production process 5 except for using the intermediate compound (M19) instead of the intermediate compound (M6).

The intermediate compound (M4) wherein n is 0 can be produced in the same manner as in Production process 5 except for using the intermediate compound (M22) instead of the intermediate compound (M6).

The intermediate compound (M37) wherein n is 0 can be produced in the same manner as in Production process 5 except for using the intermediate compound (M36) instead of the intermediate compound (M6).

The intermediate compound (M2) wherein n is 1 or 2 can be produced in the same manner as in Production process 1 except for using the intermediate compound (M2) wherein n is 0 instead of the present compound (I) wherein n is 0.

The intermediate compound (M4) wherein n is 1 or 2 can be produced in the same manner as in Production process 1 except for using the intermediate compound (M4) wherein n is 0 instead of the present compound (I) wherein n is 0.

The intermediate compound (M37) wherein n is 1 or 2 can be produced in the same manner as in Production process 1 except for using the intermediate compound (M37) wherein n is 0 instead of the present compound (I) wherein n is 0. In reaction, $V^2$ is preferably a fluorine atom or a chlorine atom.

(Production Process 15)

The intermediate compound (M30) can be produced by nitrating the intermediate compound (M29), or reacting the intermediate compound (M33) with the intermediate compound (M28). By reducing the resulting intermediate compound (M30), the intermediate compound (M1) represented by the formula (M1) wherein $A^1$ is —$NR^7$— can be produced.

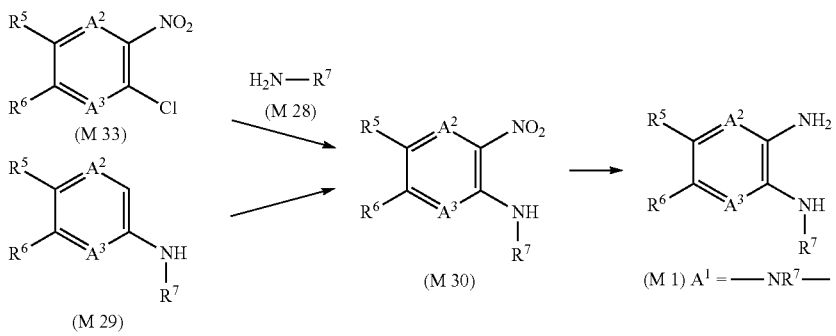

wherein the symbols are as defined in the formula (1).

The intermediate compound (M30) can be produced by reacting the intermediate compound (M33) with the intermediate compound (M28) in the presence of a base.

The reaction is generally conducted in the presence of a solvent.

Examples of the solvent to be used in the reaction include ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; and mixtures thereof.

The reaction may be conducted in the presence of a base.

Examples of the base to be used in the reaction include alkali metal hydrides such as sodium hydride; alkali metal carbonates such as sodium carbonate and potassium carbonate; tertiary amines such as triethylamine and N,N-diisopropylethylamine; and nitrogen-containing aromatic compounds such as pyridine and 4-dimethylaminopyridine.

The amount of the intermediate compound (M28) to be used in the reaction is generally 1 to 10 moles relative to 1 mole of the intermediate compound (M33).

The amount of the base to be used in the reaction is generally 0 to 10 moles relative to 1 mole of the intermediate compound (M6).

The reaction temperature of the reaction is generally within a range of 0° C. to 150° C. The reaction time of the reaction is generally within a range of 0.5 to 24 hours.

After the completion of the reaction, the intermediate compound (M30) can be isolated by post-treatments, for example, extracting the reaction mixture with an organic solvent, and drying and concentrating the organic layer. The isolated intermediate compound (M30) can be further purified by chromatography, recrystallization, and the like.

The intermediate compound (M30) can be produced by reacting the intermediate compound (M29) with a nitrating agent.

The reaction is generally conducted in the presence of a solvent. Examples of the solvent to be used in the reaction include aliphatic halogenated hydrocarbons such as dichloromethane, and chloroform; acetic acid, concentrated sulfuric acid, concentrated nitric acid, water; and mixtures thereof.

Examples of the nitrating agent to be used in the reaction include concentrated nitric acid; and the like.

The amount of the nitrating agent to be used in the reaction is generally 1 to 3 moles relative to 1 mole of the intermediate compound (M29).

The reaction temperature of the reaction is generally within a range of −10° C. to 100° C. The reaction time of the reaction is generally within a range of 0.1 to 24 hours.

After the completion of the reaction, the intermediate compound (M30) can be isolated by post-treatments, for example, pouring water to the reaction mixture, extracting the reaction mixture with an organic solvent, and drying and concentrating the organic layer. The isolated intermediate compound (M30) can be further purified by chromatography, recrystallization, and the like.

The intermediate compound (M30) wherein $R^7$ is a group other than a hydrogen atom can be produced in the same manner as in Production process 11 except for using the intermediate compound (M30) wherein $R^7$ is a hydrogen atom instead of the present compound (P2).

The intermediate compound (M1) wherein $A^1$ is —$NR^7$— can be produced by reacting the intermediate compound (M30) with hydrogen in the presence of a hydrogenating catalyst.

The reaction is generally conducted in the presence of a solvent under hydrogen atmosphere at 1 to 100 atm.

Examples of the solvent to be used in the reaction include ethers such as THF, ethylene glycol dimethyl ether, tert-butylmethyl ether, and 1,4-dioxane; esters such as ethyl acetate and butyl acetate; alcohols such as methanol and ethanol; water; and mixtures thereof.

Examples of the hydrogenating catalyst to be used in the reaction include transition metal compounds such as palladium carbon, palladium hydroxide, Raney nickel, and platinum oxide.

The amount of the hydrogen to be used in the reaction is generally 3 moles relative to 1 mole of the intermediate compound (M30).

The amount of the hydrogenating catalyst to be used in the reaction is generally 0.001 to 0.5 moles relative to 1 mole of the intermediate compound (M30).

The reaction may be conducted in the presence of an acid or a base, if necessary.

Examples of the acid to be used in the reaction include acetic acid, hydrochloric acid, and the like.

Examples of the base to be used in the reaction include tertiary amines such as triethylamine; magnesium oxide; and the like.

The reaction temperature of the reaction is generally within a range of −20° C. to 100° C. The reaction time of the reaction is generally within a range of 0.1 to 24 hours.

After the completion of the reaction, the intermediate compound (M1) wherein $A^1$ is —$NR^7$— can be isolated by post-treatments, for example, filtrating the reaction mixture, optionally extracting the reaction mixture with an organic solvent, and drying and concentrating the organic layer. The isolated intermediate compound (M1) wherein $A^1$ is —$NR^7$— can be further purified by chromatography, recrystallization, and the like.

As shown below, the intermediate compound (M30) can be produced by acetylating the intermediate compound (M29) to give the intermediate compound (M29'), nitrating the resulting intermediate compound (M29') to give the intermediate compound (M30'), and hydrolyzing the resulting intermediate compound (M30').

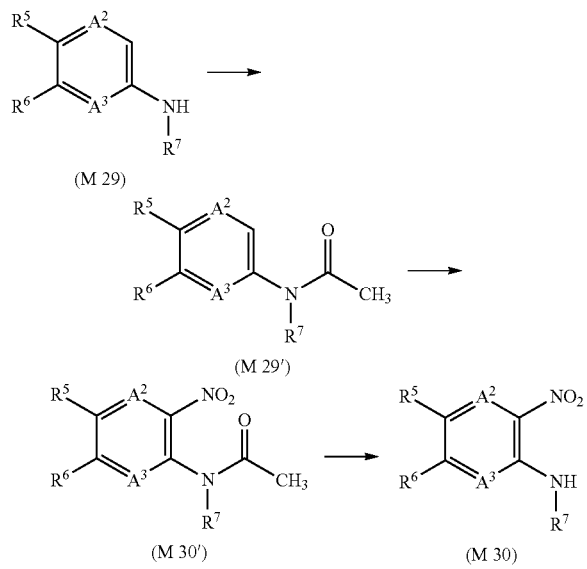

wherein the symbols are as defined in the formula (1).

The intermediate compound (M29') can be produced by reacting the intermediate compound (M29) with an acylating agent.

The reaction is generally conducted in the presence of a solvent or using the acylating agent as a solvent.

Examples of the solvent to be used in the reaction include aliphatic halogenated hydrocarbons such as dichloromethane and chloroform; ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; and mixtures thereof.

Examples of the acylating agent to be used in the reaction include acetic acid anhydride, para-acetoxynitrobenzene; and the like.

The reaction may be conducted in the presence of a base.

Examples of the base to be used in the reaction include tertiary amines such as triethylamine and N,N-diisopropylethylamine; and nitrogen-containing aromatic compounds such as pyridine and 4-dimethylaminopyridine.

The amount of the acylating agent to be used in the reaction is generally not less than 1 mole relative to 1 mole of the intermediate compound (M29).

The amount of the base to be used in the reaction is generally 0.1 to 10 moles relative to 1 mole of the intermediate compound (M29).

The reaction temperature of the reaction is generally within a range of 0° C. to 150° C. The reaction time of the reaction is generally within a range of 0.5 to 24 hours.

After the completion of the reaction, the intermediate compound (M29') can be isolated by post-treatments, for example, extracting the reaction mixture with an organic solvent, and drying and concentrating the organic layer. The isolated intermediate compound (M29') can be further purified by chromatography, recrystallization, and the like.

The intermediate compound (M30') can be produced in the same manner as in Production process 15 except for using the intermediate compound (M29') instead of the intermediate compound (M29).

The intermediate compound (M30) can be produced by hydrolyzing the intermediate compound (M30') in the presence of an acid or a base.

When the hydrolysis is conducted by using an acid, an aqueous solution of the acid is generally used as a solvent in the reaction.

Examples of the acid to be used in the reaction include mineral acids such as hydrochloric acid and sulfuric acid; and carboxylic acids such as acetic acid and trifluoroacetic acid.

The reaction temperature of the reaction is generally within a range of 0° C. to 100° C. The reaction time of the reaction is generally within a range of 0.1 to 24 hours.

After the completion of the reaction, the intermediate compound (M30) can be isolated by post-treatments, for example, extracting the reaction mixture with an organic solvent, and drying and concentrating the organic layer. The isolated intermediate compound (M30) can be further purified by chromatography, recrystallization, and the like.

When the hydrolysis is conducted by using a base, the reaction is generally conducted in the presence of a solvent.

Examples of the solvent to be used in the reaction include ethers such as THF, ethylene glycol dimethyl ether, tert-butylmethyl ether, and 1,4-dioxane; alcohols such as methanol and ethanol; water; and mixtures thereof.

Examples of the base to be used in the reaction include alkali metal hydroxides such as sodium hydroxide and potassium hydroxide; hydrazine; and the like.

The amount of the base to be used in the reaction is generally 1 to 10 moles relative to 1 mole of the intermediate compound (M30').

The reaction temperature of the reaction is generally within a range of 0° C. to 120° C. The reaction time of the reaction is generally within a range of 0.1 to 24 hours.

After the completion of the reaction, the intermediate compound (M30) can be isolated by post-treatments, for example, acidifying the reaction solution, extracting the reaction mixture with an organic solvent, and drying and concentrating the organic layer. The isolated intermediate compound (M30) can be further purified by chromatography, recrystallization, and the like.

(Production Process 16)

The intermediate compound (M1) wherein $A^1$ is —$NR^7$— can be produced by brominating the intermediate compound (M29) to give the intermediate compound (M35), and aminating the resulting intermediate compound (M35).

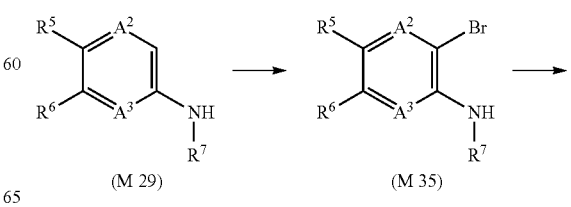

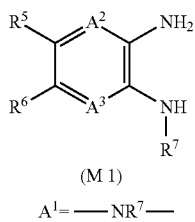

(M 1)

$A^1 = \text{—} NR^7 \text{—}$ wherein the symbols are as defined in the formula (1).

The intermediate compound (M35) can be produced by reacting the intermediate compound (M29) with a brominating agent.

The reaction is generally conducted in the presence of a solvent.

Examples of the solvent to be used in the reaction include water; acetic acid; ethers such as 1,4-dioxane, diethyl ether, and THF; esters such as ethyl acetate and butyl acetate; halogenated hydrocarbons such as dichloromethane, chloroform, carbon tetrachloride, and 1,2-dichloro ethane; nitriles such as acetonitrile; aprotic polar solvents such as DMF, NMP, and DMSO; and mixtures thereof.

Examples of the brominating agent to be used in the reaction include N-bromosuccinimide, bromine, and the like.

The amount of the brominating agent to be used in the reaction is generally 1 to 3 moles relative to 1 mole of the intermediate compound (M29).

The reaction temperature of the reaction is generally within a range of −10° C. to 100° C. The reaction time of the reaction is generally within a range of 0.1 to 24 hours.

After the completion of the reaction, the intermediate compound (M35) can be isolated by post-treatments, for example, pouring water to the reaction mixture, extracting the reaction mixture with an organic solvent, and concentrating the organic layer; pouring water to the reaction mixture, and collecting a solid by filtration; or collecting a solid formed in the reaction mixture by filtration. The isolated intermediate compound (M35) can be further purified by recrystallization, chromatography, and the like.

The intermediate compound (M1) wherein $A^1$ is —$NR^7$— can be produced by reacting the intermediate compound (M35) with an aminating agent in the presence of a copper compound.

The reaction is generally conducted in the presence of a solvent. Examples of the solvent to be used in the reaction include water; alcohols such as methanol and ethanol; ethers such as 1,4-dioxane, diethyl ether, and THF; esters such as ethyl acetate and butyl acetate; halogenated hydrocarbons such as dichloromethane, chloroform, carbon tetrachloride, and 1,2-dichloroethane; nitriles such as acetonitrile; aprotic polar solvents such as DMF, NMP, and DMSO; nitrogen-containing aromatic compounds such as pyridine and quinoline; and mixtures thereof.

Examples of the aminating agent to be used in the reaction include ammonia, aqueous ammonia, lithium amide, and the like.

Examples of the copper compound to be used in the reaction include copper, copper (I) iodide, copper (I) oxide, copper (II) oxide, acetylacetone copper (II), copper (II) acetate, copper (II) sulfate, and the like.

The reaction may be conducted in the presence of a ligand. Examples of the ligand to be used in the reaction include acetylacetone, salen, phenanthroline, and the like.

The reaction may be conducted in the presence of a base.

Examples of the base to be used in the reaction include nitrogen-containing heterocyclic compounds such as pyridine, picoline, 2,6-lutidine, DBU, and 1,5-diazabicyclo[4.3.0]-5-nonene; tertiary amines such as triethylamine and N,N-diisopropylethylamine; inorganic bases such as tripotassium phosphate, potassium carbonate, cesium carbonate, and sodium hydroxide.

The amount of the aminating agent to be used in the reaction is generally 1 to 5 moles relative to 1 mole of the intermediate compound (M35).

The amount of the copper compound to be used in the reaction is generally 0.02 to 0.2 moles relative to 1 mole of the intermediate compound (M35).

The amount of the base to be used in the reaction is generally 1 to 5 moles relative to 1 mole of the intermediate compound (M35).

The reaction temperature of the reaction is generally within a range of 30° C. to 200° C. The reaction time of the reaction is generally within a range of 0.1 to 48 hours.

After the completion of the reaction, the intermediate compound (M1) wherein $A^1$ is —$NR^7$— can be isolated by post-treatments, for example, pouring water to the reaction mixture, extracting the reaction mixture with an organic solvent, and drying and concentrating the organic layer. The isolated intermediate compound (M1) wherein $A^1$ is —$NR^7$— can be further purified by chromatography, recrystallization, and the like.

(Production Process 17)

The intermediate compound (M1) represented by the formula (M1) wherein $A^1$ is an oxygen atom can be produced by nitrating the intermediate compound (M31) to give the intermediate compound (M32), and reducing the resulting intermediate compound (M32).

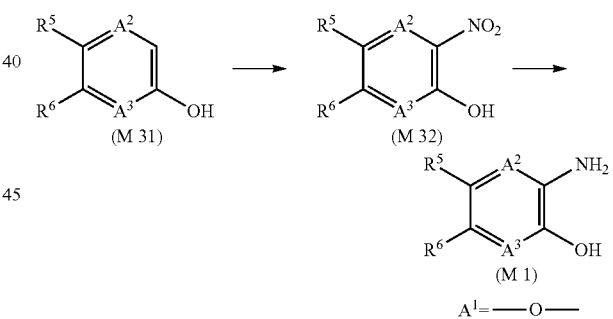

$A^1 = \text{—} O \text{—}$ wherein the symbols are as defined in the formula (1).

The intermediate compound (M32) can be produced in the same manner as in Production process 15 except for using the intermediate compound (M31) instead of the intermediate compound (M29).

The intermediate compound (M1) wherein $A^1$ is an oxygen atom can be produced in the same manner as in Production process 15 except for using the intermediate compound (M32) instead of the intermediate compound (M30).

(Production Process 18)

The intermediate compound (M1) represented by the formula (M1) wherein $A^1$ is a sulfur atom can be produced by reacting the intermediate compound (M33) with a sulfating agent to give the intermediate compound (M34), and reducing the resulting intermediate compound (M34).

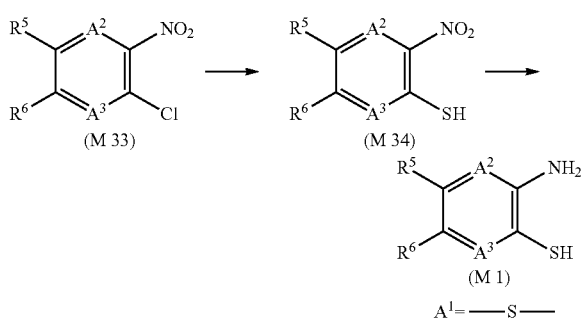

wherein the symbols are as defined in the formula (1).

The intermediate compound (M34) can be produced by reacting the intermediate compound (M33) with thiourea in the presence of a base.

The reaction is generally conducted in the presence of a solvent. Examples of the solvent to be used in the reaction include alcohols such as methanol and ethanol; water; and mixtures thereof.

Examples of the base to be used in the reaction include alkali metal hydroxide such as sodium hydroxide and potassium hydroxide.

The amount of the thiourea to be used in the reaction is generally 0.5 to 3 moles relative to 1 mole of the intermediate compound (M33).

The amount of the base to be used in the reaction is generally 1 to 10 moles relative to 1 mole of the intermediate compound (M33).

The reaction temperature of the reaction is generally within a range of 0° C. to 100° C. The reaction time of the reaction is generally within a range of 0.1 to 24 hours.

After the completion of the reaction, the intermediate compound (M34) can be isolated by post-treatments, for example, adding an acid to the reaction mixture, extracting the reaction mixture with an organic solvent, and drying and concentrating the organic layer. The isolated intermediate compound (M34) can be further purified by chromatography, recrystallization, and the like.

The intermediate, compound (M1) wherein $A^1$ is a sulfur atom can be produced by reacting the intermediate compound (M34) with a reductant.

The reduction reaction may be conducted in the presence of, for example, metal powder such as iron powder, and zinc powder; acids such as hydrochloric acid and acetic acid; and water.

The reaction is generally conducted in the presence of a solvent. Examples of the solvent to be used in the reaction include ethers such as THF, ethylene glycol dimethyl ether, tert-butylmethyl ether, and 1,4-dioxane; esters such as ethyl acetate and butyl acetate; alcohols such as methanol and ethanol; aprotic polar solvents such as DMF, NMP, and DMSO; and mixtures thereof.

Examples of the reductant to be used in the reaction include metal powders such as iron powders, zinc powders and tin dichloride powders.

The amount of the metal powder to be used in the reaction is generally 3 to 10 moles relative to 1 mole of the intermediate compound (M34).

The reaction temperature of the reaction is generally within a range of 0° C. to 100° C. The reaction time of the reaction is generally within a range of 0.1 to 24 hours.

After the completion of the reaction, the intermediate compound (M1) wherein $A^1$ is a sulfur atom can be isolated by post-treatments, for example, pouring water to the reaction mixture, extracting the reaction mixture with an organic solvent, and drying and concentrating the organic layer. The isolated intermediate compound (M1) wherein $A^1$ is a sulfur atom can be further purified by chromatography, recrystallization, and the like.

(Production Process 19)

The present compound (P7) represented by the formula (1) wherein $R^5$ is a C1-C6 perfluoroalkyl group can be produced by reacting the present compound (P4) represented by the formula (1) wherein $R^5$ is a halogen atom, the intermediate compound (M11) or the intermediate compound (M11') in the presence of a copper compound.

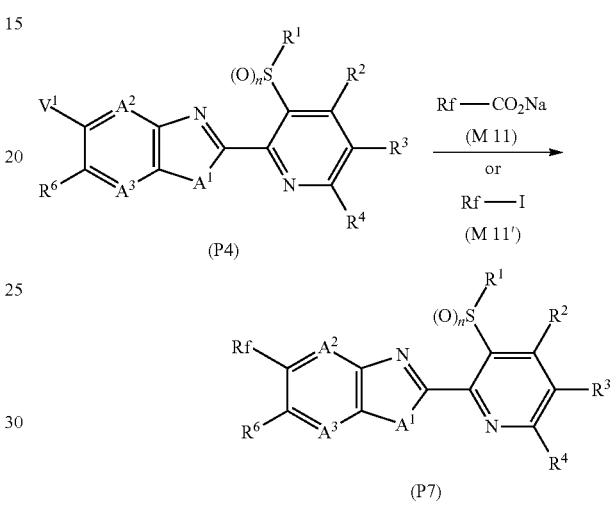

wherein $V^1$ represents a halogen atom, Rf represents a C1-C6 perfluoroalkyl group, and the other symbols are as defined in the formula (1).

The reaction is generally conducted in the presence of a solvent.

Examples of the solvent to be used in the reaction include aromatic hydrocarbons such as toluene and xylene; aprotic polar solvents such as DMF, NMP, and DMSO; and mixtures thereof.

Examples of the copper compound to be used in the reaction include copper, copper (I) iodide.

When the intermediate compound (M11) is used, the amount of the intermediate compound (M11) to be used in the reaction is generally 1 to 10 moles relative to 1 mole of the present compound (P4). The amount of the copper compound to be used in the reaction is generally 0.5 to 10 moles relative to 1 mole of the present compound (P4). The reaction temperature of the reaction is generally within a range of 100° C. to 200° C. The reaction time of the reaction is generally within a range of 0.5 to 48 hours.

When the intermediate compound (M11') is used, the reaction may be conducted in the presence of potassium fluoride. The amount of the intermediate compound (M11') to be used in the reaction is generally 1 to 10 moles relative to 1 mole of the present compound (P4). The amount of the copper compound to be used in the reaction is generally 0.1 to 10 moles relative to 1 mole of the present compound (P4). The amount of the potassium fluoride to be used in the reaction is generally 0.1 to 5 moles relative to 1 mole of the present compound (P4). The reaction temperature of the reaction is generally within a range of 0° C. to 150° C. The reaction time of the reaction is generally within a range of 0.5 to 48 hours.

After the completion of the reaction, the present compound (P7) can be isolated by post-treatments, for example, extracting the reaction mixture with an organic solvent, and drying and concentrating the organic layer. The isolated present compound (P7) can be further purified by chromatography, recrystallization, and the like.

In the reaction, $V^1$ is preferably a bromine atom and an iodine atom.

(Production Process 20)

The present compound (P9) wherein $R^5$ is —SH can be produced by reacting the present compound (P4) with a sulfating agent. The intermediate compound (P9'), which is a disulfide of the present compound (P9), can be produced by oxidizing the present compound (P9).

The amount of the ligand to be used in the reaction is generally 1 to 2 moles relative to 1 mole of the intermediate compound (P4).

The reaction temperature of the reaction is generally within a range of 50° C. to 200° C. The reaction time of the reaction is generally within a range of 0.5 to 24 hours.

After the completion of the reaction, the present compound (P9) can be isolated by post-treatments, for example, extracting the reaction mixture with an organic solvent, and drying and concentrating the organic layer. The isolated present compound (P9) can be further purified by chromatography, recrystallization, and the like.

In the reaction, $V^1$ is preferably a bromine atom and an iodine atom.

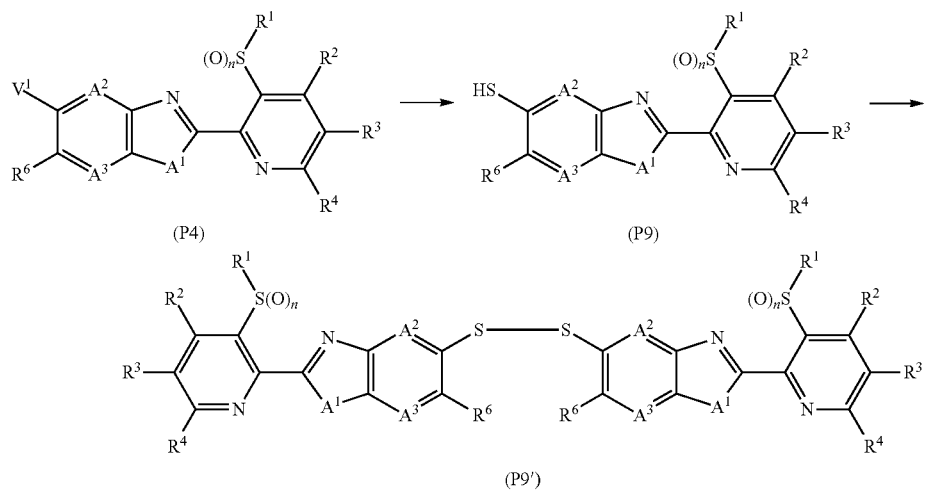

wherein $V^1$ represents a halogen atom, and the other symbols are as defined in the formula (1).

The present compound (P9) can be produced by reacting the present compound (P4) with a thioesterificating agent and a catalyst.

The reaction is generally conducted in the presence of a solvent.

Examples of the solvent to be used in the reaction include aromatic hydrocarbons such as toluene and xylene; aprotic polar solvents such as DMF, NMP, and DMSO; and mixtures thereof.

Examples of the thioesterificating agent to be used in the reaction include sodium sulfide, sodium sulfide hydrate, and thiourea.

Examples of the catalyst to be used in the reaction include copper (I) chloride, copper (I) bromide, and copper (I) iodide.

The reaction may be conducted in the presence of a ligand.

Examples of the ligand to be used in the reaction include acetylacetone, salen, phenanthroline; and the like.

The reaction may be conducted in the presence of a base.

Examples of the base to be used in the reaction include inorganic bases such as potassium carbonate, cesium carbonate, and tripotassium phosphate; and organic bases triethylamine.

The amount of the thioesterificating agent to be used in the reaction is generally 1 to 10 moles relative to mole of the intermediate compound (P4).

The amount of the catalyst to be used in the reaction is generally 0.1 to 5 moles relative to 1 mole of the intermediate compound (P4).

In the reaction, the reaction from the present compound (P9) to intermediate compound (P9') is easily progressed, and thus the intermediate compound (P9') may be produced during the synthesis of the present compound (P9).

The intermediate compound (P9') can be produced by reacting the present compound (P9) with an oxidant.

The reaction is generally conducted in the presence of a solvent.

Examples of the solvent to be used in the reaction include water; alcohols such as methanol and ethanol; ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; carboxylic acids such as acetic acid; and mixtures thereof.

Examples of the oxidant to be used in the reaction include oxygen, iodine, hydrogen peroxide solution, potassium ferricyanide, and the like.

The amount of the oxidant to be used in the reaction is generally 0.5 to 10 moles relative to 1 mole of the intermediate compound (P9).

The reaction temperature of the reaction is generally within a range of 0° C. to 100° C. The reaction time of the reaction is generally within a range of 0.1 to 24 hours.

After the completion of the reaction, the intermediate compound (P9') can be isolated by post-treatments, for example, extracting the reaction mixture with an organic solvent, and drying and concentrating the organic layer. The isolated intermediate compound (P9') can be further purified by chromatography, recrystallization, and the like.

The present compound (P9) can be produced by thioesterifying the present compound (P4) to give the intermediate compound (P9-1), and then hydrolyzing the resulting intermediate compound (P9-1).

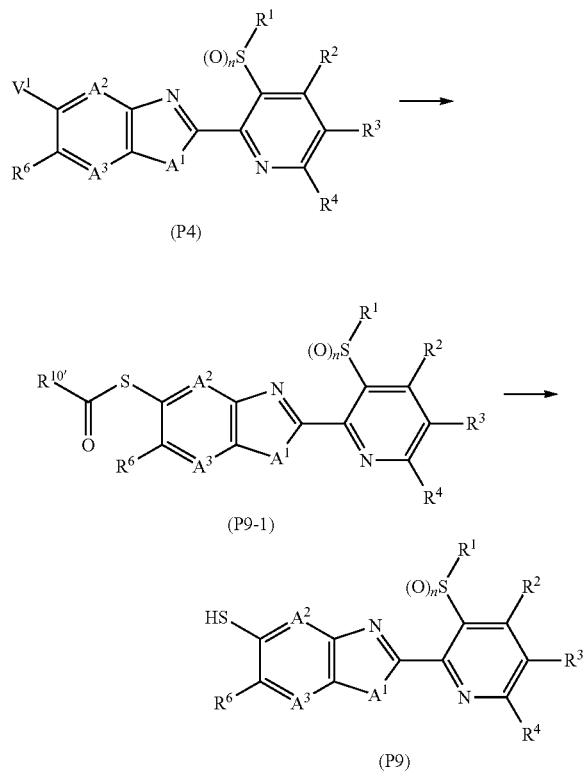

wherein $R^{10'}$ is any of the groups other than a hydrogen atom for $R^{10}$ in the formula (1), and the other symbols are as defined in the formula (1).

The intermediate compound (P9-1) can be produced by reacting the present compound (P4) with a thioesterifying agent, in the presence of a base and a catalyst.

The reaction is generally conducted in the presence of a solvent.

Examples of the solvent to be used in the reaction include aromatic hydrocarbons such as toluene and xylene; aprotic polar solvents such as DMF, NMP, and DMSO; and mixtures thereof.

Examples of the thioesterifying agent to be used in the reaction include thiobenzoic acid, and the like.

Examples of the catalyst to be used in the reaction include copper (I) chloride, copper (I) bromide, and copper (I) iodide.

The reaction may be conducted in the presence of ligand.

Examples of the ligand to be used in the reaction include acetylacetone, salen, phenanthroline; and the like.

Examples of the base to be used in the reaction include inorganic bases such as potassium carbonate, cesium carbonate, and tripotassium phosphate; and organic bases such as triethylamine.

The amount of the thioesterifying agent is generally 1 to 10 moles relative to 1 mole of the present compound (P4).

The amount of the catalyst is generally 0.1 to 5 moles relative to 1 mole of the present compound (P4).

The amount of the ligand is generally 0.1 to 5 moles relative to 1 mole of the present compound (P4).

The amount of the base is generally 1 to 2 moles relative to 1 mole of the present compound (P4).

The reaction temperature of the reaction is generally within a range of 50° C. to 200° C. The reaction time of the reaction is generally within a range of 0.5 to 24 hours.

After the completion of the reaction, the intermediate compound (P9-1) can be isolated by post-treatments, for example, extracting the reaction mixture with an organic solvent, and drying and concentrating the organic layer. The isolated intermediate compound (P9-1) can be further purified by chromatography, recrystallization, and the like.

In the reaction, $V^1$ is preferably a bromine atom and an iodine atom.

The present compound (P9) can be produced by hydrolyzing the intermediate compound (P9-1).

When the hydrolysis is conducted in the presence of an acid, an aqueous solution of the acid is generally used as a solvent.

Examples of the acid to be used in the reaction include mineral acids such as hydrochloric acid, nitric acid, phosphoric acid, and sulfuric acid; and carboxylic acids such as acetic acid and trifluoroacetic acid.

The reaction temperature of the reaction is generally within a range of 0° C. to 100° C. The reaction time of the reaction is generally within a range of 0.1 to 24 hours.

After the completion of the reaction, the present compound (P9) can be isolated by post-treatments, for example, extracting the reaction mixture with an organic solvent, and drying and concentrating the organic layer. The isolated present compound (P9) can be further purified by chromatography, recrystallization, and the like.

When the hydrolysis is conducted in the presence of a base, the reaction is generally conducted in the presence of a solvent.

Examples of the solvent to be used in the reaction include ethers such as THF, ethylene glycol dimethyl ether, tert-butylmethyl ether, and 1,4-dioxane; alcohols such as methanol and ethanol; water; and mixtures thereof.

Examples of the base to be used in the reaction include alkali metal hydroxides such as sodium hydroxide and potassium hydroxide.

The amount of the base to be used in the reaction is generally 1 to 10 moles relative to 1 mole of the intermediate compound (P9-1).

The reaction temperature of the reaction is generally within a range of 0° C. to 120° C. The reaction time of the reaction is generally within a range of 0.1 to 24 hours.

After the completion of the reaction, the present compound (P9) can be isolated by post-treatments, for example, acidifying the reaction solution, extracting the reaction mixture with an organic solvent, and drying and concentrating the organic layer. The isolated present compound (P9) can be further purified by chromatography, recrystallization, and the like.

In the reaction, the reaction from the present compound (P9) to intermediate compound (P9') is easily progressed, and thus the intermediate compound (P9') may be produced during the synthesis of the present compound (P9).

(Production Process 21)

The present compound (P10-m0) wherein $R^5$ is $—S(O)_m R^{10'}$ and m is 0 can be produced by reacting the present compound (P9) or a disulfide thereof, the intermediate compound (P9'), and the compound (M13). The present compound (P10) represented by the formula (1) wherein $R^5$ is $—S(O)_m R^{10'}$ and m is 1 or 2 can be produced by oxidizing the present compound (P10-m0) wherein m is 0.

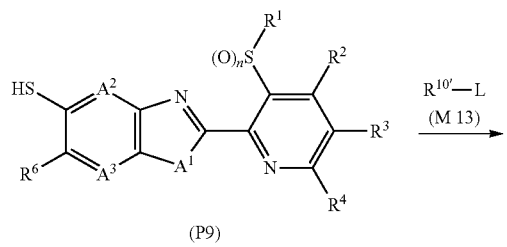

(P9)

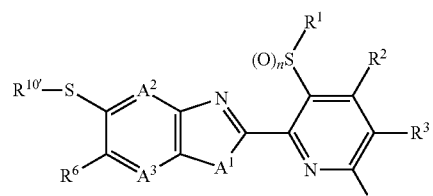

(P10 - m0)

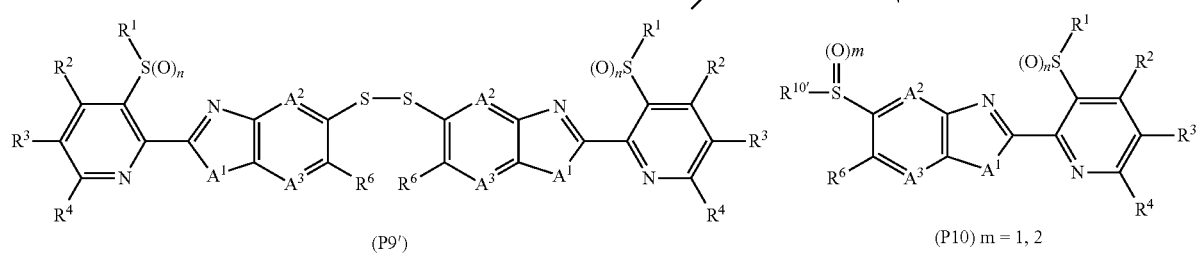

(P9')  (P10) m = 1, 2 wherein $R^{10'}$ is any of the groups other than a hydrogen atom for $R^{10}$ in the formula (1), L is a leaving group such as a chlorine atom, a bromine atom, an iodine atom, a trifluoromethanesulfonyloxy group and a methanesulfonyloxy group, and the other symbols are as defined in the formula (1).

The reaction is generally conducted in the presence of a solvent.

Examples of the solvent to be used in the reaction include ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; and mixtures thereof.

Examples of the base to be used in the reaction include alkali metal or alkaline earth metal hydrides such as sodium hydride, potassium hydride, calcium hydride; inorganic bases such as sodium carbonate and potassium carbonate; and organic bases such as triethylamine.

When the intermediate compound (P9'), which is disulfide, is used, the reaction is generally conducted in the presence of a reductant.

Examples of the reductant to be used in the reaction include sodium hydroxymethanesulfinate (trade name: Rongalite).

The amount of the base to be used in the reaction is generally 1 to 10 moles relative to 1 mole of the present compound (P9).

When the intermediate compound (P9'), which is disulfide, is used, the amount of the intermediate compound (M13) to be used in the reaction is generally 2 to 10 moles relative to 1 mole of the present compound (P9'). The amount of the base to be used in the reaction is generally 2 to 10 moles relative to 1 mole of the present compound (P9). The amount of the reductant to be used in the reaction is generally 1 to 5 moles relative to 1 mole of the present compound (P9).

The reaction temperature of the reaction is generally within a range of 0° C. to 100° C. The reaction time of the reaction is generally within a range of 0.1 to 24 hours.

After the completion of the reaction, the present compound (P10-m0) wherein m is 0 can be isolated by post-treatments, for example, extracting the reaction mixture with an organic solvent, and drying and concentrating the organic layer. The isolated present compound (P10-m0) wherein m is 0 can be further purified by chromatography, recrystallization, and the like.

Among the present compounds (P10-m0) wherein m is 0, the compound wherein $R^{10'}$ is a C1-C6 perfluoroalkyl group can be produced by reacting the intermediate compound (P9'), perfluoroalkyl iodide and a reductant.

The reaction is generally conducted in the presence of a solvent.

Examples of the solvent to be used in the reaction include ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; and mixtures thereof.

Examples of the reductant to be used in the reaction include tetrakis(dimethylamino)ethylene.

Examples of the perfluoroalkyl iodide to be used in the reaction include trifluoromethane iodide, pentafluoroethane iodide, heptafluoro-2-iodopropane, and the like.

The amount of the perfluoroalkyl iodide to be used in the reaction is generally 2 to 10 moles relative to 1 mole of the intermediate compound (P9').

The amount of the reductant to be used in the reaction is generally 1 to 5 moles relative to 1 mole of the intermediate compound (P9').

The reaction temperature of the reaction is generally within a range of –80° C. to 50° C. The reaction time of the reaction is generally within a range of 0.1 to 24 hours.

After the completion of the reaction, the present compound (P10-m0) wherein m is 0 can be isolated by post-treatments, for example, extracting the reaction mixture with an organic solvent, and drying and concentrating the organic layer. The isolated present compound (P10-m0) wherein m is 0 can be further purified by chromatography, recrystallization, and the like.

The present compound (P10) wherein m is 1 or 2 can be produced by reacting, the present compound (P10-m0) wherein m is 0 with an oxidant.

The reaction is generally conducted in the presence of a solvent.

Examples of the solvent to be used in the reaction include aliphatic halogenated hydrocarbons such as dichloromethane and chloroform; alcohols such as methanol and ethanol; acetic acid; water; and mixtures thereof.

Examples of the oxidant to be used in the reaction include m-chloroperbenzoic acid and hydrogen peroxide solution.

The reaction may be conducted in the presence of a catalyst.

Examples of the catalyst to be used in the reaction include sodium tungstate.

The amount of oxidant is generally 1 to 5 moles relative to 1 mole of the present compound (P10-m0) wherein m is 0.

The amount of catalyst is generally 0.01 to 0.5 moles relative to 1 mole of the present compound (P10-m0) wherein m is 0.

In the production of the compound wherein m is 1, the amount of the oxidant is generally 0.8 to 1.2 moles relative to 1 mole of the present compound (P10-m0) wherein m is 0. The amount of the catalyst to be used in the reaction is generally 0.05 to 0.2 moles relative to 1 mole of the present compound (P10-m0) wherein m is 0.

In the production of the compound wherein m is 2, the amount of the oxidant is generally 1.8 to 5 moles relative to 1 mole of the present compound (P10-m0) wherein m is 0. The amount of the catalyst to be used in the reaction is generally 0.05 to 0.2 moles relative to 1 mole of the present compound (P10-m0) wherein m is 0.

The reaction temperature of the reaction is generally within a range of −20° C. to 120° C. The reaction time of the reaction is generally within a range of 0.1 to 12 hours.

After the completion of the reaction, the present compound (P10) wherein m is 1 or 2 can be isolated by post-treatments, for example, extracting the reaction mixture with an organic solvent, optionally washing the mixture with an aqueous solution of a reductant (e.g., sodium sulfite and sodium thiosulfate), followed by an aqueous solution of a base (e.g., sodium hydrogen carbonate), and drying and concentrating the organic layer. The isolated present compound (P10) wherein m is 1 or 2 can be further purified by chromatography, recrystallization, and the like.

(Production Process 22)

The present compound (P11) represented by the formula (1) wherein $R^5$ is —OH can be produced via the intermediate compound (P11') from the present compound (P4).

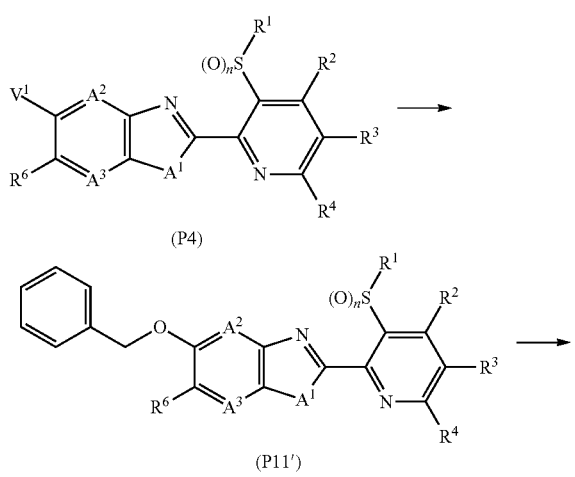

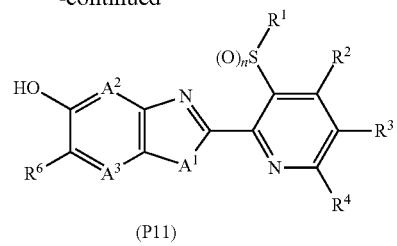

wherein $V^1$ represents a halogen atom, and the other symbols are as defined in the formula (1).

The intermediate compound (P11') can be produced by reacting the present compound (P4) with benzyl alcohol in the presence of a base.

The reaction is generally conducted in the presence of a solvent or used benzyl alcohol as a solvent.

Examples of the solvent to be used in the reaction include aromatic hydrocarbons such as toluene and xylene; aprotic polar solvents such as DMF, NMP, and DMSO; and mixtures thereof.

The reaction may be conducted in the presence of a catalyst.

Examples of the catalyst to be used in the reaction include copper (I) chloride, copper (I) bromide, and copper (I) iodide.

The reaction may be conducted in the presence of a ligand.

Examples of the ligand to be used in the reaction include acetylacetone, salen, phenanthroline; and the like.

The reaction is generally conducted in the presence of a base.

Examples of the base to be used in the reaction include inorganic bases such as potassium carbonate, cesium carbonate, and tripotassium phosphate.

The amount of the benzyl alcohol is generally 1 to 10 moles relative to 1 mole of the present compound (P4).

The amount of the catalyst is generally 0.1 to 5 moles relative to 1 mole of the present compound (P4).

The amount of the ligand is generally 0.1 to 5 moles relative to 1 mole of the present compound (P4).

The amount of the base is generally 1 to 2 moles relative to 1 mole of the present compound (P4).

The reaction temperature of the reaction is generally within a range of 50° C. to 200° C. The reaction time of the reaction is generally within a range of 0.5 to 24 hours.

After the completion of the reaction, the intermediate compound (P11') can be isolated by post-treatments, for example, extracting the reaction mixture with an organic solvent, and drying and concentrating the organic layer. The isolated intermediate compound (P11') can be further purified by chromatography, recrystallization, and the like.

In the reaction, $V^1$ is preferably a bromine atom and an iodine atom.

The present compound (P11) can be produced by reacting the intermediate compound (P11') with hydrogen in the presence of a hydrogenating catalyst.

The reaction is generally conducted in the presence of a solvent under of hydrogen atmosphere at 1 to 100 atm.

Examples of the solvent to be used in the reaction include ethers such as THF, ethylene glycol dimethyl ether, tert-butylmethyl ether, and 1,4-dioxane; esters such as ethyl acetate and butyl acetate; alcohols such as methanol and ethanol; water; and mixtures thereof.

Examples of the hydrogenating catalyst to be used in the reaction include transition metal compounds such as palladium carbon, palladium hydroxide, Raney nickel, and platinum oxide.

The amount of the hydrogen to be used in the reaction is generally 3 moles relative to 1 mole of the intermediate compound (P11').

The amount of the hydrogenating catalyst to be used in the reaction is generally 0.001 to 0.5 moles relative to 1 mole of the intermediate compound (P11').

The reaction may be conducted in the presence of an acid or a base.

Examples of the acid to be used in the reaction include acetic acid, hydrochloric acid, and the like.

Examples of the base to be used in the reaction include tertiary amines such as triethylamine; magnesium oxide; and the like.

The reaction temperature of the reaction is generally within a range of −20° C. to 100° C. The reaction time of the reaction is generally within a range of 0.1 to 24 hours.

After the completion of the reaction, the present compound (P11) can be isolated by post-treatments, for example, filtrating the reaction mixture, extracting the reaction mixture with an organic solvent, and drying and concentrating the organic layer. The isolated present compound (P11) can be further purified by chromatography, recrystallization, and the like.

(Production Process 23)

The present compound (P12) represented by the formula (1) wherein $R^5$ is —$OR^{10'}$ can be produced by reacting the present compound (P11) with the compound (M13).

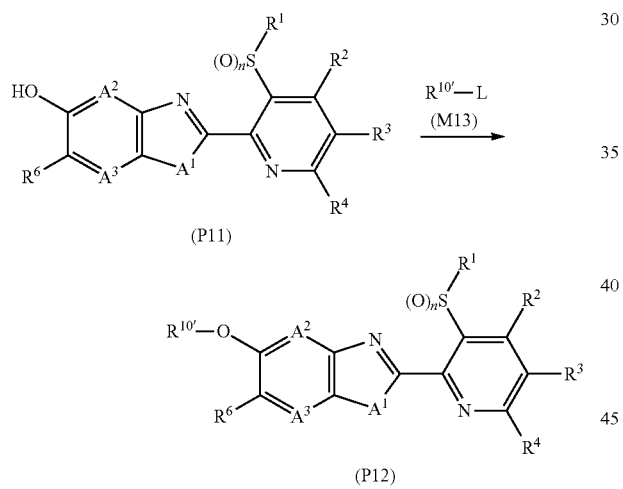

wherein $R^{10'}$ is any of the groups other than a hydrogen atom for $R^{10}$ in the formula (1), and the other symbols are as defined in the formula (1).

The reaction is generally conducted in the presence of a solvent.

Examples of the solvent to be used in the reaction include ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; and mixtures thereof.

Examples of the base to be used in the reaction include alkali metal or alkaline earth metal hydrides such as sodium hydride, potassium hydride, calcium hydride; inorganic bases such as sodium carbonate and potassium carbonate; and organic bases such as triethylamine.

The amount of the compound (M13) is generally 1 to 10 moles relative to 1 mole of the present compound (P11).

The amount of the base is generally 1 to 10 moles relative to 1 mole of the present compound (P11).

The reaction temperature of the reaction is generally within a range of 0° C. to 100° C. The reaction time of the reaction is generally within a range of 0.1 to 24 hours.

After the completion of the reaction, the present compound (P12) can be isolated by post-treatments, for example, extracting the reaction mixture with an organic solvent, and drying and concentrating the organic layer. The isolated present compound (P12) can be further purified by chromatography, recrystallization, and the like.

Among the present compounds (P12), the present compound (P12) wherein $R^{10'}$ is a trifluoromethyl group can be produced by the following Production process.

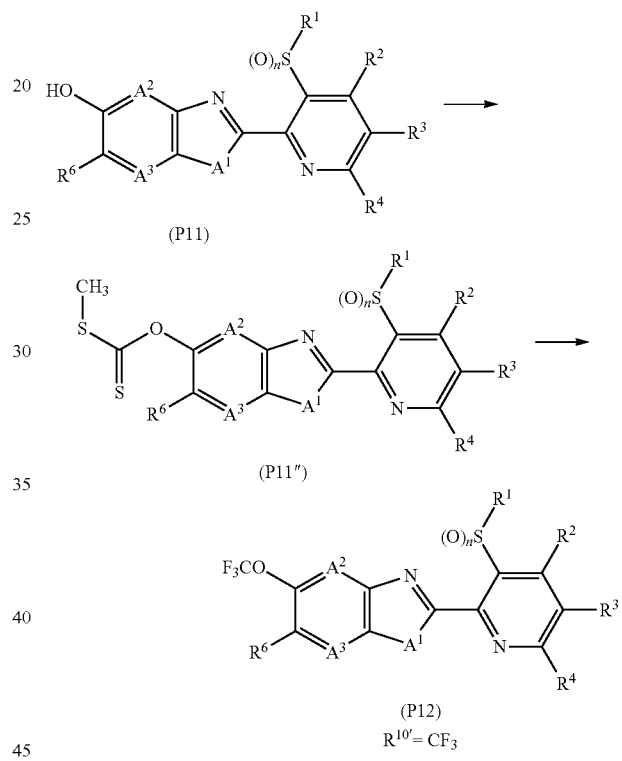

wherein the symbols are as defined in the formula (1).

The intermediate compound (P11″) can be produced by reacting the present compound (P11), a base, carbon disulfide and a methylating agent.

The reaction is conducted in the presence of a solvent.

Examples of the solvent to be used in the reaction include aprotic polar solvents such as DMF, NMP, and DMSO.

Examples of the base to be used in the reaction include alkali metal hydrides such as sodium hydride. Examples of the methylating agent to be used in the reaction include methyl iodide.

The amount of the base is generally 1 to 2 moles relative to 1 mole of the present compound (P11).

The amount of the carbon disulfide is generally 1 to 10 moles relative to 1 mole of the present compound (P11).

The amount of the methylating agent is generally 1 to 10 moles relative to 1 mole of the present compound (P11).

The reaction temperature of the reaction is generally within a range of 0° C. to 100° C. The reaction time of the reaction is generally within a range of 0.5 to 24 hours.

After the completion of the reaction, the intermediate compound (P11") can be isolated by post-treatments, for example, extracting the reaction mixture with an organic solvent, and drying and concentrating the organic layer. The isolated intermediate compound (P11") can be further purified by chromatography, recrystallization, and the like.

Among the present compounds (P12), the present compound (P12) wherein $R^{10t}$ is a trifluoromethyl group can be produced by reacting the intermediate compound (P11") with a fluorinating agent in the presence of a base.

The reaction is conducted in the presence of a solvent.

Examples of the solvent to be used in the reaction include halogenated hydrocarbons such as dichloromethane, chloroform, carbon tetrachloride, and 1,2-dichloro ethane.

The reaction is conducted in the presence of a base and a fluorinating agent.

Examples of the base to be used in the reaction include 1,3-dibromo-5,5-dimethyl hydantoin.

Examples of the fluorinating agent to be used in the reaction include tetra-n-butylammonium fluoride, and hydrogen fluoride pyridine complex.

The amount of the base to be used in the reaction is generally 1 to 10 moles relative to 1 mole of the intermediate compound (P11").

The amount of the fluorinating agent is generally 1 to 10 moles relative to 1 mole of the intermediate compound (P11").

The reaction temperature of the reaction is generally within a range of −80° C. to 50° C. The reaction time of the reaction is generally within a range of 0.5 to 24 hours.

After the completion of the reaction, the present compound (P12) wherein $R^{10t}$ is a trifluoromethyl group can be isolated by post-treatments, for example, extracting the reaction mixture with an organic solvent, and drying and concentrating the organic layer. The isolated present compound (P12) wherein $R^{10t}$ is a trifluoromethyl group can be further purified by chromatography, recrystallization, and the like.

(Production Process 25)

An N-oxide having an oxidized nitrogen atom of the present compound or the intermediate compound can be produced by reacting a compound having a nitrogen-containing heterocyclic group having a lone electron pair on the nitrogen atom with an oxidant.

Examples of the nitrogen-containing heterocyclic group to be used in the reaction include a pyridine ring.

The reaction can be conducted by, for example, a known method in the presence of a solvent such as halogenated hydrocarbons such as dichloromethane, chloroform, and chlorobenzene; alcohols such as methanol and ethanol; acetic acid; water; and the mixtures thereof, by using an oxidant such as m-chloroperbenzoic acid or hydrogen peroxide.

Examples of the intermediate compound (M3) include the following compounds.

A compound represented by the formula (M3) wherein $A^1$ is —$NR^7$—;

A compound represented by the formula (M3) wherein $A^1$ is an oxygen atom;

A compound represented by the formula (M3) wherein $A^1$ is a sulfur atom;

A compound represented by the formula (M3) wherein $A^2$ is =$CR^8$—;

A compound represented by the formula (M3) wherein $A^2$ is =$CR^8$—, and $A^3$ is a nitrogen atom;

A compound represented by the formula (M3) wherein $A^2$ is =$CR^8$—, and $A^3$ is =$CR^9$—;

A compound represented by the formula (M3) wherein $A^1$ is —$NR^7$—, and $A^2$ is =$CR^8$—;

A compound represented by the formula (M3) wherein $A^1$ is —$NR^7$—, $A^2$ is =$CR^8$—, and $A^3$ is a nitrogen atom;

A compound represented by the formula (M3) wherein $A^1$ is —$NR^7$—, $A^2$ is =$CR^8$—, and $A^3$ is =$CR^9$—;

A compound represented by the formula (M3) wherein $A^1$ is an oxygen atom, and $A^2$ is =$CR^8$—;

A compound represented by the formula (M3) wherein $A^1$ is an oxygen atom, $A^2$ is =$CR^8$—, and $A^3$ is a nitrogen atom;

A compound represented by the formula (M3) wherein $A^1$ is an oxygen atom, $A^2$ is =$CR^8$—, and $A^3$ is =$CR^9$—;

A compound represented by the formula (M3) wherein $A^1$ is a sulfur atom, and $A^2$ is =$CR^8$—;

A compound represented by the formula (M3) wherein $A^1$ is a sulfur atom, $A^2$ is =$CR^8$—, and $A^3$ is a nitrogen atom;

A compound represented by the formula (M3) wherein $A^1$ is a sulfur atom, $A^2$ is =$CR^8$—, and $A^3$ is =$CR^9$—;

A compound represented by the formula (M3), which is represented by the formula (M3-1):

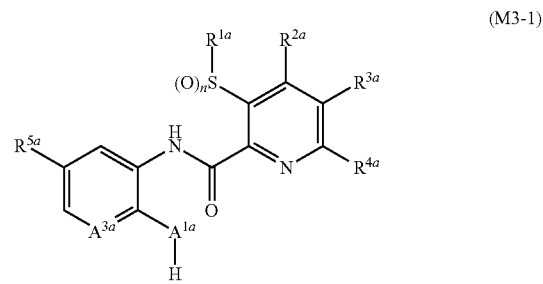

(M3-1)

wherein the symbols are as defined in the formula (1-1);

A compound represented by the formula (M3-1) wherein $A^{1a}$ is —$NR^{7a}$—;

A compound represented by the formula (M3-1) wherein $A^{1a}$ is an oxygen atom;

A compound represented by the formula (M3-1) wherein $A^{1a}$ is a sulfur atom;

A compound represented by the formula (M3-1) wherein $A^{1a}$ is —$NR^{7a}$—, and $A^{3a}$ is a nitrogen atom;

A compound represented by the formula (M3-1) wherein $A^{1a}$ is —$NR^{7a}$—, and $A^{3a}$ is =$CR^{9a}$— compound;

A compound represented by the formula (M3-1) wherein $A^{1a}$ is an oxygen atom, and $A^{3a}$ is a nitrogen atom;

A compound represented by the formula (M3-1) wherein $A^{1a}$ is an oxygen atom, and $A^{3a}$ is =$CR^{9a}$— compound;

A compound represented by the formula (M3-1) wherein $A^{1a}$ is a sulfur atom, and $A^{3a}$ is a nitrogen atom;

A compound represented by the formula (M3-1) wherein $A^{1a}$ is a sulfur atom, and $A^{3a}$ is =$CR^{9a}$— compound;

A compound represented by the formula (M3-1), which is represented by the formula (M3-2):
the formula (M3-2)

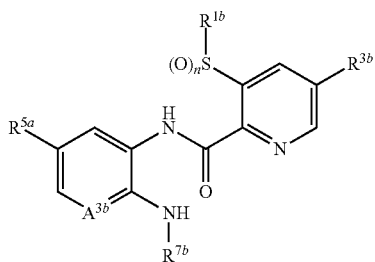

wherein the symbols are as defined in the formula (1-2);
A compound represented by the formula (M3-2) wherein $A^{3b}$ is a nitrogen atom;
A compound represented by the formula (M3-2) wherein $A^{3b}$ is $=CR^{9b}$— compound;
A compound represented by the formula (M3-1), which is represented by the formula (M3-3):

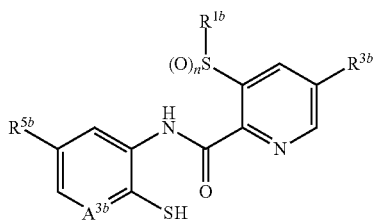

wherein the symbols are as defined in the formula (1-2);
A compound represented by the formula (M3-3) wherein $A^{3b}$ is a nitrogen atom;
A compound represented by the formula (M3-3) wherein $A^{3b}$ is $=CR^{9b}$— compound;
A compound represented by the formula (M3-1), which is represented by the formula (M3-4):

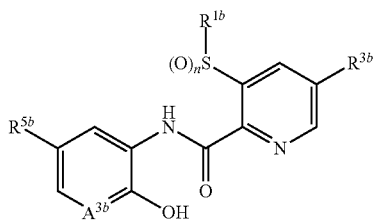

wherein the symbols are as defined in the formula (1-2);
A compound represented by the formula (M3-4) wherein $A^{3b}$ is a nitrogen atom;
A compound represented by the formula (M3-4) wherein $A^{3b}$ is $=CR^{9b}$— compound;
Examples of the intermediate compound (M6) include the following compounds.
A compound represented by the formula (M6) wherein $A^1$ is —$NR^7$—;
A compound represented by the formula (M6) wherein $A^1$ is an oxygen atom;
A compound represented by the formula (M6) wherein $A^1$ is a sulfur atom;
A compound represented by the formula (M6) wherein $A^2$ is $=CR^8$—;
A compound represented by the formula (M6) wherein $A^2$ is $=CR^8$—, and $A^3$ is a nitrogen atom;
A compound represented by the formula (M6) wherein $A^2$ is $=CR^8$—, and $A^3$ is $=CR^9$—;
A compound represented by the formula (M6) wherein $A^1$ is —$NR^7$—, and $A^2$ is $=CR^8$—;
A compound represented by the formula (M6) wherein $A^1$ is —$NR^7$—, $A^2$ is $=CR^8$—, and $A^3$ is a nitrogen atom;
A compound represented by the formula (M6) wherein $A^1$ is —$NR^7$—, $A^2$ is $=CR^8$—, and $A^3$ is $=CR^9$—;
A compound represented by the formula (M6) wherein $A^1$ is an oxygen atom, and $A^2$ is $=CR^8$—;
A compound represented by the formula (M6) wherein $A^1$ is an oxygen atom, $A^2$ is $=CR^8$—, and $A^3$ is a nitrogen atom;
A compound represented by the formula (M6) wherein $A^1$ is an oxygen atom, $A^2$ is $=CR^8$—, and $A^3$ is $=CR^9$—;
A compound represented by the formula (M6) wherein $A^1$ is a sulfur atom, and $A^2$ is $=CR^8$—;
A compound represented by the formula (M6) wherein $A^1$ is a sulfur atom, $A^2$ is $=CR^8$—, and $A^3$ is a nitrogen atom;
A compound represented by the formula (M6) wherein $A^1$ is a sulfur atom, $A^2$ is $=CR^8$—, and $A^3$ is $=CR^9$—;
A compound represented by the formula (M6), which is represented by the formula (M6-1):

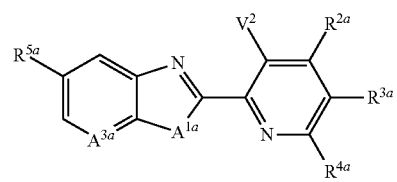

wherein $V^2$ represents a halogen atom, and the other symbols are as defined in the formula (1-1);
A compound represented by the formula (M6-1) wherein $A^{1a}$ is —$NR^{7a}$—;
A compound represented by the formula (M6-1) wherein $A^{1a}$ is an oxygen atom;
A compound represented by the formula (M6-1) wherein $A^{1a}$ is a sulfur atom;
A compound represented by the formula (M6-1) wherein $A^{1a}$ is —$NR^{7a}$—, and $A^{3a}$ is a nitrogen atom;
A compound represented by the formula (M6-1) wherein $A^{1a}$ is —$NR^{7a}$—, and $A^{3a}$ is $=CR^{9a}$— compound;
A compound represented by the formula (M6-1) wherein $A^{1a}$ is an oxygen atom, and $A^{3a}$ is a nitrogen atom;
A compound represented by the formula (M6-1) wherein $A^{1a}$ is an oxygen atom, and $A^{3a}$ is $=CR^{9a}$— compound;
A compound represented by the formula (M6-1) wherein $A^{1a}$ is a sulfur atom, and $A^{3a}$ is a nitrogen atom;
A compound represented by the formula (M6-1) wherein $A^{1a}$ is a sulfur atom, and $A^{3a}$ is $=CR^{9a}$— compound;

A compound represented by the formula (M6-1), which is represented by the formula (M6-2):

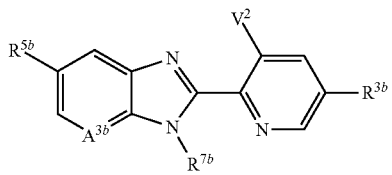

wherein $V^2$ represents a halogen atom, and the other symbols are as defined in the formula (1-2);

A compound represented by the formula (M6-2) wherein $A^{3b}$ is a nitrogen atom;

A compound represented by the formula (M6-2) wherein $A^{3b}$ is $=CR^{9b}$— compound;

A compound represented by the formula (M6-1), which is represented by the formula (M6-3):

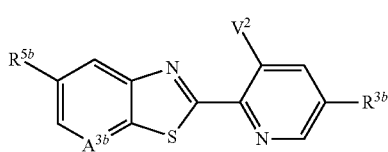

wherein $V^2$ represents a halogen atom, and the other symbols are as defined in the formula (1-2);

A compound represented by the formula (M6-3) wherein $A^{3b}$ is a nitrogen atom;

A compound represented by the formula (M6-3) wherein $A^{3b}$ is $=CR^{9b}$— compound;

A compound represented by the formula (M6-1), which is represented by the formula (M6-4):

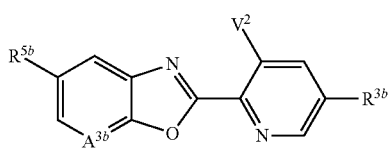

wherein $V^2$ represents a halogen atom, and the other symbols are as defined in the formula (1-2);

A compound represented by the formula (M6-4) wherein $A^{3b}$ is a nitrogen atom;

A compound represented by the formula (M6-4) wherein $A^{3b}$ is $=CR^{9b}$— compound;

Examples of the intermediate compound (M8) and a disulfide thereof (M8') include the following compounds.

A compound represented by the formula (M8) or (M8') wherein $A^1$ is $—NR^7—$;

A compound represented by the formula (M8) or (M8') wherein $A^1$ is an oxygen atom;

A compound represented by the formula (M8) or (M8') wherein $A^1$ is a sulfur atom;

A compound represented by the formula (M8) or (M8') wherein $A^2$ is $=CR^8—$;

A compound represented by the formula (M8) or (M8') wherein $A^2$ is $=CR^8—$, and $A^3$ is a nitrogen atom;

A compound represented by the formula (M8) or (M8') wherein $A^2$ is $=CR^8—$, and $A^3$ is $=CR^9—$;

A compound represented by the formula (M8) or (M8') wherein $A^1$ is $—NR^7—$, and $A^2$ is $=CR^8—$;

A compound represented by the formula (M8) or (M8') wherein $A^1$ is $—NR^7—$, $A^2$ is $=CR^8—$, and $A^3$ is a nitrogen atom;

A compound represented by the formula (M8) or (M8') wherein $A^1$ is $—NR^7—$, $A^2$ is $=CR^8—$, and $A^3$ is $=CR^9—$;

A compound represented by the formula (M8) or (M8') wherein $A^1$ is an oxygen atom, and $A^2$ is $=CR^8—$;

A compound represented by the formula (M8) or (M8') wherein $A^1$ is an oxygen atom, $A^2$ is $=CR^8—$, and $A^3$ is a nitrogen atom;

A compound represented by the formula (M8) or (M8') wherein $A^1$ is an oxygen atom, $A^2$ is $=CR^8—$, and $A^3$ is $=CR^9—$;

A compound represented by the formula (M8) or (M8') wherein $A^1$ is a sulfur atom, and $A^2$ is $=CR^8—$;

A compound represented by the formula (M8) or (M8') wherein $A^1$ is a sulfur atom, $A^2$ is $=CR^8—$, and $A^3$ is a nitrogen atom;

A compound represented by the formula (M8) or (M8') wherein $A^1$ is a sulfur atom, $A^2$ is $=CR^8—$, and $A^3$ is $=CR^9—$;

A compound represented by the formula (M8), which is represented by the formula (M8-1):

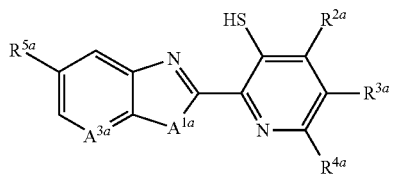

wherein the symbols are as defined in the formula (1-1), or a compound represented by the formula (M8'), which is a disulfide thereof and represented by the formula (M8'-1):

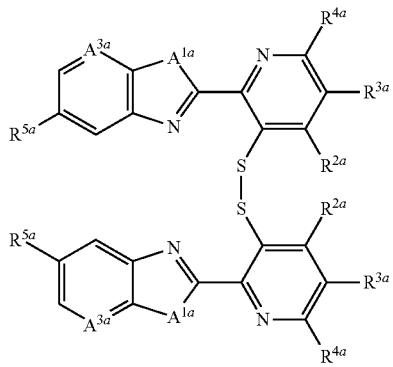

wherein the symbols are as defined in the formula (1-1);

A compound represented by the formula (M8-1) or (M8'-1) wherein $A^{1a}$ is $—NR^{7a}—$;

A compound represented by the formula (M8-1) or (M8'-1) wherein $A^{1a}$ is an oxygen atom;

A compound represented by the formula (M8-1) or (M8'-1) wherein $A^{1a}$ is a sulfur atom;

A compound represented by the formula (M8-1) or (M8'-1) wherein $A^{1a}$ is —$NR^{7a}$—, and $A^{3a}$ is a nitrogen atom;

A compound represented by the formula (M8-1) or (M8'-1) wherein $A^{1a}$ is —$NR^{7a}$—, and $A^{3a}$ is =$CR^{9a}$— compound;

A compound represented by the formula (M8-1) or (M8'-1) wherein $A^{1a}$ is an oxygen atom, and $A^{3a}$ is a nitrogen atom;

A compound represented by the formula (M8-1) or (M8'-1) wherein $A^{1a}$ is an oxygen atom, and $A^{3a}$ is =$CR^{9a}$— compound;

A compound represented by the formula (M8-1) or (M8'-1) wherein $A^{1a}$ is a sulfur atom, and $A^{3a}$ is a nitrogen atom;

A compound represented by the formula (M8-1) or (M8'-1) wherein $A^{1a}$ is a sulfur atom, and $A^{3a}$ is =$CR^{9a}$— compound;

A compound represented by the formula (M8-1), which is represented by the formula (M8-2):

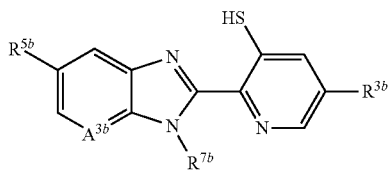

(M8-2)

wherein the symbols are as defined in the formula (1-2) or a compound represented by the formula (M8'-1), which is a disulfide thereof and represented by the formula (M8'-2):

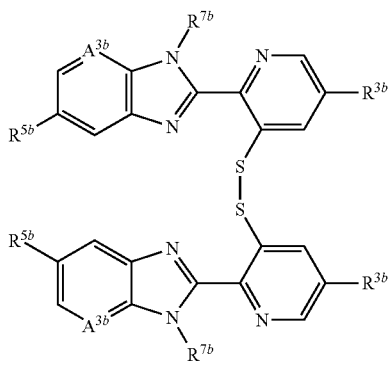

(M8'-2)

wherein the symbols are as defined in the formula (1-2);

A compound represented by the formula (M8-2) or (M8'-2) wherein $A^{3b}$ is a nitrogen atom;

A compound represented by the formula (M8-2) or (M8'-2) wherein $A^{3b}$ is =$CR^{9b}$— compound;

A compound represented by the formula (M8-1), which is represented by the formula (M8-3):

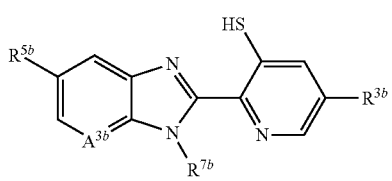

(M8-3)

wherein the symbols are as defined in the formula (1-2) or a compound represented by the formula (M8'-1), which is a disulfide thereof and represented by the formula (M8'-3):

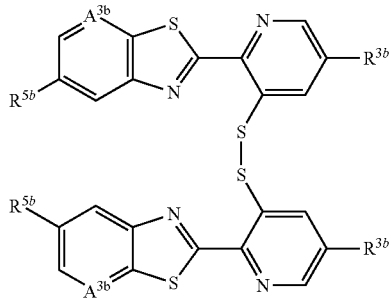

(M8'-3)

wherein the symbols are as defined in the formula (1-2).

A compound represented by the formula (M8-3) or (M8'-3) wherein $A^{3b}$ is a nitrogen atom;

A compound represented by the formula (M8-3) or (M8'-3) wherein $A^{3b}$ is =$CR^{9b}$— compound;

A compound represented by the formula (M8-1), which is represented by the formula (M8-4):

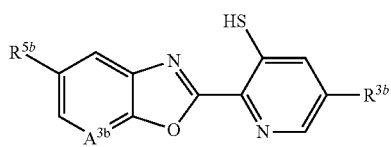

(M8-4)

wherein the symbols are as defined in the formula (1-2) or a compound represented by the formula (M8'-1), which is a disulfide thereof and represented by the formula (M8'-4):

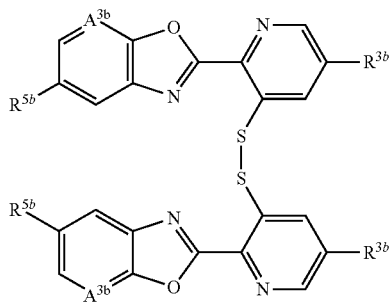

(M8'-4)

wherein the symbols are as defined in the formula (1-2).

A compound represented by the formula (M8-4) or (M8'-4) wherein $A^{3b}$ is a nitrogen atom;

A compound represented by the formula (M8-4) or (M8'-4) wherein $A^{3b}$ is =$CR^{9b}$— compound;

Examples of the intermediate compound (M20) include the following compounds.

A compound represented by the formula (M20) wherein $A^1$ is —$NR^7$—;

A compound represented by the formula (M20) wherein $A^1$ is an oxygen atom;

A compound represented by the formula (M20) wherein $A^1$ is a sulfur atom;

A compound represented by the formula (M20) wherein $A^2$ is =$CR^8$—;

A compound represented by the formula (M20) wherein $A^2$ is =$CR^8$—, and $A^3$ is a nitrogen atom;

A compound represented by the formula (M20) wherein $A^2$ is $=CR^8-$, and $A^3$ is $=CR^9-$;

A compound represented by the formula (M20) wherein $A^1$ is $-NR^7-$, and $A^2$ is $=CR^8-$;

A compound represented by the formula (M20) wherein $A^1$ is $-NR^7-$, $A^2$ is $=CR^8-$, and $A^3$ is a nitrogen atom;

A compound represented by the formula (M20) wherein $A^1$ is $-NR^7-$, $A^2$ is $=CR^8-$, and $A^3$ is $=CR^9-$;

A compound represented by the formula (M20) wherein $A^1$ is an oxygen atom, and $A^2$ is $=CR^8-$;

A compound represented by the formula (M20) wherein $A^1$ is an oxygen atom, $A^2$ is $=CR^8-$, and $A^3$ is a nitrogen atom;

A compound represented by the formula (M20) wherein $A^1$ is an oxygen atom, $A^2$ is $=CR^8-$, and $A^3$ is $=CR^9-$;

A compound represented by the formula (M20) wherein $A^1$ is a sulfur atom, and $A^2$ is $=CR^8-$;

A compound represented by the formula (M20) wherein $A^1$ is a sulfur atom, $A^2$ is $=CR^8-$, and $A^3$ is a nitrogen atom;

A compound represented by the formula (M20) wherein $A^1$ is a sulfur atom, $A^2$ is $=CR^8-$, and $A^3$ is $=CR^9-$;

A compound represented by the formula (M20) wherein $R^2$ and $R^4$ is a hydrogen atom;

A compound represented by the formula (M20), which is represented by the formula (M20-1):

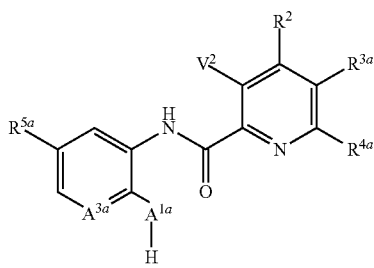

(M20-1)

wherein $V^2$ represents a halogen atom, and the other symbols are as defined in the formula (1-1);

A compound represented by the formula (M20-1) wherein $A^{1a}$ is $-NR^{7a}-$;

A compound represented by the formula (M20-1) wherein $A^{1a}$ is an oxygen atom;

A compound represented by the formula (M20-1) wherein $A^{1a}$ is a sulfur atom;

A compound represented by the formula (M20-1) wherein $A^{1a}$ is $-NR^{7a}-$, and $A^{3a}$ is a nitrogen atom;

A compound represented by the formula (M20-1) wherein $A^{1a}$ is $-NR^{7a}-$, and $A^{3a}$ is $=CR^{9a}-$ compound;

A compound represented by the formula (M20-1) wherein $A^{1a}$ is an oxygen atom, and $A^{3a}$ is a nitrogen atom;

A compound represented by the formula (M20-1) wherein $A^{1a}$ is an oxygen atom, and $A^{3a}$ is $=CR^{9a}-$ compound;

A compound represented by the formula (M20-1) wherein $A^{1a}$ is a sulfur atom, and $A^{3a}$ is a nitrogen atom;

A compound represented by the formula (M20-1) wherein $A^{1a}$ is a sulfur atom, and $A^{3a}$ is $=CR^{9a}-$ compound;

A compound represented by the formula (M20-1) wherein $R^{2a}$ and $R^{4a}$ is a hydrogen atom;

A compound represented by the formula (M20-1), which is represented by the formula (M20-2):

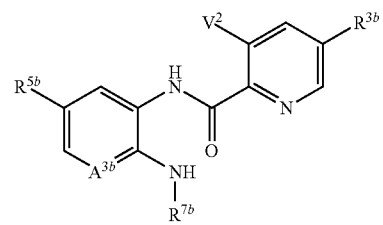

(M20-2)

wherein $V^2$ represents a halogen atom, and the other symbols are as defined in the formula (1-2);

A compound represented by the formula (M20-2) wherein $A^{3b}$ is a nitrogen atom;

A compound represented by the formula (M20-2) wherein $A^{3b}$ is $=CR^{9b}-$ compound;

A compound represented by the formula (M20-1), which is represented by the formula (M20-3):

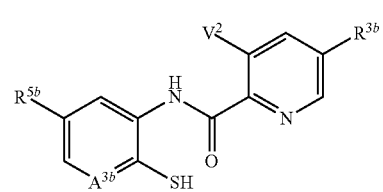

(M20-3)

wherein $V^2$ represents a halogen atom, and the other symbols are as defined in the formula (1-2);

A compound represented by the formula (M20-3) wherein $A^{3b}$ is a nitrogen atom;

A compound represented by the formula (M20-3) wherein $A^{3b}$ is $=CR^{9b}-$ compound;

A compound represented by the formula (M20-1), which is represented by the formula (M20-4):

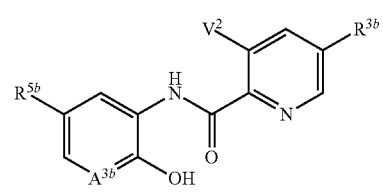

(M20-4)

wherein $V^2$ represents a halogen atom, and the other symbols are as defined in the formula (1-2);

A compound represented by the formula (M20-4) wherein $A^{3b}$ is a nitrogen atom;

A compound represented by the formula (M20-4) wherein $A^{3b}$ is $=CR^{9b}-$ compound;

As described above, the compound represented by the formula (P4) among the present compounds can be used as an intermediate in the production of the present compound. Examples of the present compound (P4) represented by the formula (1) include the following compounds.

A compound represented by the formula (P4) wherein $A^1$ is $-NR^7-$;

A compound represented by the formula (P4) wherein $A^1$ is an oxygen atom;

A compound represented by the formula (P4) wherein $A^1$ is a sulfur atom;

A compound represented by the formula (P4) wherein $A^2$ is $=CR^8—$;

A compound represented by the formula (P4) wherein $A^2$ is $=CR^8—$, and $A^3$ is a nitrogen atom;

A compound represented by the formula (P4) wherein $A^2$ is $=CR^8—$, and $A^3$ is $=CR^9—$;

A compound represented by the formula (P4) wherein $A^1$ is $—NR^7—$, and $A^2$ is $=CR^8—$;

A compound represented by the formula (P4) wherein $A^1$ is $—NR^7—$, $A^2$ is $=CR^8—$, and $A^3$ is a nitrogen atom;

A compound represented by the formula (P4) wherein $A^1$ is $—NR^7—$, $A^2$ is $=CR^8—$, and $A^3$ is $=CR^9—$;

a compound represented by the formula (P4) wherein $A^1$ is an oxygen atom, and $A^2$ is $=CR^8—$;

A compound represented by the formula (P4) wherein $A^1$ is an oxygen atom, $A^2$ is $=CR^8—$, and $A^3$ is a nitrogen atom;

A compound represented by the formula (P4) wherein $A^1$ is an oxygen atom, $A^2$ is $=CR^8—$, and $A^3$ is $=CR^9—$;

A compound represented by the formula (P4) wherein $A^1$ is a sulfur atom, and $A^2$ is $=CR^8—$;

A compound represented by the formula (P4) wherein $A^1$ is a sulfur atom, $A^2$ is $=CR^8—$, and $A^3$ is a nitrogen atom;

A compound represented by the formula (P4) wherein $A^1$ is a sulfur atom, $A^2$ is $=CR^8—$, and $A^3$ is $=CR^9—$;

A compound represented by the formula (P4), which is represented by the formula (P4-1):

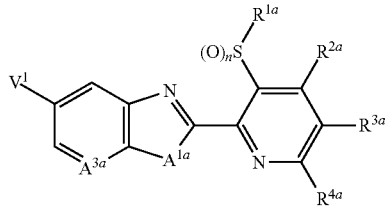

(P4-1)

wherein V represents a halogen atom, and the other symbols are as defined in the formula (1-1);

A compound represented by the formula (P4-1) wherein $A^{1a}$ is $—NR^{7a}—$;

A compound represented by the formula (P4-1) wherein $A^{1a}$ is an oxygen atom;

A compound represented by the formula (P4-1) wherein $A^{1a}$ is a sulfur atom;

A compound represented by the formula (P4-1) wherein $A^{1a}$ is $—NR^{7a}—$, and $A^{3a}$ is a nitrogen atom;

A compound represented by the formula (P4-1) wherein $A^{1a}$ is $—NR^{7a}—$, and $A^{3a}$ is $=CR^{9a}—$ compound;

A compound represented by the formula (P4-1) wherein $A^{1a}$ is an oxygen atom, and $A^{3a}$ is a nitrogen atom;

A compound represented by the formula (P4-1) wherein $A^{1a}$ is an oxygen atom, and $A^{3a}$ is $=CR^{9a}—$ compound;

A compound represented by the formula (P4-1) wherein $A^{1a}$ is a sulfur atom, and $A^{3a}$ is a nitrogen atom;

A compound represented by the formula (P4-1) wherein $A^{1a}$ is a sulfur atom, and $A^{3a}$ is $=CR^{9a}—$ compound;

A compound represented by the formula (P4-1), which is represented by the formula (P4-2):

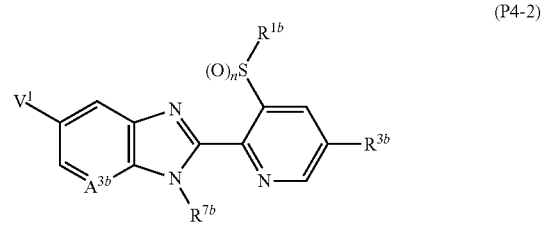

(P4-2)

wherein $V^1$ represents a halogen atom, and the other symbols are as defined in the formula (1-2);

A compound represented by the formula (P4-2) wherein $A^{3b}$ is a nitrogen atom;

A compound represented by the formula (P4-2) wherein $A^{3b}$ is $=CR^{9b}—$ compound;

A compound represented by the formula (P4-1), which is represented by the formula (P4-3):

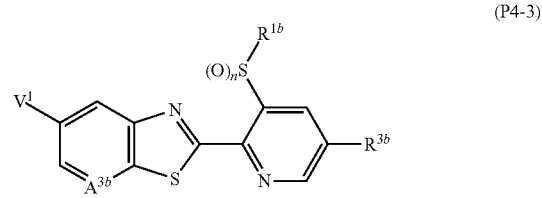

(P4-3)

wherein $V^1$ represents a halogen atom, and the other symbols are as defined in the formula (1-2);

A compound represented by the formula (P4-3) wherein $A^{3b}$ is a nitrogen atom;

A compound represented by the formula (P4-3) wherein $A^{3b}$ is $=CR^{9b}—$ compound;

A compound represented by the formula (P4-1), which is represented by the formula (P4-4):

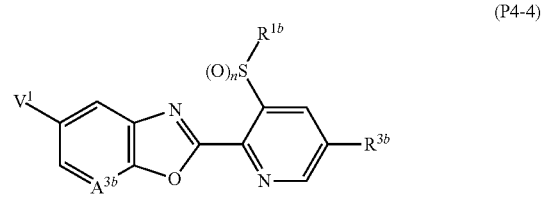

(P4-4)

wherein $V^1$ represents a halogen atom, and the other symbols are as defined in the formula (1-2);

A compound represented by the formula (P4-4) wherein $A^{3b}$ is a nitrogen atom;

A compound represented by the formula (P4-4) wherein $A^{3b}$ is $=CR^{9b}—$ compound.

As described above, the compound represented by the formula (P9) among the present compounds can be used as an intermediate in the production of the present compound. The present compound (P9) represented by the formula (1) and a disulfide thereof (P9') include the following compounds.

A compound represented by the formula (P9) or the formula (P9') wherein $A^1$ is $—NR^7—$;

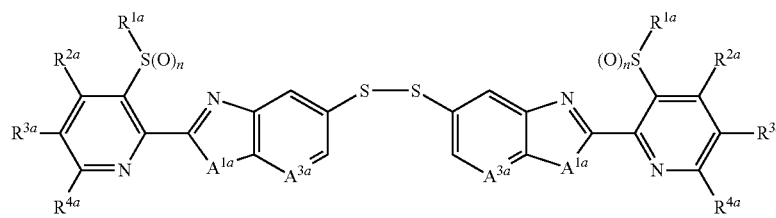

A compound represented by the formula (P9) or the formula (P9') wherein $A^1$ is an oxygen atom;
A compound represented by the formula (P9) or the formula (P9') wherein $A^1$ is a sulfur atom;
A compound represented by the formula (P9) or the formula (P9') wherein $A^2$ is $=R^8—$;
A compound represented by the formula (P9) or the formula (P9') wherein $A^2$ is $=CR^8—$, and $A^3$ is a nitrogen atom;
A compound represented by the formula (P9) or the formula (P9') wherein $A^2$ is $=CR^8—$, and $A^3$ is $=CR^8—$;
A compound represented by the formula (P9) or the formula (P9') wherein $A^1$ is $—NR^7—$, and $A^2$ is $=CR^8—$;
A compound represented by the formula (P9) or the formula (P9') wherein $A^1$ is $—NR^7—$, $A^2$ is $=CR^8—$, and $A^3$ is a nitrogen atom;
A compound represented by the formula (P9) or the formula (P9') wherein $A^1$ is $—NR^7—$, $A^2$ is $=CR^8—$, and $A^3$ is $=CR^9—$;
A compound represented by the formula (P9) or the formula (P9') wherein $A^1$ is an oxygen atom, and $A^2$ is $=CR^8—$;
A compound represented by the formula (P9) or the formula (P9') wherein $A^1$ is an oxygen atom, $A^2$ is $=CR^8—$, and $A^3$ is a nitrogen atom;
A compound represented by the formula (P9) or the formula (P9') wherein $A^1$ is an oxygen atom, $A^2$ is $=CR^8—$, and $A^3$ is $=CR^9—$;
A compound represented by the formula (P9) or the formula (P9') wherein $A^1$ is a sulfur atom, and $A^2$ is $=CR^8—$;
A compound represented by the formula (P9) or the formula (P9') wherein $A^1$ is a sulfur atom, $A^2$ is $=CR^8—$, and $A^3$ is a nitrogen atom;
A compound represented by the formula (P9) or the formula (P9') wherein $A^1$ is a sulfur atom, $A^2$ is $=CR^8—$, and $A^3$ is $=CR^9—$;
A compound represented by the formula (P9), which is represented by the formula (P9-1):

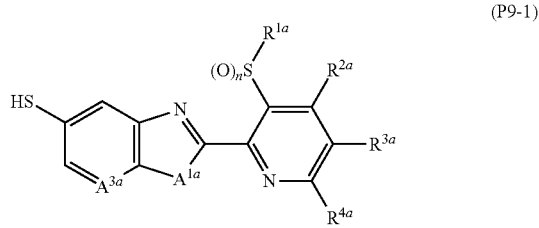

wherein the symbols are as defined in the formula (1-1), or a compound represented by the formula (M9'), which is a disulfide thereof and represented by the formula (M9'-1):

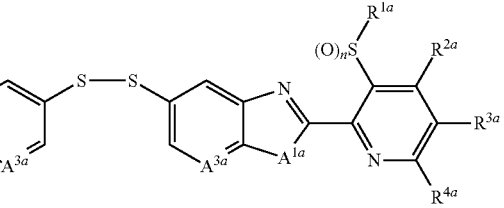

wherein the symbols are as defined in the formula (1-1);

A compound represented by the formula (P9-1) or (P9'-1) wherein $A^{1a}$ is $—NR^{7a}—$;
A compound represented by the formula (P9-1) or (P9'-1) wherein $A^{1a}$ is an oxygen atom;
A compound represented by the formula (P9-1) or (P9'-1) wherein $A^{1a}$ is a sulfur atom;
A compound represented by the formula (P9-1) or (P9'-1) wherein $A^{1a}$ is $—NR^{7a}—$ and $A^{1a}$ is a nitrogen atom;
A compound represented by the formula (P9-1) or (P9'-1) wherein $A^{1a}$ is $—NR^{7a}—$, and $A^{1a}$ is $=CR^{9a}—$ compound;
A compound represented by the formula (P9-1) or (P9'-1) wherein $A^{1a}$ is an oxygen atom, and $A^{1a}$ is a nitrogen atom;
A compound represented by the formula (P9-1) or (P9'-1) wherein $A^{1a}$ is an oxygen atom, and $A^{1a}$ is $=CR^{9a}—$ compound;
A compound represented by the formula (P9-1) or (P9'-1) wherein $A^{1a}$ is a sulfur atom, and $A^{1a}$ is a nitrogen atom;
A compound represented by the formula (P9-1) or (P9'-1) wherein $A^{1a}$ is a sulfur atom, and $A^{1a}$ is $=CR^{9a}—$ compound;
A compound represented by the formula (P9-1), which is represented by the formula (P9-2):

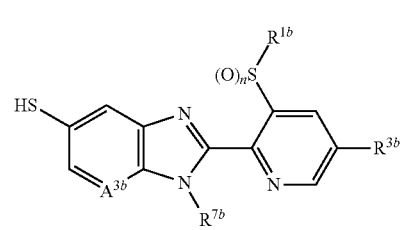

wherein the symbols are as defined in the formula (1-2), or a compound represented by the formula (M9'-1), which is a disulfide thereof and represented by the formula (M9'-2):

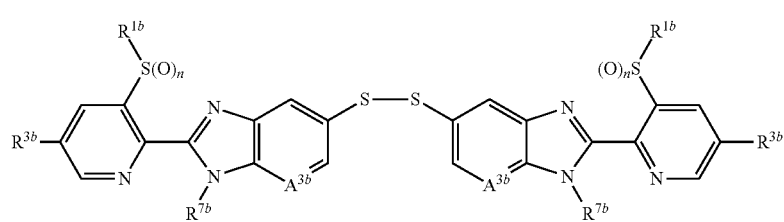

(P9'-2)

wherein, the symbols are as defined in the formula (1-2);

A compound represented by the formula (P9-2) or (P9'-2) wherein $A^{3b}$ is a nitrogen atom;

A compound represented by the formula (P9-2) or (P9'-2) wherein $A^{3b}$ is =$CR^{9b}$— compound;

A compound represented by the formula (P9-1), which is represented by the formula (P9-3):

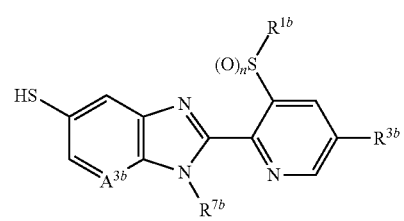

(P9-3)

wherein the symbols are as defined in the formula (1-2), or a compound represented by the formula (M9'-1), which is a disulfide thereof and represented by the formula (M9'-3):

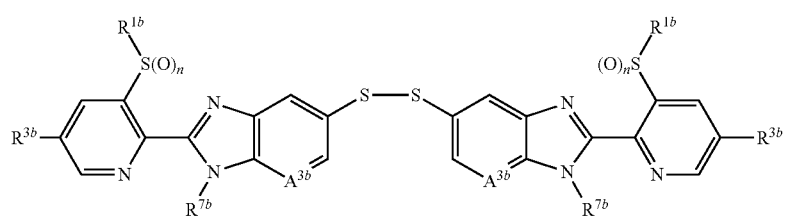

(P9'-3)

wherein the symbols are as defined in the formula (1-2);

A compound represented by the formula (P9-3) or (P9'-3) wherein $A^{3b}$ is a nitrogen atom;

A compound represented by the formula (P9-3) or (P9'-3) wherein $A^{3b}$ is =$CR^{9b}$— compound;

A compound represented by the formula (P9-1), which is represented by the formula (P9-4):

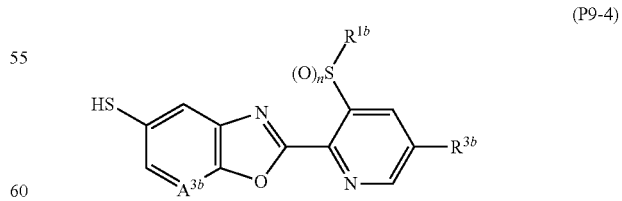

(P9-4)

wherein the symbols are as defined in the formula (1-2), or a compound represented by the formula (M9'-1), which is a disulfide thereof and represented by the formula (M9'-4):

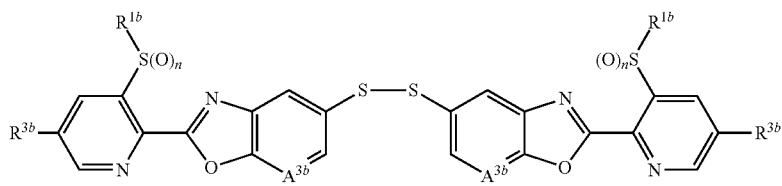

wherein the symbols are as defined in the formula (1-2);

A compound represented by the formula (P9-4) or (P9'-4) wherein $A^{3b}$ is a nitrogen atom;

A compound represented by the formula (P9-4) or (P9'-4) wherein $A^{3b}$ is $=CR^{9b}$— compound;

As described above, the compound represented by the formula (P2) among the present compounds can be used as an intermediate in the production of the present compound. The present compound (P2) represented by the formula (1) include the following compounds.

A compound represented by the formula (P2) wherein $A^2$ is $=CR^8$—;

A compound represented by the formula (P2) wherein $A^2$ is $=CR^8$—, and $A^3$ is a nitrogen atom;

A compound represented by the formula (P2) wherein $A^2$ is $=CR^8$—, and $A^3$ is $=CR^9$—;

A compound represented by the formula (P2), which is represented by the formula (P2-1):

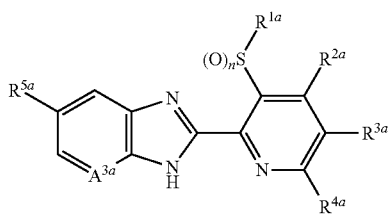

wherein the symbols are as defined in the formula (1-1);

A compound represented by the formula (P2-1) wherein $A^{3a}$ is a nitrogen atom;

A compound represented by the formula (P2-1) wherein $A^{3a}$ is $=CR^{9a}$— compound;

A compound represented by the formula (P2-1), which is represented by the formula (P2-2):

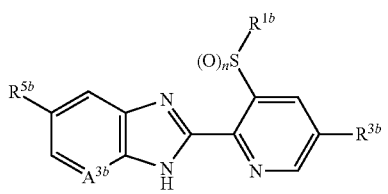

wherein the symbols are as defined in the formula (1-2);

A compound represented by the formula (P2-2) wherein $A^{3a}$ is a nitrogen atom;

A compound represented by the formula (P2-2) wherein $A^{3a}$ is $=CR^{9a}$— compound;

Examples of the intermediate compound (M2) include the following compounds.

A compound represented by the formula (M2), which is represented by the formula (M2-1):

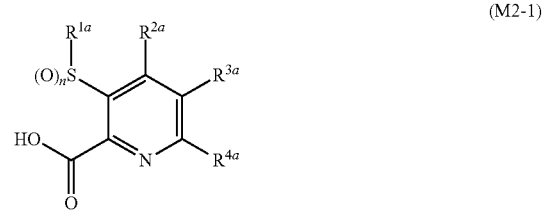

wherein the symbols are as defined in the formula (1-1);

A compound represented by the formula (M2-1) wherein $R^{1a}$ is an ethyl group or a cyclopropylmethyl group, n is 1 or 2;

A compound represented by the formula (M2-1) wherein $R^{1a}$ is an ethyl group or a cyclopropylmethyl group, $R^{3a}$ is a trifluoromethyl group;

A compound represented by the formula (M2-1), which is represented by the formula (M2-2):

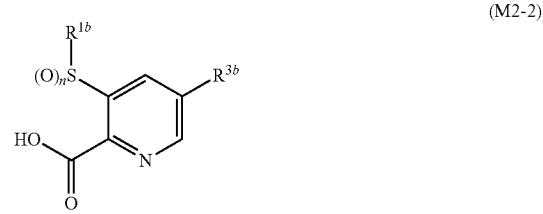

wherein the symbols are as defined in the formula (1-2);

A compound represented by the formula (M2-2) wherein $R^{1b}$ is an ethyl group or a cyclopropylmethyl group, n is 1 or 2;

A compound represented by the formula (M2-2) wherein $R^{1b}$ is an ethyl group or a cyclopropylmethyl group, $R^{3b}$ is a trifluoromethyl group;

Examples of the intermediate compound (M18) include the following compounds.

A compound represented by the formula (M18), which is represented by the formula (M18-1):

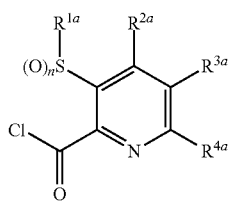

wherein the symbols are as defined in the formula (1-1);

A compound represented by the formula (M18-1) wherein $R^{1a}$ is an ethyl group or a cyclopropylmethyl group;

A compound represented by the formula (M18-1), which is represented by the formula (M18-2):

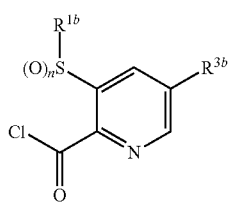

wherein the symbols are as defined in the formula (1-2);

A compound represented by the formula (M18-2) wherein $R^{1b}$ is an ethyl group or a cyclopropylmethyl group, $R^{3b}$ is a hydrogen atom;

A compound represented by the formula (M18-2) wherein $R^{1b}$ is an ethyl group or a cyclopropylmethyl group, $R^{3b}$ is a trifluoromethyl group;

Examples of the intermediate compound (M4) include the following compounds.

A compound represented by the formula (M4), which is represented by the formula (M4-1):

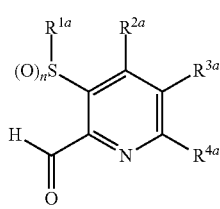

wherein the symbols are as defined in the formula (1-1);

A compound represented by the formula (M4-1) wherein $R^{1a}$ is an ethyl group or a cyclopropylmethyl group, $R^{3a}$ is a hydrogen atom;

A compound represented by the formula (M4-1) wherein $R^{1a}$ is an ethyl group or a cyclopropylmethyl group, $R^{3a}$ is a trifluoromethyl group;

A compound represented by the formula (M4-1), which is represented by the formula (M4-2):

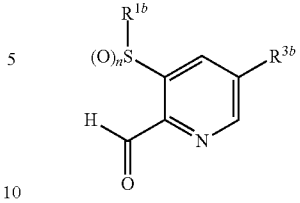

wherein the symbols are as defined in the formula (1-2);

A compound represented by the formula (M4-2) wherein $R^{1b}$ is an ethyl group or a cyclopropylmethyl group, $R^{3b}$ is a hydrogen atom;

A compound represented by the formula (M4-2) wherein $R^{1b}$ is an ethyl group or a cyclopropylmethyl group, $R^{3b}$ is a trifluoromethyl group;

Examples of the intermediate compound (M37) include the following compounds.

A compound represented by the formula (M37), which is represented by the formula (M37-1):

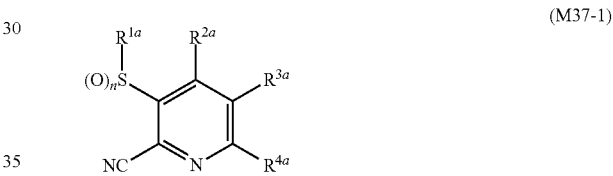

wherein the symbols are as defined in the formula (1-1);

A compound represented by the formula (M37-1) wherein $R^{1a}$ is an ethyl group or a cyclopropylmethyl group, n is 1 or 2;

A compound represented by the formula (M37-1) wherein $R^{1a}$ is an ethyl group or a cyclopropylmethyl group, $R^{3a}$ is a trifluoromethyl group;

A compound represented by the formula (M37-1), which is represented by the formula (M37-2):

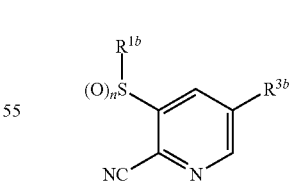

wherein the symbols are as defined in the formula (1-2);

A compound represented by the formula (M37-2) wherein $R^{1b}$ is an ethyl group or a cyclopropylmethyl group, n is 1 or 2;

A compound represented by the formula (M37-2) wherein $R^{1b}$ is an ethyl group or a cyclopropylmethyl group, $R^{3b}$ is a trifluoromethyl group.

Next, specific examples of the present compound are described below.

The present compound is represented by the formula (A):

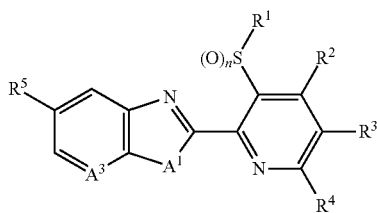

(A)

wherein $R^2$, $R^3$ and $R^4$ are independently a hydrogen atom, $R^5$ is a trifluoromethyl group, $R^1$, $A^1$, $A^3$ and n represent any one of the combinations as listed in [Table 1] to [Table 35].

TABLE 1

| $R^1$ | $A^1$ | $A^3$ | n |
|---|---|---|---|
| Me | NMe | N | 0 |
| Me | NMe | N | 1 |
| Me | NMe | N | 2 |
| Et | NMe | N | 0 |
| Et | NMe | N | 1 |
| Et | NMe | N | 2 |
| Pr | NMe | N | 0 |
| Pr | NMe | N | 1 |
| Pr | NMe | N | 2 |
| iPr | NMe | N | 0 |
| iPr | NMe | N | 1 |
| iPr | NMe | N | 2 |
| tBu | NMe | N | 0 |
| tBu | NMe | N | 1 |
| tBu | NMe | N | 2 |
| $CF_3$ | NMe | N | 0 |
| $CF_3$ | NMe | N | 1 |
| $CF_3$ | NMe | N | 2 |
| $CH_2CF_3$ | NMe | N | 0 |
| $CH_2CF_3$ | NMe | N | 1 |
| $CH_2CF_3$ | NMe | N | 2 |
| $CH=CH_2$ | NMe | N | 0 |
| $CH=CH_2$ | NMe | N | 1 |
| $CH=CH_2$ | NMe | N | 2 |

TABLE 2

| $R^1$ | $A^1$ | $A^3$ | n |
|---|---|---|---|
| $CH_2CH=CH_2$ | NMe | N | 0 |
| $CH_2CH=CH_2$ | NMe | N | 1 |
| $CH_2CH=CH_2$ | NMe | N | 2 |
| $C\equiv CH$ | NMe | N | 0 |
| $C\equiv CH$ | NMe | N | 1 |
| $C\equiv CH$ | NMe | N | 2 |
| $CH_2C\equiv CH$ | NMe | N | 0 |
| $CH_2C\equiv CH$ | NMe | N | 1 |
| $CH_2C\equiv CH$ | NMe | N | 2 |
| CycPr | NMe | N | 0 |
| CycPr | NMe | N | 1 |
| CycPr | NMe | N | 2 |
| $CH_2CycPr$ | NMe | N | 0 |
| $CH_2CycPr$ | NMe | N | 1 |
| $CH_2CycPr$ | NMe | N | 2 |
| Me | NMe | CH | 0 |
| Me | NMe | CH | 1 |
| Me | NMe | CH | 2 |
| Et | NMe | CH | 0 |
| Et | NMe | CH | 1 |
| Et | NMe | CH | 2 |
| Pr | NMe | CH | 0 |

TABLE 2-continued

| $R^1$ | $A^1$ | $A^3$ | n |
|---|---|---|---|
| Pr | NMe | CH | 1 |
| Pr | NMe | CH | 2 |

TABLE 3

| $R^1$ | $A^1$ | $A^3$ | n |
|---|---|---|---|
| iPr | NMe | CH | 0 |
| iPr | NMe | CH | 1 |
| iPr | NMe | CH | 2 |
| tBu | NMe | CH | 0 |
| tBu | NMe | CH | 1 |
| tBu | NMe | CH | 2 |
| $CF_3$ | NMe | CH | 0 |
| $CF_3$ | NMe | CH | 1 |
| $CF_3$ | NMe | CH | 2 |
| $CH_2CF_3$ | NMe | CH | 0 |
| $CH_2CF_3$ | NMe | CH | 1 |
| $CH_2CF_3$ | NMe | CH | 2 |
| $CH=CH_2$ | NMe | CH | 0 |
| $CH=CH_2$ | NMe | CH | 1 |
| $CH=CH_2$ | NMe | CH | 2 |
| $CH_2CH=CH_2$ | NMe | CH | 0 |
| $CH_2CH=CH_2$ | NMe | CH | 1 |
| $CH_2CH=CH_2$ | NMe | CH | 2 |
| $C\equiv CH$ | NMe | CH | 0 |
| $C\equiv CH$ | NMe | CH | 1 |
| $C\equiv CH$ | NMe | CH | 2 |
| $CH_2C\equiv CH$ | NMe | CH | 0 |
| $CH_2C\equiv CH$ | NMe | CH | 1 |
| $CH_2C\equiv CH$ | NMe | CH | 2 |

TABLE 4

| $R^1$ | $A^1$ | $A^3$ | n |
|---|---|---|---|
| CycPr | NMe | CH | 0 |
| CycPr | NMe | CH | 1 |
| CycPr | NMe | CH | 2 |
| $CH_2CycPr$ | NMe | CH | 0 |
| $CH_2CycPr$ | NMe | CH | 1 |
| $CH_2CycPr$ | NMe | CH | 2 |
| Me | NMe | CBr | 0 |
| Me | NMe | CBr | 1 |
| Me | NMe | CBr | 2 |
| Et | NMe | CBr | 0 |
| Et | NMe | CBr | 1 |
| Et | NMe | CBr | 2 |
| Pr | NMe | CBr | 0 |
| Pr | NMe | CBr | 1 |
| Pr | NMe | CBr | 2 |
| iPr | NMe | CBr | 0 |
| iPr | NMe | CBr | 1 |
| iPr | NMe | CBr | 2 |
| tBu | NMe | CBr | 0 |
| tBu | NMe | CBr | 1 |
| tBu | NMe | CBr | 2 |
| $CF_3$ | NMe | CBr | 0 |
| $CF_3$ | NMe | CBr | 1 |
| $CF_3$ | NMe | CBr | 2 |

TABLE 5

| $R^1$ | $A^1$ | $A^3$ | n |
|---|---|---|---|
| $CH_2CF_3$ | NMe | CBr | 0 |
| $CH_2CF_3$ | NMe | CBr | 1 |
| $CH_2CF_3$ | NMe | CBr | 2 |
| $CH=CH_2$ | NMe | CBr | 0 |
| $CH=CH_2$ | NMe | CBr | 1 |
| $CH=CH_2$ | NMe | CBr | 2 |

TABLE 5-continued

| R¹ | A¹ | A³ | n |
|---|---|---|---|
| CH$_2$CH=CH$_2$ | NMe | CBr | 0 |
| CH$_2$CH=CH$_2$ | NMe | CBr | 1 |
| CH$_2$CH=CH$_2$ | NMe | CBr | 2 |
| C≡CH | NMe | CBr | 0 |
| C≡CH | NMe | CBr | 1 |
| C≡CH | NMe | CBr | 2 |
| CH$_2$C≡CH | NMe | CBr | 0 |
| CH$_2$C≡CH | NMe | CBr | 1 |
| CH$_2$C≡CH | NMe | CBr | 2 |
| CycPr | NMe | CBr | 0 |
| CycPr | NMe | CBr | 1 |
| CycPr | NMe | CBr | 2 |
| CH$_2$CycPr | NMe | CBr | 0 |
| CH$_2$CycPr | NMe | CBr | 1 |
| CH$_2$CycPr | NMe | CBr | 2 |

TABLE 6

| R¹ | A¹ | A³ | n |
|---|---|---|---|
| Me | NH | N | 0 |
| Me | NH | N | 1 |
| Me | NH | N | 2 |
| Et | NH | N | 0 |
| Et | NH | N | 1 |
| Et | NH | N | 2 |
| Pr | NH | N | 0 |
| Pr | NH | N | 1 |
| Pr | NH | N | 2 |
| iPr | NH | N | 0 |
| iPr | NH | N | 1 |
| iPr | NH | N | 2 |
| tBu | NH | N | 0 |
| tBu | NH | N | 1 |
| tBu | NH | N | 2 |
| CF$_3$ | NH | N | 0 |
| CF$_3$ | NH | N | 1 |
| CF$_3$ | NH | N | 2 |
| CH$_2$CF$_3$ | NH | N | 0 |
| CH$_2$CF$_3$ | NH | N | 1 |
| CH$_2$CF$_3$ | NH | N | 2 |
| CH=CH$_2$ | NH | N | 0 |
| CH=CH$_2$ | NH | N | 1 |
| CH=CH$_2$ | NH | N | 2 |

TABLE 7

| R¹ | A¹ | A³ | n |
|---|---|---|---|
| CH$_2$CH=CH$_2$ | NH | N | 0 |
| CH$_2$CH=CH$_2$ | NH | N | 1 |
| CH$_2$CH=CH$_2$ | NH | N | 2 |
| C≡CH | NH | N | 0 |
| C≡CH | NH | N | 1 |
| C≡CH | NH | N | 2 |
| CH$_2$C≡CH | NH | N | 0 |
| CH$_2$C≡CH | NH | N | 1 |
| CH$_2$C≡CH | NH | N | 2 |
| CycPr | NH | N | 0 |
| CycPr | NH | N | 1 |
| CycPr | NH | N | 2 |
| CH$_2$CycPr | NH | N | 0 |
| CH$_2$CycPr | NH | N | 1 |
| CH$_2$CycPr | NH | N | 2 |
| Me | NH | CH | 0 |
| Me | NH | CH | 1 |
| Me | NH | CH | 2 |
| Et | NH | CH | 0 |
| Et | NH | CH | 1 |
| Et | NH | CH | 2 |
| Pr | NH | CH | 0 |

TABLE 7-continued

| R¹ | A¹ | A³ | n |
|---|---|---|---|
| Pr | NH | CH | 1 |
| Pr | NH | CH | 2 |

TABLE 8

| R¹ | A¹ | A³ | n |
|---|---|---|---|
| iPr | NH | CH | 0 |
| iPr | NH | CH | 1 |
| iPr | NH | CH | 2 |
| tBu | NH | CH | 0 |
| tBu | NH | CH | 1 |
| tBu | NH | CH | 2 |
| CF$_3$ | NH | CH | 0 |
| CF$_3$ | NH | CH | 1 |
| CF$_3$ | NH | CH | 2 |
| CH$_2$CF$_3$ | NH | CH | 0 |
| CH$_2$CF$_3$ | NH | CH | 1 |
| CH$_2$CF$_3$ | NH | CH | 2 |
| CH=CH$_2$ | NH | CH | 0 |
| CH=CH$_2$ | NH | CH | 1 |
| CH=CH$_2$ | NH | CH | 2 |
| CH$_2$CH=CH$_2$ | NH | CH | 0 |
| CH$_2$CH=CH$_2$ | NH | CH | 1 |
| CH$_2$CH=CH$_2$ | NH | CH | 2 |
| C≡CH | NH | CH | 0 |
| C≡CH | NH | CH | 1 |
| C≡CH | NH | CH | 2 |
| CH$_2$C≡CH | NH | CH | 0 |
| CH$_2$C≡CH | NH | CH | 1 |
| CH$_2$C≡CH | NH | CH | 2 |

TABLE 9

| R¹ | A¹ | A³ | n |
|---|---|---|---|
| CycPr | NH | CH | 0 |
| CycPr | NH | CH | 1 |
| CycPr | NH | CH | 2 |
| CH$_2$CycPr | NH | CH | 0 |
| CH$_2$CycPr | NH | CH | 1 |
| CH$_2$CycPr | NH | CH | 2 |
| Me | NH | CBr | 0 |
| Me | NH | CBr | 1 |
| Me | NH | CBr | 2 |
| Et | NH | CBr | 0 |
| Et | NH | CBr | 1 |
| Et | NH | CBr | 2 |
| Pr | NH | CBr | 0 |
| Pr | NH | CBr | 1 |
| Pr | NH | CBr | 2 |
| iPr | NH | CBr | 0 |
| iPr | NH | CBr | 1 |
| iPr | NH | CBr | 2 |
| tBu | NH | CBr | 0 |
| tBu | NH | CBr | 1 |
| tBu | NH | CBr | 2 |
| CF$_3$ | NH | CBr | 0 |
| CF$_3$ | NH | CBr | 1 |
| CF$_3$ | NH | CBr | 2 |

TABLE 10

| R¹ | A¹ | A³ | n |
|---|---|---|---|
| CH$_2$CF$_3$ | NH | CBr | 0 |
| CH$_2$CF$_3$ | NH | CBr | 1 |
| CH$_2$CF$_3$ | NH | CBr | 2 |
| CH=CH$_2$ | NH | CBr | 0 |
| CH=CH$_2$ | NH | CBr | 1 |
| CH=CH$_2$ | NH | CBr | 2 |

TABLE 10-continued

| R¹ | A¹ | A³ | n |
|---|---|---|---|
| CH₂CH=CH₂ | NH | CBr | 0 |
| CH₂CH=CH₂ | NH | CBr | 1 |
| CH₂CH=CH₂ | NH | CBr | 2 |
| C≡CH | NH | CBr | 0 |
| C≡CH | NH | CBr | 1 |
| C≡CH | NH | CBr | 2 |
| CH₂C≡CH | NH | CBr | 0 |
| CH₂C≡CH | NH | CBr | 1 |
| CH₂C≡CH | NH | CBr | 2 |
| CycPr | NH | CBr | 0 |
| CycPr | NH | CBr | 1 |
| CycPr | NH | CBr | 2 |
| CH₂CycPr | NH | CBr | 0 |
| CH₂CycPr | NH | CBr | 1 |
| CH₂CycPr | NH | CBr | 2 |

TABLE 11

| R¹ | A¹ | A³ | n |
|---|---|---|---|
| Me | N(CH₂OMe) | N | 0 |
| Me | N(CH₂OMe) | N | 1 |
| Me | N(CH₂OMe) | N | 2 |
| Et | N(CH₂OMe) | N | 0 |
| Et | N(CH₂OMe) | N | 1 |
| Et | N(CH₂OMe) | N | 2 |
| Pr | N(CH₂OMe) | N | 0 |
| Pr | N(CH₂OMe) | N | 1 |
| Pr | N(CH₂OMe) | N | 2 |
| iPr | N(CH₂OMe) | N | 0 |
| iPr | N(CH₂OMe) | N | 1 |
| iPr | N(CH₂OMe) | N | 2 |
| tBu | N(CH₂OMe) | N | 0 |
| tBu | N(CH₂OMe) | N | 1 |
| tBu | N(CH₂OMe) | N | 2 |
| CF₃ | N(CH₂OMe) | N | 0 |
| CF₃ | N(CH₂OMe) | N | 1 |
| CF₃ | N(CH₂OMe) | N | 2 |
| CH₂CF₃ | N(CH₂OMe) | N | 0 |
| CH₂CF₃ | N(CH₂OMe) | N | 1 |
| CH₂CF₃ | N(CH₂OMe) | N | 2 |
| CH=CH₂ | N(CH₂OMe) | N | 0 |
| CH=CH₂ | N(CH₂OMe) | N | 1 |
| CH=CH₂ | N(CH₂OMe) | N | 2 |

TABLE 12

| R¹ | A¹ | A³ | n |
|---|---|---|---|
| CH₂CH=CH₂ | N(CH₂OMe) | N | 0 |
| CH₂CH=CH₂ | N(CH₂OMe) | N | 1 |
| CH₂CH=CH₂ | N(CH₂OMe) | N | 2 |
| C≡CH | N(CH₂OMe) | N | 0 |
| C≡CH | N(CH₂OMe) | N | 1 |
| C≡CH | N(CH₂OMe) | N | 2 |
| CH₂C≡CH | N(CH₂OMe) | N | 0 |
| CH₂C≡CH | N(CH₂OMe) | N | 1 |
| CH₂C≡CH | N(CH₂OMe) | N | 2 |
| CycPr | N(CH₂OMe) | N | 0 |
| CycPr | N(CH₂OMe) | N | 1 |
| CycPr | N(CH₂OMe) | N | 2 |
| CH₂CycPr | N(CH₂OMe) | N | 0 |
| CH₂CycPr | N(CH₂OMe) | N | 1 |
| CH₂CycPr | N(CH₂OMe) | N | 2 |
| Me | N(CH₂OMe) | CH | 0 |
| Me | N(CH₂OMe) | CH | 1 |
| Me | N(CH₂OMe) | CH | 2 |
| Et | N(CH₂OMe) | CH | 0 |
| Et | N(CH₂OMe) | CH | 1 |
| Et | N(CH₂OMe) | CH | 2 |
| Pr | N(CH₂OMe) | CH | 0 |
| Pr | N(CH₂OMe) | CH | 1 |
| Pr | N(CH₂OMe) | CH | 2 |

TABLE 13

| R¹ | A¹ | A³ | n |
|---|---|---|---|
| iPr | N(CH₂OMe) | CH | 0 |
| iPr | N(CH₂OMe) | CH | 1 |
| iPr | N(CH₂OMe) | CH | 2 |
| tBu | N(CH₂OMe) | CH | 0 |
| tBu | N(CH₂OMe) | CH | 1 |
| tBu | N(CH₂OMe) | CH | 2 |
| CF₃ | N(CH₂OMe) | CH | 0 |
| CF₃ | N(CH₂OMe) | CH | 1 |
| CF₃ | N(CH₂OMe) | CH | 2 |
| CH₂CF₃ | N(CH₂OMe) | CH | 0 |
| CH₂CF₃ | N(CH₂OMe) | CH | 1 |
| CH₂CF₃ | N(CH₂OMe) | CH | 2 |
| CH=CH₂ | N(CH₂OMe) | CH | 0 |
| CH=CH₂ | N(CH₂OMe) | CH | 1 |
| CH=CH₂ | N(CH₂OMe) | CH | 2 |
| CH₂CH=CH₂ | N(CH₂OMe) | CH | 0 |
| CH₂CH=CH₂ | N(CH₂OMe) | CH | 1 |
| CH₂CH=CH₂ | N(CH₂OMe) | CH | 2 |
| C≡CH | N(CH₂OMe) | CH | 0 |
| C≡CH | N(CH₂OMe) | CH | 1 |
| C≡CH | N(CH₂OMe) | CH | 2 |
| CH₂C≡CH | N(CH₂OMe) | CH | 0 |
| CH₂C≡CH | N(CH₂OMe) | CH | 1 |
| CH₂C≡CH | N(CH₂OMe) | CH | 2 |

TABLE 14

| R¹ | A¹ | A³ | n |
|---|---|---|---|
| CycPr | N(CH₂OMe) | CH | 0 |
| CycPr | N(CH₂OMe) | CH | 1 |
| CycPr | N(CH₂OMe) | CH | 2 |
| CH₂CycPr | N(CH₂OMe) | CH | 0 |
| CH₂CycPr | N(CH₂OMe) | CH | 1 |
| CH₂CycPr | N(CH₂OMe) | CH | 2 |
| Me | N(CH₂OMe) | CBr | 0 |
| Me | N(CH₂OMe) | CBr | 1 |
| Me | N(CH₂OMe) | CBr | 2 |
| Et | N(CH₂OMe) | CBr | 0 |
| Et | N(CH₂OMe) | CBr | 1 |
| Et | N(CH₂OMe) | CBr | 2 |
| Pr | N(CH₂OMe) | CBr | 0 |
| Pr | N(CH₂OMe) | CBr | 1 |
| Pr | N(CH₂OMe) | CBr | 2 |
| iPr | N(CH₂OMe) | CBr | 0 |
| iPr | N(CH₂OMe) | CBr | 1 |
| iPr | N(CH₂OMe) | CBr | 2 |
| tBu | N(CH₂OMe) | CBr | 0 |
| tBu | N(CH₂OMe) | CBr | 1 |
| tBu | N(CH₂OMe) | CBr | 2 |
| CF₃ | N(CH₂OMe) | CBr | 0 |
| CF₃ | N(CH₂OMe) | CBr | 1 |
| CF₃ | N(CH₂OMe) | CBr | 2 |

TABLE 15

| R¹ | A¹ | A³ | n |
|---|---|---|---|
| CH₂CF₃ | N(CH₂OMe) | CBr | 0 |
| CH₂CF₃ | N(CH₂OMe) | CBr | 1 |
| CH₂CF₃ | N(CH₂OMe) | CBr | 2 |
| CH=CH₂ | N(CH₂OMe) | CBr | 0 |
| CH=CH₂ | N(CH₂OMe) | CBr | 1 |
| CH=CH₂ | N(CH₂OMe) | CBr | 2 |

TABLE 15-continued

| R¹ | A¹ | A³ | n |
|---|---|---|---|
| CH₂CH=CH₂ | N(CH₂OMe) | CBr | 0 |
| CH₂CH=CH₂ | N(CH₂OMe) | CBr | 1 |
| CH₂CH=CH₂ | N(CH₂OMe) | CBr | 2 |
| C≡CH | N(CH₂OMe) | CBr | 0 |
| C≡CH | N(CH₂OMe) | CBr | 1 |
| C≡CH | N(CH₂OMe) | CBr | 2 |
| CH₂C≡CH | N(CH₂OMe) | CBr | 0 |
| CH₂C≡CH | N(CH₂OMe) | CBr | 1 |
| CH₂C≡CH | N(CH₂OMe) | CBr | 2 |
| CycPr | N(CH₂OMe) | CBr | 0 |
| CycPr | N(CH₂OMe) | CBr | 1 |
| CycPr | N(CH₂OMe) | CBr | 2 |
| CH₂CycPr | N(CH₂OMe) | CBr | 0 |
| CH₂CycPr | N(CH₂OMe) | CBr | 1 |
| CH₂CycPr | N(CH₂OMe) | CBr | 2 |

TABLE 16

| R¹ | A¹ | A³ | n |
|---|---|---|---|
| Me | N(CH₂OEt) | N | 0 |
| Me | N(CH₂OEt) | N | 1 |
| Me | N(CH₂OEt) | N | 2 |
| Et | N(CH₂OEt) | N | 0 |
| Et | N(CH₂OEt) | N | 1 |
| Et | N(CH₂OEt) | N | 2 |
| Pr | N(CH₂OEt) | N | 0 |
| Pr | N(CH₂OEt) | N | 1 |
| Pr | N(CH₂OEt) | N | 2 |
| iPr | N(CH₂OEt) | N | 0 |
| iPr | N(CH₂OEt) | N | 1 |
| iPr | N(CH₂OEt) | N | 2 |
| tBu | N(CH₂OEt) | N | 0 |
| tBu | N(CH₂OEt) | N | 1 |
| tBu | N(CH₂OEt) | N | 2 |
| CF₃ | N(CH₂OEt) | N | 0 |
| CF₃ | N(CH₂OEt) | N | 1 |
| CF₃ | N(CH₂OEt) | N | 2 |
| CH₂CF₃ | N(CH₂OEt) | N | 0 |
| CH₂CF₃ | N(CH₂OEt) | N | 1 |
| CH₂CF₃ | N(CH₂OEt) | N | 2 |
| CH=CH₂ | N(CH₂OEt) | N | 0 |
| CH=CH₂ | N(CH₂OEt) | N | 1 |
| CH=CH₂ | N(CH₂OEt) | N | 2 |

TABLE 17

| R¹ | A¹ | A³ | n |
|---|---|---|---|
| CH₂CH=CH₂ | N(CH₂OEt) | N | 0 |
| CH₂CH=CH₂ | N(CH₂OEt) | N | 1 |
| CH₂CH=CH₂ | N(CH₂OEt) | N | 2 |
| C≡CH | N(CH₂OEt) | N | 0 |
| C≡CH | N(CH₂OEt) | N | 1 |
| C≡CH | N(CH₂OEt) | N | 2 |
| CH₂C≡CH | N(CH₂OEt) | N | 0 |
| CH₂C≡CH | N(CH₂OEt) | N | 1 |
| CH₂C≡CH | N(CH₂OEt) | N | 2 |
| CycPr | N(CH₂OEt) | N | 0 |
| CycPr | N(CH₂OEt) | N | 1 |
| CycPr | N(CH₂OEt) | N | 2 |
| CH₂CycPr | N(CH₂OEt) | N | 0 |
| CH₂CycPr | N(CH₂OEt) | N | 1 |
| CH₂CycPr | N(CH₂OEt) | N | 2 |
| Me | N(CH₂OEt) | CH | 0 |
| Me | N(CH₂OEt) | CH | 1 |
| Me | N(CH₂OEt) | CH | 2 |
| Et | N(CH₂OEt) | CH | 0 |
| Et | N(CH₂OEt) | CH | 1 |
| Et | N(CH₂OEt) | CH | 2 |
| Pr | N(CH₂OEt) | CH | 0 |

TABLE 17-continued

| R¹ | A¹ | A³ | n |
|---|---|---|---|
| Pr | N(CH₂OEt) | CH | 1 |
| Pr | N(CH₂OEt) | CH | 2 |

TABLE 18

| R¹ | A¹ | A³ | n |
|---|---|---|---|
| iPr | N(CH₂OEt) | CH | 0 |
| iPr | N(CH₂OEt) | CH | 1 |
| iPr | N(CH₂OEt) | CH | 2 |
| tBu | N(CH₂OEt) | CH | 0 |
| tBu | N(CH₂OEt) | CH | 1 |
| tBu | N(CH₂OEt) | CH | 2 |
| CF₃ | N(CH₂OEt) | CH | 0 |
| CF₃ | N(CH₂OEt) | CH | 1 |
| CF₃ | N(CH₂OEt) | CH | 2 |
| CH₂CF₃ | N(CH₂OEt) | CH | 0 |
| CH₂CF₃ | N(CH₂OEt) | CH | 1 |
| CH₂CF₃ | N(CH₂OEt) | CH | 2 |
| CH=CH₂ | N(CH₂OEt) | CH | 0 |
| CH=CH₂ | N(CH₂OEt) | CH | 1 |
| CH=CH₂ | N(CH₂OEt) | CH | 2 |
| CH₂CH=CH₂ | N(CH₂OEt) | CH | 0 |
| CH₂CH=CH₂ | N(CH₂OEt) | CH | 1 |
| CH₂CH=CH₂ | N(CH₂OEt) | CH | 2 |
| C≡CH | N (CH₂OEt) | CH | 0 |
| C≡CH | N (CH₂OEt) | CH | 1 |
| C≡CH | N (CH₂OEt) | CH | 2 |
| CH₂C≡CH | N (CH₂OEt) | CH | 0 |
| CH₂C≡CH | N (CH₂OEt) | CH | 1 |
| CH₂C≡CH | N (CH₂OEt) | CH | 2 |

TABLE 19

| R¹ | A¹ | A³ | n |
|---|---|---|---|
| CycPr | N (CH₂OEt) | CH | 0 |
| CycPr | N (CH₂OEt) | CH | 1 |
| CycPr | N (CH₂OEt) | CH | 2 |
| CH₂CycPr | N (CH₂OEt) | CH | 0 |
| CH₂CycPr | N (CH₂OEt) | CH | 1 |
| CH₂CycPr | N (CH₂OEt) | CH | 2 |
| Me | N (CH₂OEt) | CBr | 0 |
| Me | N (CH₂OEt) | CBr | 1 |
| Me | N (CH₂OEt) | CBr | 2 |
| Et | N (CH₂OEt) | CBr | 0 |
| Et | N (CH₂OEt) | CBr | 1 |
| Et | N (CH₂OEt) | CBr | 2 |
| Pr | N (CH₂OEt) | CBr | 0 |
| Pr | N (CH₂OEt) | CBr | 1 |
| Pr | N (CH₂OEt) | CBr | 2 |
| iPr | N (CH₂OEt) | CBr | 0 |
| iPr | N (CH₂OEt) | CBr | 1 |
| iPr | N (CH₂OEt) | CBr | 2 |
| tBu | N (CH₂OEt) | CBr | 0 |
| tBu | N (CH₂OEt) | CBr | 1 |
| tBu | N (CH₂OEt) | CBr | 2 |
| CF₃ | N (CH₂OEt) | CBr | 0 |
| CF₃ | N (CH₂OEt) | CBr | 1 |
| CF₃ | N (CH₂OEt) | CBr | 2 |

TABLE 20

| R¹ | A¹ | A³ | n |
|---|---|---|---|
| CH₂CF₃ | N (CH₂OEt) | CBr | 0 |
| CH₂CF₃ | N (CH₂OEt) | CBr | 1 |
| CH₂CF₃ | N (CH₂OEt) | CBr | 2 |
| CH=CH₂ | N (CH₂OEt) | CBr | 0 |
| CH=CH₂ | N (CH₂OEt) | CBr | 1 |
| CH=CH₂ | N (CH₂OEt) | CBr | 2 |

TABLE 20-continued

| R¹ | A¹ | A³ | n |
|---|---|---|---|
| CH$_2$CH=CH$_2$ | N (CH$_2$OEt) | CBr | 0 |
| CH$_2$CH=CH$_2$ | N (CH$_2$OEt) | CBr | 1 |
| CH$_2$CH=CH$_2$ | N (CH$_2$OEt) | CBr | 2 |
| C≡CH | N (CH$_2$OEt) | CBr | 0 |
| C≡CH | N (CH$_2$OEt) | CBr | 1 |
| C≡CH | N (CH$_2$OEt) | CBr | 2 |
| CH$_2$C≡CH | N (CH$_2$OEt) | CBr | 0 |
| CH$_2$C≡CH | N (CH$_2$OEt) | CBr | 1 |
| CH$_2$C≡CH | N (CH$_2$OEt) | CBr | 2 |
| CycPr | N (CH$_2$OEt) | CBr | 0 |
| CycPr | N (CH$_2$OEt) | CBr | 1 |
| CycPr | N (CH$_2$OEt) | CBr | 2 |
| CH$_2$CycPr | N (CH$_2$OEt) | CBr | 0 |
| CH$_2$CycPr | N (CH$_2$OEt) | CBr | 1 |
| CH$_2$CycPr | N (CH$_2$OEt) | CBr | 2 |

TABLE 21

| R¹ | A¹ | A³ | n |
|---|---|---|---|
| Me | N (CH$_2$C≡CH) | N | 0 |
| Me | N (CH$_2$C≡CH) | N | 1 |
| Me | N (CH$_2$C≡CH) | N | 2 |
| Et | N (CH$_2$C≡CH) | N | 0 |
| Et | N (CH$_2$C≡CH) | N | 1 |
| Et | N (CH$_2$C≡CH) | N | 2 |
| Pr | N (CH$_2$C≡CH) | N | 0 |
| Pr | N (CH$_2$C≡CH) | N | 1 |
| Pr | N (CH$_2$C≡CH) | N | 2 |
| iPr | N (CH$_2$C≡CH) | N | 0 |
| iPr | N (CH$_2$C≡CH) | N | 1 |
| iPr | N (CH$_2$C≡CH) | N | 2 |
| tBu | N (CH$_2$C≡CH) | N | 0 |
| tBu | N (CH$_2$C≡CH) | N | 1 |
| tBu | N (CH$_2$C≡CH) | N | 2 |
| CF$_3$ | N (CH$_2$C≡CH) | N | 0 |
| CF$_3$ | N (CH$_2$C≡CH) | N | 1 |
| CF$_3$ | N (CH$_2$C≡CH) | N | 2 |
| CH$_2$CF$_3$ | N (CH$_2$C≡CH) | N | 0 |
| CH$_2$CF$_3$ | N (CH$_2$C≡CH) | N | 1 |
| CH$_2$CF$_3$ | N (CH$_2$C≡CH) | N | 2 |
| CH=CH$_2$ | N (CH$_2$C≡CH) | N | 0 |
| CH=CH$_2$ | N (CH$_2$C≡CH) | N | 1 |
| CH=CH$_2$ | N (CH$_2$C≡CH) | N | 2 |

TABLE 22

| R¹ | A¹ | A³ | n |
|---|---|---|---|
| CH$_2$CH=CH$_2$ | N (CH$_2$C≡CH) | N | 0 |
| CH$_2$CH=CH$_2$ | N (CH$_2$C≡CH) | N | 1 |
| CH$_2$CH=CH$_2$ | N (CH$_2$C≡CH) | N | 2 |
| C≡CH | N (CH$_2$C≡CH) | N | 0 |
| C≡CH | N (CH$_2$C≡CH) | N | 1 |
| C≡CH | N (CH$_2$C≡CH) | N | 2 |
| CH$_2$C≡CH | N (CH$_2$C≡CH) | N | 0 |
| CH$_2$C≡CH | N (CH$_2$C≡CH) | N | 1 |
| CH$_2$C≡CH | N (CH$_2$C≡CH) | N | 2 |
| CycPr | N (CH$_2$C≡CH) | N | 0 |
| CycPr | N (CH$_2$C≡CH) | N | 1 |
| CycPr | N (CH$_2$C≡CH) | N | 2 |
| CH$_2$CycPr | N (CH$_2$C≡CH) | N | 0 |
| CH$_2$CycPr | N (CH$_2$C≡CH) | N | 1 |
| CH$_2$CycPr | N (CH$_2$C≡CH) | N | 2 |
| Me | N (CH$_2$C≡CH) | CH | 0 |
| Me | N (CH$_2$C≡CH) | CH | 1 |
| Me | N (CH$_2$C≡CH) | CH | 2 |
| Et | N (CH$_2$C≡CH) | CH | 0 |
| Et | N (CH$_2$C≡CH) | CH | 1 |
| Et | N (CH$_2$C≡CH) | CH | 2 |
| Pr | N (CH$_2$C≡CH) | CH | 0 |
| Pr | N (CH$_2$C≡CH) | CH | 1 |
| Pr | N (CH$_2$C≡CH) | CH | 2 |

TABLE 23

| R¹ | A¹ | A³ | n |
|---|---|---|---|
| iPr | N (CH$_2$C≡CH) | CH | 0 |
| iPr | N (CH$_2$C≡CH) | CH | 1 |
| iPr | N (CH$_2$C≡CH) | CH | 2 |
| tBu | N (CH$_2$C≡CH) | CH | 0 |
| tBu | N (CH$_2$C≡CH) | CH | 1 |
| tBu | N (CH$_2$C≡CH) | CH | 2 |
| CF$_3$ | N (CH$_2$C≡CH) | CH | 0 |
| CF$_3$ | N (CH$_2$C≡CH) | CH | 1 |
| CF$_3$ | N (CH$_2$C≡CH) | CH | 2 |
| CH$_2$CF$_3$ | N (CH$_2$C≡CH) | CH | 0 |
| CH$_2$CF$_3$ | N (CH$_2$C≡CH) | CH | 1 |
| CH$_2$CF$_3$ | N (CH$_2$C≡CH) | CH | 2 |
| CH=CH$_2$ | N (CH$_2$C≡CH) | CH | 0 |
| CH=CH$_2$ | N (CH$_2$C≡CH) | CH | 1 |
| CH=CH$_2$ | N (CH$_2$C≡CH) | CH | 2 |
| CH$_2$CH=CH$_2$ | N (CH$_2$C≡CH) | CH | 0 |
| CH$_2$CH=CH$_2$ | N (CH$_2$C≡CH) | CH | 1 |
| CH$_2$CH=CH$_2$ | N (CH$_2$C≡CH) | CH | 2 |
| C≡CH | N (CH$_2$C≡CH) | CH | 0 |
| C≡CH | N (CH$_2$C≡CH) | CH | 1 |
| C≡CH | N (CH$_2$C≡CH) | CH | 2 |
| CH$_2$C≡CH | N (CH$_2$C≡CH) | CH | 0 |
| CH$_2$C≡CH | N (CH$_2$C≡CH) | CH | 1 |
| CH$_2$C≡CH | N (CH$_2$C≡CH) | CH | 2 |

TABLE 24

| R¹ | A¹ | A³ | n |
|---|---|---|---|
| CycPr | N (CH$_2$C≡CH) | CH | 0 |
| CycPr | N (CH$_2$C≡CH) | CH | 1 |
| CycPr | N (CH$_2$C≡CH) | CH | 2 |
| CH$_2$CycPr | N (CH$_2$C≡CH) | CH | 0 |
| CH$_2$CycPr | N (CH$_2$C≡CH) | CH | 1 |
| CH$_2$CycPr | N (CH$_2$C≡CH) | CH | 2 |
| Me | N (CH$_2$C≡CH) | CBr | 0 |
| Me | N (CH$_2$C≡CH) | CBr | 1 |
| Me | N (CH$_2$C≡CH) | CBr | 2 |
| Et | N (CH$_2$C≡CH) | CBr | 0 |
| Et | N (CH$_2$C≡CH) | CBr | 1 |
| Et | N (CH$_2$C≡CH) | CBr | 2 |
| Pr | N (CH$_2$C≡CH) | CBr | 0 |
| Pr | N (CH$_2$C≡CH) | CBr | 1 |
| Pr | N (CH$_2$C≡CH) | CBr | 2 |
| iPr | N (CH$_2$C≡CH) | CBr | 0 |
| iPr | N (CH$_2$C≡CH) | CBr | 1 |
| iPr | N (CH$_2$C≡CH) | CBr | 2 |
| tBu | N (CH$_2$C≡CH) | CBr | 0 |
| tBu | N (CH$_2$C≡CH) | CBr | 1 |
| tBu | N (CH$_2$C≡CH) | CBr | 2 |
| CF$_3$ | N (CH$_2$C≡CH) | CBr | 0 |
| CF$_3$ | N (CH$_2$C≡CH) | CBr | 1 |
| CF$_3$ | N (CH$_2$C≡CH) | CBr | 2 |

TABLE 25

| R¹ | A¹ | A³ | n |
|---|---|---|---|
| CH$_2$CF$_3$ | N (CH$_2$C≡CH) | CBr | 0 |
| CH$_2$CF$_3$ | N (CH$_2$C≡CH) | CBr | 1 |
| CH$_2$CF$_3$ | N (CH$_2$C≡CH) | CBr | 2 |
| CH=CH$_2$ | N (CH$_2$C≡CH) | CBr | 0 |
| CH=CH$_2$ | N (CH$_2$C≡CH) | CBr | 1 |
| CH=CH$_2$ | N (CH$_2$C≡CH) | CBr | 2 |

TABLE 25-continued

| R¹ | A¹ | A³ | n |
|---|---|---|---|
| CH₂CH=CH₂ | N (CH₂C≡CH) | CBr | 0 |
| CH₂CH=CH₂ | N (CH₂C≡CH) | CBr | 1 |
| CH₂CH=CH₂ | N (CH₂C≡CH) | CBr | 2 |
| C≡CH | N (CH₂C≡CH) | CBr | 0 |
| C≡CH | N (CH₂C≡CH) | CBr | 1 |
| C≡CH | N (CH₂C≡CH) | CBr | 2 |
| CH₂C≡CH | N (CH₂C≡CH) | CBr | 0 |
| CH₂C≡CH | N (CH₂C≡CH) | CBr | 1 |
| CH₂C≡CH | N (CH₂C≡CH) | CBr | 2 |
| CycPr | N (CH₂C≡CH) | CBr | 0 |
| CycPr | N (CH₂C≡CH) | CBr | 1 |
| CycPr | N (CH₂C≡CH) | CBr | 2 |
| CH₂CycPr | N (CH₂C≡CH) | CBr | 0 |
| CH₂CycPr | N (CH₂C≡CH) | CBr | 1 |
| CH₂CycPr | N (CH₂C≡CH) | CBr | 2 |

TABLE 26

| R¹ | A¹ | A³ | n |
|---|---|---|---|
| Me | O | N | 0 |
| Me | O | N | 1 |
| Me | O | N | 2 |
| Et | O | N | 0 |
| Et | O | N | 1 |
| Et | O | N | 2 |
| Pr | O | N | 0 |
| Pr | O | N | 1 |
| Pr | O | N | 2 |
| iPr | O | N | 0 |
| iPr | O | N | 1 |
| iPr | O | N | 2 |
| tBu | O | N | 0 |
| tBu | O | N | 1 |
| tBu | O | N | 2 |
| CF₃ | O | N | 0 |
| CF₃ | O | N | 1 |
| CF₃ | O | N | 2 |
| CH₂CF₃ | O | N | 0 |
| CH₂CF₃ | O | N | 1 |
| CH₂CF₃ | O | N | 2 |
| CH=CH₂ | O | N | 0 |
| CH=CH₂ | O | N | 1 |
| CH=CH₂ | O | N | 2 |

TABLE 27

| R¹ | A¹ | A³ | n |
|---|---|---|---|
| CH₂CH=CH₂ | O | N | 0 |
| CH₂CH=CH₂ | O | N | 1 |
| CH₂CH=CH₂ | O | N | 2 |
| C≡CH | O | N | 0 |
| C≡CH | O | N | 1 |
| C≡CH | O | N | 2 |
| CH₂C≡CH | O | N | 0 |
| CH₂C≡CH | O | N | 1 |
| CH₂C≡CH | O | N | 2 |
| CycPr | O | N | 0 |
| CycPr | O | N | 1 |
| CycPr | O | N | 2 |
| CH₂CycPr | O | N | 0 |
| CH₂CycPr | O | N | 1 |
| CH₂CycPr | O | N | 2 |
| Me | O | CH | 0 |
| Me | O | CH | 1 |
| Me | O | CH | 2 |
| Et | O | CH | 0 |
| Et | O | CH | 1 |
| Et | O | CH | 2 |
| Pr | O | CH | 0 |

TABLE 27-continued

| R¹ | A¹ | A³ | n |
|---|---|---|---|
| Pr | O | CH | 1 |
| Pr | O | CH | 2 |

TABLE 28

| R¹ | A¹ | A³ | n |
|---|---|---|---|
| iPr | O | CH | 0 |
| iPr | O | CH | 1 |
| iPr | O | CH | 2 |
| tBu | O | CH | 0 |
| tBu | O | CH | 1 |
| tBu | O | CH | 2 |
| CF₃ | O | CH | 0 |
| CF₃ | O | CH | 1 |
| CF₃ | O | CH | 2 |
| CH₂CF₃ | O | CH | 0 |
| CH₂CF₃ | O | CH | 1 |
| CH₂CF₃ | O | CH | 2 |
| CH=CH₂ | O | CH | 0 |
| CH=CH₂ | O | CH | 1 |
| CH=CH₂ | O | CH | 2 |
| CH₂CH=CH₂ | O | CH | 0 |
| CH₂CH=CH₂ | O | CH | 1 |
| CH₂CH=CH₂ | O | CH | 2 |
| C≡CH | O | CH | 0 |
| C≡CH | O | CH | 1 |
| C≡CH | O | CH | 2 |
| CH₂C≡CH | O | CH | 0 |
| CH₂C≡CH | O | CH | 1 |
| CH₂C≡CH | O | CH | 2 |

TABLE 29

| R¹ | A¹ | A³ | n |
|---|---|---|---|
| CycPr | O | CH | 0 |
| CycPr | O | CH | 1 |
| CycPr | O | CH | 2 |
| CH₂CycPr | O | CH | 0 |
| CH₂CycPr | O | CH | 1 |
| CH₂CycPr | O | CH | 2 |
| Me | O | CBr | 0 |
| Me | O | CBr | 1 |
| Me | O | CBr | 2 |
| Et | O | CBr | 0 |
| Et | O | CBr | 1 |
| Et | O | CBr | 2 |
| Pr | O | CBr | 0 |
| Pr | O | CBr | 1 |
| Pr | O | CBr | 2 |
| iPr | O | CBr | 0 |
| iPr | O | CBr | 1 |
| iPr | O | CBr | 2 |
| tBu | O | CBr. | 0 |
| tBu | O | CBr | 1 |
| tBu | O | CBr | 2 |
| CF₃ | O | CBr | 0 |
| CF₃ | O | CBr | 1 |
| CF₃ | O | CBr | 2 |

TABLE 30

| R¹ | A¹ | A³ | n |
|---|---|---|---|
| CH₂CF₃ | O | CBr | 0 |
| CH₂CF₃ | O | CBr | 1 |
| CH₂CF₃ | O | CBr | 2 |
| CH=CH₂ | O | CBr | 0 |
| CH=CH₂ | O | CBr | 1 |
| CH=CH₂ | O | CBr | 2 |

TABLE 30-continued

| R¹ | A¹ | A³ | n |
|---|---|---|---|
| CH₂CH=CH₂ | O | CBr | 0 |
| CH₂CH=CH₂ | O | CBr | 1 |
| CH₂CH=CH₂ | O | CBr | 2 |
| C≡CH | O | CBr | 0 |
| C≡CH | O | CBr | 1 |
| C≡CH | O | CBr | 2 |
| CH₂C≡CH | O | CBr | 0 |
| CH₂C≡CH | O | CBr | 1 |
| CH₂C≡CH | O | CBr | 2 |
| CycPr | O | CBr | 0 |
| CycPr | O | CBr | 1 |
| CycPr | O | CBr | 2 |
| CH₂CycPr | O | CBr | 0 |
| CH₂CycPr | O | CBr | 1 |
| CH₂CycPr | O | CBr | 2 |

TABLE 31

| R¹ | A¹ | A³ | n |
|---|---|---|---|
| Me | S | N | 0 |
| Me | S | N | 1 |
| Me | S | N | 2 |
| Et | S | N | 0 |
| Et | S | N | 1 |
| Et | S | N | 2 |
| Pr | S | N | 0 |
| Pr | S | N | 1 |
| Pr | S | N | 2 |
| iPr | S | N | 0 |
| iPr | S | N | 1 |
| iPr | S | N | 2 |
| tBu | S | N | 0 |
| tBu | S | N | 1 |
| tBu | S | N | 2 |
| CF₃ | S | N | 0 |
| CF₃ | S | N | 1 |
| CF₃ | S | N | 2 |
| CH₂CF₃ | S | N | 0 |
| CH₂CF₃ | S | N | 1 |
| CH₂CF₃ | S | N | 2 |
| CH=CH₂ | S | N | 0 |
| CH=CH₂ | S | N | 1 |
| CH=CH₂ | S | N | 2 |

TABLE 32

| R¹ | A¹ | A³ | n |
|---|---|---|---|
| CH₂CH=CH₂ | S | N | 0 |
| CH₂CH=CH₂ | S | N | 1 |
| CH₂CH=CH₂ | S | N | 2 |
| C≡CH | S | N | 0 |
| C≡CH | S | N | 1 |
| C≡CH | S | N | 2 |
| CH₂C≡CH | S | N | 0 |
| CH₂C≡CH | S | N | 1 |
| CH₂C≡CH | S | N | 2 |
| CycPr | S | N | 0 |
| CycPr | S | N | 1 |
| CycPr | S | N | 2 |
| CH₂CycPr | S | N | 0 |
| CH₂CycPr | S | N | 1 |
| CH₂CycPr | S | N | 2 |
| Me | S | CH | 0 |
| Me | S | CH | 1 |
| Me | S | CH | 2 |
| Et | S | CH | 0 |
| Et | S | CH | 1 |
| Et | S | CH | 2 |
| Pr | S | CH | 0 |

TABLE 32-continued

| R¹ | A¹ | A³ | n |
|---|---|---|---|
| Pr | S | CH | 1 |
| Pr | S | CH | 2 |

TABLE 33

| R¹ | A¹ | A³ | n |
|---|---|---|---|
| iPr | S | CH | 0 |
| iPr | S | CH | 1 |
| iPr | S | CH | 2 |
| tBu | S | CH | 0 |
| tBu | S | CH | 1 |
| tBu | S | CH | 2 |
| CF₃ | S | CH | 0 |
| CF₃ | S | CH | 1 |
| CF₃ | S | CH | 2 |
| CH₂CF₃ | S | CH | 0 |
| CH₂CF₃ | S | CH | 1 |
| CH₂CF₃ | S | CH | 2 |
| CH=CH₂ | S | CH | 0 |
| CH=CH₂ | S | CH | 1 |
| CH=CH₂ | S | CH | 2 |
| CH₂CH=CH₂ | S | CH | 0 |
| CH₂CH=CH₂ | S | CH | 1 |
| CH₂CH=CH₂ | S | CH | 2 |
| C≡CH | S | CH | 0 |
| C≡CH | S | CH | 1 |
| C≡CH | S | CH | 2 |
| CH₂C≡CH | S | CH | 0 |
| CH₂C≡CH | S | CH | 1 |
| CH₂C≡CH | S | CH | 2 |

TABLE 34

| R¹ | A¹ | A³ | n |
|---|---|---|---|
| CycPr | S | CH | 0 |
| CycPr | S | CH | 1 |
| CycPr | S | CH | 2 |
| CH₂CycPr | S | CH | 0 |
| CH₂CycPr | S | CH | 1 |
| CH₂CycPr | S | CH | 2 |
| Me | S | CBr | 0 |
| Me | S | CBr | 1 |
| Me | S | CBr | 2 |
| Et | S | CBr | 0 |
| Et | S | CBr | 1 |
| Et | S | CBr | 2 |
| Pr | S | CBr | 0 |
| Pr | S | CBr | 1 |
| Pr | S | CBr | 2 |
| iPr | S | CBr | 0 |
| iPr | S | CBr | 1 |
| iPr | S | CBr | 2 |
| tBu | S | CBr | 0 |
| tBu | S | CBr | 1 |
| tBu | S | CBr | 2 |
| CF₃ | S | CBr | 0 |
| CF₃ | S | CBr | 1 |
| CF₃ | S | CBr | 2 |

TABLE 35

| R¹ | A¹ | A³ | n |
|---|---|---|---|
| CH₂CF₃ | S | CBr | 0 |
| CH₂CF₃ | S | CBr | 1 |
| CH₂CF₃ | S | CBr | 2 |
| CH=CH₂ | S | CBr | 0 |
| CH=CH₂ | S | CBr | 1 |
| CH=CH₂ | S | CBr | 2 |

TABLE 35-continued

| R$^1$ | A$^1$ | A$^3$ | n |
|---|---|---|---|
| CH$_2$CH=CH$_2$ | S | CBr | 0 |
| CH$_2$CH=CH$_2$ | S | CBr | 1 |
| CH$_2$CH=CH$_2$ | S | CBr | 2 |
| C≡CH | S | CBr | 0 |
| C≡CH | S | CBr | 1 |
| C≡CH | S | CBr | 2 |
| CH$_2$C≡CH | S | CBr | 0 |
| CH$_2$C≡CH | S | CBr | 1 |
| CH$_2$C≡CH | S | CBr | 2 |
| CycPr | S | CBr | 0 |
| CycPr | S | CBr | 1 |
| CycPr | S | CBr | 2 |
| CH$_2$CycPr | S | CBr | 0 |
| CH$_2$CycPr | S | CBr | 1 |
| CH$_2$CycPr | S | CBr | 2 |

In the above [Table 1] to [Table 35], Me represents a methyl group, Et represents an ethyl group, Pr represents a n-propyl group, iPr represents isopropyl group, tBu represents a tert-butyl group, and CycPr represents cyclopropyl group.

A compound represented by the formula (A) wherein R$^2$ is a fluorine atom, R$^3$ and R$^4$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^3$ is a fluorine atom, R$^2$ and R$^4$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^4$ is a fluorine atom, R$^2$ and R$^3$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^2$ is a chlorine atom, R$^3$ and R$^4$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein is a chlorine atom, R$^2$ and R$^4$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^4$ is a chlorine atom, R$^2$ and R$^3$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^2$ is a bromine atom, R$^3$ and R$^4$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^3$ is a bromine atom, R$^2$ and R$^4$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^4$ is a bromine atom, R$^2$ and R$^3$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^2$ is a methyl group, R$^3$ and R$^4$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^3$ is a methyl group, R$^2$ and R$^4$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^4$ is a methyl group, R$^2$ and R$^3$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^2$ is a trifluoromethyl group, R$^3$ and R$^4$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^3$ is a trifluoromethyl group, R$^2$ and R$^4$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^4$ is a trifluoromethyl group, R$^2$ and R$^3$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^3$ is a pentafluoroethyl group, R$^2$ and R$^4$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^3$ is a trifluoromethoxy group, R$^2$ and R$^4$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^3$ is a 2-pyridyl group, R$^2$ and R$^4$ are independently a hydrogen atom, R$^5$ is a trifluoromethyl group, and R$^1$, A$^1$, and n represent any one of the combinations as listed in [Table 1] to [Table 35].

A compound represented by the formula (A) wherein R$^3$ is a 3-chloro-2-pyridyl group, R$^2$ and R$^4$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^3$ is a 2-pyrimidinyl group, R$^2$ and R$^4$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^3$ is —SF$_5$, R$^2$ and R$^4$ are independently a hydrogen atom, R$^5$ is a trifluoromethyl group, and R$^1$, A$^1$, A$^3$ and n represent any one of the combinations as listed in [Table 1] to [Table 35].

A compound represented by the formula (A) wherein R$^2$, R$^3$ and R$^4$ are independently a hydrogen atom, R$^5$ is a pentafluoroethyl group, and R$^1$, A$^1$, A$^3$ and n represent any one of the combinations as listed in [Table 1] to [Table 35].

A compound represented by the formula (A) wherein R$^2$ is a fluorine atom, R$^3$ and R$^4$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^3$ is a fluorine atom, $R^2$ and $R^4$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^4$ is a fluorine atom, $R^2$ and $R^3$ are independently a hydrogen atom, $R^5$ is a pentafluoroethyl group, and $R^1$, $A^1$, $A^3$ and represent any one of the combinations as listed in [Table 1] to [Table 35].

A compound represented by the formula (A) wherein $R^2$ is a chlorine atom, $R^3$ and $R^4$ are independently a hydrogen atom, $R^5$ is a pentafluoroethyl group, $R^1$, $A^1$, $A^3$ and represent any one of the combinations as listed in [Table 1] to [Table 35]

A compound represented by the formula (A) wherein $R^3$ is a chlorine atom, $R^2$ and $R^4$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^4$ is a chlorine atom, $R^2$ and $R^3$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^2$ is a bromine atom, $R^3$ and $R^4$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^3$ is a bromine atom, $R^2$ and $R^4$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^4$ is a bromine atom, $R^2$ and $R^3$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^2$ is a methyl group, $R^3$ and $R^4$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^3$ is a methyl group, $R^2$ and $R^4$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^4$ is a methyl group, $R^2$ and $R^3$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^2$ is a trifluoromethyl group, $R^3$ and $R^4$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^3$ is a trifluoromethyl group, $R^2$ and $R^4$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^4$ is a trifluoromethyl group, $R^2$ and $R^3$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^3$ is a pentafluoroethyl group, $R^2$ and $R^4$ are independently a hydrogen atom, $R^5$ is a pentafluoroethyl group, and $R^1$, $A^3$ and n represent any one of the combinations as listed in [Table 1] to [Table 35].

A compound represented by the formula (A) wherein $R^3$ is a trifluoromethoxy group, $R^2$ and $R^4$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^3$ is a 2-pyridyl group, $R^2$ and $R^4$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^3$ is a 3-chloro-2-pyridyl group, $R^2$ and $R^4$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^3$ is a 2-pyrimidinyl group, $R^2$ and $R^4$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^3$ is —$SF_5$, $R^2$ and $R^4$ are independently a hydrogen atom, $R^5$ is a pentafluoroethyl group, and $R^1$, $A^1$, $A^3$ and n represent any one of the combinations as listed in [Table 1] to [Table 35].

A compound represented by the formula (A) wherein $R^2$, $R^3$ and $R^4$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^2$ is a fluorine atom, $R^3$ and $R^4$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^3$ is a fluorine atom, $R^2$ and $R^4$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^4$ is a fluorine atom, $R^2$ and $R^3$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^2$ is a chlorine atom, $R^3$ and $R^4$ are independently a hydrogen atom, $R^5$ is a heptafluoroisopropyl group, $R^1$, $A^1$, $A^3$ and n represent any one of the combinations as listed in [Table 1] to [Table 35].

A compound represented by the formula (A) wherein $R^3$ is a chlorine atom, $R^2$ and $R^4$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^4$ is a chlorine atom, $R^2$ and $R^3$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^2$ is a bromine atom, $R^3$ and $R^4$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^3$ is a bromine atom, $R^2$ and $R^4$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^4$ is a bromine atom, $R^2$ and $R^3$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^2$ is a methyl group, $R^3$ and $R^4$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^3$ is a methyl group, $R^2$ and $R^4$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^4$ is a methyl group, $R^2$ and $R^3$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^2$ is a trifluoromethyl group, $R^3$ and $R^4$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^3$ is a trifluoromethyl group, $R^2$ and $R^4$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^4$ is a trifluoromethyl group, $R^2$ and $R^3$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^3$ is a pentafluoroethyl group, $R^2$ and $R^4$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^3$ is a trifluoromethoxy group, $R^2$ and $R^4$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^3$ is a 2-pyridyl group, $R^2$ and $R^4$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^3$ is a 3-chloro-2-pyridyl group, $R^2$ and $R^4$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^3$ is a 2-pyrimidinyl group, $R^2$ and $R^4$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^3$ is —$SF_5$, $R^2$ and $R^4$ are independently a hydrogen atom, $R^5$ is a heptafluoroisopropyl group, and $R^1$, $A^1$, $A^3$ and n represent any one of the combinations as listed in [Table 1] to [Table 35].

A compound represented by the formula (A) wherein $R^2$, $R^3$ and $R^4$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^2$ is a fluorine atom, $R^3$ and $R^4$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^3$ is a fluorine atom, $R^2$ and $R^4$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^4$ is a fluorine atom, $R^2$ and $R^3$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^2$ is a chlorine atom, $R^3$ and $R^4$ are independently a hydrogen atom, $R^5$ is a trifluoromethoxy group, $R^1$, $A^1$, $A^3$ and n represent any one of the combinations as listed in [Table 1] to [Table 35]

A compound represented by the formula (A) wherein $R^3$ is a chlorine atom, $R^2$ and $R^4$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^4$ is a chlorine atom, $R^2$ and $R^3$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^2$ is a bromine atom, $R^3$ and $R^4$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^3$ is a bromine atom, $R^2$ and $R^4$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^4$ is a bromine atom, $R^2$ and $R^3$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^2$ is a methyl group, $R^3$ and $R^4$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^3$ is a methyl group, $R^2$ and $R^4$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^4$ is a methyl group, $R^2$ and $R^3$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^2$ is a trifluoromethyl group, $R^3$ and $R^4$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^3$ is a trifluoromethyl group, $R^2$ and $R^4$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^4$ is a trifluoromethyl group, $R^2$ and $R^3$ are independently hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^3$ is a pentafluoroethyl group, $R^2$ and $R^4$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^3$ is a trifluoromethoxy group, $R^2$ and $R^4$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^3$ is a 2-pyridyl group, $R^2$ and $R^4$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^3$ is a 3-chloro-2-pyridyl group, $R^2$ and $R^4$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^3$ is a 2-pyrimidinyl group, $R^2$ and $R^4$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^3$ is —$SF_5$, $R^2$ and $R^4$ are independently a hydrogen atom, $R^5$ is a trifluoromethoxy group, and $R^1$, $A^1$, $A^3$ and n represent any one of the combinations as listed in [Table 1] to [Table 35].

A compound represented by the formula (A) wherein $R^2$, $R^3$ and $R^4$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^2$ is a fluorine atom, $R^3$ and $R^4$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^3$ is a fluorine atom, $R^2$ and $R^4$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^4$ is a fluorine atom, $R^2$ and $R^3$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^2$ is a chlorine atom, $R^3$ and $R^4$ are independently a hydrogen atom, $R^5$ is a trifluoromethylsulfanyl group, $R^1$, $A^1$, $A^3$ and n represent any one of the combinations as listed in [Table 1] to [Table 35]

A compound represented by the formula (A) wherein $R^3$ is a chlorine atom, $R^2$ and $R^4$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^4$ is a chlorine atom, $R^2$ and $R^3$ are independently a hydrogen atom, $R^5$ is a trifluoromethylsulfanyl group, and $R^1$, $A^1$, $A^3$ and n represent any one of the combinations as listed in [Table 1] to [Table 35]

A compound represented by the formula (A) wherein $R^2$ is a bromine atom, $R^3$ and $R^4$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^3$ is a bromine atom, $R^2$ and $R^4$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^4$ is a bromine atom, $R^2$ and $R^3$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^2$ is a methyl group, $R^3$ and $R^4$ are independently a hydrogen atom, $R^5$ is a trifluoromethylsulfanyl group, and $R^1$, $A^1$, $A^3$ and n represent any one of the combinations as listed, in [Table 1] to [Table 35].

A compound represented by the formula (A) wherein $R^3$ is a methyl group, $R^2$ and $R^4$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^4$ is a methyl group, $R^2$ and $R^3$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^2$ is a trifluoromethyl group, $R^3$ and $R^4$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^3$ is a trifluoromethyl group, $R^2$ and $R^4$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^4$ is a trifluoromethyl group, $R^2$ and $R^3$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^3$ is a pentafluoroethyl group, $R^2$ and $R^4$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^3$ is a trifluoromethoxy group, $R^2$ and $R^4$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^3$ is a 2-pyridyl group, $R^2$ and $R^4$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^3$ is a 3-chloro-2-pyridyl group, $R^2$ and $R^4$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^3$ is a 2-pyrimidinyl group, $R^2$ and $R^4$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^3$ is —$SF_5$, $R^2$ and $R^4$ are independently a hydrogen atom, $R^5$ is a trifluoromethylsulfanyl group, and $R^1$, $A^1$, $A^3$ and n represent any one of the combinations as listed in [Table 1] to [Table 35].

A compound represented by the formula (A) wherein $R^2$, $R^3$ and $R^4$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^2$ is a fluorine atom, $R^3$ and $R^4$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^3$ is a fluorine atom, $R^2$ and $R^4$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^4$ is a fluorine atom, $R^2$ and $R^3$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^2$ is a chlorine atom, $R^3$ and $R^4$ are independently a hydrogen atom, $R^5$ is a trifluoromethylsulfinyl group, $R^1$, $A^1$, $A^3$ and n represent any one of the combinations as listed in [Table 1] to [Table 35]

A compound represented by the formula (A) wherein $R^3$ is a chlorine atom, $R^2$ and $R^4$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^4$ is a chlorine atom, $R^2$ and $R^3$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^2$ is a bromine atom, $R^3$ and $R^4$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^3$ is a bromine atom, $R^2$ and $R^4$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^4$ is a bromine atom, $R^2$ and $R^3$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^2$ is a methyl group, $R^3$ and $R^4$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^3$ is a methyl group, $R^2$ and $R^4$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^4$ is a methyl group, $R^2$ and $R^3$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^2$ is a trifluoromethyl group, $R^3$ and $R^4$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^3$ is a trifluoromethyl group, $R^2$ and $R^4$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^4$ is a trifluoromethyl group, $R^2$ and $R^3$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^3$ is a pentafluoroethyl group, $R^2$ and $R^4$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^3$ is a trifluoromethoxy group, $R^2$ and $R^4$ are independently a hydrogen atom, is a trifluoromethylsulfinyl group, and $R^1$, $A^1$, $A^3$ and n represent any one of the combinations as listed in [Table 1] to [Table 35].

A compound represented by the formula (A) wherein $R^3$ is a 2-pyridyl group, $R^2$ and $R^4$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^3$ is a 3-chloro-2-pyridyl group, $R^2$ and $R^4$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^3$ is a 2-pyrimidinyl group, $R^2$ and $R^4$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^3$ is —$SF_5$, $R^2$ and $R^4$ are independently a hydrogen atom, $R^5$ is a trifluoromethylsulfinyl group, and $R^1$, $A^1$, $A^3$ and n represent any one of the combinations as listed in [Table 1] to [Table 35].

A compound represented by the formula (A) wherein $R^2$, $R^3$ and $R^4$ are independently a hydrogen atom, $R^5$ is a trifluoromethylsulfonyl group, and $R^1$, $A^1$, $A^3$ and represent any one of the combinations as listed in [Table 1] to [Table 35].

A compound represented by the formula (A) wherein $R^2$ is a fluorine atom, $R^3$ and $R^4$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^3$ is a fluorine atom, $R^2$ and $R^4$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^4$ is a fluorine atom, $R^2$ and $R^3$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^2$ is a chlorine atom, $R^3$ and $R^4$ are independently a hydrogen atom, $R^5$ is a trifluoromethylsulfonyl group, and $R^1$, $A^1$, $A^3$ and n represent any one of the combinations as listed in [Table 1] to [Table 35]

A compound represented by the formula (A) wherein $R^3$ is a chlorine atom, $R^2$ and $R^4$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^4$ is a chlorine atom, $R^2$ and $R^3$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^2$ is a bromine atom, $R^3$ and $R^4$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^3$ is a bromine atom, $R^2$ and $R^4$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^4$ is a bromine atom, $R^2$ and $R^3$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^2$ is a methyl group, $R^3$ and $R^4$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^3$ is a methyl group, $R^2$ and $R^4$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^4$ is a methyl group, $R^2$ and $R^3$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^2$ is a trifluoromethyl group, $R^3$ and $R^4$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^3$ is a trifluoromethyl group, $R^2$ and $R^4$ are independently a hydrogen atom; $R^5$ is a trifluoromethylsulfonyl group, and $R^1$, $A^1$, $A^3$ and n represent any one of the combinations as listed in [Table 1] to [Table 35].

A compound represented by the formula (A) wherein $R^4$ is a trifluoromethyl group, $R^2$ and $R^3$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^3$ is a pentafluoroethyl group, $R^2$ and $R^4$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^3$ is a trifluoromethoxy group, $R^2$ and $R^4$ are independently a hydrogen atom, is a trifluoromethylsulfonyl group, and $R^1$, $A^1$, $A^3$ and n represent any one of the combinations as listed in [Table 1] to [Table 35].

A compound represented by the formula (A) wherein $R^3$ is a 2-pyridyl group, $R^2$ and $R^4$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^3$ is a 3-chloro-2-pyridyl group, $R^2$ and $R^4$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^3$ is a 2-pyrimidinyl group, $R^2$ and $R^4$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^3$ is —$SF_5$, $R^2$ and $R^4$ are independently a hydrogen atom, $R^5$ is a trifluoromethylsulfonyl group, and $R^1$, $A^1$, $A^3$ and n represent any one of the combinations as listed in [Table 1] to [Table 35].

A compound represented by the formula (A) wherein $R^2$, $R^3$ and $R^4$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^2$ is a fluorine atom, $R^3$ and $R^4$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^3$ is a fluorine atom, $R^2$ and $R^4$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^4$ is a fluorine atom, $R^2$ and $R^3$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^2$ is a chlorine atom, $R^3$ and $R^4$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^3$ is a chlorine atom, $R^2$ and $R^4$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^4$ is a chlorine atom, $R^2$ and $R^3$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^2$ is a bromine atom, $R^3$ and $R^4$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^3$ is a bromine atom, $R^2$ and $R^4$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^4$ is a bromine atom, $R^2$ and $R^3$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^2$ is a methyl group, $R^3$ and $R^4$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^3$ is a methyl group, $R^2$ and $R^4$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^4$ is a methyl group, $R^2$ and $R^3$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^2$ is a trifluoromethyl group, $R^3$ and $R^4$ are independently a hydrogen atom, $R^5$ is a bromine atom, and $R^1$, $A^1$, $A^3$ and n represent any one of the combinations as listed in [Table 1] to [Table 35]

A compound represented by the formula (A) wherein $R^3$ is a trifluoromethyl group, $R^2$ and $R^4$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^4$ is a trifluoromethyl group, $R^2$ and $R^3$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^3$ is a pentafluoroethyl group, $R^2$ and $R^4$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^3$ is a trifluoromethoxy group, $R^2$ and $R^4$ are independently a hydrogen atom, $R^5$ is a bromine atom, and $R^1$, $A^1$, $A^3$ and represent any one of the combinations as listed in [Table 1] to [Table 35]

A compound represented by the formula (A) wherein $R^3$ is a 2-pyridyl group, $R^2$ and $R^4$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^3$ is a 3-chloro-2-pyridyl, group, $R^2$ and $R^4$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^3$ is a 2-pyrimidinyl group, $R^2$ and $R^4$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^3$ is —$SF_5$, $R^2$ and $R^4$ are independently a hydrogen atom, $R^5$ is a bromine atom, and $R^1$, $A^1$, $A^3$ and n represent any one of the combinations as listed in [Table 1] to [Table 35].

A compound represented by the formula (A) wherein $R^2$, $R^3$ and $R^4$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^2$ is a fluorine atom, $R^3$ and $R^4$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^3$ is a fluorine atom, $R^2$ and $R^4$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^4$ is a fluorine atom, $R^2$ and $R^3$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^2$ is a chlorine atom, $R^3$ and $R^4$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^3$ is a chlorine atom, $R^2$ and $R^4$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^4$ is a chlorine atom, $R^2$ and $R^3$ are independently a hydrogen atom, $R^5$ is a iodine atom, and $R^1$, $A^1$, $A^3$ and n represent any one of the combinations as listed in. [Table 1] to [Table 35].

A compound represented by the formula (A) wherein $R^2$ is a bromine atom, $R^3$ and $R^4$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^3$ is a bromine atom, $R^2$ and $R^4$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^4$ is a bromine atom, $R^2$ and $R^3$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^2$ is a methyl group, $R^3$ and $R^4$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^3$ is a methyl group, $R^2$ and $R^4$ are independently a hydrogen atom, $R^5$ is a iodine atom, and $R^1$, $A^1$, $A^3$ and n represent any one of the combinations as listed in [Table 1] to [Table 35]

A compound represented by the formula (A) wherein $R^4$ is a methyl group, $R^2$ and $R^3$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^2$ is a trifluoromethyl group, $R^3$ and $R^4$ are independently a hydrogen atom, $R^5$ is a iodine atom, and $R^1$, $A^1$, $A^3$ and n represent any one of the combinations as listed in [Table 1] to [Table 35]

A compound represented by the formula (A) wherein $R^3$ is a trifluoromethyl group, $R^2$ and $R^4$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^4$ is a trifluoromethyl group, $R^2$ and $R^3$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^3$ is a pentafluoroethyl group, $R^2$ and $R^4$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^3$ is a trifluoromethoxy group, $R^2$ and $R^4$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^3$ is a 2-pyridyl group, $R^2$ and $R^4$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^3$ is a 3-chloro-2-pyridyl group, $R^2$ and $R^4$ are independently hydrogen atom, $R^5$ is a iodine atom, and $R^1$, $A^1$, $A^3$ and n represent any one of the combinations as listed in [Table 1] to [Table 35].

A compound represented by the formula (A) wherein $R^3$ is a 2-pyrimidinyl group, $R^2$ and $R^4$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^3$ is $-SF_5$, $R^2$ and $R^4$ are independently a hydrogen atom, $R^5$ is a iodine atom, and $R^1$, $A^1$, $A^3$ and n represent any one of the combinations as listed in [Table 1] to [Table 35].

A compound represented by the formula (A) wherein $R^2$, $R^3$ and $R^4$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^2$ is a fluorine atom, $R^3$ and $R^4$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^3$ is a fluorine atom, $R^2$ and $R^4$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^4$ is a fluorine atom, $R^2$ and $R^3$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^2$ is a chlorine atom, $R^3$ and $R^4$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^3$ is a chlorine atom, $R^2$ and $R^4$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^4$ is a chlorine atom, $R^2$ and $R^3$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^2$ is a bromine atom, $R^3$ and $R^4$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^3$ is a bromine atom, $R^2$ and $R^4$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^4$ is a bromine atom, $R^2$ and $R^3$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^2$ is a methyl group, $R^3$ and $R^4$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^3$ is a methyl group, $R^2$ and $R^4$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^4$ is a methyl group, $R^2$ and $R^3$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^2$ is a trifluoromethyl group, $R^3$ and $R^4$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^3$ is a trifluoromethyl group, $R^2$ and $R^4$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^4$ is a trifluoromethyl group, $R^2$ and $R^3$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^3$ is a pentafluoroethyl group, $R^2$ and $R^4$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^3$ is a trifluoromethoxy group, $R^2$ and $R^4$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^3$ is a 2-pyridyl group, $R^2$ and $R^4$ are independently a hydrogen atom, $R^5$ is $-SF_5$, and $R^1$, $A^1$, $A^3$ and n represent any one of the combinations as listed in [Table 1] to [Table 35].

A compound represented by the formula (A) wherein $R^3$ is a 3-chloro-2-pyridyl group, $R^2$ and $R^4$ are independently a hydrogen atom, $R^5$ is —$SF_5$, and $R^1$, $A^1$, $A^3$ and n represent any one of the combinations as listed in [Table 1] to [Table 35].

A compound represented by the formula (A) wherein $R^3$ is a 2-pyrimidinyl group, $R^2$ and $R^4$ are independently hydrogen atom, $R^5$ is —$SF_5$, and $R^1$, $A^1$, $A^3$ and n represent any one of the combinations as listed in [Table 1] to [Table 35].

A compound represented by the formula (A) wherein $R^3$ is —$SF_5$, $R^2$ and $R^4$ are independently a hydrogen atom, $R^5$ is —$SF_5$, and $R^1$, $A^1$, $A^3$ and n represent any one of the combinations as listed in [Table 1] to [Table 35].

A compound represented by the formula (A) wherein $A^3$ is =N(→O)—, $R^2$, $R^3$ and $R^4$ are independently a hydrogen atom, $R^5$ is a trifluoromethyl group, and $R^1$, $A^1$, and n represent any one of the combinations as listed in [Table 1] to [Table 35].

A compound represented by the formula (A) wherein $A^3$ is =N(→O)—, $R^2$, $R^3$ and $R^4$ are independently a hydrogen atom, $R^5$ is a pentafluoroethyl group, and $R^1$, $A^1$, and n represent any one of the combinations as listed in [Table 1] to [Table 35].

A compound represented by the formula (A) wherein $A^3$ is =(→N)—, $R^2$, $R^3$ and $R^4$ are independently a hydrogen atom, $R^5$ is a trifluoromethylsulfonyl group, and $R^1$, $A^1$, and n represent any one of the combinations as listed in [Table 1] to [Table 35].

A compound represented by the formula (A) wherein $A^3$ is =N(→O)—, $R^3$ is a trifluoromethyl group, $R^2$ and $R^4$ are independently a hydrogen atom, $R^5$ is a trifluoromethyl group, and $R^1$, $A^1$, and n represent any one of the combinations as listed in [Table 1] to [Table 35].

A compound represented by the formula (A) wherein $A^3$ is =N(→O)—, $R^3$ is a trifluoromethyl group, $R^2$ and $R^4$ are independently a hydrogen atom, $R^5$ is a pentafluoroethyl group, and $R^1$, $A^1$, and n represent any one of the combinations as listed in [Table 1] to [Table 35].

A compound represented by the formula (A) wherein $A^3$ is =N(→O)—, $R^3$ is a trifluoromethyl group, $R^2$ and $R^4$ are independently a hydrogen atom, $R^5$ is trifluoromethylsulfonyl group, and $R^1$, $A^1$, and n represent any one of the combinations as listed in [Table 1] to [Table 35].

A compound represented by the formula (A) wherein $A^3$ is =N(→O)—, $R^3$ is a pentafluoroethyl group, $R^2$ and $R^4$ are independently a hydrogen atom, $R^5$ is a trifluoromethyl group, and $R^1$, $A^1$, and n represent any one of the combinations as listed in [Table 1] to [Table 35].

A compound represented by the formula (A) wherein $A^3$ is =N(→O)—, $R^3$ is a pentafluoroethyl group, $R^2$ and $R^4$ are independently a hydrogen atom, $R^5$ is a pentafluoroethyl group, and $R^1$, $A^1$, and n represent any one of the combinations as listed in [Table 1] to [Table 35].

A compound represented by the formula (A) wherein $A^3$ is =N(→O)—, $R^3$ is a pentafluoroethyl group, $R^2$ and $R^4$ are independently a hydrogen atom, $R^5$ is trifluoromethylsulfonyl group, and $R^1$, $A^1$, and n represent any one of the combinations as listed in [Table 1] to [Table 35].

Examples of pests on which the compound of the present invention exhibits a controlling effect include arthropod pests such as harmful insects and harmful mites, and more specifically, the following pests.

Hemiptera:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), green rice leafhopper (*Nephotettix virescens*), and tea green leafhopper (*Empoasca onukii*); aphids (Aphididae) such as cotton aphid (*Aphis gossypii*), green peach aphid (*Ryzus persicae*), cabbage aphid (*Brevicoryne brassicae*), piraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), and stink bug (*Halyomorpha mista*); whiteflies (Aleyrodidae) such as greenhouse whitefly (*Trialeurodes vaporariorum*), sweetpotato whitefly (*Bemisia tabaci*), silverleaf whitefly (*Bemisia argentifolii*), citrus whitefly (*Dialeurodes citri*), and citrus spiny white fly (*Aleurocanthus spiniferus*); scales (Coccidae) such as Calformia red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*), Japanese mealybug (*Planococcus kraunhiae*), Cosmstock mealybug (*Pseudococcus longispinis*), and white peach scale (*Pseudaulacaspis pentagona*); lace bugs (Tingidae); cimices such as *Cimex lectularius*; psyllids (Psyllidae); etc.

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes* honmai.), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); Carposinidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback (*Plutella xylostella*); gelechiid moths (Gelechiidae) such as pink bollworm (*Pectinophora gossypiella*), and potato tubeworm (*Phthorimaea operculella*); tiger moths and allies (Arctiidae) such as fall webworm (*Hyphantria cunea*); tineid moths (Tineidae) such as casemaking clothes moth (*Tinea translucens*), and webbing clothes moth (*Tineola bisselliella*); etc.

Thysanoptera:

Thrips (Thripidae) such as yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), etc.

Diptera:

Culices such as common mosquito (*Culex pipiens pallens*), *Cluex tritaeniorhynchus*, and *Cluex quinquefasciatus*; *Aedes* spp. such as yellow fever mosquito (*Aedes aegypti*), and Asian tiger mosquito (*Aedes albopictus*); *Anopheles* spp. such as *Anopheles sinensis*; chironomids (Chironomidae); house flies (Muscidae) such as *Musca domestica*, and *Muscina stabulans*; blow flies (Calliphoridae); flesh flies (Sarcophagidae); little house flies (Fanniidae); anthomyiid flies (Anthomyiidae) such as seedcorn fly (*Delia platura*), and onion fly (*Delia antiqua*); leafminer flies (Agromyzidae) such as rice leafminer (*Agromyza oryzae*), little rice leafminer (*Hydrellia griseola*), tomato leafminer (*Liriomyza sativae*), legume leafminer (*Liriomyza trifolii*), and garden pea leafminer (*Chromatomyia horticola*); gout flies (Chloropidae) such as rice stem maggot (*Chlorops oryzae*); fruit flies (Tephritidae) such as melon fly (*Dacus cucurbitae*), and Mediterranean fruit fly (*Ceratitis capitata*); Drosophilidae; humpbacked flies (Phoridae) such as *Megaselia spiracularis*; moth flies (Psychodidae) such as *Clogmia albipunctata*; Simuliidae; Tabanidae such as horsefly (*Tabanus trigonus*); stable flies, etc.

Coleoptera:

Corn root worms (*Diabrotica* spp.) such as Western corn root worm (*Diabrotica virgifera* virgifera), and Sourthern corn root worm (*Diabrotica undecimpunctata howardi*); scarabs (Scarabaeidae) such as cupreous chafer (*Anomala cuprea*), soybean beetle (*Anomala rufocuprea*), and Japanese beetle (*Popillia japonica*); weevils such as maize weevil (*Sitophilus zeamais*), rice water weevil (*Lissorhoptrus oryzophilus*), azuki bean weevil (*Callosobruchus chinensis*), rice curculio (*Echinocnemus squameus*), boll weevil (*Anthonomus grandis*), and hunting billbug (*Sphenophorus venatus*); darkling beetles (Tenebrionidae) such as yellow mealworm (*Tenebrio molitor*), and red flour beetle (*Tribolium castaneum*); leaf beetles (Chrysomelidae) such as rice leaf beetle (*Oulema oryzae*), cucurbit leaf beetle (*Aulacophora femoralis*), striped flea beetle (*Phyllotreta striolata*), and Colorado potato beetle (*Leptinotarsa decemlineata*); dermestid beetles (Dermestidae) such as varied carper beetle (*Anthrenus verbasci*), and hide beetle (*Dermestes maculates*); deathwatch beetles (Anobiidae) such as cigarette beetle (*Lasioderma serricorne*); *Epilachna* such as Twenty-eight-spotted ladybird (*Epilachna vigintioctopunctata*); bark beetles (Scolytidae) such as powder-post beetle (*Lyctus brunneus*), and pine shoot beetle (*Tomicus piniperda*); false powder-post beetles (Bostrychidae); spider beetles (Ptinidae); longhorn beetles (Cerambycidae) such as white-spotted longicorn beetle (*Anoplophora malasiaca*); click beetles (*Agriotes* spp.); *Paederus fuscipens*, etc.

Orthoptera:

Asiatic locust (*Locusta migratoria*), African mole cricket (*Gryllotalpa africana*), rice grasshopper (*Oxya yezoensis*), rice grasshopper (*Oxya japonica*), Gryllidae, etc.

Shiphonaptera:

Cat flea (*Ctenocephalides felis*), dog flea (*Ctenocephalides canis*), human flea (*Pulex irritans*), oriental rat flea (*Xenopsylla cheopis*), etc.

Anoplura:

Human body louse (*Pediculus humanus corporis*), crab louse (*Phthirus pubis*), short-nosed cattle louse (*Haematopinus eurysternus*), sheep louse (*Dalmalinia ovis*), hog louse (*Haematopinus suis*), dog louse (*Linognathus setosus*), etc.

Damalinia:

Sheep body louse (*Dalmalinia ovis*), cattle biting louse (*Dalmalinia bovis*), chicken louse (*Menopon gallinae*), dog louse (*Trichodectes canis*), cat louse (*Felicola subrostrata*) etc.

Hymenoptera:

Ants (Formicidae) such as pharaoh ant (*Monomorium pharaosis*), negro ant (*Formica fusca japonica*), black house ant (*Ochetellus glaber*), *Pristomyrmex pungens*, *Pheidole noda*, leaf-cutting ant (*Acromyrmex* spp.), and fire ant (*Solenopsis* spp.); hornets (Vespidae); bethylid wasps (Betylidae); sawflies (Tenthredinidae) such as cabbage sawfly (*Athalia rosae*), and *Athalia japonica*, etc.

Nematoda:

Rice white-tip nematode (*Aphelenchoides besseyi*), strawberry bud nematode (*Nothotylenchus acris*), southern root-knot nematode (*Meloidogyne incognita*), northern root-knot nematode (*Meloidogyne hapla*), Javanese root-knot nematode (*Meloidogyne javanica*), soybean cyst nematode (*Heterodera glycines*), potato cyst nematode (*Globodera rostochiensis*), coffee root-lesion nematode (*Pratylenchus coffeae*), California root-lesion nematode (*Pratylenchus neglectus*), etc.

Blattodea:

German cockroach (*Blattella germanica*), smokybrown cockroach (*Periplaneta fuliginosa*), American cockroach (*Periplaneta americana*), *Periplaneta brunnea*, oriental cockroach (*Blatta orientalis*);

Isoptera:

Termites such as Japanese subterranean termite (*Reticulitermes speratus*), Formosan subterranean termite (*Coptotermes formosanus*), western drywood termite (*Incisitermes minor*), Daikoku drywood termite (*Cryptotermes domesticus*), *Odontotermes formosanus*, *Neotermes koshunensis*, *Glyptotermes satsumesis*, *Glyptotermes nakajimai*, *Glyptotermes fuscus*, *Glyptotermes kodamai*, *Glyptotermes kushimensis*, Japanese dampwood termite (*Hodotermopsis japonica*), *Coptotermes guangzhoensis*, *Reticulitermes miyatakei*, eastern subterranean termite (*Reticulitermes flavipes amamianus*), *Reticulitermes* sp., *Nasutitermes takasagoesis*, *Pericapritermes nitobei*, *Sinocapritermes mushae*, *Reticuliterumes flavipes*, *Reticulitermes hesperus*, *Reticulitermes virginicus*, *Reticulitermes tibialis*, *Heterotermes aureus*, and *Zootermopsis nevadensis*, etc.

Acarina:

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as pink citrus rust mite (*Aculops pelekassi*), *Phyllocoptruta citri*, tomato rust mite (*Aculops lycopersici*), purple tea mite (*Calacarus carinatus*), pink tea rust mite (*Acaphylla theavagran*), *Eriophyes chibaensis*, and apple rust mite (*Aculus schlechtendali*); tarosonemid mites (Tarsonemidae) such as broad mite (*Polyphagotarsonemus latus*); false spider mites (Tenuipalpidae) such as *Brevipalpus phoenicis*; Tuckerellidae; ticks (Ixodidae) such as *Haemaphysalis longicornis*, *Haemaphysalis flava*, *Dermacentor taiwanicus*, American dog tick (*Dermacentor variabilis*), *Ixodes ovatus*, *Ixodes persulcatus*, black leg tick (*Ixodes scapularis*), lone star tick (*Amblyomma americanum*), *Boophilus microplus*, and *Rhipicephalus sanguineus*; Psoroptidae such as ear mite (*Otodectes cynotis*); itch mites (Sarcoptidae) such as *Sarcoptes scabiei*; follicle mites (Demodicidae) such as dog follicle mite (*Demodex canis*); acarid mites (Acaridae) such as mold mite (*Tyrophagus putrescentiae*), and *Tyrophagus similis*; house dust mites (Pyroglyphidae) such as *Dermatophagoides farinae*, and *Dermatophagoides ptrenyssnus*; cheyletide mites (Cheyletidae) such as *Cheyletus eruditus*, *Cheyletus malaccensis*, and *Cheyletus moorei*; parasitoid mites (Dermanyssidae) such as tropical rat mite (*Ornithonyssus bacoti*), northern fowl mite (*Ornithonyssus sylviarum*), and poultry red mite (*Dermanyssus gallinae*); chiggers (Trombiculidae) such as *Leptotrombidium akamushi*; spiders (Araneae) such as Japanese foliage spider (*Chiracanthium japonicum*), redback spider (*Latrodectus hasseltii*), etc.

Chilopoda: house centipede (*Thereuonema hilgendorfi*), *Scolopendra subspinipes*, etc.;

Diplopoda: garden millipede (*Oxidus gracilis*), *Nedyopus tambanus*, etc.;

Isopoda: common pill bug (*Armadillidium vulgare*), etc.;

Gastropoda: *Limax marginatus*, *Limax flavus*, etc.

The pest control agent of the present invention comprises the present compound and an inert carrier. The pest control agent of the present invention generally comprises the present compound in combination with a solid carrier, a liquid carrier and/or a gaseous carrier, and if necessary, a surfactant or other formulation additives and takes the form of emulsifiable concentrate, oil solution, dusts, granules, wettable powder, suspension concentrate, microcapsules, aerosol, smoking agent, poison bait, resin formulation, shampoo formulation, paste, foam, carbon dioxide gas formulation, tablet or the like. The pesticidal composition of the present invention may be processed into mosquito coil, electric mosquito mat, electric mosquito liquid, smoking agent, fumigant, sheet, spot-on pesticide, or oral pesticide, and then be used.

The pesticidal composition of the present invention generally contains 0.01 to 95% by weight of the compound of the present invention.

Examples of the solid carrier to be used for formulation include a fine power and a granule of clays (e.g., kaolin clay, diatomite, bentonite, Fubasami clay, and acid clay), synthetic hydrated silicon oxide, talc, ceramic, other inorganic minerals (e.g., sericite, quartz, sulfur, activated carbon, calcium carbonate, and hydrated silica), and chemical fertilizers (e.g., ammonium sulfate, ammonium phosphate, ammonium nitrate, urea, and ammonium chloride) as well as synthetic resins (e.g., polypropylene, polyacrylonitrile, polyester resins such as methyl polymethacrylate and polyethylene terephthalate, nylon resins such as nylon-6, nylon-11, and nylon-66, polyamide resins, polyvinyl chloride, polyvinylidene chloride, and vinyl chloride-propylene copolymer).

Examples of the liquid carrier include water, alcohols (e.g., methanol, ethanol, isopropyl alcohol, butanol, hexanol, benzyl alcohol, ethylene glycol, propylene glycol, and phenoxyethanol), ketones (e.g., acetone, methyl ethyl ketone, and cyclohexanone), aromatic hydrocarbons (e.g., toluene, xylene, ethylbenzene, dodecylbenzene, phenylxylylethane, and methylnaphthalene), aliphatic hydrocarbons (e.g., hexane, cyclohexane, kerosine, and light oil), esters (e.g., ethyl acetate, butyl acetate, isopropyl mylistate, ethyl oleate, diisopropyl adipate, diisobutyl adipate, and propyleneglycol monomethyl ether acetate), nitriles (e.g., acetonitrile and isobutyronitrile), ethers (e.g., diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, and 3-methoxy-3-methyl-1-butanol), acid amides (e.g., N,N-dimethylformamide and N,N-dimethylacetamide), halogenated hydrocarbons (e.g., dichloromethane, trichloroethane, and tetrachlorocarbon), sulfoxides (e.g., dimethylsulfoxide), propylene carbonate, and vegetable oils (e.g., soy bean oil and cotton seed oil).

Examples of the gaseous carrier include fluorocarbons, butane gas, liquefied petroleum gas (LPG), dimethyl ether, and carbon dioxide.

Examples of the surfactant include nonionic surfactant such as polyoxyethylene alkyl ether, polyoxyethylene alkylaryl ether, and polyethyleneglycol fatty acid ester; and anionic surfactant such as alkylsulfonic acid salts, alkylbenzenesulfonic acid salts, and alkylsulfuric acid salts.

Examples of the other formulation additives include binders, dispersants, colorants and stabilizers, and particularly for example, casein, gelatin, polysaccharides (e.g., starch, gum arabic, cellulose derivatives, and alginic acid), lignin derivatives, synthetic water-soluble polymers (e.g., polyvinyl alcohol, polyvinylpyrrolidone, and polyacrylic acid), PAP (acidic isopropyl phosphate), BHT (2,6-di-t-butyl-4-methylphenol), and BHA (a mixture of 2-t-butyl-4-methoxyphenol and 3-t-butyl-4-methoxyphenol).

Examples of a base material for the resin formulation include vinyl chloride polymers, and polyurethane. To the base material, if necessary, a plasticizer such as phthalate (e.g., dimethyl phthalate, dioctyl phthalate, etc.), adipate, stearic acid or the like may be added. The resin formulation is prepared by kneading the compound of the present invention into the base material, using a conventional kneader, followed by molding such as injection molding, extrusion molding, press molding or the like. The resulting resin formulation may be formed into the shape of a plate, a film, a tape, a net, a string or the like via a further step of molding, cutting, or the like, if necessary. These resin formulations may be used, for example, the form of an animal collar, an animal ear tag, a sheet, a lead, or a horticultural post.

Examples of a base material of the poison bait include cereal powder, vegetable oil, sugar, and crystalline cellulose. To the base material, if necessary, an antioxidant such as dibutylhydroxytoluene, or nordihydroguaiaretic acid, a preservative such as dehydroacetic acid, an agent for preventing children or pets from erroneously eating such as hot pepper powder, a pest-attractive perfume such as cheese perfume, onion perfume or peanut oil or the like may be added.

The method for controlling a pest of the present invention is applying an effective amount of the present compound to a pest directly and/or a habitat of a pest (e.g., plant, soil, indoor, and in-body of animals). The present compound is generally used as the pest control agent of the present invention in the method for controlling pests of the present invention.

When the pest control agent of the present invention is used for a control of pests in agriculture, the application amount is usually 1 to 10,000 g as the present compound per 10,000 $m^2$. When the pest control agent of the present invention is a formulation of emulsion, wettable powder or flowable, it is generally applied after a dilution with water to have an active ingredient concentration of 0.01 to 10,000 ppm. When the pest control agent of the present invention is a formulation of granules or dusts, they are generally applied as such.

The formulations and the dilute aqueous solutions of the formulation may be sprayed directly to the plant to be protected from pests, or may be applied to the soil to control the pests living in a soil.

Furthermore, the resin formulation of sheet or strip form can be applied by a method such as winding around plants, stretching in the vicinity of plants, and laying on the soil surface at the plant bottom.

When the pest control agent of the present invention is used for a control of pests in indoor, the application amount is usually 0.01 to 1,000 mg as the present compound per 1 $m^2$ in case of application for plane surface, and 0.01 to 500 mg as the present compound per 1 $m^3$ in case of application for space. When the pest control agent of the present invention is a formulation of emulsions, wettable powders or flowables, they are usually applied after a dilution with water to have an active ingredient concentration of 0.1 to 1,000 ppm. When the pest control agent of the present invention is a formulation of oil solutions, aerosols, smoking agents and poison baits, they are usually applied as such.

When the pesticidal composition of the present invention is used for controlling external parasites of livestock such as a cow, a horse, a pig, a sheep, a goat and a chicken, or small animals such as a dog, a cat, a rat and a mouse, it can be applied to said animals by a known method in the veterinary field. Specifically, when systemic control is intended, the pesticidal composition of the present invention is administered, for example, as a tablet, a mixture with feed, a suppository or an injection (e.g., intramuscularly, subcutaneously, intravenously, intraperitoneally, etc.). When non-systemic control is intended, a method of using the pesticidal composition of the present invention includes spraying, pour-on treatment or a spot-on treatment with the pesticidal composition in the form of an oil solution or an aqueous liquid, washing an animal with the pesticidal composition in the form of a shampoo formulation, and attachment of a collar or a ear tag made of the pesticidal composition in the form of a resin formulation to an animal. When administered to an animal, the amount of the compound of the present invention is usually in the range of 0.1 to 1,000 mg per 1 kg body weight of the animal.

The pest control agent of the present invention could be used in farmlands on which "crops" shown below are cultivated.

Agricultural crops: corn, rice, wheat, barley, rye, oat, sorghum, cotton, soybean, peanut, sarrazin, sugar beet, rapeseed, sunflower, sugar cane, and tobacco;

Vegetables: Solanaceae vegetables (e.g., eggplant, tomato, green pepper, hot pepper, and potato), Cucurbitaceae vegetables (e.g., cucumber, pumpkin, zucchini, watermelon, and melon), Cruciferae vegetables (e.g., Japanese radish, turnip, horseradish, kohlrabi, Chinese cabbage, cabbage, brown mustard, broccoli, and cauliflower), Compositae vegetables (e.g., burdock, garland chrysanthemum, artichoke, and lettuce), Liliaceae vegetables (e.g., Welsh onion, onion, garlic, and asparagus), Umbelliferae vegetables (e.g., carrot, parsley, celery, and parsnip), Chenopodiaceae vegetables (e.g., spinach, and Swiss chard), Labiatae vegetables (e.g., Japanese basil, mint, and basil), strawberry, sweat potato, yam, and aroid;

Fruit trees: pomaceous fruits (e.g., apple, common pear, Japanese pear, Chinese quince, and quince), stone fleshy fruits (e.g., peach, plum, nectarine, Japanese plum, cherry, apricot, and prune), citrus plants (e.g., Satsuma mandarin, orange, lemon, lime, and grapefruit), nuts (e.g., chestnut, walnut, hazel nut, almond, pistachio, cashew nut, and macadamia nut), berry fruits (e.g., blueberry, cranberry, blackberry, and raspberry), grape, persimmon, olive, loquat, banana, coffee, date, coconut palm, and oil palm;

Trees other fruit trees: tea, mulberry, flowering trees (e.g., azalea, japonica, hydrangea, sasanqua, *Illicium anisatum*, cherry tree, tulip poplar, crepe myetle, and orange osmanthus), street trees (e.g., ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, and horse-chestnut), sweet viburnum, *Podocarpus macrophyllus*, Japanese cedar, Japanese cypress, croton, spindle tree, and Chainese howthorn.

Lawn: zoysia (e.g., Japanese lawn grass and mascarene grass), Bermuda grass (e.g., *Cynodon dactylon*), bent grass (e.g., creeping bent grass, *Agrostis stolonifera*, and *Agrostis tenuis*), bluegrass (e.g., Kentucky bluegrass and rough bluegrass), fescue (e.g., tall fescue, chewing fescue, and creeping fescue), ryegrass (e.g., darnel and perennial ryegrass), cocksfoot, and timothy grass;

Others: flowers (e.g., rose, carnation, chrysanthemum, Eustoma grandiflorum Shinners, gypsophila, gerbera, pot marigold, salvia, petunia, verbena, tulip, aster, gentian, lily, pansy, cyclamen, orchid, lily of the valley, lavender, stock, ornamental kale, primula, poinsettia, gladiolus, cattleya, daisy, cymbidium, and begonia), biofuel plants (e.g., Jatropha, curcas, safflower, Camelina alyssum, switchgrass, miscanthus, reed canary grass, Arundo donax, kenaf, cassava, willow, and algae), and foliage plant.

The "crops" include genetically modified crops.

The pest control agent of the present invention can be used as a mixture with or together with other insecticides, acaricides, nematocides, fungicides, plant growth regulators, herbicides, and synergists. Examples of active ingredients of the insecticide, the acaricide, the nematocide, the fungicide, the herbicide, and the synergist are shown below.

Examples of active ingredients of the insecticides include:
(1) Organic Phosphorus Compounds:
  acephate, aluminium phosphide, butathiofos, cadusafos, chlorethoxyfos, chlorfenvinphos, chlorpyrifos, chlorpyrifos-methyl, cyanophos: CYAP, diazinon, DCIP (dichlorodiisopropyl ether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, Hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, and cadusafos.
(2) Carbamate Compounds:
  alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, and aldicarb.
(3) Synthetic Pyrethroid Compounds:
  acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetra fluoro-4-(methoxymethyl)benzyl(EZ)-(1RS,3RS;1RS, 3SR)-2,2-dimethyl-3-prop-1-enylcyclopropane carboxylate, 2,3,5,6-tetrafluoro-4-methylbenzyl(EZ)-(1RS,3RS;1RS, 3SR)-2,2-dimethyl-3-prop-1-enylcyclopropane carboxylate, and 2,3,5,6-tetrafluoro-4-(methoxymethyl)benzyl(1RS,3RS; 1RS,3SR)-2,2-dimethyl-3-(2-methyl-1-propenyl)cyclopropane carboxylate, 2,3,5,6-tetrafluoro-4-(methoxymethyl) benzyl(EZ)-(1RS,3RS;1RS,3SR)-2,2-dimethyl-3-(2-cyano-1-propenyl)cyclopropane carboxylate.
(4) Nereistoxin Compounds:
  cartap, bensultap, thiocyclam, monosultap, and bisultap.
(5) Neonicotinoid Compounds:
  imidacloprid, nitenpyram, acetamiprid, thiamethoxam, thiacloprid, dinotefuran, and clothianidin.

(6) Benzoylurea Compounds:
chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, and triazuron.

(7) Phenylpyrazole Compounds:
acetoprole, ethiprole, fipronil, vaniliprole, pyriprole, and pyrafluprole.

(8) Bt Toxin Insecticides:
live spores derived from and crystal toxins produced from Bacillus thuringiesis and a mixture thereof;

(9) Hydrazine Compounds:
chromafenozide, halofenozide, methoxyfenozide, and tebufenozide.

(10) Organic Chlorine Compounds:
aldrin, dieldrin, dienochlor, endosulfan, and methoxychlor.

(11) Other Insecticides:
machine oil, nicotine-sulfate; avermectin-B, bromopropylate, buprofezin, chlrphenapyr, cyantraniliprole, cyromazine, D-D (1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, sulfoxaflor, Sulfur, metaflumizone, spirotetramat, pyrifluquinazone, spinetoram, chlorantraniliprole, tralopyril, cyantraniliprole, a compound represented by the following formula (K):

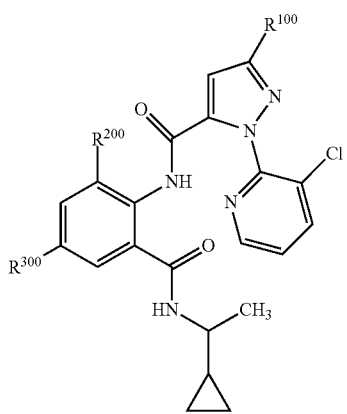

wherein
$R^{100}$ represents chlorine, bromine or a trifluoromethyl group,
$R^{200}$ represents chlorine, bromine or a methy group,
$R^{300}$ represents chlorine, bromine or a cyano group, and
A compound represented by the following formula (L):

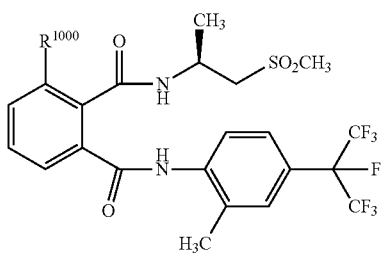

wherein
$R^{1000}$ represents chlorine, bromine or iodine.

Examples of active ingredients of the acaricides include acequinocyl, amitraz, benzoximate, bifenaate, bromopropylate, chinomethionat, chlorobenzilate, CPCBS (chlorfenson), clofentezine, cyflumetofen, dicofol, etoxazole, fenbutatin oxide, fenothiocarb, fenpyroximate, fluacrypyrim, fluproxyfen, hexythiazox, propargite: BPPS, polynactins, pyridaben, Pyrimidifen, tebufenpyrad, tetradifon, spirodiclofen, spiromesifen, spirotetramat, amidoflumet, and cyenopyrafen.

Examples of active ingredients of the nematicides include DCIP, fosthiazate, levamisol, methylsothiocyanate, morantel tartarate, and imicyafos.

Examples of active ingredients of the fungicides include azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol;
cyclic amine fungicidal compounds such as fenpropimorph, tridemorph, and fenpropidin;
benzimidazole fungicidal compounds such as carbendezim, benomyl, thiabendazole, and thiophanate-methyl;
procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid; proquinazid; isotianil and tiadinil.

Examples of active ingredients of the herbicides and the phytohormone agents include:
(1) phenoxyfatty acid herbicidal compounds such as 2,4-PA, MCP, MCPS, phenothiol, mecoprop, fluoroxypyr, triclopyr, clomeprop, and naproanilide.
(2) benzoic acid herbicidal compounds such as 2,3,6-TBA, dicamba, clopyralid, picloram, aminopyralid, quinclorac, and quinmerac.
(3) urea herbicidal compounds such as diuron, linuron, chlortoluron, isoproturon, fluometuron, isouron, tebuthiuron, methabenzthiazuron, cumyluron, daimuron, and methyldaimuron.
(4) triazine herbicidal compounds such as atrazine, ametoryn, cyanazine, simazine, propazine, simetryn, dimethametryn, prometryn, metribuzin, triaziflam, and indaziflam.
(5) bipyridinium herbicidal compounds such as paraquat, and diquat.
(6) hydroxybenzonitrile herbicidal compounds such as bromoxynil, and ioxynil.
(7) dinitroaniline herbicidal compounds such as pendimethalin, prodiamine, and trifluralin.
(8) organic phosphorus herbicidal compounds such as amiprofos-methyl, butamifos, bensulide, piperophos, anilofos, glyphosate, glufosinate, glufosinate-P, and bialaphos.
(9) carbamate herbicidal compounds such as di-allate, triallate, EPTC, butylate, benthiocarb, esprocarb, molinate, dimepiperate, swep, chlorpropham, phenmedipham, phenisopham, pyributicarb, and asulam.
(10) acid amide herbicidal compounds such as propanil, propyzamide, bromobutide) and etobenzanid.
(11) chloroacetanilide herbicidal compounds such as acetochlor, alachlor, butachlor, dimethenamid, propachlor, metazachlor, metolachlor, pretilachlor, thenylchlor, and pethoxamid.

(12) diphenylether herbicidal compounds such as acifluorfen-sodium, bifenox, oxyfluorfen, lactofen), fomesafen, chlomethoxynil, and aclonifen.
(13) cyclic imide herbicidal compounds such as oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.
(14) pyrazole herbicidal compounds such as benzofenap, pyrazolate, pyrazoxyfen, topramezone, and pyrasulfotole.
(15) triketone herbicidal compounds such as isoxaflutole, benzobicyclon, sulcotrione, mesotrione, tembotrione, and tefuryltrione.
(16) aryloxyphenoxypropionic acid herbicidal compounds such as clodinafop-propargyl, cyhalofop-butyl, diclofop-methyl, fenoxaprop-ethyl, fluazifop-butyl, haloxyfop-methyl, and quizalofop-ethyl, metamifop.
(17) trioneoxime herbicidal compounds such as alloxydim-sodium, sethoxydim, butroxydim, clethodim, cloproxydim, cycloxydim, tepraloxydim, tralkoxydim, and profoxydim.
(18) sulfonylurea herbicidal compounds such as chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.
(19) imidazolinone herbicidal compounds such as imazamethabenz-methyl, imazamethapyr, imazamox, imazapyr, imazaquin, and imazethapyr.
(20) sulfonamide herbicidal compounds such as flumetsulam, metosulam, diclosulam, florasulam, cloransulam-methyl, penoxsulam, and pyroxsulam.
(21) pyrimidinyloxybenzoic acid herbicidal compounds such as pyrithiobac-sodium, bispyribac-sodium, pyriminobac-methyl, pyribenzoxim, pyriftalid, and pyrimisulfan.
(22) other herbicidal compounds such as bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.

Examples of active ingredients of the synergists include piperonyl butoxide, sesamex, sulfoxide, N-(2-ethylhexyl)-8,9,10-trinorborn-5-ene-2,3-dicarboximide (MGK 264), N-declyimidazole, WARF-antiresistant, TBPT, TPP, IBP, PSCP, methyl iodide ($CH_3I$), t-phenylbutenone, diethylmaleate, DMC, FDMC, ETP, and ETN.

EXAMPLES

Hereinafter, the present invention is described in more detail by reference to Production Examples, Reference Production Examples, Formulation Examples and Test Examples which the present invention is not limited to.

Firstly, Production Examples of the present compound are described below.

Production Example 1(1)

A mixture of $N^2$-methyl-5-trifluoromethylpyridin-2,3-diamine (0.76 g), 3-fluoropyridin-2-carboaldehyde (0.50 g), sodium hydrogen sulfite (0.50 g) and DMF (3 ml) was stirred at 120° C. for 8 hours. To the cooled reaction mixture was added saturated aqueous sodium hydrogen carbonate solution, and extracted with ethyl acetate. The organic layer was washed with water, dried over anhydrous magnesium sulfate, and concentrated under reduced pressure. The residue was subjected to silica gel column chromatography to give 2-(3-fluoropyridin-2-yl)-3-methyl-6-trifluoromethyl-3H-imidazo[4,5-b]pyridine (0.43 g), which is hereinafter referred to as "intermediate compound (M6-2)".

Intermediate Compound (M6-2)

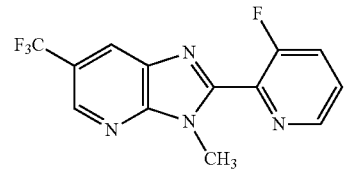 [SMILES: Cn1c(-c2ncccc2F)nc2cc(C(F)(F)F)cnc21]

$^1$H-NMR ($CDCl_3$) δ: 8.75 (1H, d), 8.66-8.63 (1H, m), 8.40 (1H, d), 7.73-7.67 (1H, m), 7.56-7.51 (1H, m), 4.16 (3H, s).

Production Example 1(2)

To a mixture of the intermediate compound (M6-2) (1.23 g) and DMF (3.5 ml) was added sodium ethanethiolate (0.48 g) while ice-cooling, and the mixture was stirred at room temperature for 2 hours. To the reaction mixture was added water, and the mixture was extracted with ethyl acetate. The organic layer was washed with water, dried over anhydrous magnesium sulfate, and concentrated under reduced pressure. The resulting residue was subjected to silica gel column chromatography to give 2-(3-ethylsulfanyl pyridin-2-yl)-3-methyl-6-trifluoromethyl-3H-imidazo[4,5-b]pyridine (1.39 g), which is hereinafter referred to as "the present compound 1".

The Present Compound 1

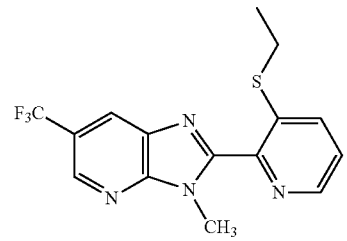 [SMILES: CCSc1cccnc1-c1nc2cc(C(F)(F)F)cnc2n1C]

$^1$H-NMR ($CDCl_3$) δ: 8.73 (1H, d), 8.53 (1H, dd), 8.39 (1H, d), 7.80 (1H, dd), 7.40 (1H, dd), 4.04 (3H, s), 2.97 (2H, q), 1.35 (3H, t).

Production Examples 2 and 3

To a mixture of 2-(3-ethylsulfanyl pyridin-2-yl)-3-methyl-6-trifluoromethyl-3H-imidazo[4,5-b]pyridine (0.62 g) and chloroform (10 ml) was added m-chloroperbenzoic acid (purity: not less than 65%) (0.79 g) while ice-cooling, and then the mixture was stirred at room temperature for 5 hours. To the reaction mixture was poured saturated aqueous sodium hydrogen carbonate solution, and the mixture was extracted with chloroform. The organic layer was washed with water, dried over anhydrous magnesium sulfate, and concentrated under reduced pressure. The resulting residue was subjected to silica gel column chromatography to give 2-(3-ethylsulfinyl pyridin-2-yl)-3-methyl-6-trifluoromethyl-3H-imidazo[4,5-b]pyridine (87 mg), which is hereinafter referred to as "the present compound 2", and 2-(3-ethylsulfonylpyridin-2-yl)-3-methyl-6-trifluoromethyl-3H-imidazo[4,5-b]pyridine (0.49 g), which is hereinafter referred to as "the present compound 3".
The Present Compound 2

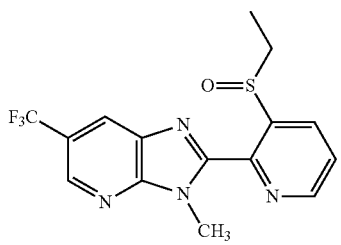 [SMILES: CCS(=O)c1cccnc1-c1nc2cc(C(F)(F)F)cnc2n1C]

$^1$H-NMR (CDCl$_3$) δ: 8.85 (1H, dd), 8.77 (1H, s), 8.67 (1H, dd), 8.34 (1H, s), 7.69 (1H, dd), 4.36 (3H, s), 3.72-3.62 (1H, m), 3.14-3.04 (1H, m), 1.47 (3H, t).
The Present Compound 3

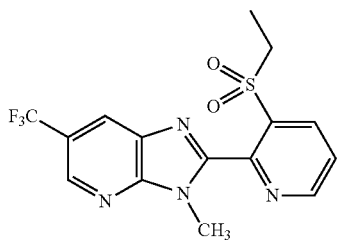 [SMILES: CCS(=O)(=O)c1cccnc1-c1nc2cc(C(F)(F)F)cnc2n1C]

$^1$H-NMR (CDCl$_3$) δ: 9.01 (1H, dd), 8.76 (1H, s), 8.55 (1H, dd), 8.31 (1H, s), 7.74 (1H, dd), 3.88 (3H, s), 3.83 (2H, q), 1.37 (3H, t).

Production Example 4(1)

A mixture of N$^2$-methyl-5-trifluoromethylpyridin-2,3-diamine (0.70 g), 3-chloro-5-trifluoromethylpyridin-2-carboxylic acid (0.53 g), WSC (0.82 g), HOBt (42 mg) and pyridine (4.5 ml) was stirred at 60° C. for 4 hours. To the cooled reaction mixture was added water, and the mixture was extracted with ethyl acetate. The organic layer was washed with water, dried over anhydrous magnesium sulfate, and concentrated under reduced pressure to give an intermediate compound (M20-3).
Intermediate Compound (M20-3)

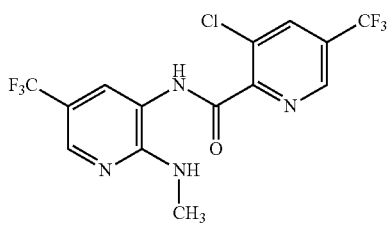 [SMILES: CNc1ncc(C(F)(F)F)cc1NC(=O)c1ncc(C(F)(F)F)cc1Cl]

A mixture of the resulting intermediate compound (M3-4) (total amount), p-toluenesulfonic acid monohydrate (1.04 g) and N-methylpyrrolidinone (4 ml) was stirred while heating to 150° C. for 2.5 hours. To the cooled reaction mixture was added saturated aqueous sodium hydrogen carbonate solution, and the mixture was extracted with ethyl acetate. The organic layer was washed with water, dried over anhydrous magnesium sulfate, and concentrated under reduced pressure. The resulting residue was subjected to silica gel column chromatography to give 2-(3-chloro-5-trifluoromethylpyridin-2-yl)-3-methyl-6-trifluoromethyl-3H-imidazo[4,5-b]pyridine (0.71 g), which is hereinafter referred to as "intermediate compound (M6-3)".
Intermediate Compound (M6-3)

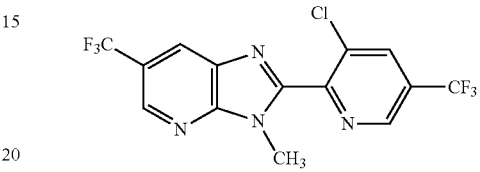

$^1$H-NMR (CDCl$_3$) δ: 8.96 (1H, d), 8.79 (1H, d), 8.42 (1H, d), 8.22 (1H, d), 4.02 (3H, s).

Production Example 4(2)

To a mixture of 2-(3-chloro-5-trifluoromethylpyridin-2-yl)-3-methyl-6-trifluoromethyl-3H-imidazo[4,5-b]pyridine (0.71 g) and DMF (4 ml) was added sodium ethanethiolate (0.24 g) while ice-cooling, and the mixture was stirred at room temperature for 1 hour. To the reaction mixture was added water, and the mixture was extracted with ethyl acetate. The organic layer was washed with water, dried over anhydrous magnesium sulfate, and concentrated under reduced pressure to give 2-(3-ethylsulfanyl-5-trifluoromethylpyridin-2-yl)-3-methyl-6-trifluoromethyl-3H-imidazo[4,5-b]pyridine (0.76 g), which is hereinafter referred to as "the present compound 4".
The Present Compound 4

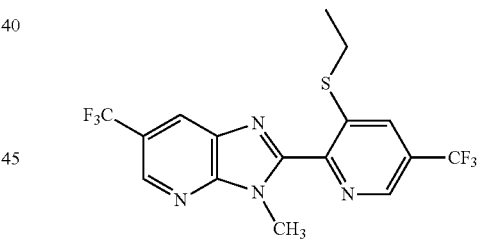

$^1$H-NMR (CDCl$_3$) δ: 8.77 (1H, d), 8.75 (1H, d), 8.43 (1H, d), 7.93 (1H, d), 4.11 (3H, s), 3.02 (2H, q), 1.40 (3H, t).

Production Example 5

To a mixture of 2-(3-ethylsulfanyl-5-trifluoromethylpyridin-2-yl)-3-methyl-6-trifluoromethyl-3H-imidazo[4,5-b]pyridine (0.61 g) and chloroform (10 ml) was added m-chloroperbenzoic acid (purity: not less than 65%) (0.66 g) while ice-cooling, and the mixture was stirred at room temperature for 10 hours. To the reaction mixture were added aqueous 10% sodium thiosulfate solution and saturated aqueous sodium hydrogen carbonate solution, and the mixture was extracted with chloroform. The organic layer was washed with water, dried over anhydrous magnesium sulfate, and concentrated under reduced pressure to give 2-(3-ethylsulfonyl-5-trifluoromethylpyridin-2-yl)-3-methyl-6-trifluoromethyl-3H-imidazo[4,5-b]pyridine (0.62 g), which is hereinafter referred to as "the present compound 5".

The Present Compound 5

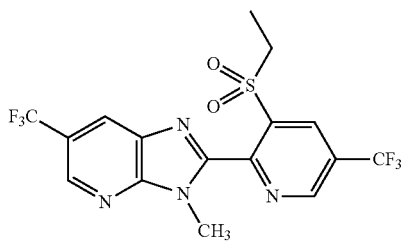 [SMILES: CCS(=O)(=O)c1cc(C(F)(F)F)cnc1-c1nc2cc(C(F)(F)F)cnc2n1C]

¹H-NMR (CDCl₃) δ: 9.25 (1H, d), 8.80 (1H, d), 8.79 (1H, d), 8.34 (1H, d), 3.96 (2H, q), 3.94 (3H, s), 1.42 (3H, t).

Production Example 6

A mixture of 2-(3-ethylsulfanyl-pyridin-2-yl)-6-iodo-3-methyl-3H-imidazo[4,5-b]pyridine (835 mg), sodium pentafluoropropionate (2.0 g), copper iodide (2.0 g), NMP (10 ml) and xylene (50 ml) was stirred while heating to 150° C. for 8 hours. After allowing to cool to room temperature, to the reaction mixture were added 40% aqueous ammonia solution and saturated aqueous sodium hydrogen carbonate solution and the mixture was extracted with ethyl acetate. The organic layer was dried over sodium sulfate, and concentrated under reduced pressure. The residue was subjected to silica gel column chromatography to give 2-(3-ethylsulfanyl-pyridin-2-yl)-3-methyl-6-pentafluoroethyl-3H-imidazo[4,5-b]pyridine (303 mg) which is hereinafter referred to as "the present compound 6".

The Present Compound 6

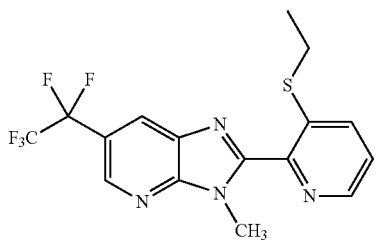

¹H-NMR (CDCl₃) δ: 8.69 (1H, d), 8.52 (1H, dd), 8.40 (1H, d), 7.80 (1H, dd), 7.39 (1H, dd), 4.06 (3H, s), 2.97 (2H, q), 1.34 (3H, t).

Production Examples 7 and 8

To a mixture of 2-(3-ethylsulfanyl-pyridin-2-yl)-3-methyl-6-pentafluoroethyl-3H-imidazo[4,5-b]pyridine (254 mg) and chloroform (10 ml) was added m-chloroperbenzoic acid (purity: not less than 65%) (266 mg) while ice-cooling. The mixture was heated to room temperature and then stirred for 0.5 hours. To the mixture were poured saturated aqueous sodium hydrogen carbonate solution and saturated aqueous sodium thiosulfate solution, and the mixture was extracted with chloroform. The organic layer was dried over magnesium sulfate and concentrated under reduced pressure. The residue was subjected to silica gel column chromatography to give 2-(3-ethane sulfinyl-pyridin-2-yl)-3-methyl-6-pentafluoroethyl-3H-imidazo[4,5-b]pyridine (8 mg), which is hereinafter referred to as "the present compound 7"), and 2-(3-ethanesulfonyl-pyridin-2-yl)-3-methyl-6-pentafluoro-ethyl-3H-imidazo[4,5-b]pyridine (235 mg), which is hereinafter referred to as "the present compound 8".

The Present Compound 7

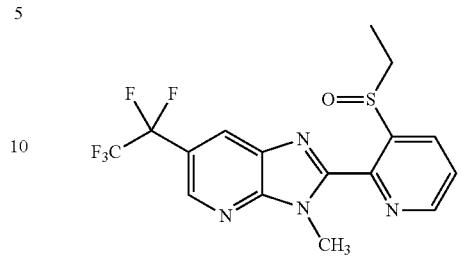

¹H-NMR (CDCl₃) δ: 8.85 (1H, dd), 8.72 (1H, d), 8.68 (1H, dd), 8.31 (1H, d), 7.69 (1H, dd), 4.36 (3H, s), 3.72-3.61 (1H, m), 3.17-3.06 (1H, m), 1.47 (3H, t).

The Present Compound 8

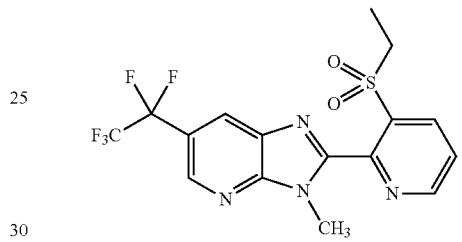

¹H-NMR (CDCl₃) δ: 9.00 (1H, dd), 8.72 (1H, d), 8.55 (1H, dd), 8.30 (1H, d), 7.73 (1H, dd), 3.89 (3H, s), 3.84 (2H, q), 1.37 (3H, t).

Production Example 9(1)

To a mixture of 5-iodo-N²-methyl-pyridin-2,3-diamine (1.9 g) and pyridine (6 ml) were added WSC (1.28 g), HOBt (86 mg) and 3-chloro-pyridin-2-carboxylic acid (1.3 g), and the mixture was stirred at room temperature for 9 hours. To this reaction mixture was added water, and the mixture was filtered to collect the precipitated powder. The collected powder was washed with chloroform to give 3-chloro-pyridin-2-carboxylic acid (5-iodo-2-methylamino-pyridin-3-yl)-amide (3.6 g), which is hereinafter referred to as "intermediate compound (M20-7)".

Intermediate Compound (M20-7)

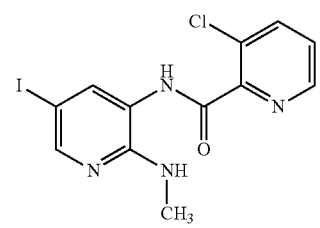 [SMILES: CNc1ncc(I)cc1NC(=O)c1ncccc1Cl]

¹H-NMR (DMSO-d⁶) δ: 9.95 (1H, s), 8.65 (1H, d), 8.15-8.10 (2H, m), 8.00 (1H, d), 7.65 (1H, dd), 6.30 (1H, d), 2.81 (3H, d).

Production Example 9(2)

A mixture of the intermediate compound (M20-7) (3.4 g), p-toluenesulfonic acid monohydrate (5.8 g), DMF (30 ml)

and toluene (120 ml) was stirred while heating to 130° C. for 12 hours. After allowing to cool to room temperature, to the mixture was poured saturated aqueous sodium hydrogen carbonate solution, and the mixture was extracted with ethyl acetate. The organic layer was dried over sodium sulfate, and concentrated under reduced pressure. The residue was subjected to silica gel column chromatography to give 2-(3-chloro-pyridin-2-yl)-6-iodo-3-methyl-3H-imidazo[4,5-b]pyridine (2.0 g), which is hereinafter referred to as "intermediate compound (M6-7)".

Intermediate Compound (M6-7)

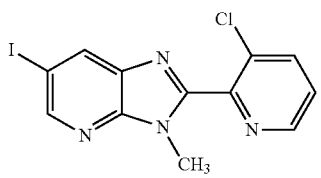

$^1$H-NMR (CDCl$_3$) δ: 8.70 (1H, d), 8.66-8.63 (1H, m), 8.47-8.44 (1H, m), 7.95 (1H, d), 7.45 (1H, dd), 3.90 (3H, s).

Production Example 9(3)

A mixture of the intermediate compound (M6-7) (2.0 g), sodium ethanethiolate (888 mg) and DMF (45 ml) was stirred while heating at 50° C. for 12 hours. After allowing to cool to room temperature, to the mixture was poured saturated aqueous sodium hydrogen carbonate solution, and the mixture was extracted with ethyl acetate. The organic layer was dried over sodium sulfate, and concentrated under reduced pressure. The residue was subjected to silica gel column chromatography to give 2-(3-ethylsulfanyl-pyridin-2-yl)-6-iodo-3-methyl-3H-imidazo[4,5-b]pyridine (1.0 g), which is hereinafter referred to as "the present compound 9".

The Present Compound 9

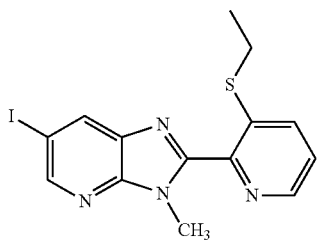

$^1$H-NMR (CDCl$_3$) δ: 8.61 (1H, d), 8.51 (1H, dd), 8.45 (1H, d), 7.76 (1H, dd), 7.37 (1H, dd), 3.96 (3H, s), 2.94 (2H, q), 1.33 (3H, t).

Production Example 10(1)

A mixture of 3-amino-5-trifluoromethylpyridin-2-thiol (0.45 g), 3-chloro-5-trifluoromethylpyridin-2-carboxylic acid (0.55 g), WSC (0.67 g), HOBt (31 mg) and pyridine (4.5 ml) was stirred at 60° C. for 4 hours. To the cooled reaction mixture was added water, and the mixture was extracted with ethyl acetate. The organic layer was washed with water, dried over anhydrous magnesium sulfate, and concentrated under reduced pressure to give intermediate compound (M20-9).

Intermediate Compound (M20-9)

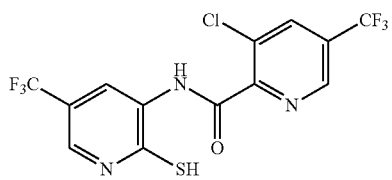 [SMILES: O=C(Nc1cc(C(F)(F)F)cnc1S)c1ncc(C(F)(F)F)cc1Cl]

A mixture of the resulting intermediate compound (M20-9) (total amount), p-toluenesulfonic acid monohydrate (1.04 g) and N-methylpyrrolidinone (3.5 ml) was stirred while heating to 150° C. for 2 hours. To the cooled reaction mixture was added saturated aqueous sodium hydrogen carbonate solution, and extracted with ethyl acetate. The organic layer was washed with water, dried over anhydrous magnesium sulfate, and concentrated under reduced pressure. The resulting residue was subjected to silica gel column chromatography to give 2-(3-chloro-5-trifluoromethylpyridin-2-yl)-6-(trifluoromethyl)thiazolo[5,4-b]pyridine (0.29 g), which is hereinafter referred to as "intermediate compound (M6-9)".

Intermediate Compound (M6-9)

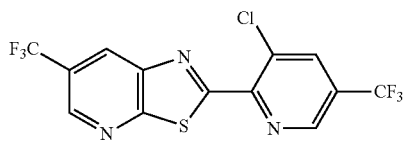 [SMILES: FC(F)(F)c1cnc(-c2nc3cc(C(F)(F)F)cnc3s2)c(Cl)c1]

$^1$H-NMR (CDCl$_3$) δ: 8.94 (1H, d), 8.90 (1H, d), 8.69 (1H, d), 8.19 (1H, d).

Production Example 10(2)

2-(3-ethylsulfanyl-5-trifluoromethylpyridin-2-yl)-6-(trifluoromethyl)thiazolo[5,4-b]pyridine (hereinafter referred to as "the present compound 10") was synthesized in the same manner as in Production Example 4(2) except for using the intermediate compound (M6-9) instead of 2-(3-chloro-5-trifluoromethylpyridin-2-yl)-3-methyl-6-trifluoromethyl-3H-imidazo[4,5-b]pyridine.

The Present Compound 10

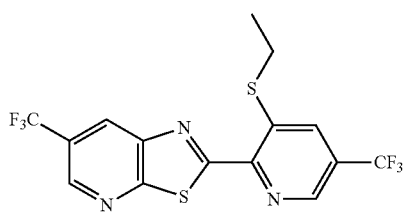 [SMILES: CCSc1cc(C(F)(F)F)cnc1-c1nc2cc(C(F)(F)F)cnc2s1]

$^1$H-NMR (CDCl$_3$) δ: 8.91 (1H, d), 8.70-8.67 (2H, m), 7.91 (1H, s), 3.09 (2H, q), 1.51 (3H, t).

Production Example 11

2-(3-ethylsulfonyl-5-trifluoromethylpyridin-2-yl)-6-(trifluoromethyl)thiazolo[5,4-b]pyridine (hereinafter referred to as "the present compound 11") was synthesized in the same manner as in Production Example 5 except for using 2-(3-ethylsulfanyl-5-trifluoromethylpyridin-2-yl)-6-(trifluoromethyl)thiazolo[5,4-b]pyridine instead of 2-(3-ethylsulfanyl-5-trifluoromethylpyridin-2-yl)-3-methyl-6-trifluoromethyl-3H-imidazo[4,5-b]pyridine.

The Present Compound 11

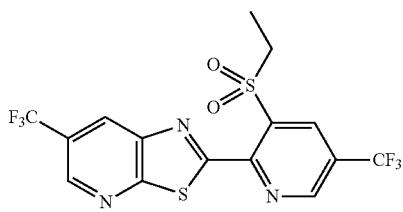 [SMILES: CCS(=O)(=O)c1cc(C(F)(F)F)cnc1-c1nc2cc(C(F)(F)F)cnc2s1]

$^1$H-NMR (CDCl$_3$) δ: 9.19 (1H, d), 8.98 (1H, d), 8.89 (1H, d), 8.61 (1H, d), 4.17 (2H, q), 1.49 (3H, t).

Production Example 12(1)

A mixture of 3-amino-5-trifluoromethylpyridin-2-thiol (0.45 g), 3-chloropyridin-2-carboxylic acid (0.39 g), WSC (0.67 g), HOBt (31 mg) and pyridine (4 ml) was stirred at room temperature for 12 hours. To the reaction mixture was added water, and the mixture was filtered to collect a solid. The resulting solid was washed with water, followed by n-hexane, and dried to give 3-chloropyridin-2-carboxylic acid (2-mercapto-5-trifluoromethylpyridin-3-yl)-amide (0.45 g), which is hereinafter referred to as "intermediate compound (M20-11)".

Intermediate Compound (M20-11)

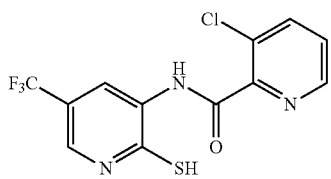 [SMILES: O=C(Nc1cc(C(F)(F)F)cnc1S)c1ncccc1Cl]

Production Example 12(2)

A mixture of the intermediate compound (M20-11) (0.45 g), p-toluenesulfonic acid monohydrate (0.70 g) and NMP (4 ml) was stirred at 150° C. for 2 hours. To the cooled reaction mixture was added saturated aqueous sodium hydrogen carbonate solution, and extracted with ethyl acetate. The organic layer was washed with water, dried over anhydrous magnesium sulfate, and concentrated under reduced pressure. The resulting residue was subjected to silica gel column chromatography to give 2-(3-chloropyridin-2-yl)-6-(trifluoromethyl)thiazolo[5,4-b]pyridine (0.47 g), which is hereinafter referred to as "intermediate compound (M6-11)".

Intermediate Compound (M6-11)

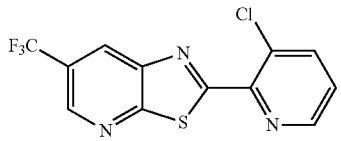 [SMILES: FC(F)(F)c1cnc2sc(-c3ncccc3Cl)nc2c1]

Production Example 12(3)

2-(3-ethylsulfanyl-2-yl)-6-(trifluoromethyl)thiazolo[5,4-b]pyridine (hereinafter referred to as "the present compound 41") was synthesized in the same manner as in Production Example 1(2) except for using the intermediate compound (M6-11) instead of 2-(3-fluoropyridin-2-yl)-3-methyl-6-trifluoromethyl-3H-imidazo[4,5-b]pyridine.

The Present Compound 41

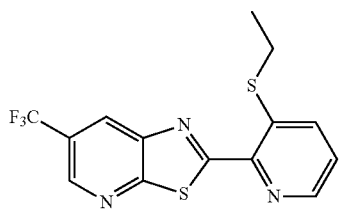 [SMILES: CCSc1cccnc1-c1nc2cc(C(F)(F)F)cnc2s1]

$^1$H-NMR (CDCl$_3$) δ: 8.87 (1H, d), 8.64 (1H, d), 8.48 (1H, dd), 7.76 (1H, dd), 7.37 (1H, dd), 3.06 (2H, q), 1.49 (3H, t).

Production Example 12(4)

To a mixture of 2-(3-ethylsulfanyl-2-yl)-6-(trifluoromethyl)thiazolo[5,4-b]pyridine (0.36 g) and chloroform (5 ml) was added m-chloroperbenzoic acid (purity: not less than 65%) (0.56 g), and the mixture was stirred at room temperature for 12 hours. To the reaction mixture were poured aqueous 10% sodium thiosulfate solution and saturated aqueous sodium hydrogen carbonate solution, and the mixture was extracted with chloroform. The organic layer was washed with water, dried over anhydrous magnesium sulfate, and concentrated under reduced pressure to give 2-(3-ethylsulfonyl-2-yl)-6-(trifluoromethyl)thiazolo[5,4-b]pyridine (0.27 g), which is hereinafter referred to as "the present compound 12", and 2-(3-ethylsulfonyl-2-yl)-6-(trifluoromethyl)thiazolo[5,4-b]pyridine 4-oxide (91 mg), which is hereinafter referred to as "the present compound 22".

The Present Compound 12

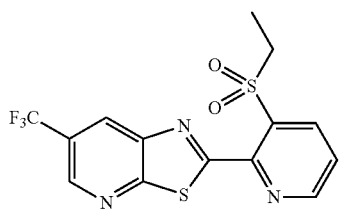 [SMILES: CCS(=O)(=O)c1cccnc1-c1nc2cc(C(F)(F)F)cnc2s1]

$^1$H-NMR (CDCl$_3$) δ: 8.98-8.93 (2H, m), 8.66 (1H, dd), 8.57 (1H, d), 7.69 (1H, dd), 4.13 (2H, q), 1.45 (3H, t).

The Present Compound 22

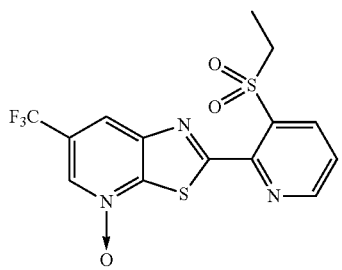 [SMILES: CCS(=O)(=O)c1cccnc1-c1nc2cc(C(F)(F)F)c[n+]([O-])c2s1]

$^1$H-NMR (CDCl$_3$) δ: 8.96 (1H, dd), 8.68 (1H, dd), 8.62 (1H, s), 8.20 (1H, s), 7.74 (1H, dd), 4.06 (2H, q), 1.44 (3H, t).

Production Example 13(1)

A mixture of 2-(3-ethylsulfanyl-pyridin-2-yl)-6-iodo-3-methyl-3H-imidazo[4,5-b]pyridine (1.1 g), copper iodide (160 mg), sodium sulfide 9-hydrate (2.7 g) and DMF (10 ml) was stirred at 110° C. for 5 hours. To the reaction mixture was added water, and the mixture was extracted with ethyl acetate. The organic layer was dried over sodium sulfate, and concentrated under reduced pressure. The residue was subjected to silica gel column chromatography to give a compound represented by the formula

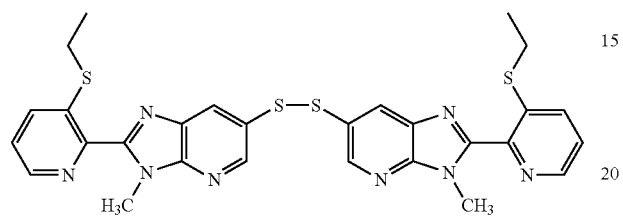

(710 mg), which is hereinafter referred tows "intermediate compound (P9'-1)".

Intermediate Compound (P9'-1)

$^1$H-NMR (DMSO-D$_6$) δ: 8.56-8.55 (2H, m), 8.53-8.50 (2H, m), 8.38-8.36 (2H, m), 8.04 (2H, d), 7.61-7.56 (2H, m), 3.87 (6H, brs), 3.00 (4H, q), 1.23-1.16 (6H, m).

Production Example 13(2)

A mixture of the intermediate compound (P9'-1) (710 mg) and DMF (12 ml) was cooled to −60° C., and thereto was added trifluoroiodomethane (10 g). To this mixture was added dropwise tetrakis(dimethylamino)ethylene (1.2 ml) at −40° C. The mixture was warmed to −10° C., and stirred at −10° C. for 5 hours. To the reaction mixture was added water, and the mixture was extracted with ethyl acetate. The organic layer was dried over sodium sulfate, and concentrated under reduced pressure. The residue was subjected to silica gel column chromatography to give 2-(3-ethylsulfanyl-pyridin-2-yl)-3-methyl-6-trifluoromethylsulfanyl-3H-imidazo[4,5-b]pyridine (530 mg), which is hereinafter referred to as "the present compound 13".

The Present Compound 13

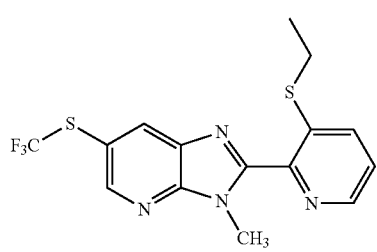 [SMILES: CCSc1cccnc1-c1nc2cc(SC(F)(F)F)cnc2n1C]

$^1$H-NMR (CDCl$_3$) δ: 8.67 (1H, d), 8.52 (1H, dd), 8.46 (1H, d), 7.79 (1H, dd), 7.39 (1H, dd), 4.03 (3H, s), 2.97 (2H, q), 1.36 (3H, t).

Production Examples 14 and 15

A mixture of 2-(3-ethylsulfanyl-pyridin-2-yl)-3-methyl-6-trifluoromethylsulfanyl-3H-imidazo[4,5-b]pyridine (200 mg), m-chloroperbenzoic acid (purity: not less than 65%) (230 mg) and chloroform (10 ml) was stirred while ice-cooling for 5 hours. To the reaction mixture was poured saturated aqueous sodium hydrogen carbonate solution, and the mixture was extracted with chloroform. The organic layer was dried over sodium sulfate, and concentrated under reduced pressure. The residue was subjected to silica gel column chromatography to give 2-(3-ethylsulfinyl-pyridin-2-yl)-3-methyl-6-trifluoromethylsulfanyl-3H-imidazo[4,5-b]pyridine (89 mg), which is hereinafter referred to as "the present compound 14", and 2-(3-ethylsulfonyl-pyridin-2-yl)-3-methyl-6-trifluoromethylsulfanyl-3H-imidazo[4,5-b]pyridine (130 mg), which is hereinafter referred to as "the present compound 15".

The Present Compound 14

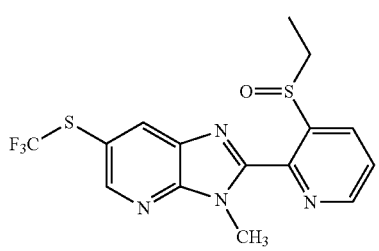 [SMILES: CCS(=O)c1cccnc1-c1nc2cc(SC(F)(F)F)cnc2n1C]

$^1$H-NMR (CDCl$_3$) δ: 8.87-8.83 (1H, m), 8.73-8.64 (2H, m), 8.41 (1H, d), 7.72-7.66 (1H, m), 4.34 (3H, s), 3.72-3.62 (1H, m), 3.17-3.05 (1H, m), 1.47 (3H, t).

The Present Compound 15

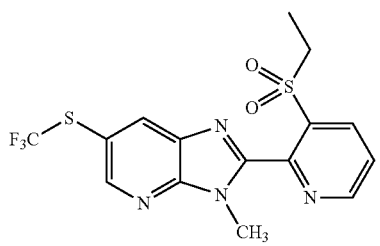 [SMILES: CCS(=O)(=O)c1cccnc1-c1nc2cc(SC(F)(F)F)cnc2n1C]

$^1$H-NMR (CDCl$_3$) δ: 9.01-8.98 (1H, m), 8.71 (1H, d), 8.55-8.52 (1H, m), 8.39 (1H, d), 7.72 (1H, dd), 3.90-3.81 (5H, m), 1.36 (3H, t).

Production Example 16

To a mixture of 2-(3-ethylsulfanyl-pyridin-2-yl)-3-methyl-6-trifluoromethylsulfanyl-3H-imidazo[4,5-b]pyridine acetonitrile (5 ml) was added 30% hydrogen peroxide solution (2 ml) at 40° C. The mixture was heated to 80° C. and then stirred for 24 hours. To the mixture was added saturated aqueous sodium thiosulfate solution, and the mixture was extracted with ethyl acetate. The organic layer was dried over sodium sulfate, and concentrated under reduced pressure. The residue was subjected to silica gel column chromatography to give 2-(3-ethylsulfonyl-pyridin-2-yl)-3-methyl-6-trifluoromethylsulfonyl-3H-imidazo[4,5-b]pyridine (280 mg), which is hereinafter referred to as "the present compound 16".

The Present Compound 16

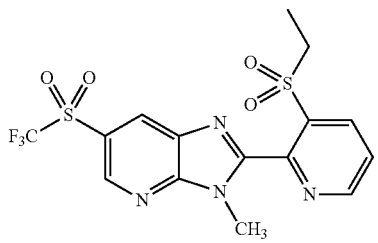 [SMILES: CCS(=O)(=O)c1cccnc1-c1nc2cc(S(=O)(=O)C(F)(F)F)cnc2n1C]

¹H-NMR (CDCl₃) δ: 9.08 (1H, d), 9.04 (1H, dd), 8.71 (1H, d), 8.57 (1H, dd), 7.79 (1H, dd), 3.93 (3H, s), 3.82 (2H, q), 1.38 (3H, t).

Production Example 17(1)

A mixture of N²-methyl-5-pentafluoroethyl-pyridin-2,3-diamine (590 mg), 3-chloro-5-trifluoromethyl-pyridin-2-carboxylic acid (560 mg), WSC (520 mg), HOBt (35 mg), and pyridine (5 ml) was stirred at room temperature for 5 hours. To the reaction mixture was added water, and the mixture was extracted with ethyl acetate. The organic layer was dried over sodium sulfate, and concentrated under reduced pressure to give intermediate compound (M20-17).
Intermediate Compound (M20-17)

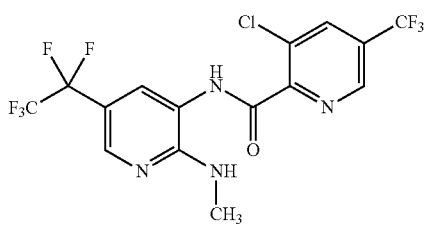 [SMILES: CNc1ncc(C(F)(F)C(F)(F)F)cc1NC(=O)c1ncc(C(F)(F)F)cc1Cl]

The resulting intermediate compound (M20-17) was dissolved in a mixed solvent of DMF (7.5 ml) and toluene (30 ml), thereto was added p-toluenesulfonic acid monohydrate (1.5 g), and the mixture was stirred at 160° C. for 6 hours. The reaction mixture was allowed to cool to room temperature, thereto was poured saturated aqueous sodium hydrogen carbonate solution, and the mixture was extracted with t-butylmethyl ether. The organic layer was dried over sodium sulfate, and concentrated under reduced pressure. The residue was subjected to silica gel column chromatography to give 2-(3-chloro-5-trifluoromethyl-pyridin-2-yl)-3-methyl-6-pentafluoroethyl-3H-imidazo[4,5-b]pyridine (540 mg), which is hereinafter referred to as "intermediate compound (M6-17)".
Intermediate Compound (M6-17)

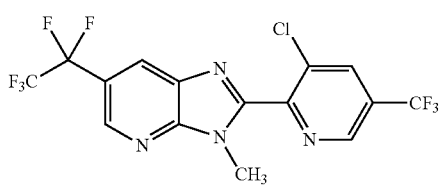

¹H-NMR (CDCl₃) δ: 8.96 (1H, d), 8.74 (1H, d), 8.40 (1H, d), 8.23 (1H, d), 4.03 (3H, s).

Production Example 17(2)

2-(3-ethylsulfanyl-5-trifluoromethyl-pyridin-2-yl)-3-methyl-6-pentafluoroethyl-3H-imidazo[4,5-b]pyridine (hereinafter referred to as "the present compound 17") was synthesized in the same manner as in Production Example 1(2) except for using the intermediate compound (M6-17) instead of 2-(3-fluoropyridin-2-yl)-3-methyl-6-trifluoromethyl-3H-imidazo[4,5-b]pyridine.
The Present Compound 17

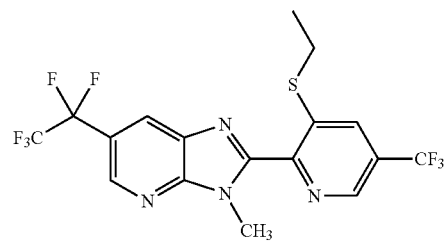 [SMILES: CCSc1cc(C(F)(F)F)cnc1-c1nc2cc(C(F)(F)C(F)(F)F)cnc2n1C]

¹H-NMR (CDCl₃) δ: 8.75 (1H, d), 8.71 (1H, d), 8.42 (1H, d), 7.93 (1H, d), 4.12 (3H, s), 3.03 (2H, q), 1.41 (3H, t).

Production Examples 18 and 19

2-(3-ethylsulfinyl-5-trifluoromethyl-pyridin-2-yl)-3-methyl-6-pentafluoroethyl-3H-imidazo[4,5-b]pyridine (hereinafter referred to as "the present compound 18") and 2-(3-ethylsulfonyl-5-trifluoromethyl-pyridin-2-yl)-3-methyl-6-pentafluoroethyl-3H-imidazo[4,5-b]pyridine (hereinafter referred to as "the present compound 19") were synthesized in the same manner as in Production Examples 2 and 3 except for using 2-(3-ethylsulfanyl-5-trifluoromethyl-pyridin-2-yl)-3-methyl-6-pentafluoroethyl-3H-imidazo[4,5-b]pyridine instead of 2-(3-ethylsulfanyl pyridin-2-yl)-3-methyl-6-trifluoromethyl-3H-imidazo[4,5-b]pyridine.
The Present Compound 18

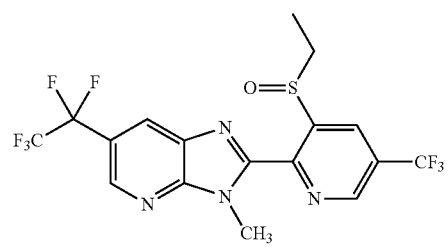 [SMILES: CCS(=O)c1cc(C(F)(F)F)cnc1-c1nc2cc(C(F)(F)C(F)(F)F)cnc2n1C]

¹H-NMR (CDCl₃) δ: 9.10 (1H, d), 8.94 (1H, d), 8.76 (1H, d), 8.36 (1H, d), 4.41 (3H, s), 3.76-3.66 (1H, m), 3.18-3.07 (1H, m), 1.49 (3H, t).
The Present Compound 19

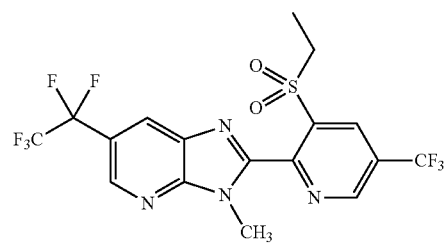

¹H-NMR (CDCl₃) δ: 9.27 (1H, d), 8.80 (1H, d), 8.76 (1H, s), 8.34 (1H, s), 4.01-3.94 (5H, m), 1.41 (3H, t).

Production Example 20

To a mixture of 2-(3-ethylsulfonyl-pyridin-2-yl)-3-methyl-6-trifluoromethylsulfanyl-3H-imidazo[4,5-b]pyridine (500 mg) and chloroform (10 ml) was added m-chloroperbenzoic acid (purity: not less than 65%) (429 mg) while ice-cooling, and the mixture was stirred at room temperature for 1 hour and at 50° C. for 2 hours. To the reaction mixture were poured aqueous sodium thiosulfate solution and aqueous sodium hydrogen carbonate solution, and the mixture was extracted with chloroform. The organic layer was dried over sodium sulfate, and concentrated under reduced pressure. The residue was subjected to silica gel column chromatography to give 2-(3-ethylsulfonyl-pyridin-2-yl)-3-methyl-6-trifluoromethylsulfinyl-3H-imidazo[4,5-b]pyridine (353 mg), which is hereinafter referred to as "the present compound 20".

The Present Compound 20

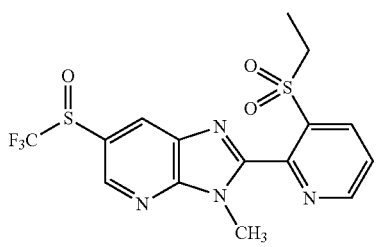 [SMILES: CCS(=O)(=O)c1cccnc1-c1nc2cc(S(=O)C(F)(F)F)cnc2n1C]

¹H-NMR (CDCl₃) δ: 9.02 (1H, dd), 8.77 (1H, d), 8.60-8.52 (2H, m), 7.75 (1H, dd), 3.91 (3H, s), 3.83 (2H, q), 1.38 (3H, t).

Production Example 21(1)

To a mixture of 4-iodo-2-nitro-phenyl amine (2.0 g), 60% sodium hydride (oil) (330 mg), and DMF (20 ml) was added dropwise iodomethane (470 µL) while ice-cooling. The reaction mixture was heated to room temperature, and then stirred for 2 hours. To the reaction mixture was added water, and the mixture was extracted with ethyl acetate. The organic layer was dried over sodium sulfate, and concentrated under reduced pressure. The residue was subjected to silica gel column chromatography to give (4-iodo-2-nitro-phenyl)-methyl-amine (2.0 g).

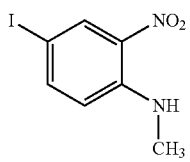

Production Example 21(2)

A mixture of an iron powder (1.7 g), acetic acid (2.2 ml), ethanol (80 ml), and water (25 ml) was stirred at 70° C. To the reaction mixture was added dropwise a mixture of (4-iodo-2-nitro-phenyl)-methyl-amine (2.0 g) and ethanol (20 ml). After that, the mixture was stirred at 70° C. for 6 hours. Then, the reaction mixture was filtrated and thoroughly washed with THF. The resulting filtrate was concentrated under reduced pressure. To the resulting residue was poured saturated aqueous sodium hydrogen carbonate solution, and the mixture was extracted with ethyl acetate. The organic layer was dried over sodium sulfate, and concentrated under reduced pressure. The residue was subjected to silica gel column chromatography to give 4-iodo-N-methyl-benzene-1,2-diamine (1.6 g).

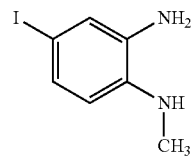

Production Example 21(3)

A mixture of 4-iodo-N¹-methyl-benzene-1,2-diamine (850 mg), 3-chloro-pyridin-2-carboxylic acid (590 mg), WSC (790 mg), HOBt (46 mg), and pyridine (10 ml) was stirred at 100° C. for 12 hours. To the reaction mixture was added water, and the mixture was extracted with ethyl acetate. The organic layer was dried over sodium sulfate, and concentrated under reduced pressure. The residue was subjected to silica gel column chromatography to give 2-(3-chloro-pyridin-2-yl)-5-iodo-1-methyl-1H-benzimidazole (930 mg), which is hereinafter referred to as "intermediate compound (M6-21)".

Intermediate Compound (M6-21)

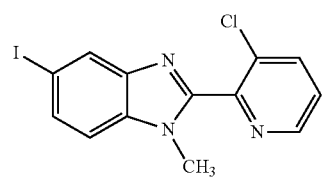 [SMILES: Cn1c(-c2ncccc2Cl)nc2cc(I)ccc21]

Production Example 21(4)

2-(3-ethylsulfanyl-pyridin-2-yl)-5-iodo-1-methyl-1H-benzimidazole (hereinafter referred as "the present compound 21") was synthesized in the same manner as in Production Example 1(2) except for using the intermediate compound (M6-21) instead of 2-(3-fluoropyridin-2-yl)-3-methyl-6-trifluoromethyl-3H-imidazo[4,5-b]pyridine.

The Present Compound 21

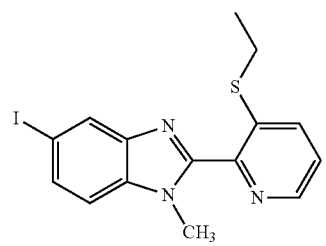 [SMILES: CCSc1cccnc1-c1nc2cc(I)ccc2n1C]

¹H-NMR (CDCl₃) δ: 8.49 (1H, dd), 8.22 (1H, d), 7.75 (1H, d), 7.62 (1H, dd), 7.35 (1H, dd), 7.21 (1H, d), 3.87 (3H, s), 2.92 (2H, q), 1.32 (3H, t).

Production Example 22(1)

A mixture of 4-amino phenyl sulfur pentafluoride (5.2 g), acetic acid anhydride (2.7 ml), triethylamine (6.6 ml) and chloroform (20 ml) was stirred at room temperature for 3 hours. To the reaction mixture was poured water, and the mixture was extracted with chloroform. The resulting residue was subjected to recrystallization with hexane and ethyl acetate to give 4-acetoamide phenyl sulfur pentafluoride (5.4 g).

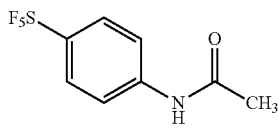

Production Example 22(2)

To a mixture of 4-acetoamide phenyl sulfur pentafluoride (5.4 g) and sulfuric acid (15 ml) was added dropwise fuming nitric acid (905 ml) while ice-cooling. After that, the mixture was stirred at room temperature for 3 hours. The reaction mixture was poured onto ice, and the precipitated crystal was collected by filtration. The crystal was washed with water and dried to give 4-amino-3-nitro phenyl sulfur pentafluoride (5.2 g).

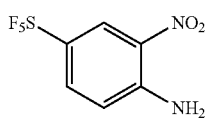

Production Example 22(3)

To a mixture 4-amino-3-nitro-phenyl sulfur pentafluoride (2.0 g), 60% sodium hydride (oil) (310 mg) and DMF (15 ml) was added dropwise iodomethane (447 μL) while ice-cooling. After that, the mixture was stirred at room temperature for 3 hours. To the reaction mixture was poured water, and the precipitated solid was collected by filtration. The solid was washed with water and dried to give methyl-(2-nitro-4-pentafluorosulfanyl-phenyl)-amine (2.0 g).

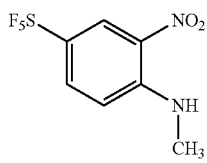

¹H-NMR (CDCl₃) δ: 8.60 (1H, d), 8.28 (1H, brs), 7.78 (1H, dd), 6.89 (1H, d), 3.10 (3H, d).

Production Example 22(4)

N¹-methyl-4-pentafluorosulfanyl-benzene-1,2-diamine was synthesized in the same manner as in Production Example 21(2) except for using methyl-(2-nitro-4-pentafluorosulfanyl-phenyl)-amine instead of (4-iodo-2-nitro-phenyl)-methyl-amine.

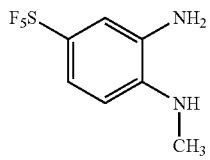

Production Example 22(5)

3-chloro-pyridin-2-carboxylic acid (2-methylamino-5-pentafluorosulfanyl-phenyl)-amide (hereinafter referred to as "intermediate compound (M20-23)") was synthesized in the same manner as in Production Example 9(1) except for using N¹-methyl-4-pentafluorosulfanyl-benzene-1,2-diamine instead of 5-iodo-N²-methyl-pyridin-2,3-diamine.

Intermediate compound (M20-23)

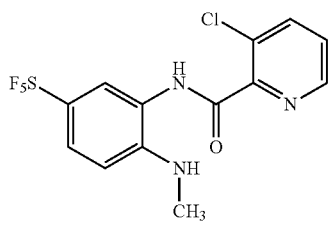

¹H-NMR (CDCl₃) δ: 9.57 (1H, s), 8.55 (1H, dd), 7.91 (1H, dd), 7.81 (1H, d), 7.59 (1H, dd), 7.50-7.45 (1H, m), 6.71 (1H, d), 4.52 (1H, d), 2.93 (3H, d).

Production Example 22(6)

To a mixture of the intermediate compound (M20-23) (405 mg) and DMF (10 ml) was added sodium ethanethiolate (193 mg) while ice-cooling, and then the mixture was stirred at room temperature for 8 hours and 60° C. for 2 hours. To the reaction mixture was added water, and the mixture was extracted with ethyl acetate. The organic layer was washed with water, dried over anhydrous magnesium sulfate, and concentrated under reduced pressure. The resulting residue was subjected to silica gel column chromatography to give 2-(3-ethylsulfanyl-5-trifluoromethyl-pyridin-2-yl)-1-methyl-5-pentafluorosulfanyl-1H-benzimidazole (411 mg), which is hereinafter referred to as "the present compound 23".

The Present Compound 23

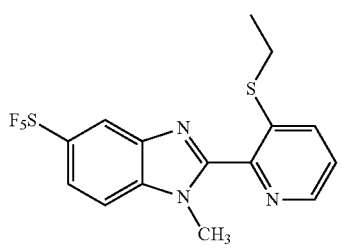

¹H-NMR (CDCl₃) δ: 8.50 (1H, dd), 8.33 (1H, d), 7.79-7.74 (2H, m), 7.46-7.43 (1H, m), 7.37 (1H, dd), 3.92 (3H, s), 2.94 (2H, q), 1.33 (3H, t).

Production Example 23

2-(3-ethylsulfonyl-pyridin-2-yl)-1-methyl-5-pentafluoro-sulfanyl-1H-benzimidazole (hereinafter referred to as "the present compound 24") was synthesized in the same manner as in Production Example 11 except for using 2-(3-ethylsulfanyl-pyridin-2-yl)-1-methyl-5-pentafluorosulfanyl-1H-benzimidazole instead of 2-(3-ethylsulfanyl-5-trifluoromethylpyridin-2-yl)-3-methyl-6-trifluoromethyl-3H-imidazo[4,5-b]pyridine.

The Present Compound 24

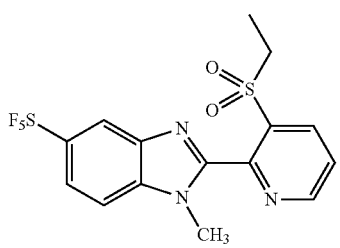

¹H-NMR (CDCl₃) δ: 8.96 (1H, dd), 8.50 (1H, dd), 8.24 (1H, d), 7.79 (1H, dd), 7.68 (1H, dd), 7.48 (1H, d), 3.82 (2H, q), 3.75 (3H, s), 1.34 (3H, t).

Production Example 24(1)

3-chloro-5-trifluoromethyl-pyridin-2-carboxylic acid (5-iodo-2-methylamino-pyridin-3-yl)-amide (hereinafter referred to as "intermediate compound (M20-35)") was synthesized in the same manner as in Production Example 9(1) except for using 3-chloro-5-trifluoromethyl-pyridin-2-carboxylic acid instead of 3-chloro-pyridin-2-carboxylic acid.

Intermediate Compound (M20-35)

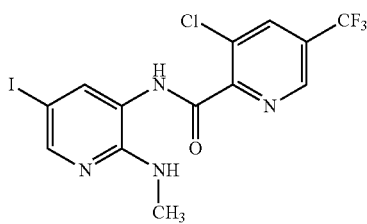 [SMILES: CNc1ncc(I)cc1NC(=O)c1ncc(C(F)(F)F)cc1Cl]

¹H-NMR (CDCl₃) δ: 9.33 (1H, s), 8.80 (1H, d), 8.28 (1H, d), 8.17 (1H, d), 8.00 (1H, d), 4.60 (1H, s), 3.01 (3H, d).

Production Example 24(2)

2-(3-chloro-5-trifluoromethyl-pyridin-2-yl)-6-iodo-3-methyl-3H-imidazo[4,5-b]pyridine (hereinafter referred to as "intermediate compound (M6-35)") was synthesized in the same manner as in Production Example 9(2) except for using the intermediate compound (M20-35) instead of 3-chloro-pyridin-2-carboxylic acid (5-iodo-2-methylamino-pyridin-3-yl)-amide.

Intermediate Compound (M6-35)

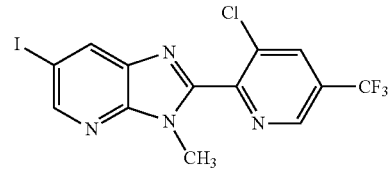 [SMILES: Cn1c(-c2ncc(C(F)(F)F)cc2Cl)nc2cc(I)cnc21]

¹H-NMR (CDCl₃) δ: 8.95 (1H, s), 8.68 (1H, s), 8.49 (1H, s), 8.20 (1H, s), 3.95 (3H, s).

Production Example 24(3)

2-(3-ethylsulfanyl-5-trifluoromethyl-pyridin-2-yl)-6-iodo-3-methyl-3H-imidazo[4,5-b]pyridine (hereinafter referred to as "the present compound 42") was synthesized in the same manner as in Production Example 1(2) except for using the intermediate compound (M6-35) instead of 2-(3-fluoropyridin-2-yl)-3-methyl-6-trifluoromethyl-3H-imidazo[4,5-b]pyridine.

The Present Compound 42

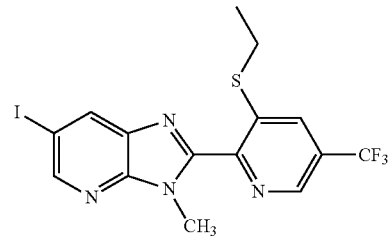

¹H-NMR (CDCl₃) δ: 8.73 (1H, s), 8.65 (1H, d), 8.49 (1H, d), 7.91 (1H, s), 4.04 (3H, s), 3.01 (2H, q), 1.39 (3H, t).

Production Example 24(4)

A mixture of 2-(3-ethylsulfanyl-5-trifluoromethyl-pyridin-2-yl)-6-iodo-3-methyl-3H-imidazo[4,5-b]pyridine (900 mg), thiobenzoic acid 3 (20 μL), copper iodide (45 mg), 1,10-phenanthroline (85 mg), diisopropylethylamine (940 μL), and toluene (25 ml) was stirred at 110° C. for 8 hours. To the reaction mixture was added water, and the mixture was extracted with ethyl acetate. The organic layer was dried over sodium sulfate, and concentrated under reduced pressure. The residue was subjected to silica gel column chromatography to give thiobenzoic acid S-[2-(3-ethylsulfanyl-5-trifluoromethyl-pyridin-2-yl)-3-methyl-3H-imidazo[4,5-b]pyridine]ester (990 mg).

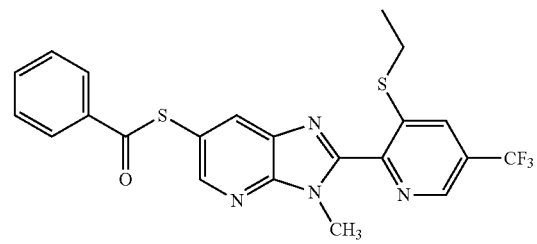 [SMILES: CCSc1cc(C(F)(F)F)cnc1-c1nc2cc(SC(=O)c3ccccc3)cnc2n1C]

$^1$H-NMR (CDCl$_3$) δ: 8.74 (1H, s), 8.54 (1H, d), 8.33 (1H, d), 8.07 (2H, dd), 7.92 (1H, s), 7.63 (1H, t), 7.51 (2H, t), 4.10 (3H, s), 3.01 (2H, q), 1.39 (3H, t).

Production Example 24(5)

A mixture of thiobenzoic acid S-[2-(3-ethylsulfanyl-5-trifluoromethyl-pyridin-2-yl)-3-methyl-3H-imidazo[4,5-b]pyridine]ester (1.8 g), potassium carbonate (1.1 g), and methanol (20 ml) was stirred at room temperature for 4.5 hours. To the reaction mixture was poured saturated aqueous ammonium chloride solution, and the mixture was extracted with ethyl acetate. The organic layer was washed with saturated aqueous sodium hydrogen carbonate solution, dried over sodium sulfate, and concentrated under reduced pressure to give 2-(3-ethylsulfanyl-5-trifluoromethyl-pyridin-2-yl)-3-methyl-3H-imidazo[4,5-b]pyridin-6-thiol (1.2 g), which is hereinafter referred to as "the present compound 43".
The Present Compound 43

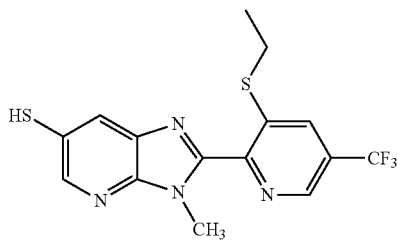 [SMILES: CCSc1cc(C(F)(F)F)cnc1-c1nc2cc(S)cnc2n1C]

$^1$H-NMR (CDCl$_3$) δ: 8.73 (1H, s), 8.46 (1H, d), 8.19 (1H, d), 7.90 (1H, s), 4.04 (3H, s), 3.01 (2H, q), 1.39 (3H, t).

Production Example 24(6)

To a mixture of 2-(3-ethylsulfanyl-5-trifluoromethyl-pyridin-2-yl)-3-methyl-3H-imidazo[4,5-b]pyridin-6-thiol (1.2 g), iodine (20 mg), and DMF (30 ml) was stirred at room temperature under air atmosphere for 12 hours. The reaction mixture was concentrated, and then the residue was subjected to silica gel column chromatography to give a compound represented by the formula:

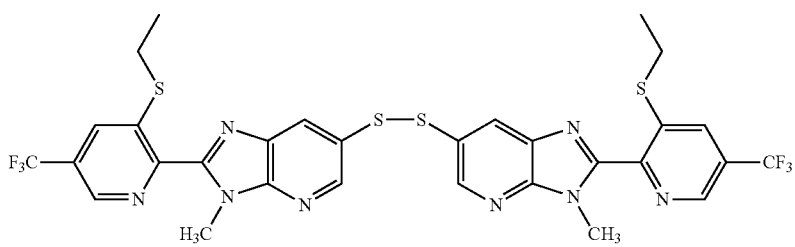 [SMILES: CCSc1cc(C(F)(F)F)cnc1-c1nc2cc(SSc3cnc4c(c3)nc(-c3ncc(C(F)(F)F)cc3SCC)n4C)cnc2n1C]

(800 mg), which is hereinafter referred to as "intermediate compound (P9'-4)".

Intermediate Compound (P9'-4)

$^1$H-NMR (CDCl$_3$) δ: 8.73 (2H, s), 8.52 (2H, d), 8.35 (2H, d), 7.91 (2H, d), 4.06 (6H, s), 3.04-2.98 (4H, m), 1.39 (6H, t).

Production Example 24(7)

2-(3-ethylsulfanyl-5-trifluoromethyl-pyridin-2-yl)-3-methyl-6-trifluoromethylsulfanyl-3H-imidazo[4,5-b]pyridine (hereinafter referred to as "the present compound 28") was synthesized in the same manner as in Production Example 13(2) except for using the intermediate compound (P9'-4) instead of the intermediate compound (P9'-1).
The Present Compound 28

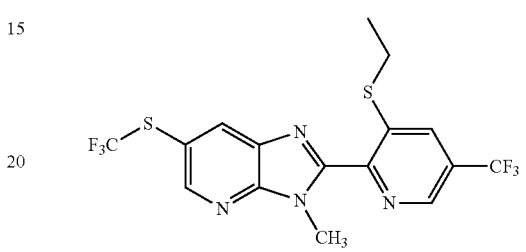

$^1$H-NMR (CDCl$_3$) δ: 8.75 (1H, d), 8.71 (1H, d), 8.50 (1H, d), 7.93 (1H, d), 4.10 (3H, s), 3.03 (2H, q), 1.41 (3H, t).

Production Example 24(8)

To a mixture of 2-(3-ethylsulfanyl-5-trifluoromethyl-pyridin-2-yl)-3-methyl-6-trifluoromethylsulfanyl-3H-imidazo[4,5-b]pyridine (299 mg) and chloroform (30 ml) was added m-chloroperbenzoic acid (purity: not less than 65%) (0.34 g) while ice-cooling, and the mixture was stirred while ice-cooling for 5 hours. To the reaction mixture were poured saturated aqueous sodium hydrogen carbonate solution and saturated aqueous sodium thiosulfate solution, and the mixture was extracted with chloroform. The organic layer was dried over magnesium sulfate and concentrated under reduced pressure. The resulting residue was subjected to silica gel column chromatography to give 2-(3-ethylsulfonyl-5-trifluoromethyl-pyridin-2-yl)-3-methyl-6-trifluoromethylsulfanyl-3H-imidazo[4,5-b]pyridine (0.24 g), which is hereinafter referred to as "the present compound 44".

The Present Compound 44

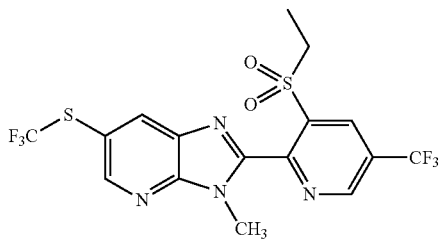 [SMILES: CCS(=O)(=O)c1cc(C(F)(F)F)cnc1-c1nc2cc(SC(F)(F)F)cnc2n1C]

$^1$H-NMR (CDCl$_3$) δ: 9.24 (1H, d), 8.79 (1H, d), 8.74 (1H, d), 8.40 (1H, d), 3.97 (2H, q), 3.93 (3H, s), 1.42 (3H, t).

Production Example 24(9)

2-(3-ethylsulfonyl-5-trifluoromethyl-pyridin-2-yl)-3-methyl-6-trifluoromethylsulfonyl-3H-imidazo[4,5-b]pyridine (hereinafter referred to as "the present compound 25") was synthesized in the same manner as in Production Example 16 except for using 2-(3-ethylsulfanyl-5-trifluoromethyl-pyridin-2-yl)-3-methyl-6-trifluoromethylsulfanyl-3H-imidazo[4,5-b]pyridine instead of 2-(3-ethylsulfanyl-pyridin-2-yl)-3-methyl-6-trifluoromethylsulfanyl-3H-imidazo[4,5-b]pyridine.

The Present Compound 25

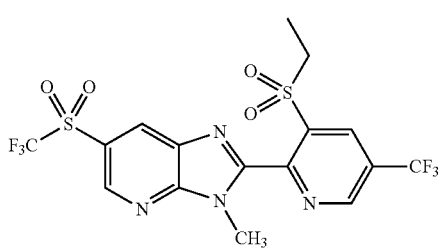 [SMILES: CCS(=O)(=O)c1cc(C(F)(F)F)cnc1-c1nc2cc(S(=O)(=O)C(F)(F)F)cnc2n1C]

$^1$H-NMR (CDCl$_3$) δ: 9.28 (1H, d), 9.10 (1H, d), 8.80 (1H, d), 8.72 (1H, d), 3.98 (3H, s), 3.93 (2H, q), 1.43 (3H, t).

Production Example 25

A mixture of 2-(3-ethylsulfanyl-pyridin-2-yl)-5-iodo-1-methyl-1H-benzimidazole (340 mg), copper iodide (410 mg), sodium pentafluoropropionate (800 mg), NMP (5 ml), and xylene (5 ml) was stirred at 160° C. for 5 hours. The reaction mixture was allowed to cool to room temperature, and then saturated aqueous sodium hydrogen carbonate solution and 28% ammonia solution were poured thereto. Then, the mixture was extracted with t-butylmethyl ether. The organic layer was dried over sodium sulfate, and concentrated under reduced pressure. The residue was subjected to silica gel column chromatography to give 2-(3-ethylsulfanyl-pyridin-2-yl)-1-methyl-5-pentafluoroethyl-1H-benzimidazole (240 mg), which is hereinafter referred to as "the present compound 26".

The Present Compound 26

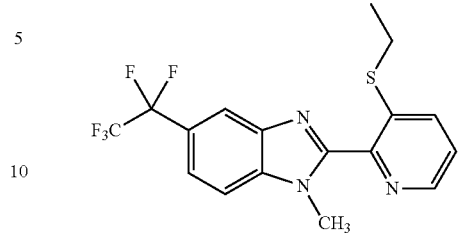

$^1$H-NMR (CDCl$_3$) δ: 8.50 (1H, dd), 8.16 (1H, s), 7.77 (1H, dd), 7.57 (1H, d), 7.53 (1H, d), 7.36 (1H, dd), 3.93 (3H, s), 2.94 (2H, q), 1.33 (3H, t).

Production Example 26

2-(3-ethylsulfonyl-pyridin-2-yl)-1-methyl-5-pentafluoroethyl-1H-benzimidazole (hereinafter referred to as "the present compound 27") was synthesized in the same manner as in Production Example 5 except for using 2-(3-ethylsulfanyl-pyridin-2-yl)-1-methyl-5-pentafluoroethyl-1H-benzimidazole instead of 2-(3-ethylsulfanyl-5-trifluoromethylpyridin-2-yl)-3-methyl-6-trifluoromethyl-3H-imidazo[4,5-b]pyridine.

The Present Compound 27

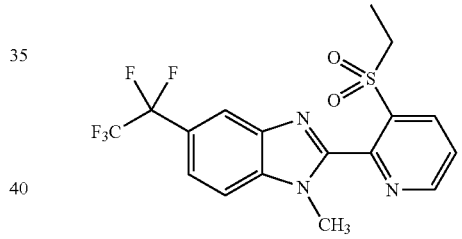

$^1$H-NMR (CDCl$_3$) δ: 8.98 (1H, dd), 8.53 (1H, dd), 8.06 (1H, s), 7.70 (1H, dd), 7.60 (1H, d), 7.56 (1H, d), 3.86-3.78 (5H, m), 1.34 (3H, t).

Production Example 27

To a mixture of 2-(3-ethylsulfanyl-5-trifluoromethylpyridin-2-yl)-3-methyl-6-trifluoromethylsulfanyl-3H-imidazo[4,5-b]pyridine (0.18 g) and chloroform (4 ml) was added m-chloroperbenzoic acid (purity: not less than 65%) (0.21 g) while ice-cooling, and then the mixture was stirred while ice-cooling for 5 minutes. To the reaction mixture were poured saturated aqueous sodium hydrogen carbonate solution and saturated aqueous sodium thiosulfate solution, and the mixture was extracted with chloroform. The organic layer was dried over magnesium sulfate, and concentrated under reduced pressure. The resulting residue was subjected to silica gel column chromatography to give 2-(3-ethylsulfanyl-5-trifluoromethylpyridin-2-yl)-3-methyl-6-trifluoromethylsulfanyl-3H-imidazo[4,5-b]pyridine (0.16 g), which is hereinafter referred to as "the present compound 29".

The Present Compound 29

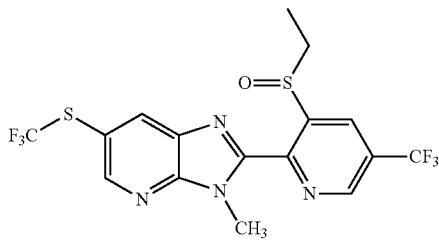 [SMILES: CCS(=O)c1cc(C(F)(F)F)cnc1-c1nc2cc(SC(F)(F)F)cnc2n1C]

¹H-NMR (CDCl₃) δ: 9.10-9.07 (1H, m), 8.94-8.91 (1H, m), 8.77-8.74 (1H, m), 8.46-8.44 (1H, m), 4.38 (3H, s), 3.76-3.65 (1H, m), 3.16-3.05 (1H, m), 1.49 (3H, t).

Production Example 28(1)

3-chloro-pyridin-2-carboxylic acid (2-methylamino-5-trifluoromethyl-phenyl)-amide (hereinafter referred to as "intermediate compound (M20-29)") was synthesized in the same manner as in Production Example 9(1) except for using N¹-methyl-4-trifluoromethyl-benzene-1,2-diamine instead of 5-iodo-N²-methyl-pyridin-2,3-diamine.

Intermediate Compound (M20-29)

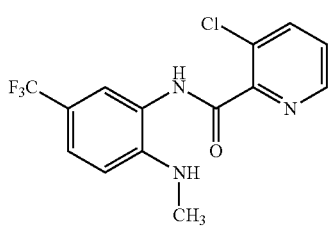

¹H-NMR (CDCl₃) δ: 9.56 (1H, s), 8.55-8.54 (1H, m), 7.91 (1H, dd), 7.70 (1H, d), 7.49-7.43 (3H, m), 6.79 (1H, d), 2.93 (3H, d).

Production Example 28(2)

A mixture of the intermediate compound (M20-29) (800 mg), sodium ethanethiolate (350 mg), and DMF (10 ml) was stirred at 100° C. for 5 hours. To the reaction mixture was added saturated aqueous sodium hydrogen carbonate solution, and then the mixture was extracted with ethyl acetate. The organic layer was dried over sodium sulfate, and concentrated under reduced pressure. The residue was subjected to silica gel column chromatography to give 2-(3-ethylsulfanyl-pyridin-2-yl)-1-methyl-5-trifluoromethyl-1H-benzimidazole (410 mg), which is hereinafter referred to as "the present compound 30".

The Present Compound 30

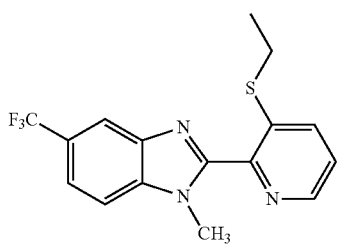

¹H-NMR (CDCl₃) δ: 8.51 (1H, dd), 8.17 (1H, d), 7.78 (1H, dd), 7.61 (1H, dd), 7.52 (1H, d), 7.38 (1H, dd), 3.93 (3H, s), 2.94 (2H, q), 1.33 (3H, t).

Production Example 29, 30

2-(3-ethylsulfinyl-pyridin-2-yl)-1-methyl-5-trifluoromethyl-1H-benzimidazole (hereinafter referred to as "the present compound 31") and 2-(3-ethylsulfonyl-pyridin-2-yl)-1-methyl-5-trifluoromethyl-1H-benzimidazole (hereinafter referred to as "the present compound 32") were synthesized in the same manner as in Production Examples 2 and 3 except for using 2-(3-ethylsulfanyl-pyridin-2-yl)-1-methyl-5-trifluoromethyl-1H-benzimidazole instead of 2-(3-ethylsulfanyl pyridin-2-yl)-3-methyl-6-trifluoromethyl-3H-imidazo[4,5-b]pyridine.

The Present Compound 31

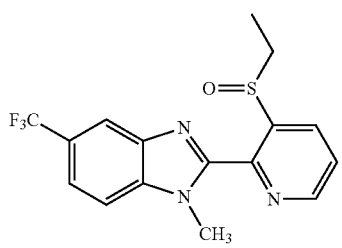 [SMILES: CCS(=O)c1cccnc1-c1nc2cc(C(F)(F)F)ccc2n1C]

¹H-NMR (CDCl₃) δ: 8.77 (1H, d), 8.61 (1H, d), 8.05 (1H, s), 7.61 (1H, dd), 7.55 (1H, d), 7.48 (1H, d), 4.20 (3H, s), 3.73-3.61 (1H, m), 3.11-3.00 (1H, m), 1.47 (3H, t).

The Present Compound 32

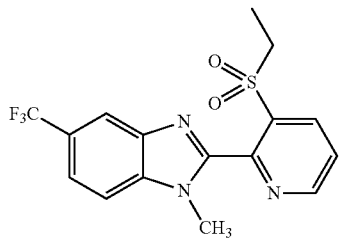

¹H-NMR (CDCl₃) δ: 8.95 (1H, dd), 8.50 (1H, dd), 8.09 (1H, d), 7.66 (1H, dd), 7.61 (1H, d), 7.53 (1H, d), 3.83 (2H, q), 3.75 (3H, s), 1.33 (3H, t).

Production Example 31(1)

3-chloro-5-trifluoromethyl-pyridin-2-carboxylic acid (2-methylamino-5-trifluoromethyl-phenyl)-amide (hereinafter referred to as "intermediate compound (M20-31)") was synthesized in the same manner as in Production Example 9(1) except for using N¹-methyl-4-trifluoromethyl-benzene-1,2-diamine and 3-chloro-5-trifluoromethylpyridin-2-carboxylic acid instead of 5-iodo-N²-methyl-pyridin-2,3-diamine and 3-chloro-pyridin-2-carboxylic acid.

Intermediate Compound (M20-31)

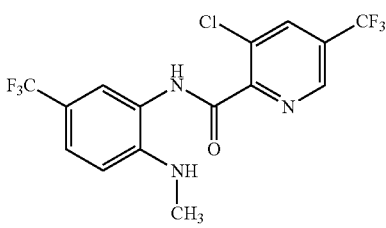 [SMILES: CNc1ccc(C(F)(F)F)cc1NC(=O)c1ncc(C(F)(F)F)cc1Cl]

¹H-NMR (CDCl₃) δ: 9.42 (1H, s), 8.80 (1H, d), 8.16 (1H, d), 7.71 (1H, s), 7.47 (1H, d), 6.81 (1H, d), 4.32 (1H, s), 2.93 (3H, d).

Production Example 31(2)

2-(3-ethylsulfanyl-5-trifluoromethyl-pyridin-2-yl)-1-methyl-5-trifluoromethyl-1H-benzimidazole (hereinafter referred to as "the present compound 33") and 3-ethylsulfanyl-5-trifluoromethyl-pyridin-2-carboxylic acid (2-methylamino-5-trifluoromethyl-phenyl)-amide (hereinafter referred to as "intermediate compound (M3-32)") were synthesized in the same manner as in Production Example 28(2) except for using the intermediate compound (M20-31) instead of 3-chloro-pyridin-2-carboxylic acid (2-methylamino-5-trifluoromethyl-phenyl)-amide.

The Present Compound 33

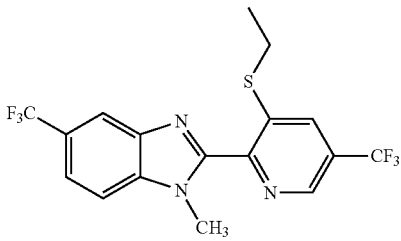 [SMILES: CCSc1cc(C(F)(F)F)cnc1-c1nc2cc(C(F)(F)F)ccc2n1C]

¹H-NMR (CDCl₃) δ: 8.72 (1H, d), 8.21 (1H, d), 7.91 (1H, d), 7.63 (1H, d), 7.54 (1H, d), 4.00 (3H, s), 3.00 (2H, q), 1.38 (3H, t).

Intermediate Compound (M3-32)

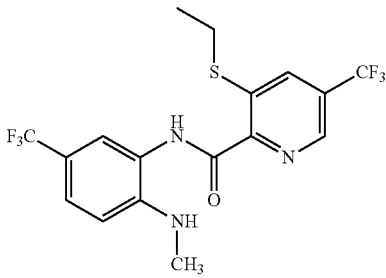 [SMILES: CCSc1cc(C(F)(F)F)cnc1C(=O)Nc1cc(C(F)(F)F)ccc1NC]

¹H-NMR (CDCl₃) δ: 9.64 (1H, s), 8.53 (1H, d), 7.86 (1H, s), 7.76 (1H, d), 7.41 (1H, dd), 6.76 (1H, d), 4.35 (1H, d), 2.96 (2H, q), 2.90 (3H, d), 1.44 (3H, t).

Production Examples 32 and 33

2-(3-ethylsulfinyl-5-trifluoromethyl-pyridin-2-yl)-1-methyl-5-trifluoromethyl-1H-benzimidazole (hereinafter referred to as "the present compound 34") and 2-(3-ethylsulfonyl-5-trifluoromethyl-pyridin-2-yl)-1-methyl-5-trifluoromethyl-1H-benzimidazole (hereinafter referred to as "the present compound 35") were synthesized in the same manner as in Production Examples 2 and 3 except for using 2-(3-ethylsulfanyl-5-trifluoromethyl-pyridin-2-yl)-1-methyl-5-trifluoromethyl-1H-benzimidazole instead of 2-(3-ethylsulfanyl pyridin-2-yl)-3-methyl-6-trifluoromethyl-3H-imidazo[4,5-b]pyridine.

The Present Compound 34

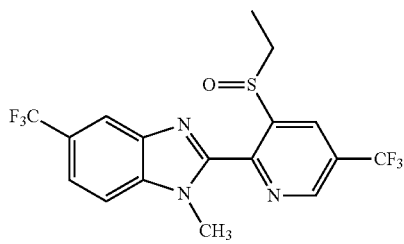 [SMILES: CCS(=O)c1cc(C(F)(F)F)cnc1-c1nc2cc(C(F)(F)F)ccc2n1C]

¹H-NMR (CDCl₃) δ: 9.05 (1H, d), 8.91 (1H, d), 8.12 (1H, d), 7.67 (1H, dd), 7.60 (1H, d), 4.32 (3H, s), 3.80-3.70 (1H, m), 3.15-3.05 (1H, m), 1.51 (3H, t).

The Present Compound 35

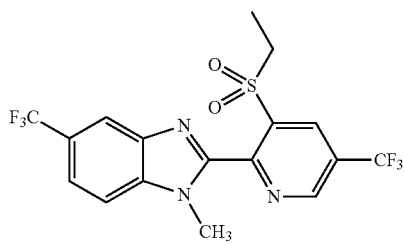 [SMILES: CCS(=O)(=O)c1cc(C(F)(F)F)cnc1-c1nc2cc(C(F)(F)F)ccc2n1C]

¹H-NMR (CDCl₃) δ: 9.22 (1H, d), 8.77 (1H, d), 8.10 (1H, d), 7.66 (1H, dd), 7.57 (1H, d), 3.98 (2H, q), 3.84 (3H, s), 1.40 (3H, t).

Production Example 34, 35

To a mixture of 2-(3-ethylsulfonylpyridin-2-yl)-3-methyl-6-trifluoromethyl-3H-imidazo[4,5-b]pyridine (550 mg) and chloroform (15 ml) was added m-chloroperbenzoic acid (purity: not less than 65%) (750 mg), and the mixture was heated under reflux for 20 hours. To the reaction mixture was poured aqueous 10% sodium thiosulfate solution, and the mixture was extracted with chloroform. The organic layer was washed with saturated aqueous sodium hydrogen carbonate solution, dried over anhydrous magnesium sulfate, and concentrated under reduced pressure. The resulting residue was subjected to silica gel column chromatography to give 2-(3-ethylsulfonyl-1-oxy pyridin-2-yl)-3-methyl-6-trifluoromethyl-3H-imidazo[4,5-b]pyridine (168 mg), which is hereinafter referred to as "the present compound 36" and 2-(3-ethylsulfonylpyridin-2-yl)-3-methyl-6-trifluoromethyl-3H-imidazo[4,5-b]pyridine 4-oxide (73 mg), which is hereinafter referred to as "the present compound 37".

The Present Compound 36

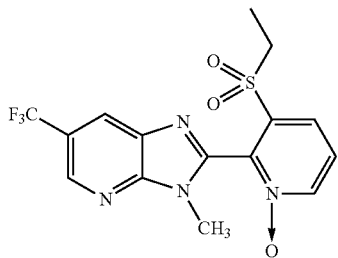 [SMILES: CCS(=O)(=O)c1ccc[n+]([O-])c1-c1nc2cc(C(F)(F)F)cnc2n1C]

¹H-NMR (CDCl₃) δ: 8.79 (1H, d), 8.54 (1H, dd), 8.33 (1H, d), 7.99 (1H, dd), 7.69 (1H, dd), 3.85-3.74 (4H, m), 3.52-3.42 (1H, m), 1.34 (3H, t).

The Present Compound 37

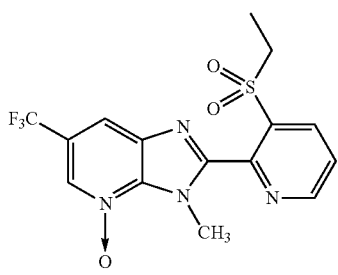 [SMILES: CCS(=O)(=O)c1cccnc1-c1nc2cc(C(F)(F)F)c[n+]([O-])c2n1C]

¹H-NMR (CDCl₃) δ: 9.03 (1H, dd), 8.53 (1H, dd), 8.47 (1H, d), 7.92 (1H, d), 7.77 (1H, dd), 4.29 (3H, s), 3.69 (2H, q), 1.36 (3H, t).

Production Example 36(1)

2-(3-chloro-5-trifluoromethyl-pyridin-2-yl)-5-iodo-1-methyl-1H-benzimidazole (hereinafter referred to as "intermediate compound (M6-41)") was synthesized in the same manner as in Production Example 4(1) except for using 4-iodo-N¹-methyl-benzene-1,2-diamine instead of N²-methyl-5-trifluoromethylpyridin-2,3-diamine.

Intermediate Compound (M6-41)

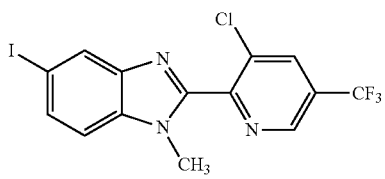

¹H-NMR (CDCl₃) δ: 8.92 (1H, d), 8.23 (1H, d), 8.17 (1H, d), 7.66 (1H, dd), 7.23 (1H, d), 3.85 (3H, s).

Production Example 36(2)

2-(3-ethylsulfanyl-5-trifluoromethyl-pyridin-2-yl)-5-iodo-1-methyl-1H-benzimidazole (hereinafter referred to as "the present compound 45") was synthesized in the same manner as in Production Example 1(2) except for using the intermediate compound (M6-41) instead of 2-(3-fluoropyridin-2-yl)-3-methyl-6-trifluoromethyl-3H-imidazo[4,5-b]pyridine.

The Present Compound 45

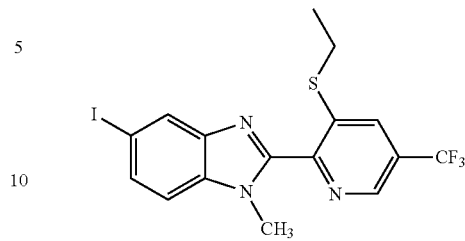

Production Example 36(3)

2-(3-ethylsulfanyl-5-trifluoromethyl-pyridin-2-yl)-1-methyl-5-pentafluoroethyl-1H-benzimidazole (hereinafter referred to as "the present compound 38") was synthesized in the same manner as in Production Example 25 except for using 2-(3-ethylsulfanyl-5-trifluoromethyl-pyridin-2-yl)-5-iodo-1-methyl-1H-benzimidazole instead of 2-(3-ethylsulfanyl-pyridin-2-yl)-5-iodo-1-methyl-1H-benzimidazole.

The Present Compound 38

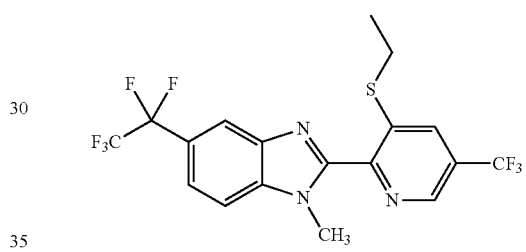

¹H-NMR (CDCl₃) δ: 8.72 (1H, d), 8.20 (1H, s), 7.91 (1H, d), 7.60 (1H, d), 7.55 (1H, d), 4.00 (3H, s), 3.01 (2H, q), 1.39 (3H, t).

Production Example 37, 38

2-(3-ethylsulfinyl-5-trifluoromethyl-pyridin-2-yl)-1-methyl-5-pentafluoroethyl-1H-benzimidazole (hereinafter referred to as "the present compound 39") and 2-(3-ethylsulfonyl-5-trifluoromethyl-pyridin-2-yl)-1-methyl-5-pentafluoroethyl-1H-benzimidazole (hereinafter referred to as "the present compound 40") were synthesized in the same manner as in Production Examples 2 and 3 except for using 2-(3-ethylsulfanyl-5-trifluoromethyl-pyridin-2-yl)-1-methyl-5-pentafluoroethyl-1H-benzimidazole instead of 2-(3-ethylsulfanylpyridin-2-yl)-3-methyl-6-trifluoromethyl-3H-imidazo[4,5-b]pyridine.

The Present Compound 39

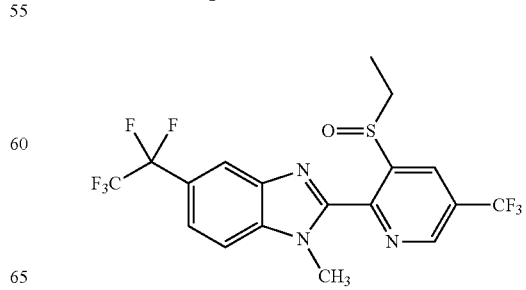

$^1$H-NMR (CDCl$_3$) δ: 9.05 (1H, d), 8.91 (1H, d), 8.10 (1H, s), 7.66-7.60 (2H, m), 4.33 (3H, s), 3.80-3.69 (1H, m), 3.17-3.07 (1H, m), 1.50 (3H, t).

The Present Compound 40

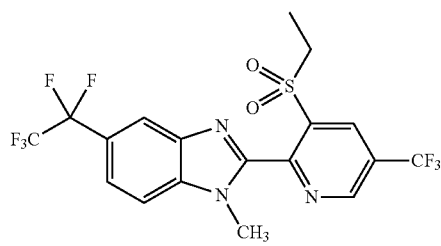 [SMILES: CCS(=O)(=O)c1cc(C(F)(F)F)cnc1-c1nc2cc(C(F)(F)C(F)(F)F)ccc2n1C]

$^1$H-NMR (CDCl$_3$) δ: 9.22 (1H, d), 8.77 (1H, d), 8.08 (1H, s), 7.63 (1H, d), 7.58 (1H, d), 3.99 (2H, q), 3.84 (3H, s), 1.40 (3H, t).

Production Example 39(1)

To a mixture of methyl-(2-nitro-4-trifluoromethyl-phenyl)-amine (16 g) and acetonitrile (200 ml) was added N-bromosuccinimide (15 g) while ice-cooling. The reaction mixture was stirred at room temperature for 5 hours. To the resulting reaction mixture was poured saturated aqueous sodium hydrogen carbonate solution, and then the mixture was extracted with ethyl acetate. The organic layer was dried over magnesium sulfate, and concentrated under reduced pressure. The residue was subjected to silica gel column chromatography to give (2-bromo-6-nitro-4-trifluoromethyl-phenyl)-methyl-amine (15 g).

(2-bromo-6-nitro-4-trifluoromethyl-phenyl)-methyl-amine

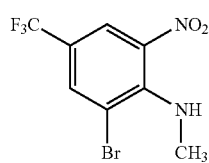

$^1$H-NMR (CDCl$_3$) δ: 8.12 (1H, s), 7.86 (1H, s), 6.48 (1H, brs), 3.07 (3H, d).

Production Example 39(2)

To a mixture of an iron powder (11 g), acetic acid (12 ml), THF (40 ml), and water (10 ml) was added dropwise a mixture of (2-bromo-6-nitro-4-trifluoromethyl-phenyl)-methyl-amine (10 g) and THF (50 ml) while stirring and heating at 70° C. After that, the mixture was stirred at 70° C. for 3 hours. The resulting reaction mixture was filtered through celite (registered trademark), and washed with THF. The resulting filtrate was concentrated under reduced pressure. To the resulting residue was poured 10% sodium hydroxide aqueous solution, and the mixture was extracted with ethyl acetate. The organic layer was dried over magnesium sulfate, and concentrated under reduced pressure to give 3-bromo-N$^2$-methyl-5-trifluoromethyl-benzene-1,2-diamine (11 g).

3-bromo-N$^2$-methyl-5-trifluoromethyl-benzene-1,2-diamine

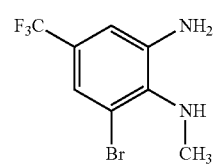

Production Example 39(3)

3-chloro-pyridin-2-carboxylic acid (3-bromo-2-methylamino-5-trifluoromethyl-phenyl)-amide (hereinafter referred to as "intermediate compound (M20-43)") was synthesized in the same manner as in Production Example 9(1) except for using 3-bromo-N$^2$-methyl-5-trifluoromethyl-benzene-1,2-diamine instead of 5-iodo-N$^2$-methyl-pyridin-2,3-diamine.

Intermediate Compound (M20-43)

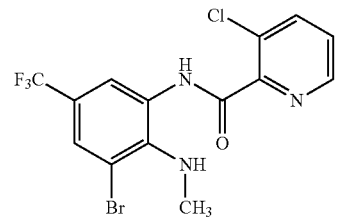 [SMILES: CNc1c(Br)cc(C(F)(F)F)cc1NC(=O)c1ncccc1Cl]

$^1$H-NMR (CDCl$_3$) δ: 10.63 (1H, s), 8.77 (1H, d), 8.58 (1H, dd), 7.91 (1H, dd), 7.56 (1H, d), 7.47 (1H, dd), 3.75-3.68 (1H, m), 2.83 (3H, d).

Production Example 39(4)

2-(3-ethylsulfanyl-pyridin-2-yl)-7-bromo-1-methyl-5-trifluoromethyl-1H-benzimidazole (hereinafter referred to as "the present compound 75"), 3-ethylsulfanyl-pyridin-2-carboxylic acid (3-bromo-2-methylamino-5-trifluoromethyl-phenyl)-amide (hereinafter referred to as "intermediate compound (M3-42)") and 2-(3-chloro-pyridin-2-yl)-7-bromo-1-methyl-5-trifluoromethyl-1H-benzimidazole (hereinafter referred to as "intermediate compound (M6-43)") were synthesized in the same manner as in Production Example 28(2) except for using the intermediate compound (M20-43) instead of the intermediate compound (M20-29).

The Present Compound 75

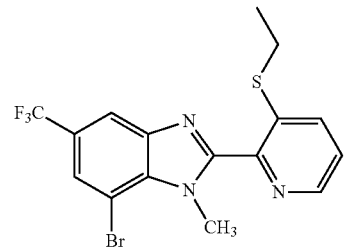 [SMILES: CCSc1cccnc1-c1nc2cc(C(F)(F)F)cc(Br)c2n1C]

¹H-NMR (CDCl₃) δ: 8.54 (1H, dd), 8.08 (1H, d), 7.79 (1H, dd), 7.72 (1H, d), 7.40 (1H, dd), 4.13 (3H, s), 2.94 (2H, q), 1.32 (3H, t).

Intermediate Compound (M3-42)

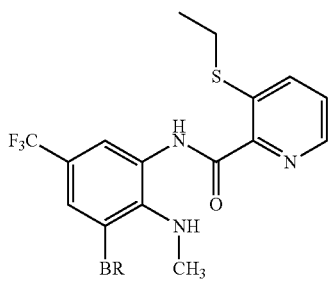

¹H-NMR (CDCl₃) δ: 10.80 (1H, s), 8.82 (1H, s), 8.38 (1H, dd), 7.74 (1H, d), 7.54 (1H, s), 7.42 (1H, dd), 3.75-3.65 (1H, brm), 2.97 (2H, q), 2.82 (3H, d), 1.45 (3H, t).

Intermediate Compound (M6-43)

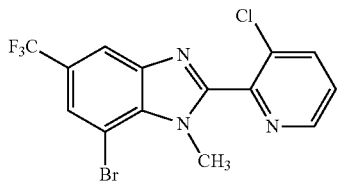 [SMILES: Cn1c(-c2ncccc2Cl)nc2cc(C(F)(F)F)cc(Br)c21]

¹H-NMR (CDCl₃) δ: 8.71 (1H, dd), 8.08 (1H, d), 7.95 (1H, dd), 7.74 (1H, d), 7.47 (1H, dd), 4.09 (3H, s).

Production Example 40

2-(3-ethylsulfonyl-pyridin-2-yl)-7-bromo-1-methyl-5-trifluoromethyl-1H-benzimidazole (hereinafter referred to as "the present compound 46") was synthesized in the same manner as in Production Example 5 except for using 2-(3-ethylsulfanyl-pyridin-2-yl)-7-bromo-1-methyl-5-trifluoromethyl-1H-benzimidazole instead of 2-(3-ethylsulfanyl-5-trifluoromethylpyridin-2-yl)-3-methyl-6-trifluoromethyl-3H-imidazo[4,5-b]pyridine.

The Present Compound 46

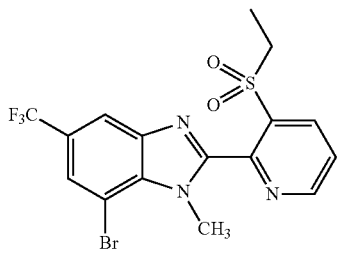 [SMILES: CCS(=O)(=O)c1cccnc1-c1nc2cc(C(F)(F)F)cc(Br)c2n1C]

¹H-NMR (CDCl₃) δ: 8.99 (1H, dd), 8.51 (1H, dd), 8.00 (1H, d), 7.75 (1H, d), 7.72 (1H, dd), 4.03 (3H, s), 3.73 (2H, q), 1.33 (3H, t).

Production Examples 41 and 42

A mixture of 2-(3-ethylsulfanyl-5-trifluoromethylpyridin-2-yl)-3-methyl-6-trifluoromethyl-3H-imidazo[4,5-b]pyridine (1.0 g), m-chloroperbenzoic acid (purity: not less than 65%) (2.72 g) and chloroform (5 ml) was refluxed for 8 hours, and m-chloroperbenzoic acid (purity: not less than 65%) (2.0 g) was added thereto, and the mixture was further refluxed for 5 hours. To the cooled reaction mixture was poured aqueous 10% sodium thiosulfate solution, and the mixture was extracted with chloroform. The organic layer was washed with saturated aqueous sodium hydrogen carbonate solution, dried over anhydrous magnesium sulfate, and concentrated under reduced pressure to give 2-(3-ethylsulfonyl-5-trifluoromethylpyridin-2-yl)-3-methyl-6-trifluoromethyl-3H-imidazo[4,5-b]pyridine 4-oxide (362 mg), which is hereinafter referred to as "the present compound 48", and 2-(3-ethylsulfonyl-1-oxy-5-trifluoromethylpyridin-2-yl)-3-methyl-6-trifluoromethyl-3H-imidazo[4,5-b]pyridine (45 g), which is hereinafter referred to as "the present compound 51".

The Present Compound 48

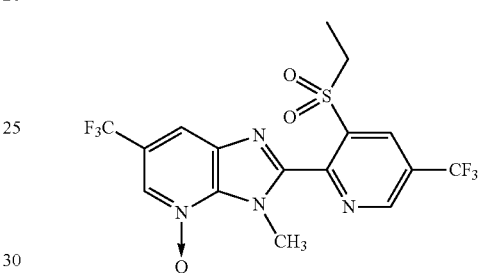

1H-NMR (CDCl3) δ: 9.27 (1H, d), 8.76 (1H, d), 8.49 (1H, d), 7.94 (1H, d), 4.33 (3H, s), 3.80 (2H, q), 1.40 (3H, t).

The Present Compound 51

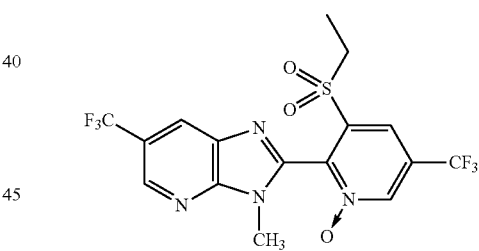

1H-NMR (CDCl3) δ: 8.75 (1H, s), 8.50 (1H, s), 8.12 (1H, s), 7.94 (1H, s), 4.28 (3H, s), 3.75-3.65 (1H, m), 3.55-3.44 (1H, m), 1.38 (3H, t).

Production Example 43(1)

A mixture of 2-chloro-3-nitro-5-trifluoromethylpyridine (2.60 g), 2,2,2-trifluoroethylamine (0.79 g), N,N-diisopropylethylamine (1.04 g) and N-methyl-2-pyrrolidone (5 ml) was stirred at room temperature for 10 hours. To the reaction mixture was poured aqueous 10% citric acid solution, and then the mixture was extracted with ethyl acetate. The organic layer was washed with water, dried over sodium sulfate, and concentrated under reduced pressure to give (3-nitro-5-trifluoromethylpyridin-2-yl)-(2,2,2-trifluoroethyl)amine (1.83 g).

(3-nitro-5-trifluoromethylpyridin-2-yl)-(2,2,2-trifluoroethyl)amine

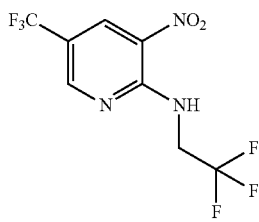

¹H-NMR (CDCl₃) δ: 8.72 (1H, d), 8.68 (1H, d), 8.59 (1H, brs), 4.54-4.41 (2H, m).

Production Example 43(2)

A mixture of an iron powder (2.12 g), ethanol 6 ml), water 4 ml) and acetic acid 0.1 ml) was added dropwise a mixture of (3-nitro-5-trifluoromethylpyridin-2-yl)-(2,2,2-trifluoroethyl)amine (1.83 g) and ethanol (10 ml) at 70° C., and then the mixture was stirred at 70° C. for 1 hour. After allowing to cool, the cooled reaction mixture was filtrated. To the filtrate was added water, and then the mixture was extracted with ethyl acetate. The organic layer was washed with water, dried over sodium sulfate, and concentrated under reduced pressure to give $N^2$-(2,2,2-trifluoroethyl)-5-trifluoromethylpyridin-2,3-diamine (1.59 g).

$N^2$-(2,2,2-trifluoroethyl)-5-trifluoromethylpyridin-2,3-diamine

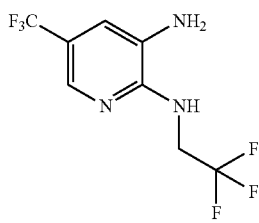 [SMILES: Nc1cc(C(F)(F)F)cnc1NCC(F)(F)F]

¹H-NMR (CDCl₃) δ: 8.04-8.02 (1H, m), 7.10-7.07 (1H, m), 4.81 (1H, brs), 4.31-4.20 (2H, m), 3.34 (2H, brs).

Production Example 43(3)

A mixture of $N^2$-(2,2,2-trifluoroethyl)-5-ethylsulfanylpyridin-2-carboxylic acid (0.37 g), WSC (0.46 g), HOBt (27 mg) and pyridine (2 ml) was stirred at room temperature for 3 hours. To the reaction mixture was poured aqueous 10% citric acid solution, and then the mixture was extracted with ethyl acetate. The organic layer was washed with water, dried over sodium sulfate, and concentrated under reduced pressure to give 3-ethylsulfanyl pyridin-2-carboxylic acid [2-(2,2,2-trifluoroethyl)amino-5-trifluoromethylpyridin-3-yl]amide (0.75 g), which is hereinafter referred to as "intermediate compound (M3-43)".

Intermediate Compound (M3-43)

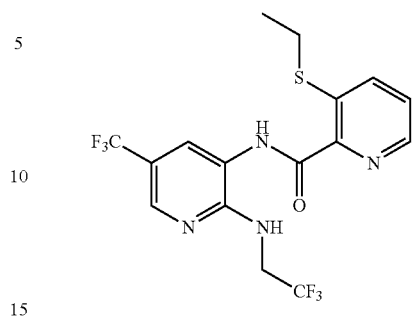

Production Example 43(4)

A mixture of the intermediate compound (M3-43) (0.75 g) and acetic acid (5 ml) was stirred while heating under reflux for 2 days. After cooling to room temperature, the mixture was concentrated under reduced pressure. The crude product was subjected to silica gel column chromatography to give 2-(3-ethylsulfanylpyridin-2-yl)-3-(2,2,2-trifluoroethyl)-6-trifluoromethyl-3H-imidazo[4,5-b]pyridine (0.53 g), which is hereinafter referred to as "the present compound 65".

The Present Compound 65

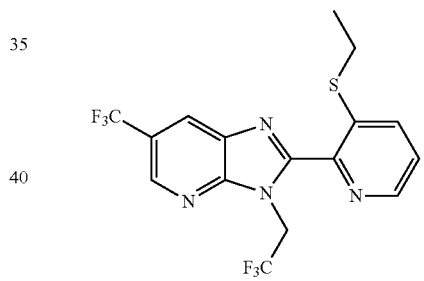

¹H-NMR (CDCl₃) δ: 8.77-8.74 (1H, m), 8.48 (1H, dd), 8.45-8.42 (1H, m), 7.82 (1H, dd), 7.40 (1H, dd), 5.64 (2H, q), 2.99 (2H, q), 1.35 (3H, t).

Production Example 44(1)

A mixture of $N^2$-(2,2,2-trifluoroethyl)-5-trifluoromethylpyridin-2,3-diamine (0.52 g), 3-ethylsulfanyl-5-trifluoromethylpyridin-2-carboxylic acid (0.50 g), WSC (0.46 g), HOBt (27 mg) and pyridine (2 ml) was stirred at room temperature for 3 hours. To the reaction mixture was poured aqueous 10% citric acid solution, and then the mixture was extracted with ethyl acetate. The organic layer was washed with water, dried over sodium sulfate, and concentrated under reduced pressure to give 3-ethylsulfanyl-5-trifluoromethylpyridin-2-carboxylic acid [2-(2,2,2-trifluoroethyl)amino-5-trifluoromethylpyridin-3-yl]amide (0.89 g), which is hereinafter referred to as "intermediate compound (M3-44)".

Intermediate Compound (M3-44)

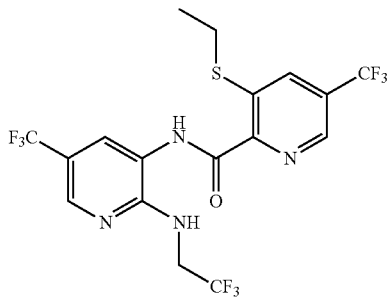 [SMILES: CCSc1cc(C(F)(F)F)cnc1C(=O)Nc1cc(C(F)(F)F)cnc1NCC(F)(F)F]

Production Example 44(2)

A mixture of the intermediate compound (M3-44) (0.89 g), p-toluenesulfonic acid monohydrate (1.14 g), N-methyl-2-pyrrolidone (10 ml) and xylene (10 ml) was heated under reflux while dehydrating with the Dean-Stark apparatus for 8 hours, and then the reaction mixture was allowed to cool. To the cooled reaction mixture was added water, and the mixture was extracted with ethyl acetate. The organic layer was washed with water, dried over sodium sulfate, and concentrated under reduced pressure. The crude product was subjected to silica gel column chromatography to give 2-(3-ethylsulfanyl-5-trifluoromethylpyridin-2-yl)-3-(2,2,2-trifluoroethyl)-6-trifluoromethyl-3H-imidazo[4,5-b]pyridine (0.76 g), which is hereinafter referred to as "the present compound 66".

The Present Compound 66

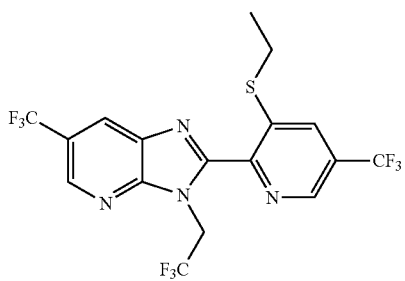 [SMILES: CCSc1cc(C(F)(F)F)cnc1-c1nc2cc(C(F)(F)F)cnc2n1CC(F)(F)F]

$^1$H-NMR (CDCl$_3$) δ: 8.80 (1H, d), 8.70 (1H, d), 8.48 (1H, d), 7.96 (1H, d), 5.67 (2H, q), 3.04 (2H, q), 1.40 (3H, t).

Production Example 45

To a mixture of the present compound 65 (0.32 g) and chloroform (2 ml) was added m-chloroperbenzoic acid (purity: not less than 65%) (0.36 g) while ice-cooling. The mixture was heated to room temperature, and stirred 1 hour. To the mixture were added saturated aqueous sodium hydrogen carbonate solution and saturated aqueous sodium thiosulfate solution, and then the mixture was extracted with chloroform. The organic layer was washed with water, dried over sodium sulfate, and concentrated under reduced pressure. The crude product was subjected to silica gel column chromatography to give 2-(3-ethylsulfonylpyridin-2-yl)-3-(2,2,2-trifluoroethyl)-6-trifluoromethyl-3H-imidazo[4,5-b]pyridine (0.32 g), which is hereinafter referred to as "the present compound 67".

The Present Compound 67

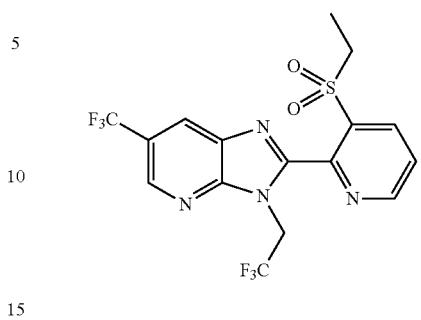

$^1$H-NMR (CDCl$_3$) δ: 8.98 (1H, dd), 8.80 (1H, d), 8.59 (1H, dd), 8.37 (1H, d), 7.75 (1H, dd), 5.31 (2H, q), 3.95 (2H, q), 1.40 (3H, t).

Production Example 46

To a mixture of the present compound 66 (0.32 g) and chloroform (2 ml) was added m-chloroperbenzoic acid (purity: not less than 65%) (0.31 g) while ice-cooling. The mixture was heated to room temperature, and stirred for hour. To the mixture were poured saturated aqueous sodium hydrogen carbonate solution and saturated aqueous sodium thiosulfate solution, and the mixture was extracted with chloroform. The organic layer was washed with water, dried over sodium sulfate, and concentrated under reduced pressure. The resulting crude product was washed with hexane to give 2-(3-ethylsulfonyl-5-trifluoromethylpyridin-2-yl)-3-(2,2,2-trifluoroethyl)-6-trifluoromethyl-3H-imidazo[4,5-b]pyridine (0.28 g), which is hereinafter referred to as "the present compound 68".

The Present Compound 68

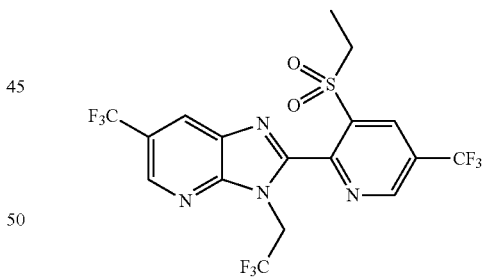

$^1$H-NMR (CDCl$_3$) δ: 9.22 (1H, d), 8.83-8.83 (2H, m), 8.40 (1H, d), 5.36 (2H, q), 4.05 (2H, q), 1.45 (3H, t).

Production Example 47(1)

A mixture of 2-chloro-5-iodopyridine (20.0 g), sodium pentafluoropropionate (77.8 g), copper (I) iodide (31.8 g), xylene (84 ml) and N-methylpyrrolidone (84 ml) was heated to 160° C., and stirred while heating under reflux 6 hours. The reaction mixture was cooled to room temperature, and water was poured thereto. Then, the mixture was extracted with methyl-tert-butyl ether. The organic layer was dried over sodium sulfate, and concentrated under reduced pressure to give 2-chloro-5-pentafluoroethyl pyridine.

2-chloro-5-pentafluoroethyl pyridine

$^1$H-NMR (CDCl$_3$) δ: 8.65-8.62 (1H, m), 7.85-7.81 (1H, m), 7.48-7.44 (1H, m)

Production Example 47(2)

A mixture of the half amount of 2-chloro-5-pentafluoroethyl pyridine obtained in Production Example 47(1), zinc (II) cyanide (14.4 g), tetrakistriphenylphosphine palladium (2.42 g) and N-methyl pyrrolidone (84 ml) was heated to 80° C., and stirred for 2.5 hours. The reaction mixture was cooled to room temperature, and water and methyl-tert-butyl ether were poured thereto. The resulting precipitate was filtrated through celite (registered trademark), and the residue was washed with methyl-test-butyl ether. The filtrate was extracted with methyl-tert-butyl ether. The organic layer was dried over sodium sulfate, and concentrated under reduced pressure. The crude product was subjected to silica gel column chromatography to give 2-cyano-5-pentafluoroethyl pyridine (4.19 g).

2-cyano-5-pentafluoroethyl pyridine

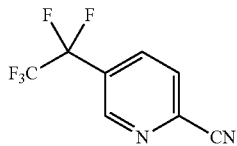 [SMILES: N#Cc1ccc(C(F)(F)C(F)(F)F)cn1]

$^1$H-NMR (CDCl$_3$) δ: 8.97-8.96 (1H, m), 8.12-8.09 (1H, m), 7.90-7.87 (1H, m)

Production Example 47(3)

A mixture of water (17 ml) and concentrated sulfuric acid (17 ml) was heated to 100° C., and thereto was added dropwise 2-cyano-5-pentafluoroethyl pyridine (3.81 g) while heating. Then, the mixture was stirred at 100° C. for 2.5 hours. After cooling to room temperature, the reaction mixture was poured to ice water. The precipitated solid was filtrated and washed with water. The resulting solid was dried under reduced pressure to give 5-pentafluoropyridin-2-carboxylic acid (3.52 g).

5-pentafluoropyridin-2-carboxylic acid

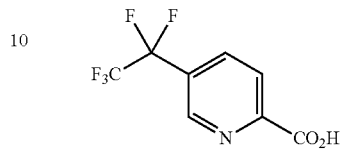

$^1$H-NMR (CDCl$_3$) δ: 8.92-8.88 (1H, m), 8.44-8.39 (1H, m), 8.25-8.20 (1H, m)

Production Example 47(4)

A mixture of tetramethyl piperidine (5.5 ml) and THF (58 ml) was cooled to −78° C., and thereto was added dropwise a solution of 1.6M n-butyl lithium in hexane. After heating to room temperature, the mixture was stirred for 10 minutes. The mixture was cooled to −78° C. again, and thereto was added dropwise a solution of 5-pentafluoropyridin-2-carboxylic acid (3.52 g) in THF. Then, the mixture was stirred at −78° C. for 1 hour, and thereto was added dropwise diethyl disulfide (4.0 ml) at −78°. After heating to room temperature, the mixture was stirred for 1 hour. To the reaction mixture was poured 1N hydrochloric acid, followed by a 5N aqueous sodium hydroxide solution. Then, the aqueous layer was washed with methyl-tert-butyl ether, and thereto was poured 12N hydrochloric acid. The precipitated solid was filtrated, and dissolved in methyl-tert-butyl ether. The solid was dried over sodium sulfate, and concentrated under reduced pressure to give 3-ethylsulfanyl-5-pentafluoroethyl pyridin-2-carboxylic acid (1.99 g), which is hereinafter referred to as "intermediate compound (M2-7)".

Intermediate Compound (M2-7)

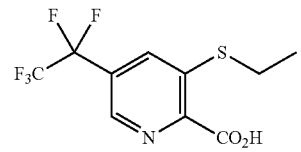 [SMILES: CCSc1cc(C(F)(F)C(F)(F)F)cnc1C(=O)O]

$^1$H-NMR (CDCl$_3$) δ: 8.51-8.50 (1H, m), 7.89-7.87 (1H, m), 3.01 (2H, q), 1.46 (3H, t)

Production Example 47(5)

A mixture of N$^2$-methyl-5-trifluoromethylpyridin-2,3-diamine (0.50 g), the intermediate compound (M2-7) (0.79 g), WSC (0.37 g), HOBt (35 mg) and pyridine (5 ml) was stirred at room temperature for 3 hours. To the reaction mixture was poured water, and then the mixture was extracted with methyl-tert-butyl ether. The organic layer was dried over magnesium sulfate and concentrated under reduced pressure to give 3-ethylsulfanyl-5-pentafluoroethyl pyridin-2-carboxylic acid (2-methylamino-5-trifluoromethylpyridin-3-yl) amide, which is hereinafter referred to as "intermediate compound (M3-45)".

Intermediate Compound (M3-45)

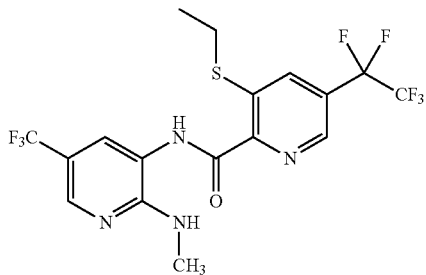 [SMILES: CCSc1cc(C(F)(F)C(F)(F)F)cnc1C(=O)Nc1cc(C(F)(F)F)cnc1NC]

¹H-NMR (CDCl₃) δ: 9.57 (1H, brs), 8.54-8.52 (1H, m), 8.37-8.35 (1H, m), 7.94-7.92 (1H, m), 7.89-7.87 (1H, m), 4.97 (1H, brs), 3.08 (3H, d), 2.99 (2H, q), 1.45 (3H, t)

A mixture of the total amount of the resulting intermediate compound (M3-45) and acetic acid (5 ml) was heated to 120° C., and stirred while heating under reflux for 3 hours. After cooling to room temperature, the mixture was concentrated under reduced pressure. The crude product was subjected to silica gel column chromatography to give 2-(3-ethylsulfanyl-5-pentafluoroethylpyridin-2-yl)-3-methyl-6-trifluoromethyl-3H-imidazo[4,5-b]pyridine (0.77 g), which is hereinafter referred to as "the present compound 71".

The Present Compound 71

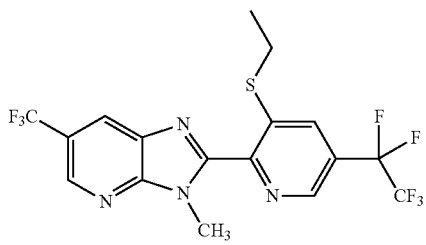 [SMILES: CCSc1cc(C(F)(F)C(F)(F)F)cnc1-c1nc2cc(C(F)(F)F)cnc2n1C]

¹H-NMR (CDCl₃) δ: 8.78-8.76 (1H, m), 8.71-8.69 (1H, m), 8.44-8.42 (1H, m), 7.91-7.89 (1H, m), 4.13 (3H, s), 3.02 (2H, q), 1.39 (3H, t)

Production Example 48

To a mixture of the present compound 71 (0.47 g) and chloroform (10 ml) was added m-chloroperbenzoic acid (purity: not less than 65%) (0.57 g) while ice-cooling. Then, the mixture was heated to room temperature, and stirred for 1 hour. To the mixture were poured saturated aqueous sodium hydrogen carbonate solution and saturated aqueous sodium thiosulfate solution, and then the mixture was extracted with chloroform. The organic layer was dried over sodium sulfate, and concentrated under reduced pressure. The crude product was subjected to silica gel column chromatography to give 2-(3-ethylsulfonyl-5-pentafluoroethylpyridin-2-yl)-3-methyl-6-trifluoromethyl-3H-imidazo[4,5-b]pyridine (0.39 g), which is hereinafter referred to as "the present compound 72".

The Present Compound 72

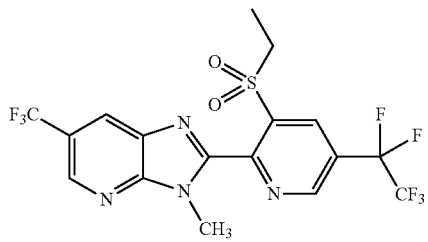 [SMILES: CCS(=O)(=O)c1cc(C(F)(F)C(F)(F)F)cnc1-c1nc2cc(C(F)(F)F)cnc2n1C]

¹H-NMR (CDCl₃) δ: 9.21-9.19 (1H, m), 8.81-8.79 (1H, m), 8.76-8.75 (1H, m), 8.35-8.33 (1H, m), 3.99-3.93 (5H, m), 1.41 (3H, t)

Production Example 49

A mixture of N²-methyl-5-pentafluoroethylpyridin-2,3-diamine (0.50 g), the intermediate compound (M2-7) (0.62 g), WSC (0.29 g), HOBt (28 mg) and pyridine (4 ml) was stirred at room temperature for 3 hours. To the reaction mixture was poured water, and the mixture was extracted with methyl-tert-butyl ether. The organic layer was dried over magnesium sulfate and concentrated under reduced pressure to give 3-ethylsulfanyl-5-pentafluoroethylpyridin-2-carboxylic acid (2-methylamino-5-pentafluoroethyl pyridin-3-yl)amide, which is hereinafter referred to as "intermediate compound (M3-46)".

Intermediate Compound (M3-46)

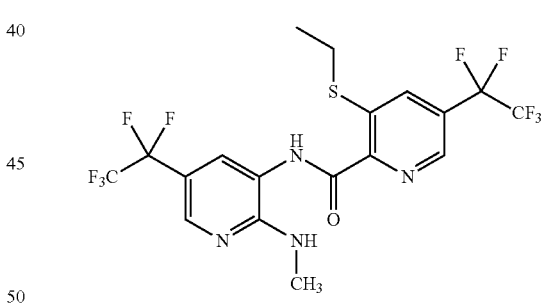

¹H-NMR (CDCl₃) δ: 9.59 (1H, brs), 8.54-8.52 (1H, m), 8.32-8.30 (1H, m), 7.89-7.87 (1H, m), 7.85-7.83 (1H, m), 5.04 (1H, brs), 3.09 (3H, d), 2.99 (2H, q), 1.45 (3H, t)

A mixture of the total amount of the resulting intermediate compound (M3-46) and acetic acid (4 ml) was heated to 120° C., and stirred while heating under reflux for 3 hours. After cooling to room temperature, the mixture was concentrated under reduced pressure. The crude product was subjected to silica gel column chromatography to give 2-(3-ethylsulfanyl-5-pentafluoroethylpyridin-2-yl)-3-methyl-6-pentafluoroethyl-3H-imidazo[4,5-b]pyridine (0.84 g), which is hereinafter referred to as "the present compound 73".

The Present Compound 73

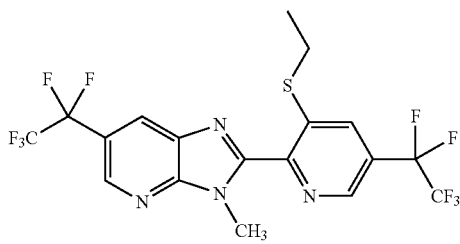 [SMILES: CCSc1cc(C(F)(F)C(F)(F)F)cnc1-c1nc2cc(C(F)(F)C(F)(F)F)cnc2n1C]

¹H-NMR (CDCl₃) δ: 8.72-8.69 (2H, m), 8.42-8.41 (1H, m), 7.90-7.89 (1H, m), 4.15-4.12 (3H, m), 3.02 (2H, q), 1.40 (3H, t)

Production Example 50

To the mixture of the present compound 73 (0.54 g) and chloroform (11 ml) was added m-chloroperbenzoic acid (purity: not less than 65%) (0.59 g) while ice-cooling. The mixture was heated to room temperature, and stirred for hour. To the mixture were poured saturated aqueous sodium hydrogen carbonate solution and saturated aqueous sodium thiosulfate solution, and then the mixture was extracted with chloroform. The organic layer was dried over sodium sulfate, and concentrated under reduced pressure. The crude product was subjected to silica gel column chromatography to give 2-(3-ethylsulfonyl-5-pentafluoroethyl pyridin-2-yl)-3-methyl-6-pentafluoroethyl-3H-imidazo[4,5-b]pyridine (0.34 g), which is hereinafter referred to as "the present compound 74".

The Present Compound 74

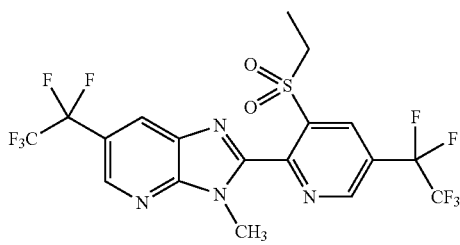 [SMILES: CCS(=O)(=O)c1cc(C(F)(F)C(F)(F)F)cnc1-c1nc2cc(C(F)(F)C(F)(F)F)cnc2n1C]

¹H-NMR (CDCl₃) δ: 9.21-9.20 (1H, m), 8.77-8.74 (2H, m), 8.32-8.31 (1H, m), 4.00-3.94 (5H, m), 1.41 (3H, t)

The compounds as described in Production Examples and the compounds produced in the same manner as in Production Examples are shown below.

A compound represented by the formula (1):

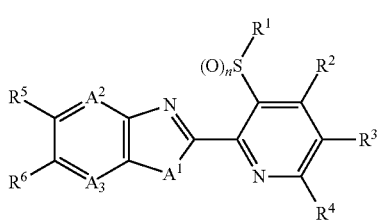

wherein $R^1, R^2, R^3, R^4, R^5, R^6, A^1, A^2, A^3$ and n are any of the combinations as listed in [Table 36] to [Table 58].

TABLE 36

| The present compound | $R^1$ | $R^2$ | $R^3$ | $R^4$ | $R^5$ | $R^6$ | $A^1$ | $A^2$ | $A^3$ | n |
|---|---|---|---|---|---|---|---|---|---|---|
| 1 | Et | H | H | H | CF₃ | H | NMe | CH | N | 0 |
| 2 | Et | H | H | H | CF₃ | H | NMe | CH | N | 1 |
| 3 | Et | H | H | H | CF₃ | H | NMe | CH | N | 2 |
| 4 | Et | H | CF₃ | H | CF₃ | H | NMe | CH | N | 0 |
| 5 | Et | H | CF₃ | H | CF₃ | H | NMe | CH | N | 2 |
| 6 | Et | H | H | H | CF₂CF₃ | H | NMe | CH | N | 0 |
| 7 | Et | H | H | H | CF₂CF₃ | H | NMe | CH | N | 1 |
| 8 | Et | H | H | H | CF₂CF₃ | H | NMe | CH | N | 2 |
| 9 | Et | H | H | H | I | H | NMe | CH | N | 0 |
| 10 | Et | H | CF₃ | H | CF₃ | H | S | CH | N | 0 |
| 11 | Et | H | CF₃ | H | CF₃ | H | S | CH | N | 2 |
| 12 | Et | H | H | H | CF₃ | H | S | CH | N | 2 |
| 13 | Et | H | H | H | SCF₃ | H | NMe | CH | N | 0 |
| 14 | Et | H | H | H | SCF₃ | H | NMe | CH | N | 1 |
| 15 | Et | H | H | H | SCF₃ | H | NMe | CH | N | 2 |
| 16 | Et | H | H | H | SO₂CF₃ | H | NMe | CH | N | 2 |
| 17 | Et | H | CF₃ | H | CF₂CF₃ | H | NMe | CH | N | 0 |
| 18 | Et | H | CF₃ | H | CF₂CF₃ | H | NMe | CH | N | 1 |
| 19 | Et | H | CF₃ | H | CF₂CF₃ | H | NMe | CH | N | 2 |
| 20 | Et | H | H | H | SOCF₃ | H | NMe | CH | N | 2 |
| 21 | Et | H | H | H | I | H | NMe | CH | CH | 0 |
| 22* | Et | H | H | H | CF₃ | H | S | CH | N | 2 |
| 23 | Et | H | H | H | SF₅ | H | NMe | CH | CH | 0 |
| 24 | Et | H | H | H | SF₅ | H | NMe | CH | CH | 2 |
| 25 | Et | H | CF₃ | H | SO₂CF₃ | H | NMe | CH | N | 2 |

TABLE 37

| The present compound | $R^1$ | $R^2$ | $R^3$ | $R^4$ | $R^5$ | $R^6$ | $A^1$ | $A^2$ | $A^3$ | n |
|---|---|---|---|---|---|---|---|---|---|---|
| 26 | Et | H | H | H | CF₂CF₃ | H | NMe | CH | CH | 0 |
| 27 | Et | H | H | H | CF₂CF₃ | H | NMe | CH | CH | 2 |
| 28 | Et | H | CF₃ | H | SCF₃ | H | NMe | CH | N | 0 |
| 29 | Et | H | CF₃ | H | SCF₃ | H | NMe | CH | N | 1 |
| 30 | Et | H | H | H | CF₃ | H | NMe | CH | CH | 0 |
| 31 | Et | H | H | H | CF₃ | H | NMe | CH | CH | 1 |
| 32 | Et | H | H | H | CF₃ | H | NMe | CH | CH | 2 |
| 33 | Et | H | CF₃ | H | CF₃ | H | NMe | CH | CH | 0 |
| 34 | Et | H | CF₃ | H | CF₃ | H | NMe | CH | CH | 1 |
| 35 | Et | H | CF₃ | H | CF₃ | H | NMe | CH | CH | 2 |
| 36* | Et | H | H | H | CF₃ | H | NMe | CH | N | 2 |
| 37* | Et | H | H | H | CF₃ | H | NMe | CH | N | 2 |
| 38 | Et | H | CF₃ | H | CF₂CF₃ | H | NMe | CH | CH | 0 |
| 39 | Et | H | CF₃ | H | CF₂CF₃ | H | NMe | CH | CH | 1 |
| 40 | Et | H | CF₃ | H | CF₂CF₃ | H | NMe | CH | CH | 2 |
| 41 | Et | H | H | H | CF₃ | H | S | CH | N | 0 |
| 42 | Et | H | CF₃ | H | I | H | NMe | CH | N | 0 |
| 43 | Et | H | CF₃ | H | SH | H | NMe | CH | N | 0 |
| 44 | Et | H | CF₃ | H | SCF₃ | H | NMe | CH | N | 2 |
| 45 | Et | H | CF₃ | H | I | H | NMe | CH | CH | 0 |
| 46 | Et | H | H | H | CF₃ | H | NMe | CH | CBr | 2 |
| 47* | Et | H | H | H | CF₂CF₃ | H | NMe | CH | CH | 2 |
| 48* | Et | H | CF₃ | H | CF₃ | H | NMe | CH | N | 2 |
| 49 | Et | H | H | H | OCF₃ | H | NMe | CH | CH | 0 |
| 50 | Et | H | H | H | OCF₃ | H | NMe | CH | CH | 2 |

TABLE 38

| The present compound | R¹ | R² | R³ | R⁴ | R⁵ | R⁶ | A¹ | A² | A³ | n |
|---|---|---|---|---|---|---|---|---|---|---|
| 51* | Et | H | $CF_3$ | H | $CF_3$ | H | NMe | CH | N | 2 |
| 52 | Et | H | H | H | $CF_3$ | H | S | CH | CH | 0 |
| 53 | Et | H | H | H | $CF_3$ | H | S | CH | CH | 2 |
| 54 | Et | H | $CF_3$ | H | $CF_3$ | H | S | CH | CH | 0 |
| 55 | Et | H | $CF_3$ | H | $CF_3$ | H | S | CH | CH | 2 |
| 56 | Et | H | H | H | $CF_3$ | OMe | NMe | CH | CH | 2 |
| 57 | Et | H | H | H | $C(OH)_2CF_3$ | H | NMe | CH | N | 0 |
| 58 | Et | H | H | H | $C(OH)_2CF_3$ | H | NMe | CH | N | 2 |
| 59 | Et | H | $CF_3$ | H | $CO_2Me$ | H | NMe | CH | N | 0 |
| 60 | Et | H | $CF_3$ | H | $SOCF_3$ | H | NMe | CH | N | 2 |
| 61 | Et | H | H | H | $SCF_3$ | H | NMe | CH | CH | 0 |
| 62 | Et | H | H | H | $SCF_3$ | H | NMe | CH | CH | 1 |
| 63 | Et | H | H | H | $SCF_3$ | H | NMe | CH | CH | 2 |
| 64 | Et | H | H | H | $SO_2CF_3$ | H | NMe | CH | CH | 2 |
| 65 | Et | H | H | H | $CF_3$ | H | $NCH_2CF_3$ | CH | N | 0 |
| 66 | Et | H | $CF_3$ | H | $CF_3$ | H | $NCH_2CF_3$ | CH | N | 0 |
| 67 | Et | H | H | H | $CF_3$ | H | $NCH_2CF_3$ | CH | N | 2 |
| 68 | Et | H | $CF_3$ | H | $CF_3$ | H | $NCH_2CF_3$ | CH | N | 2 |
| 69 | Et | H | $CF_3$ | H | $CO_2Me$ | H | NMe | CH | N | 2 |
| 70* | Et | H | $CF_3$ | H | $CO_2Me$ | H | NMe | CH | N | 2 |
| 71 | Et | H | $CF_2CF_3$ | H | $CF_3$ | H | NMe | CH | N | 0 |
| 72 | Et | H | $CF_2CF_3$ | H | $CF_3$ | H | NMe | CH | N | 2 |
| 73 | Et | H | $CF_2CF_3$ | H | $CF_2CF_3$ | H | NMe | CH | N | 0 |
| 74 | Et | H | $CF_2CF_3$ | H | $CF_2CF_3$ | H | NMe | CH | N | 2 |
| 75 | Et | H | H | H | $CF_3$ | H | NMe | CH | CBr | 0 |

TABLE 39

| The present compound | R¹ | R² | R³ | R⁴ | R⁵ | R⁶ | A¹ | A² | A³ | n |
|---|---|---|---|---|---|---|---|---|---|---|
| 76 | Et | H | H | H | $CF_3$ | H | NH | CH | N | 0 |
| 77 | Et | H | H | H | $CF_3$ | H | NH | CH | N | 2 |
| 78 | Et | H | $CF_3$ | H | $CF_3$ | H | NH | CH | N | 0 |
| 79 | Et | H | $CF_3$ | H | $CF_3$ | H | NH | CH | N | 2 |
| 80 | Et | H | H | H | $CF_3$ | H | O | CH | N | 0 |
| 81 | Et | H | H | H | $CF_3$ | H | O | CH | N | 2 |
| 82 | Et | H | $CF_3$ | H | $CF_3$ | H | O | CH | N | 0 |
| 83 | Et | H | $CF_3$ | H | $CF_3$ | H | O | CH | N | 2 |
| 84 | Et | H | H | H | $CF_3$ | H | O | CH | CH | 0 |
| 85 | Et | H | H | H | $CF_3$ | H | O | CH | CH | 2 |
| 86 | Et | H | $CF_3$ | H | $CF_3$ | H | O | CH | CH | 0 |
| 87 | Et | H | $CF_3$ | H | $CF_3$ | H | O | CH | CH | 2 |
| 88 | Et | H | H | H | $CF_3$ | Cl | NMe | CH | N | 2 |
| 89 | Et | H | $CF_3$ | H | $CF_3$ | Cl | NMe | CH | N | 2 |
| 90 | Et | H | H | H | $CF_3$ | SEt | NMe | CH | N | 2 |
| 91 | Et | H | $CF_3$ | H | $CF_3$ | SEt | NMe | CH | N | 2 |
| 92 | Et | H | H | H | $CF_3$ | OH | NMe | CH | N | 2 |
| 93 | Et | H | $CF_3$ | H | $CF_3$ | OH | NMe | CH | N | 2 |
| 94 | Et | H | H | H | $CF_3$ | OMe | NMe | CH | N | 2 |
| 95 | Et | H | $CF_3$ | H | $CF_3$ | OMe | NMe | CH | N | 2 |
| 96 | Et | H | H | H | $CF_3$ | SMe | NMe | CH | N | 2 |
| 97 | Et | H | $CF_3$ | H | $CF_3$ | SMe | NMe | CH | N | 2 |
| 98 | Et | H | H | H | $CF_3$ | $NMe_2$ | NMe | CH | N | 2 |
| 99 | Et | H | $CF_3$ | H | $CF_3$ | $NMe_2$ | NMe | CH | N | 2 |
| 100 | Et | H | H | H | $CF_3$ | Ph | NMe | CH | N | 2 |

TABLE 40

| The present compound | R¹ | R² | R³ | R⁴ | R⁵ | R⁶ | A¹ | A² | A³ | n |
|---|---|---|---|---|---|---|---|---|---|---|
| 101 | Et | H | $CF_3$ | H | $CF_3$ | Ph | NMe | CH | N | 2 |
| 102 | $CH_2CycPr$ | H | H | H | $CF_3$ | H | NMe | CH | N | 2 |
| 103 | $CH_2CycPr$ | H | $CF_3$ | H | $CF_3$ | H | NMe | CH | N | 2 |
| 104 | $CF_3$ | H | H | H | $CF_3$ | H | NMe | CH | N | 2 |
| 105 | $CF_3$ | H | $CF_3$ | H | $CF_3$ | H | NMe | CH | N | 2 |
| 106 | $CH_2CF_3$ | H | H | H | $CF_3$ | H | NMe | CH | N | 2 |
| 107 | $CH_2CF_3$ | H | $CF_3$ | H | $CF_3$ | H | NMe | CH | N | 2 |
| 108 | Et | Cl | H | H | $CF_3$ | H | NMe | CH | N | 2 |
| 109 | Et | H | Cl | H | $CF_3$ | H | NMe | CH | N | 2 |
| 110 | Et | H | H | Cl | $CF_3$ | H | NMe | CH | N | 2 |
| 111 | Et | H | 2-pyridyl | H | $CF_3$ | H | NMe | CH | N | 2 |
| 112 | Et | H | 2-pyrimidinyl | H | $CF_3$ | H | NMe | CH | N | 2 |
| 113 | Et | H | 3-chloro-2-pyridyl | H | $CF_3$ | H | NMe | CH | N | 2 |
| 114 | Et | H | 3-chloro-5-trifluoromethyl-2-pyridyl | H | $CF_3$ | H | NMe | CH | N | 2 |
| 115 | Et | H | $OCF_3$ | H | $CF_3$ | H | NMe | CH | N | 2 |
| 116 | Et | H | $SCF_3$ | H | $CF_3$ | H | NMe | CH | N | 2 |
| 117 | Et | H | $SOCF_3$ | H | $CF_3$ | H | NMe | CH | N | 2 |

TABLE 40-continued

| The present compound | $R^1$ | $R^2$ | $R^3$ | $R^4$ | $R^5$ | $R^6$ | $A^1$ | $A^2$ | $A^3$ | n |
|---|---|---|---|---|---|---|---|---|---|---|
| 118 | Et | H | $SO_2CF_3$ | H | $CF_3$ | H | NMe | CH | N | 2 |
| 119 | Et | H | $CF(CF_3)_2CF_3$ | H | $CF_3$ | H | NMe | CH | N | 2 |
| 120 | Et | H | $CF_2CF_2CF_3$ | H | $CF_3$ | H | NMe | CH | N | 2 |
| 121 | Et | H | Br | H | $CF_3$ | H | NMe | CH | N | 2 |
| 122 | Et | H | I | H | $CF_3$ | H | NMe | CH | N | 2 |
| 123 | Et | H | Me | H | $CF_3$ | H | NMe | CH | N | 2 |
| 124 | Et | H | OMe | H | $CF_3$ | H | NMe | CH | N | 2 |
| 125 | Et | H | H | H | $CF(CF_3)_2$ | H | NMe | CH | N | 2 |

TABLE 41

| The present compound | $R^1$ | $R^2$ | $R^3$ | $R^4$ | $R^5$ | $R^6$ | $A^1$ | $A^2$ | $A^3$ | n |
|---|---|---|---|---|---|---|---|---|---|---|
| 126 | Et | H | $CF_3$ | H | $CF(CF_3)_2$ | H | NMe | CH | N | 2 |
| 127 | Et | H | $CF_3$ | H | $SF_5$ | H | NMe | CH | N | 2 |
| 128 | Et | H | H | H | $CF_2CF_2CF_3$ | H | NMe | CH | N | 2 |
| 129 | Et | H | $CF_3$ | H | $CF_2CF_2CF_3$ | H | NMe | CH | N | 2 |
| 130 | Et | H | H | H | $SCF_2CF_3$ | H | NMe | CH | N | 2 |
| 131 | Et | H | $CF_3$ | H | $SCF_2CF_3$ | H | NMe | CH | N | 2 |
| 132 | Et | H | H | H | $SO_2CF_2CF_3$ | H | NMe | CH | N | 2 |
| 133 | Et | H | $CF_3$ | H | $SO_2CF_2CF_3$ | H | NMe | CH | N | 2 |
| 134 | Et | H | H | H | $CF_3$ | H | $NCH_2OMe$ | CH | N | 2 |
| 135 | Et | H | $CF_3$ | H | $CF_3$ | H | $NCH_2OMe$ | CH | N | 2 |
| 136 | Et | H | H | H | $CF_3$ | H | $NCH_2C\equiv CH$ | CH | N | 2 |
| 137 | Et | H | $CF_3$ | H | $CF_3$ | H | $NCH_2C\equiv CH$ | CH | N | 2 |
| 138 | Et | H | H | H | $CF_3$ | H | NMe | CH | CCN | 2 |
| 139 | Et | H | $CF_3$ | H | $CF_3$ | H | NMe | CH | CCN | 2 |
| 140 | Et | H | H | H | $CF_3$ | H | NMe | CH | CF | 2 |
| 141 | Et | H | $CF_3$ | H | $CF_3$ | H | NMe | CH | CF | 2 |
| 142 | Et | H | H | H | $CF_3$ | H | NMe | CH | CMe | 2 |
| 143 | Et | H | $CF_3$ | H | $CF_3$ | H | NMe | CH | CMe | 2 |
| 144 | Et | H | H | H | $CF_3$ | H | NMe | CH | COMe | 2 |
| 145 | Et | H | $CF_3$ | H | $CF_3$ | H | NMe | CH | COMe | 2 |
| 146 | Et | H | H | H | $CF_3$ | H | NMe | CH | $CSCH_2CH_3$ | 2 |
| 147 | Et | H | $CF_3$ | H | $CF_3$ | H | NMe | CH | $CSCH_2CH_3$ | 2 |
| 148 | Et | H | H | H | $CF_3$ | H | NMe | CH | $CSO_2CH_2CH_3$ | 2 |
| 149 | Et | H | $CF_3$ | H | $CF_3$ | H | NMe | CH | $CSO_2CH_2CH_3$ | 2 |
| 150 | Me | H | H | H | $CF_3$ | H | NMe | CH | N | 0 |

TABLE 42

| The present compound | $R^1$ | $R^2$ | $R^3$ | $R^4$ | $R^5$ | $R^6$ | $A^1$ | $A^2$ | $A^3$ | n |
|---|---|---|---|---|---|---|---|---|---|---|
| 151 | Me | H | H | H | $CF_3$ | H | NMe | CH | N | 1 |
| 152 | Me | H | H | H | $CF_3$ | H | NMe | CH | N | 2 |
| 153 | Pr | H | H | H | $CF_3$ | H | NMe | CH | N | 0 |
| 154 | Pr | H | H | H | $CF_3$ | H | NMe | CH | N | 1 |
| 155 | Pr | H | H | H | $CF_3$ | H | NMe | CH | N | 2 |
| 156 | $CH_2CH=CH_2$ | H | H | H | $CF_3$ | H | NMe | CH | N | 0 |
| 157 | $CH_2CH=CH_2$ | H | H | H | $CF_3$ | H | NMe | CH | N | 2 |
| 158 | iPr | H | H | H | $CF_3$ | H | NMe | CH | N | 0 |
| 159 | iPr | H | H | H | $CF_3$ | H | NMe | CH | N | 1 |
| 160 | iPr | H | H | H | $CF_3$ | H | NMe | CH | N | 2 |
| 161 | tBu | H | H | H | $CF_3$ | H | NMe | CH | N | 0 |
| 162 | tBu | H | H | H | $CF_3$ | H | NMe | CH | N | 1 |
| 163 | tBu | H | H | H | $CF_3$ | H | NMe | CH | N | 2 |
| 164 | $CF_3$ | H | H | H | $CF_3$ | H | NMe | CH | N | 0 |
| 165 | $CF_3$ | H | H | H | $CF_3$ | H | NMe | CH | N | 1 |
| 166 | Et | H | H | H | $CF_3$ | H | NEt | CH | N | 0 |
| 167 | Et | H | H | H | $CF_3$ | H | NEt | CH | N | 1 |
| 168 | Et | H | H | H | $CF_3$ | H | NEt | CH | N | 2 |
| 169 | Et | H | H | H | $CF_3$ | H | NPr | CH | N | 0 |
| 170 | Et | H | H | H | $CF_3$ | H | NPr | CH | N | 1 |
| 171 | Et | H | H | H | $CF_3$ | H | NPr | CH | N | 2 |
| 172 | Et | H | H | H | $CF_3$ | H | NiPr | CH | N | 0 |
| 173 | Et | H | H | H | $CF_3$ | H | NiPr | CH | N | 1 |

TABLE 42-continued

| The present compound | R¹ | R² | R³ | R⁴ | R⁵ | R⁶ | A¹ | A² | A³ | n |
|---|---|---|---|---|---|---|---|---|---|---|
| 174 | Et |  | H | H | CF₃ | H | NiPr | CH | N | 2 |
| 175 | Et |  | H | H | CF₃ | H | NCycPr | CH | N | 0 |

TABLE 43

| The present compound | R¹ | R² | R³ | R⁴ | R⁵ | R⁶ | A¹ | A² | A³ | n |
|---|---|---|---|---|---|---|---|---|---|---|
| 176 | Et | H | H | H | CF₃ | H | NCycPr | CH | N | 1 |
| 177 | Et | H | H | H | CF₃ | H | NCycPr | CH | N | 2 |
| 178 | Et | H | H | H | CF₃ | H | NCH₂OEt | CH | N | 0 |
| 179 | Et | H | H | H | H | CF₃ | NCH₂OEt | N | CH | 0 |
| 180 | Et | H | H | H | CF₃ | H | NCH₂OEt | CH | N | 1 |
| 181 | Et | H | H | H | CF₃ | H | NCH₂OEt | CH | N | 2 |
| 182 | Et | H | H | H | CF₃ | H | NCH₂OMe | CH | N | 0 |
| 183 | Et | H | H | H | Me | H | NMe | CH | N | 0 |
| 184 | Et | H | H | H | Me | H | NMe | CH | N | 1 |
| 185 | Et | H | H | H | Me | H | NMe | CH | N | 2 |
| 186 | Et | H | H | H | Br | H | NMe | CH | N | 0 |
| 187 | Et | H | H | H | Br | H | NMe | CH | N | 1 |
| 188 | Et | H | H | H | Br | H | NMe | CH | N | 2 |
| 189 | Et | H | H | H | I | H | NMe | CH | N | 1 |
| 190 | Et | H | H | H | I | H | NMe | CH | N | 2 |
| 191 | Et | H | H | H | CN | H | NMe | CH | N | 0 |
| 192 | Et | H | H | H | CN | H | NMe | CH | N | 1 |
| 193 | Et | H | H | H | CN | H | NMe | CH | N | 2 |
| 194 | Et | H | H | H | CHO | H | NMe | CH | N | 0 |
| 195 | Et | H | H | H | CF₂H | H | NMe | CH | N | 0 |
| 196 | Et | H | H | H | CF₂H | H | NMe | CH | N | 1 |
| 197 | Et | H | H | H | CF₂H | H | NMe | CH | N | 2 |
| 198 | Et | H | H | H | Ph | H | NMe | CH | N | 0 |
| 199 | Et | H | H | H | Ph | H | NMe | CH | N | 2 |
| 200 | Et | H | H | H | 2-fluoro-phenyl | H | NMe | CH | N | 0 |

TABLE 44

| The present compound | R¹ | R² | R³ | R⁴ | R⁵ | R⁶ | A¹ | A² | A³ | n |
|---|---|---|---|---|---|---|---|---|---|---|
| 201 | Et | H | H | H | 2-fluoro-phenyl | H | NMe | CH | N | 1 |
| 202 | Et | H | H | H | 2-fluoro-phenyl | H | NMe | CH | N | 2 |
| 203 | Et | H | H | H | 3-fluoro-phenyl | H | NMe | CH | N | 0 |
| 204 | Et | H | H | H | 3-fluoro-phenyl | H | NMe | CH | N | 1 |
| 205 | Et | H | H | H | 3-fluoro-phenyl | H | NMe | CH | N | 2 |
| 206 | Et | H | H | H | 4-fluoro-phenyl | H | NMe | CH | N | 0 |
| 207 | Et | H | H | H | 4-fluoro-phenyl | H | NMe | CH | N | 2 |
| 208 | Et | H | H | H | H | CF₃ | NMe | N | CH | 0 |
| 209 | Me | H | H | H | CF₃ | H | NMe | CH | CH | 0 |
| 210 | Et | H | H | H | CF₃ | H | NMe | CH | CCl | 0 |
| 211 | Et | H | H | H | CF₃ | H | NMe | CH | CCl | 1 |
| 212 | Et | H | H | H | CF₃ | H | NMe | CH | CCl | 2 |
| 213 | Et | H | H | H | CF₃ | H | NMe | CH | CBr | 1 |
| 214 | Me | H | H | H | CF₃ | H | O | CH | CH | 0 |
| 215 | Et | H | H | H | CF₃ | H | O | CH | CH | 1 |
| 216 | Et | H | H | H | CF₃ | H | O | CH | N | 1 |
| 217 | Me | H | H | H | CF₃ | H | S | CH | CH | 0 |
| 218 | Et | H | H | H | CF₃ | H | S | CH | CH | 1 |
| 219 | Et | Cl | H | H | CF₃ | H | NMe | CH | N | 0 |
| 220 | Et | Cl | H | H | CF₃ | H | NMe | CH | N | 1 |
| 221 | Et | H | H | H | COCF₃ | H | NMe | CH | N | 0 |
| 222 | Et | H | H | H | Cl | H | NMe | CH | N | 0 |

TABLE 44-continued

| The present compound | R¹ | R² | R³ | R⁴ | R⁵ | R⁶ | A¹ | A² | A³ | n |
|---|---|---|---|---|---|---|---|---|---|---|
| 223 | Et | H | H | H | Cl | H | NMe | CH | N | 1 |
| 224 | Et | H | H | H | Cl | H | NMe | CH | N | 2 |
| 225 | Et | H | H | H | Br | H | NMe | CCHO | N | 0 |

TABLE 45

| The present compound | R¹ | R² | R³ | R⁴ | R⁵ | R⁶ | A¹ | A² | A³ | n |
|---|---|---|---|---|---|---|---|---|---|---|
| 226 | Et | H | H | SEt | CF₃ | H | NMe | CH | N | 0 |
| 227 | Et | H | H | H | CF₃ | H | NCH₂OEt | CH | CH | 0 |
| 228 | Et | H | H | H | H | CF₃ | NCH₂OEt | N | CH | 0 |
| 229 | Et | H | H | H | CF₃ | H | NCH₂CO₂Me | CH | N | 0 |
| 230 | Et | H | H | H | CF₃ | H | NCH₂CO₂Et | CH | N | 0 |
| 231 | Et | H | H | H | CF₃ | H | N(CH₂)₂OMe | CH | N | 0 |
| 232 | Et | H | H | H | CF₃ | H | NCH₂SMe | CH | N | 0 |
| 233 | Et | H | H | H | CF₃ | H | N(CH₂)₂SMe | CH | N | 0 |
| 234 | Et | H | H | H | CF₃ | H | NBu | CH | N | 0 |
| 235 | Et | H | H | H | CF₃ | H | NCO₂tBu | CH | N | 0 |
| 236 | Et | H | H | H | CH(OH)CF₃ | H | NMe | CH | N | 0 |
| 237 | Et | H | H | H | CHFCF₃ | H | NMe | CH | N | 0 |
| 238 | Et | H | F | H | CF₃ | H | NMe | CH | N | 0 |
| 239 | Et | H | F | H | CF₃ | H | NMe | CH | N | 1 |
| 240 | Et | H | F | H | CF₃ | H | NMe | CH | N | 2 |
| 241 | Et | OMe | H | H | CF₃ | H | NMe | CH | N | 0 |
| 242 | Et | OMe | H | H | CF₃ | H | NMe | CH | N | 1 |
| 243 | Et | H | OMe | H | CF₃ | H | NMe | CH | N | 0 |
| 244 | Et | H | OMe | H | CF₃ | H | NMe | CH | N | 1 |
| 245 | Et | H | OH | H | CF₃ | H | NMe | CH | N | 0 |
| 246 | Et | H | H | H | NH₂ | H | NMe | CH | N | 0 |
| 247 | Et | H | H | H | CHFCF₃ | H | NMe | CH | N | 1 |
| 248 | Et | H | H | H | CHFCF₃ | H | NMe | CH | N | 2 |
| 249 | Et | H | H | H | CF₂CF₂CF₃ | H | NMe | CH | N | 0 |
| 250 | Et | H | H | H | CF₂CF₂CF₃ | H | NMe | CH | N | 1 |

TABLE 46

| The present compound | R¹ | R² | R³ | R⁴ | R⁵ | R⁶ | A¹ | A² | A³ | n |
|---|---|---|---|---|---|---|---|---|---|---|
| 251 | Et | Cl | H | H | CF₂CF₃ | H | NMe | CH | N | 1 |
| 252 | Et | Cl | H | H | CF₂CF₃ | H | NMe | CH | N | 2 |
| 253 | Et | H | Cl | H | CF₃ | H | NMe | CH | N | 0 |
| 254 | Et | H | Cl | H | CF₃ | H | NMe | CH | N | 1 |
| 255 | Et | H | Cl | H | CF₂CF₃ | H | NMe | CH | N | 1 |
| 256 | Et | H | H | Cl | CF₃ | H | NMe | CH | N | 0 |
| 257 | Et | H | H | Cl | CF₃ | H | NMe | CH | N | 1 |
| 258 | Et | H | H | OMe | CF₃ | H | NMe | CH | N | 0 |
| 259 | Et | H | H | OMe | CF₃ | H | NMe | CH | N | 1 |
| 260 | Et | H | H | OMe | CF₃ | H | NMe | CH | N | 2 |
| 261 | Et | H | H | H | SH | H | NMe | CH | N | 0 |
| 262 | Et | H | H | H | Et | H | NMe | CH | N | 0 |
| 263 | Et | H | H | H | iPr | H | NMe | CH | N | 0 |
| 264 | Et | H | H | H | NHEt | H | NMe | CH | N | 0 |
| 265 | Et | H | H | H | NEt₂ | H | NMe | CH | N | 0 |
| 266 | Et | H | H | H | tBu | H | NMe | CH | N | 0 |
| 267 | Et | H | H | H | H | CF₃ | NMe | CH | N | 0 |
| 268 | Et | F | H | H | CF₃ | H | NMe | CH | N | 0 |
| 269 | Et | F | H | H | CF₃ | H | NMe | CH | N | 1 |
| 270 | Et | F | H | H | CF₃ | H | NMe | CH | N | 2 |
| 271 | Et | H | H | H | H | CF₃ | NMe | CH | N | 1 |
| 272 | Et | H | H | H | H | CF₃ | NMe | CH | N | 2 |
| 273 | Et | H | H | H | NMe₂ | H | NMe | CH | N | 0 |
| 274 | Et | H | H | H | pyrrolidin-1-yl | H | NMe | CH | N | 0 |
| 275 | Et | H | H | H | NHCOMe | H | NMe | CH | N | 0 |

TABLE 47

| The present compound | R¹ | R² | R³ | R⁴ | R⁵ | R⁶ | A¹ | A² | A³ | n |
|---|---|---|---|---|---|---|---|---|---|---|
| 276 | Et | H | H | H | CH₂CF₃ | H | NMe | CH | N | 0 |
| 277 | Et | H | H | H | CF₃ | H | NMe | N | CH | 0 |
| 278 | Et | H | H | H | CF₃ | H J | NMe | N | CH | 1 |
| 279 | Et | H | H | H | CF₃ | H | NMe | N | CH | 2 |
| 280 | Et | H | H | H | NMeCOMe | H | NMe | CH | N | 0 |
| 281 | Et | H | H | H | NH2 | H | NMe | CH | N | 1 |
| 282 | Et | H | CF₃ | H | CF₃ | H | NMe | CH | N | 1 |

TABLE 47-continued

| The present compound | R¹ | R² | R³ | R⁴ | R⁵ | R⁶ | A¹ | A² | A³ | n |
|---|---|---|---|---|---|---|---|---|---|---|
| 283 | Et | H | H | H | NHCOCF₃ | H | NMe | CH | N | 0 |
| 284 | Et | H | H | H | NHCOCF₃ | H | NMe | CH | N | 1 |
| 285 | Et | H | H | H | NHCOCF₃ | H | NMe | CH | N | 2 |
| 286 | Et | H | H | H | 2-CF₃—Ph | H | NMe | CH | N | 0 |
| 287 | Et | H | H | H | 3-CF₃—Ph | H | NMe | CH | N | 0 |
| 288 | Et | H | H | H | 4-CF₃—Ph | H | NMe | CH | N | 0 |
| 289 | Et | H | H | H | CF₃ | H | S | CH | N | 1 |
| 290 | CH₂CF₃ | H | H | H | CF₃ | H | NMe | CH | N | 0 |
| 291 | CH₂CF₃ | H | H | H | CF₃ | H | NMe | CH | N | 1 |
| 292 | Et | Me | H | H | CF₃ | H | NMe | CH | N | 0 |
| 293 | Et | Me | H | H | CF₃ | H | NMe | CH | N | 1 |
| 294 | Et | Me | H | H | CF₃ | H | NMe | CH | N | 2 |
| 295 | Et | H | Me | H | CF₃ | H | NMe | CH | N | 0 |
| 296 | Et | H | Me | H | CF₃ | H | NMe | CH | N | 1 |
| 297 | Et | H | H | H | 2-CF₃—Ph | H | NMe | CH | N | 1 |
| 298 | Et | H | H | H | 2-CF₃—Ph | H | NMe | CH | N | 2 |
| 299 | Et | H | H | H | 3-CF₃—Ph | H | NMe | CH | N | 1 |
| 300 | Et | H | H | H | 3-CF₃—Ph | H | NMe | CH | N | 2 |

TABLE 48

| The present compound | R¹ | R² | R³ | R⁴ | R⁵ | R⁶ | A¹ | A² | A³ | n |
|---|---|---|---|---|---|---|---|---|---|---|
| 301 | Et | H | H | H | 4-CF₃—Ph | H | NMe | CH | N | 1 |
| 302 | Et | H | H | H | 4-CF₃—Ph | H | NMe | CH | N | 2 |
| 303 | Et | H | CF₃ | CF₃ | H | NMe | CH | N | 0 |
| 304 | Et | H | CF₃ | CF₃ | H | NMe | CH | N | 1 |
| 305 | Et | H | CF₃ | CF₃ | H | NMe | CH | N | 2 |
| 306 | Et | H | H | H | 2-chlorophenyl | H | NMe | CH | N | 0 |
| 307 | Et | H | H | H | 3-chlorophenyl | H | NMe | CH | N | 0 |
| 308 | Et | H | H | H | 4-chlorophenyl | H | NMe | CH | N | 0 |
| 309 | Et | H | H | H | 6-chloro-3-pyridyl | H | NMe | CH | N | 0 |
| 310 | Et | H | H | H | 5-fluoro-3-pyridyl | H | NMe | CH | N | 0 |
| 311 | Et | H | H | H | 3-pyridyl | H | NMe | CH | N | 0 |
| 312 | Et | H | H | H | 4-pyridyl | H | NMe | CH | N | 0 |
| 313 | Et | H | H | H | 4-chloro-1-pyrazolyl | H | NMe | CH | N | 0 |
| 314 | Et | H | H | H | 2-chlorophenyl | H | NMe | CH | N | 1 |
| 315 | Et | H | H | H | 2-chlorophenyl | H | NMe | CH | N | 2 |
| 316 | Et | H | H | H | 3-chlorophenyl | H | NMe | CH | N | 1 |
| 317 | Et | H | H | H | 3-chlorophenyl | H | NMe | CH | N | 2 |
| 318 | Et | H | H | H | 4-chlorophenyl | H | NMe | CH | N | 2 |
| 319 | Et | H | H | H | 4-pyridyl | H | NMe | CH | N | 1 |
| 320 | Et | H | H | H | 4-pyridyl | H | NMe | CH | N | 2 |
| 321 | Et | H | H | H | 6-chloro-3-pyridyl | H | NMe | CH | N | 2 |
| 322 | Et | H | H | H | 5-fluoro-3-pyridyl | H | NMe | CH | N | 1 |
| 323 | Et | H | H | H | 5-fluoro-3-pyridyl | H | NMe | CH | N | 2 |
| 324 | Et | H | H | H | 4-chloro-1-pyrazolyl | H | NMe | CH | N | 2 |
| 325 | Et | H | H | H | 3-chloro-1-triazolyl | H | NMe | CH | N | 0 |

TABLE 49

| The present compound | R¹ | R² | R³ | R⁴ | R⁵ | R⁶ | A¹ | A² | A³ | n |
|---|---|---|---|---|---|---|---|---|---|---|
| 326 | Et | H | H | H | 4-CF₃-imidazole | H | NMe | CH | N | 0 |
| 327 | Et | H | H | H | 2-nitro-phenyl | H | NMe | CH | N | 0 |
| 328 | Et | H | H | H | 3-nitro-phenyl | H | NMe | CH | N | 0 |
| 329 | Et | H | H | H | 2-cyano-phenyl | H | NMe | CH | N | 0 |
| 330 | Et | H | H | H | 3-cyano-phenyl | H | NMe | CH | N | 0 |
| 331 | Et | H | H | H | 4-cyano-phenyl | H | NMe | CH | N | 0 |
| 332 | Et | H | H | H | 3-CF₃-triazolyl | H | NMe | CH | N | 0 |
| 333 | Et | H | H | H | 3-CF₃-5-Me-triazolyl | H | NMe | CH | N | 0 |
| 334 | Et | H | H | H | 3-chloro-1-triazolyl | H | NMe | CH | N | 2 |
| 335 | Et | H | H | H | 4-CF₃-imidazolyl | H | NMe | CH | N | 1 |
| 336 | Et | H | Br | H | CF₃ | H | NMe | CH | N | 0 |
| 337 | Et | H | Br | H | CF₃ | H | NMe | CH | N | 1 |
| 338 | Et | H | CN | H | CF₃ | H | NMe | CH | N | 0 |
| 339 | Et | H | CN | H | CF₃ | H | NMe | CH | N | 1 |

TABLE 49-continued

| The present compound | R¹ | R² | R³ | R⁴ | R⁵ | R⁶ | A¹ | A² | A³ | n |
|---|---|---|---|---|---|---|---|---|---|---|
| 340 | Et | H | CN | H | $CF_3$ | H | NMe | CH | N | 2 |
| 341 | Et | H | $CF_2CF_3$ | H | $CF_3$ | H | NMe | CH | N | 1 |
| 342 | Et | H | CHO | H | $CF_3$ | H | NMe | CH | N | 0 |
| 343 | Et | H | Ph | H | $CF_3$ | H | NMe | CH | N | 0 |
| 344 | Et | H | H | H | SMe | H | NMe | CH | N | 0 |
| 345 | Et | H | H | H | $SO_2Me$ | H | NMe | CH | N | 2 |
| 346 | Et | H | H | H | SEt | H | NMe | CH | N | 0 |
| 347 | Et | H | H | H | $SO_2Et$ | H | NMe | CH | N | 2 |
| 348 | Et | H | H | H | SiPr | H | NMe | CH | N | 0 |
| 349 | Et | H | H | H | $SO_2iPr$ | H | NMe | CH | N | 2 |
| 350 | Et | H | H | H | $SCH_2CF_3$ | H | NMe | CH | N | 0 |

TABLE 50

| The present compound | R¹ | R² | R³ | R⁴ | R⁵ | R⁶ | A¹ | A² | A³ | n |
|---|---|---|---|---|---|---|---|---|---|---|
| 351 | Et | H | H | H | $SO_2CH_2CF_3$ | H | NMe | CH | N | 2 |
| 352 | Et | H | H | H | $SCH_2CH=CH_2$ | H | NMe | CH | N | 0 |
| 353 | Et | H | H | H | $SCF_2CF_3$ | H | NMe | CH | N | 0 |
| 354 | Et | H | H | H | $SCF_2CF_2CF_3$ | H | NMe | CH | N | 0 |
| 355 | Et | H | H | H | $SCF(CF_3)_2$ | H | NMe | CH | N | 0 |
| 356 | Et | H | H | H | $CH(OH)CF_3$ | H | NMe | CH | N | 0 |
| 357 | Et | H | H | H | $CH(Cl)CF_3$ | H | NMe | CH | N | 0 |
| 358 | Et | H | H | H | OH | H | NMe | CH | N | 0 |
| 359 | Et | H | H | H | OH | H | NMe | CH | N | 2 |
| 360 | Et | H | H | H | $OCF_2Br$ | H | NMe | CH | N | 2 |
| 361 | Et | H | H | H | $OCF_3$ | H | NMe | CH | N | 2 |
| 362 | Et | H | H | H | $SCF_2CF_3$ | H | NMe | CH | N | 1 |
| 363 | Et | H | H | H | $SCF_2CF_2CF_3$ | H | NMe | CH | N | 1 |
| 364 | Et | H | H | H | $SCF_2CF_2CF_3$ | H | NMe | CH | N | 2 |
| 365 | Et | H | H | H | StBu | H | NMe | CH | N | 0 |
| 366 | Et | H | H | H | $SO_2tBu$ | H | NMe | CH | N | 2 |
| 367 | Et | H | $CF_3$ | H | Br | H | NMe | CH | N | 0 |
| 368 | Et | H | $CF_3$ | H | Br | H | NMe | CH | N | 1 |
| 369 | Et | H | $CF_3$ | H | Br | H | NMe | CH | N | 2 |
| 370 | Et | H | H | H | $SCH=C=CH_2$ | H | NMe | CH | N | 0 |
| 371 | Et | H | H | H | $SO_2CH=C=CH_2$ | H | NMe | CH | N | 2 |
| 372 | Et | H | H | H | $SO_2CH_2CH=CH_2$ | H | NMe | CH | N | 2 |
| 373 | Et | H | I | H | $CF_2CF_3$ | H | NMe | CH | N | 2 |
| 374 | Et | H | $NO_2$ | H | $CF_3$ | H | NMe | CH | N | 0 |
| 375 | Et | H | $NO_2$ | H | $CF_3$ | H | NMe | CH | N | 1 |

TABLE 51

| The present compound | R¹ | R² | R³ | R⁴ | R⁵ | R⁶ | A¹ | A² | A³ | n |
|---|---|---|---|---|---|---|---|---|---|---|
| 376 | Et | H | $NO_2$ | H | $CF_3$ | H | NMe | CH | N | 2 |
| 377 | Et | H | I | H | $SCF_3$ | H | NMe | CH | N | 2 |
| 378 | Et | H | I | H | $SO_2CF_3$ | H | NMe | CH | N | 2 |
| 379 | Et | H | Br | H | $CF_2CF_3$ | H | NMe | CH | N | 2 |
| 380 | Et | H | Cl | H | $CF_3$ | H | S | CH | N | 0 |
| 381 | Et | H | Cl | H | $CF_3$ | H | S | CH | N | 2 |
| 382 | Et | H | H | H | $C(OH)(CF_3)_2$ | H | NMe | CH | N | 0 |
| 383 | Et | H | H | H | $C(Cl)(CF_3)_2$ | H | NMe | CH | N | 0 |
| 384 | Et | H | H | H | $C(Cl)(CF_3)_2$ | H | NMe | CH | N | 1 |
| 385 | Et | H | H | H | $C(Cl)(CF_3)_2$ | H | NMe | CH | N | 2 |
| 386 | Et | H | Cl | H | $CF_2CF_3$ | H | NMe | CH | N | 2 |
| 387 | Et | H | H | H | H | $CF(CF_3)_2$ | NMe | CH | CH | 0 |
| 388 | Et | H | H | H | $CF(CF_3)_2$ | H | NMe | CH | CH | 0 |
| 389 | Et | H | $CF_3$ | H | I | H | NMe | CH | N | 2 |
| 390 | Et | H | H | H | $CF_2CF_3$ | H | NMe | CH | CH | 1 |
| 391 | Et | H | H | H | $SF_5$ | H | NMe | CH | CH | 1 |
| 392 | Et | H | $CF_3$ | H | $SF_5$ | H | NMe | CH | CH | 0 |
| 393 | Et | H | $CF_3$ | H | $SF_5$ | H | NMe | CH | CH | 1 |
| 394 | Et | H | Me | H | $CF_2CF_3$ | H | NMe | CH | N | 0 |
| 395 | Et | H | Me | H | $CF_2CF_3$ | H | NMe | CH | N | 1 |
| 396 | Et | H | Me | H | $CF_2CF_3$ | H | NMe | CH | N | 2 |

TABLE 51-continued

| The present compound | R$^1$ | R$^2$ | R$^3$ | R$^4$ | R$^5$ | R$^6$ | A$^1$ | A$^2$ | A$^3$ | n |
|---|---|---|---|---|---|---|---|---|---|---|
| 397 | Et | H | H | H | I | H | S | CH | N | 0 |
| 398 | Et | H | CF$_3$ | H | I | H | S | CH | N | 0 |
| 399 | Et | H | H | H | CF$_2$CF$_3$ | H | S | CH | N | 0 |
| 400 | Et | H | CF$_3$ | H | CF$_2$CF$_3$ | H | S | CH | N | 0 |

TABLE 52

| The present compound | R$^1$ | R$^2$ | R$^3$ | R$^4$ | R$^5$ | R$^6$ | A$^1$ | A$^2$ | A$^3$ | n |
|---|---|---|---|---|---|---|---|---|---|---|
| 401 | Et | H | H | H | CF$_2$CF$_3$ | H | S | CH | N | 2 |
| 402 | Et | H | CF$_3$ | H | CF$_2$CF$_3$ | H | S | CH | N | 2 |
| 403 | Et | H | H | H | H | CF$_3$ | S | N | CH | 0 |
| 404 | Et | H | H | H | H | CF$_3$ | S | N | CH | 2 |
| 405 | Et | H | CH=CH$_2$ | H | CF$_3$ | H | NMe | CH | N | 2 |
| 406 | Et | H | Et | H | CF$_3$ | H | NMe | CH | N | 2 |
| 407 | Et | H | H | H | SO$_2$NMe$_2$ | H | NMe | CH | N | 1 |
| 408 | Et | H | H | H | SO$_2$NMe$_2$ | H | NMe | CH | N | 2 |
| 409 | Et | H | H | H | CF$_3$ | H | NMe | CH | CNH$_2$ | 0 |
| 410 | Et | H | Br | H | SCF$_3$ | H | NMe | CH | N | 2 |
| 411 | Et | H | H | H | CF$_3$ | H | NMe | CH | CNMe$_2$ | 0 |
| 412 | Et | H | CF$_3$ | H | CF$_3$ | H | NMe | CH | CNH$_2$ | 0 |
| 413 | Et | H | CF$_3$ | H | CF$_3$ | H | NMe | CH | CNMe$_2$ | 0 |
| 414 | Et | H | SF$_5$ | H | CF$_3$ | H | NMe | CH | N | 0 |
| 415 | Et | H | SF$_5$ | H | CF$_3$ | H | NMe | CH | N | 1 |
| 416 | Et | H | SF$_5$ | H | CF$_3$ | H | NMe | CH | N | 2 |
| 417 | Et | H | H | H | CF(CF$_3$)$_2$ | H | NH | CH | CH | 0 |
| 418 | Et | H | H | H | Br | H | NMe | CCF$_2$H | N | 0 |
| 419 | Et | H | H | H | Br | H | NMe | CCF$_2$H | N | 1 |
| 420 | Et | H | H | H | Br | H | NMe | CCF$_2$H | N | 2 |
| 421 | Et | H | H | H | Br | H | NMe | CiPr | N | 0 |
| 422 | Et | H | H | H | CF$_3$ | H | NH | CH | N | 1 |
| 423 | Et | H | H | H | CF$_3$ | H | NH | CH | CH | 0 |
| 424 | Et | H | CF$_3$ | H | CF$_3$ | H | NEt | CH | N | 2 |
| 425 | Et | H | CF$_3$ | H | CF$_3$ | H | NCH$_2$CH=CH$_2$ | CH | N | 2 |

TABLE 53

| The present compound | R$^1$ | R$^2$ | R$^3$ | R$^4$ | R$^5$ | R$^6$ | A$^1$ | A$^2$ | A$^3$ | n |
|---|---|---|---|---|---|---|---|---|---|---|
| 426 | Et | H | CF$_3$ | H | CF$_3$ | H | NCH$_2$CN | CH | N | 2 |
| 427 | Et | H | CF$_3$ | H | H | CF$_3$ | NCH$_2$CN | N | CH | 2 |
| 428 | Et | H | CF$_3$ | H | CF$_3$ | H | NCH$_2$OEt | CH | N | 2 |
| 429 | Et | H | CF$_3$ | H | H | CF$_3$ | NCH$_2$OEt | N | CH | 2 |
| 430 | Et | H | CF$_3$ | H | CF$_3$ | H | NCH$_2$SMe | CH | N | 2 |
| 431 | Et | H | CF$_3$ | H | CF$_3$ | H | NPr | CH | N | 2 |
| 432 | Et | H | CF$_3$ | H | CF$_3$ | H | N(CH$_2$)$_3$CH$_3$ | CH | N | 2 |
| 433 | Et | H | CF$_3$ | H | CF$_3$ | H | NCH$_2$CO$_2$Me | CH | N | 2 |
| 434 | Et | H | CF$_3$ | H | H | CF$_3$ | NCH$_2$CO$_2$Me | N | CH | 2 |
| 435 | Et | H | CF$_3$ | H | CF$_3$ | H | NCH$_2$CH=CCl$_2$ | CH | N | 2 |
| 436 | Et | H | CF$_3$ | H | CF$_3$ | H | NCO$_2$tBu | CH | N | 2 |
| 437 | Et | H | CF$_3$ | H | CF$_3$ | H | NCO$_2$Me | CH | N | 2 |
| 438 | Et | H | CF$_3$ | H | CF$_3$ | H | NCOMe | CH | N | 2 |
| 439 | Et | H | OCF$_3$ | H | CF$_3$ | H | NMe | CH | N | 0 |
| 440 | Et | H | OCF$_3$ | H | CF$_3$ | H | NMe | CH | N | 1 |
| 441 | Et | H | CF$_2$CF$_2$CF$_2$CF$_3$ | H | CF$_3$ | H | NMe | CH | N | 2 |
| 442 | Et | H | NH$_2$ | H | CF$_3$ | H | NMe | CH | N | 2 |
| 443 | Et | H | NHCOCF$_3$ | H | CF$_3$ | H | NMe | CH | N | 2 |
| 444 | Et | H | iPr | H | CF$_3$ | H | NMe | CH | N | 2 |
| 445 | Et | H | CHO | H | CF$_3$ | H | NMe | CH | N | 2 |
| 446 | CH$_2$CH$_2$CH$_2$CH$_3$ | H | H | H | CF$_3$ | H | NMe | CH | N | 0 |
| 447 | CH$_2$CO$_2$Me | H | H | H | CF$_3$ | H | NMe | CH | N | 0 |
| 448 | CH$_2$CH=CCl$_2$ | H | H | H | CF$_3$ | H | NMe | CH | N | 0 |
| 449 | CH$_2$C≡CCH$_3$ | H | H | H | CF$_3$ | H | NMe | CH | N | 0 |
| 450 | CH$_2$CN | H | H | H | CF$_3$ | H | NMe | CH | N | 0 |

TABLE 54

| The present compound | R¹ | R² | R³ | R⁴ | R⁵ | R⁶ | A¹ | A² | A³ | n |
|---|---|---|---|---|---|---|---|---|---|---|
| 451 | CH$_2$tBu | H | H | H | CF$_3$ | H | NMe | CH | N | 0 |
| 452 | CH$_2$CH$_2$CN | H | H | H | CF$_3$ | H | NMe | CH | N | 0 |
| 453 | CH$_2$CycBu | H | H | H | CF$_3$ | H | NMe | CH | N | 0 |
| 454 | CF$_2$Br | H | H | H | CF$_3$ | H | NMe | CH | N | 0 |
| 455 | Et | H | CF$_2$H | H | CF$_3$ | H | NMe | CH | N | 2 |
| 456 | Et | H | CH$_2$OH | H | CF$_3$ | H | NMe | CH | N | 2 |
| 457 | (CH$_2$)$_3$CH$_3$ | H | H | H | CF$_3$ | H | NMe | CH | N | 2 |
| 458 | CH$_2$CO$_2$Me | H | H | H | CF$_3$ | H | NMe | CH | N | 2 |
| 459 | CH$_2$CH=CCl$_2$ | H | H | H | CF$_3$ | H | NMe | CH | N | 2 |
| 460 | CH$_2$C≡CCH$_3$ | H | H | H | CF$_3$ | H | NMe | CH | N | 2 |
| 461 | CH$_2$CN | H | H | H | CF$_3$ | H | NMe | CH | N | 2 |
| 462 | CH$_2$tBu | H | H | H | CF$_3$ | H | NMe | CH | N | 2 |
| 463 | CH$_2$CH$_2$CN | H | H | H | CF$_3$ | H | NMe | CH | N | 2 |
| 464 | CH$_2$CycBu | H | H | H | CF$_3$ | H | NMe | CH | N | 2 |
| 465 | CF$_2$Br | H | H | H | CF$_3$ | H | NMe | CH | N | 2 |
| 466 | Et | H | CH$_2$F | H | CF$_3$ | H | NMe | CH | N | 2 |
| 467 | CH=CH$_2$ | H | H | H | CF$_3$ | H | NMe | CH | N | 0 |
| 468 | CH=CH$_2$ | H | H | H | CF$_3$ | H | NMe | CH | N | 1 |
| 469 | CH=CH$_2$ | H | H | H | CF$_3$ | H | NMe | CH | N | 2 |
| 470 | Et | H | H | H | H | CF$_3$ | S | CH | N | 0 |
| 471 | Et | H | H | H | H | CF$_3$ | S | CH | N | 2 |
| 472 | Et | H | OCF$_3$ | H | CF$_2$CF$_3$ | H | NMe | CH | N | 0 |
| 473 | Et | H | OCF$_3$ | H | CF$_2$CF$_3$ | H | NMe | CH | N | 1 |
| 474 | Et | H | OCF$_3$ | H | CF$_2$CF$_3$ | H | NMe | CH | N | 2 |
| 475 | Et | H | CF$_3$ | H | CF$_3$ | H | NMe | CH | CMe | 0 |

TABLE 55

| The present compound | R¹ | R² | R³ | R⁴ | R⁵ | R⁶ | A¹ | A² | A³ | n |
|---|---|---|---|---|---|---|---|---|---|---|
| 476 | Et | H | CF$_3$ | H | CF$_3$ | H | NMe | CH | CMe | 1 |
| 477 | Et | H | CF$_3$ | H | CF$_3$ | H | NMe | CH | CF | 0 |
| 478 | Et | H | CF$_3$ | H | CF$_3$ | H | NMe | CH | CF | 1 |
| 479 | CH$_2$CycPr | H | H | H | CF$_3$ | H | NMe | CH | N | 0 |
| 480 | CH$_2$CycPr | H | H | H | CF$_3$ | H | NMe | CH | N | 1 |
| 481 | Et | H | CF$_3$ | H | CF$_3$ | H | NMe | CH | CBr | 0 |
| 482 | Et | H | CF$_3$ | H | CF$_3$ | H | NMe | CH | CSCH$_2$CH$_3$ | 0 |
| 483 | CH$_2$C≡CH | H | H | H | CF$_3$ | H | NMe | CH | N | 0 |
| 484 | CH$_2$C≡CH | H | H | H | CF$_3$ | H | NMe | CH | N | 2 |
| 485 | Et | H | C≡CH | H | CF$_3$ | H | NMe | CH | N | 2 |
| 486 | Et | H | 4-trifluoromethyl-2-pyridyl | H | CF$_3$ | H | NMe | CH | N | 2 |
| 487 | Et | H | OCF$_3$ | H | SCF$_3$ | H | NMe | CH | N | 0 |
| 488 | Et | H | OCF$_3$ | H | SCF$_3$ | H | NMe | CH | N | 1 |
| 489 | Et | H | OCF$_3$ | H | SCF$_3$ | H | NMe | CH | N | 2 |
| 490 | Et | H | CF$_3$ | H | CF$_3$ | H | NMe | CH | CBr | 1 |
| 491 | Et | H | CF$_3$ | H | CF$_3$ | H | NMe | CH | CBr | 2 |
| 492 | Et | H | H | H | 2-pyridyl | H | NMe | CH | N | 0 |
| 493 | Et | H | H | H | 2-pyridyl | H | NMe | CH | N | 2 |
| 494 | Et | H | H | H | 2-furyl | H | NMe | CH | N | 0 |
| 495 | Et | H | H | H | 2-furyl | H | NMe | CH | N | 2 |
| 496 | Et | H | H | H | 2-thienyl | H | NMe | CH | N | 0 |
| 497 | Et | H | H | H | 2-thienyl | H | NMe | CH | N | 2 |
| 498 | Et | H | H | H | CH=CH$_2$ | H | NMe | CH | N | 0 |
| 499 | Et | H | H | H | CH=CH$_2$ | H | NMe | CH | N | 2 |
| 500 | Et | H | H | H | COMe | H | NMe | CH | N | 0 |

TABLE 56

| The present compound | R¹ | R² | R³ | R⁴ | R⁵ | R⁶ | A¹ | A² | A³ | n |
|---|---|---|---|---|---|---|---|---|---|---|
| 501 | Et | H | H | H | COMe | H | NMe | CH | N | 2 |
| 502 | Et | H | H | H | CH$_2$CH=CH$_2$ | H | NMe | CH | N | 0 |
| 503 | Et | H | H | H | CF$_3$ | H | N-(6-Chloro-pyridin-3-ylmethyl) | CH | N | 2 |

TABLE 56-continued

| The present compound | R¹ | R² | R³ | R⁴ | R⁵ | R⁶ | A¹ | A² | A³ | n |
|---|---|---|---|---|---|---|---|---|---|---|
| 504 | Et | H | $CF_3$ | H | $CF_3$ | H | N-(6-Chloro-pyridin-3-ylmethyl) | CH | N | 2 |
| 505 | Et | H | H | H | $CF_3$ | H | N-(2-Chloro-thiazol-5-ylmethyl) | CH | N | 2 |
| 506 | Et | H | $CF_3$ | H | $CF_3$ | H | N-(2-Chloro-thiazol-5-ylmethyl) | CH | N | 2 |
| 507 | Et | H | H | H | $CF_3$ | CN | NMe | CH | N | 2 |
| 508 | Et | H | $CF_3$ | H | $CF_3$ | CN | NMe | CH | N | 2 |
| 509 | Et | H | H | H | $CF_3$ | H | N-(2-Chloro-thiazol-5-ylmethyl) | CH | N | 0 |
| 510 | Et | H | $CF_3$ | H | $CF_3$ | H | N-(2-Chloro-thiazol-5-ylmethyl) | CH | N | 0 |
| 511* | Et | H | H | H | $CF_3$ | H | NMe | CH | N | 2 |
| 512* | Et | H | $CF_3$ | H | $CF_3$ | H | NMe | CH | N | 2 |
| 513 | Et | H | H | H | $CF_3$ | H | NMe | CH | COMe | 0 |
| 514 | Et | H | H | H | $CF_3$ | H | NMe | CH | CSMe | 0 |
| 515 | Et | H | H | H | $CF_3$ | H | NMe | CH | $CSO_2Me$ | 2 |
| 516 | Et | H | H | H | $CF_3$ | H | NMe | CH | CSPh | 0 |
| 517 | Et | H | H | H | $CF_3$ | H | NMe | CH | $CSO_2Ph$ | 2 |
| 518 | Et | H | H | H | $CF_3$ | H | NMe | CH | $CSO_2CH_2CF_3$ | 2 |
| 519 | Et | H | H | H | $CF_3$ | H | NMe | CH | CCN | 0 |
| 520 | Et | H | $CF_3$ | H | $CF_3$ | H | NMe | $CNMe_2$ | N | 2 |
| 521 | Et | H | $CF_3$ | H | $CF_3$ | $CO_2H$ | NMe | CH | N | 2 |
| 522 | Et | H | $CF_3$ | H | $CF_3$ | $CONH_2$ | NMe | CH | N | 2 |
| 523* | Et | H | $CF_3$ | H | $CF_2CF_3$ | H | NMe | CH | N | 2 |
| 524* | Et | H | $CF_3$ | H | $CF_2CF_3$ | H | NMe | CH | N | 2 |
| 525 | Et | H | $CF_3$ | H | $CO_2H$ | H | NMe | CH | N | 0 |

TABLE 57

| The present compound | R¹ | R² | R³ | R⁴ | R⁵ | R⁶ | A¹ | A² | A³ | n |
|---|---|---|---|---|---|---|---|---|---|---|
| 526 | Et | H | H | H | $CF_3$ | H | NMe | CH | CCN | 1 |
| 527 | Et | H | H | H | $CF_3$ | H | NH | CH | $CCF_3$ | 0 |
| 528 | Et | H | $C(OMe)_3$ | H | $CF_2CF_3$ | H | NMe | CH | N | 2 |
| 529 | Et | H | H | H | H | $CF_3$ | NMe | $CCF_3$ | CH | 0 |
| 530 | Et | H | H | H | H | $CF_3$ | NMe | $CCF_3$ | CH | 2 |
| 531 | Et | H | H | H | $CF_3$ | H | NMe | CH | $CCF_3$ | 2 |
| 532 | Me | H | $CF_3$ | H | $CF_2CF_3$ | H | NMe | CH | N | 0 |
| 533 | Me | H | $CF_3$ | H | $CF_2CF_3$ | H | NMe | CH | N | 2 |
| 534 | Pr | H | $CF_3$ | H | $CF_2CF_3$ | H | NMe | CH | N | 0 |
| 535 | Pr | H | $CF_3$ | H | $CF_2CF_3$ | H | NMe | CH | N | 2 |
| 536 | iPr | H | $CF_3$ | H | $CF_2CF_3$ | H | NMe | CH | N | 0 |
| 537 | iPr | H | $CF_3$ | H | $CF_2CF_3$ | H | NMe | CH | N | 2 |
| 538 | Bu | H | $CF_3$ | H | $CF_2CF_3$ | H | NMe | CH | N | 0 |
| 539 | Bu | H | $CF_3$ | H | $CF_2CF_3$ | H | NMe | CH | N | 2 |
| 540 | $CH(CH_3)CH_2CH_3$ | H | $CF_3$ | H | $CF_2CF_3$ | H | NMe | CH | N | 0 |
| 541 | $CH(CH_3)CH_2CH_3$ | H | $CF_3$ | H | $CF_2CF_3$ | H | NMe | CH | N | 2 |
| 542 | $CH_2CH(CH_3)_2$ | H | $CF_3$ | H | $CF_2CF_3$ | H | NMe | CH | N | 0 |
| 543 | $CH_2CH(CH_3)_2$ | H | $CF_3$ | H | $CF_2CF_3$ | H | NMe | CH | N | 2 |
| 544 | tBu | H | $CF_3$ | H | $CF_2CF_3$ | H | NMe | CH | N | 0 |
| 545 | tBu | H | $CF_3$ | H | $CF_2CF_3$ | H | NMe | CH | N | 2 |
| 546 | CycPen | H | $CF_3$ | H | $CF_2CF_3$ | H | NMe | CH | N | 0 |
| 547 | CycPen | H | $CF_3$ | H | $CF_2CF_3$ | H | NMe | CH | N | 2 |
| 548 | CycHex | H | $CF_3$ | H | $CF_2CF_3$ | H | NMe | CH | N | 0 |
| 549 | CycHex | H | $CF_3$ | H | $CF_2CF_3$ | H | NMe | CH | N | 2 |
| 550 | $CH_2CF_3$ | H | $CF_3$ | H | $CF_2CF_3$ | H | NMe | CH | N | 0 |

TABLE 58

| The present compound | R¹ | R² | R³ | R⁴ | R⁵ | R⁶ | A¹ | A² | A³ | n |
|---|---|---|---|---|---|---|---|---|---|---|
| 551 | CH₂CF₃ | H | CF₃ | H | CF₂CF₃ | H | NMe | CH | N | 2 |
| 552 | Et | H | CF₃ | H | CN | H | NMe | CH | N | 0 |
| 553 | Et | H | H | H | CF₃ | H | NMe | CH | CCF₃ | 0 |
| 554 | Et | H | CF₃ | H | CF₂CF₃ | H | N-(4-methoxy-benzyl) | CH | N | 0 |
| 555 | Et | H | CF₃ | H | H | CF₂CF₃ | N-(4-methoxy-benzyl) | N | CH | 0 |

In the above [Table 36] to [Table 58], the symbol "*" in the present compound represents N-oxide. Specifically, the following compounds are mentioned.

The Present Compound 22

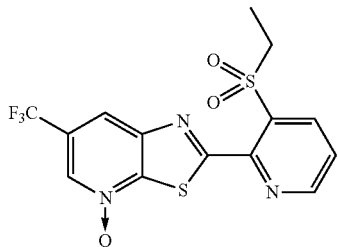 [SMILES: CCS(=O)(=O)c1cccnc1-c1nc2cc(C(F)(F)F)c[n+]([O-])c2s1]

The Present Compound 36

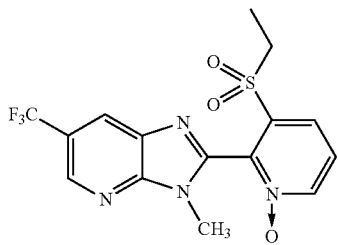 [SMILES: CCS(=O)(=O)c1ccc[n+]([O-])c1-c1nc2cc(C(F)(F)F)cnc2n1C]

The Present Compound 37

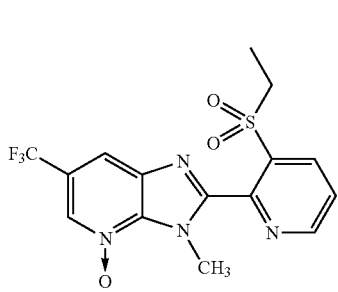 [SMILES: CCS(=O)(=O)c1cccnc1-c1nc2cc(C(F)(F)F)c[n+]([O-])c2n1C]

The Present Compound 47

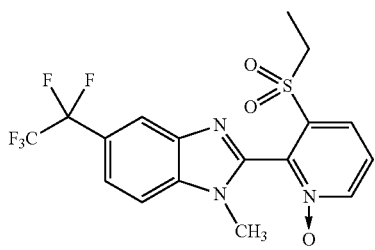 [SMILES: CCS(=O)(=O)c1ccc[n+]([O-])c1-c1nc2cc(C(F)(F)C(F)(F)F)ccc2n1C]

The Present Compound 48

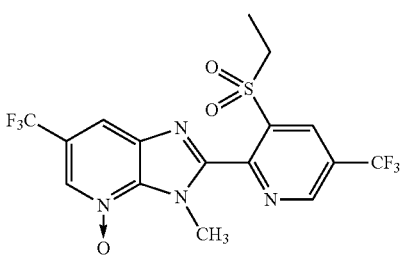 [SMILES: CCS(=O)(=O)c1cc(C(F)(F)F)cnc1-c1nc2cc(C(F)(F)F)c[n+]([O-])c2n1C]

The Present Compound 51

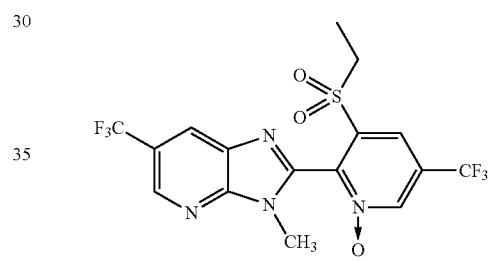

The Present Compound 70

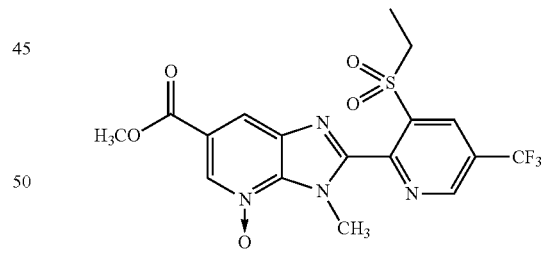

The Present Compound 511

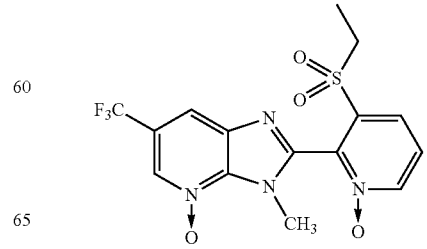

The Present Compound 512

The Present Compound 523

The Present Compound 524

In the above [Table 36] to [Table 58], "Me" represents a methyl group, "Et" represents an ethyl group, "Pr" represents a propyl group, "iPr" represents an isopropyl group, "Bu" represents a butyl group, "tBu" represents a tert-butyl group, "CycPr" represents a cyclopropyl group, "CycBu" represents a cyclobutyl group, "CycPen" represents a cyclopentyl group, "CycHex" represents a cyclohexyl group, "Ph" represents a phenyl group, "2-CF$_3$-Ph" represents a 2-trifluoromethylphenyl group, "3-CF$_3$-Ph" represents a 3-trifluoromethylphenyl group, "4-CF$_3$-Ph" represents a 4-trifluoromethylphenyl group, "3-CF$_3$-triazolyl" represents a 3-trifluoromethyl-(1H-1,2,4-triazol)-1-yl group, "3-CF$_3$-5-Me-triazolyl" represents a 3-trifluoromethyl-5-methyl-(1H-1,2,4-triazol)-1-yl group, and "4-CF$_3$-imidazolyl" represents a 4-trifluoromethylimidazole-1-yl group.

Hereinafter, $^1$H-NMR data of the present compounds listed in [Table 36] to [Table 58] are shown.

The Present Compound 47
$^1$H-NMR (CDCl$_3$) δ: 8.53 (1H, dd), 8.07 (1H, s), 7.98 (1H, dd), 7.65 (1H, dd), 7.62-7.56 (2H, m), 3.90-3.77 (1H, m), 3.75 (3H, s), 3.52-3.42 (1H, m), 1.33 (3H, t).

The Present Compound 49
$^1$H-NMR (CDCl$_3$) δ: 8.61-7.00 (6H, m), 3.90 (3H, s), 2.94 (2H, q), 1.33 (3H, t).

The Present Compound 50
$^1$H-NMR (CDCl$_3$) δ: 8.93 (1H, dd), 8.49 (1H, dd), 7.68-7.62 (2H, m), 7.43 (1H, d), 7.25 (1H, d), 3.84 (2H, q), 3.73 (3H, s), 1.31 (3H, q).

The Present Compound 52
$^1$H-NMR (CDCl$_3$) δ: 8.48-8.44 (2H, m), 8.05 (1H, d), 7.74 (1H, dd), 7.65 (1H, dd), 7.35 (1H, dd), 3.05 (2H, q), 1.49 (3H, t).

The Present Compound 53
$^1$H-NMR (CDCl$_3$) δ: 8.92 (1H, dd), 8.65 (1H, dd), 8.37 (1H, s), 8.11 (1H, d), 7.72 (1H, dd), 7.66 (1H, dd), 4.19 (2H, q), 1.45 (3H, t).

The Present Compound 54
$^1$H-NMR (CDCl$_3$) δ: 8.66 (1H, s), 8.50 (1H, s), 8.08 (1H, d), 7.90 (1H, s), 7.69 (1H, dd), 3.08 (2H, q), 1.52 (3H, t).

The Present Compound 55
$^1$H-NMR (CDCl$_3$) δ: 9.15 (1H, d), 8.88 (1H, d), 8.40 (1H, s), 8.14 (1H, d), 7.76 (1H, dd), 4.24 (2H, q), 1.49 (3H, t).

The Present Compound 56
$^1$H-NMR (CDCl$_3$) δ: 8.95 (1H, dd), 8.49 (1H, dd), 8.00 (1H, s), 7.66 (1H, dd), 6.96 (1H, s), 3.97 (3H, s), 3.84 (2H, q), 3.73 (3H, s), 1.34 (3H, t).

The Present Compound 57
$^1$H-NMR (DMSO-D$_6$) δ: 8.67 (1H, d), 8.56 (1H, dd), 8.23 (1H, d), 8.05 (1H, d), 7.91 (2H, s), 7.59 (1H, dd), 3.86 (3H, s), 3.00 (2H, q), 1.21 (3H, t).

The Present Compound 58
$^1$H-NMR (CDCl$_3$) δ: 9.20 (1H, d), 9.01 (1H, dd), 8.74 (1H, d), 8.54 (1H, dd), 7.76 (1H, dd), 3.89 (3H, s), 3.86-3.76 (2H, m), 1.37 (3H, t).

The Present Compound 59
$^1$H-NMR (CDCl$_3$) δ: 9.18 (1H, d), 8.82 (1H, d), 8.74 (1H, s), 7.92 (1H, s), 4.10 (3H, s), 4.00 (3H, s), 3.02 (2H, q), 1.40 (3H, t).

The Present Compound 60
$^1$H-NMR (CDCl$_3$) δ: 9.26 (1H, s), 8.82-8.78 (2H, m), 8.61 (1H, s), 3.99-3.91 (5H, m), 1.42 (3H, t).

The Present Compound 61
$^1$H-NMR (CDCl$_3$) δ: 8.50 (1H, dd), 8.22 (1H, d), 7.77 (1H, dd), 7.63 (1H, dd), 7.46 (1H, d), 7.39-7.34 (1H, m), 3.92 (3H, s), 2.95 (2H, q), 1.34 (3H, t).

The Present Compound 62
$^1$H-NMR (CDCl$_3$) δ: 8.79 (1H, d), 8.63 (1H, d), 8.13 (1H, s), 7.66-7.60 (2H, m), 7.49 (1H, d), 4.23 (3H, s), 3.74-3.64 (1H, m), 3.13-3.03 (1H, m), 1.47 (3H, t).

The Present Compound 63
$^1$H-NMR (CDCl$_3$) δ: 8.95 (1H, dd), 8.50 (1H, dd), 8.12 (1H, d), 7.69-7.61 (2H, m), 7.48 (1H, d), 3.86-3.80 (2H, m), 3.75 (3H, s), 1.34 (3H, t).

The Present Compound 64
$^1$H-NMR (CDCl$_3$) δ: 8.91 (1H, dd), 8.46-8.40 (2H, m), 7.91 (1H, d), 7.69-7.61 (2H, m), 3.75-3.68 (5H, m), 1.25 (3H, t).

The Present Compound 69
$^1$H-NMR (CDCl$_3$) δ: 9.25 (1H, d), 9.20 (1H, d), 8.78 (1H, d), 8.73 (1H, d), 4.02-3.95 (5H, m), 3.94 (3H, s), 1.41 (3H, t).

The Present Compound 70
$^1$H-NMR (CDCl$_3$) δ: 9.26 (1H, d), 8.86 (1H, d), 8.76 (1H, d), 8.36 (1H, d), 4.34 (3H, s), 4.01 (3H, s), 3.81 (2H, q), 1.40 (3H, t).

The Present Compound 76
$^1$H-NMR (CDCl$_3$) δ: 8.75 (1H, s), 8.48 (2H, dd), 7.77 (1H, dd), 7.38 (1H, dd), 3.07 (2H, q), 1.50 (3H, t). (No NH proton was detected)

The Present Compound 77
¹H-NMR (CDCl₃) δ: 12.11 (1H, s), 8.98 (1H, dd), 8.80 (1H, s), 8.70 (1H, dd), 8.45 (1H, s), 7.70 (1H, dd), 4.30 (2H, q), 1.43 (3H, t).
The Present Compound 78
¹H-NMR (CDCl₃) δ: 8.75-8.70 (2H, m), 8.34 (1H, s), 7.96 (1H, d), 3.14-3.07 (2H, m), 1.48 (3H, t). (No NH proton was detected)
The Present Compound 79
¹H-NMR (CDCl₃) δ: 11.63 (1H, brs), 9.19 (1H, d), 8.93 (1H, d), 8.83 (1H, d), 8.48 (1H, d), 4.35 (2H, q), 1.47 (3H, t).
The Present Compound 80
¹H-NMR (CDCl₃) δ: 8.75 (1H, dd), 8.62 (1H, dd), 8.46 (1H, d), 7.81 (1H, dd), 7.45 (1H, dd), 3.07 (2H, q), 1.46 (3H, t).
The Present Compound 81
¹H-NMR (CDCl₃) δ: 9.06 (1H, dd), 8.79 (1H, d), 8.58 (1H, dd), 8.43 (1H, d), 7.78 (1H, dd), 3.88 (2H, q), 1.44 (3H, t).
The Present Compound 82
¹H-NMR (CDCl₃) δ: 8.82 (1H, s), 8.79 (1H, s), 8.50 (1H, s), 7.96 (1H, s), 3.11 (2H, q), 1.50 (3H, t).
The Present Compound 83
¹H-NMR (CDCl₃) δ: 9.29 (1H, s), 8.84 (1H, s), 8.81 (1H, d), 8.47 (1H, d), 3.96 (2H, q), 1.48 (3H, t).
The Present Compound 84
¹H-NMR (CDCl₃) δ: 8.59 (1H, dd), 8.24-8.21 (1H, m), 7.81-7.76 (2H, m), 7.69 (1H, dd), 7.42 (1H, dd), 3.06 (2H, q), 1.47 (3H, t).
The Present Compound 85
¹H-NMR (CDCl₃) δ: 9.03 (1H, dd), 8.60 (1H, dd), 8.16-8.13 (1H, m), 7.82-7.71 (3H, m), 4.01 (2H, q), 1.43 (3H, t).
The Present Compound 86
¹H-NMR (CDCl₃) δ: 8.79 (1H, dd), 8.26 (1H, dd), 7.94 (1H, d), 7.81 (1H, dd), 7.76-7.72 (1H, m), 3.11 (2H, q), 1.50 (3H, t).
The Present Compound 87
¹H-NMR (CDCl₃) δ: 9.25 (1H, d), 8.83 (1H, d), 8.18 (1H, s), 7.85-7.76 (2H, m), 4.08 (2H, q), 1.47 (3H, t).
The Present Compound 89
¹H-NMR (CDCl₃) δ: 9.25 (1H, d), 8.78 (1H, d), 8.43 (1H, s), 3.97-3.87 (5H, m), 1.41 (3H, t).
The Present Compound 99
¹H-NMR (CDCl₃) δ: 9.20 (1H, d), 8.76 (1H, d), 8.26 (1H, s), 4.02 (2H, q), 3.84 (3H, s), 3.04 (6H, s), 1.41 (3H, t).
The Present Compound 130
¹HNMR (CDCl₃) δ: 9.01 (1H, dd), 8.68 (1H, d), 8.55 (1H, dd), 8.37 (1H, d), 7.74 (1H, dd), 3.87 (3H, s), 3.83 (2H, q), 1.37 (3H, t).
The Present Compound 138
¹H-NMR (CDCl₃) δ: 9.02 (1H, dd), 8.54 (1H, dd), 8.28 (1H, s), 7.95 (1H, s), 7.77 (1H, dd), 4.06 (3H, s), 3.74 (2H, q), 1.35 (3H, t).
The Present Compound 144
¹H-NMR (CDCl₃) δ: 9.00-8.95 (1H, m), 8.54-8.47 (1H, m), 7.71-7.64 (2H, m), 6.94 (1H, s), 4.00 (3H, s), 3.96 (3H, s), 3.81-3.70 (2H, m), 1.37-1.29 (3H, m).
The Present Compound 190
¹H-NMR (CDCl₃) δ: 8.99 (1H, dd), 8.65 (1H, d), 8.53 (1H, dd), 8.38 (1H, d), 7.71 (1H, dd), 3.83-3.80 (5H, m), 1.35 (3H, t).
The Present Compound 255
¹H-NMR (CDCl₃) δ: 8.78 (1H, d), 8.73-8.71 (1H, m), 8.65 (1H, d), 8.31-8.30 (1H, m), 4.35 (3H, s), 3.73-3.63 (1H, m), 3.16-3.06 (1H, m), 1.48 (3H, t)
The Present Compound 386
¹H-NMR (CDCl₃) δ: 8.95 (1H, d), 8.72-8.71 (1H, m), 8.53 (1H, d), 8.30-8.28 (1H, m), 3.94-3.87 (5H, m), 1.40 (3H, t).
The Present Compound 505
¹H-NMR (CDCl₃) δ: 9.05 (1H, dd), 8.79 (1H, t), 8.60 (1H, dd), 8.33 (1H, d), 7.78 (1H, dd), 7.58 (1H, s), 5.66 (2H, s), 3.98 (2H, q), 1.40 (3H, t).
The Present Compound 506
¹H-NMR (CDCl₃) δ: 9.30 (1H, d), 8.84 (1H, d), 8.82 (1H, d), 8.36 (1H, d), 7.64 (1H, s), 5.70 (2H, s), 4.09 (2H, q), 1.45 (3H, t).
The Present Compound 508
¹H-NMR (CDCl₃) δ: 9.28 (1H, d), 8.79 (1H, d), 8.48 (1H, s), 3.96 (3H, s), 3.89 (2H, q), 1.42 (3H, t).
The Present Compound 509
¹H-NMR (CDCl₃) δ: 8.75 (1H, d), 8.58 (1H, dd), 8.42 (1H, d), 7.82 (1H, dd), 7.66 (1H, s), 7.44 (1H, dd), 5.96 (2H, s), 2.98 (2H, q), 1.37 (3H, t).
The Present Compound 510
¹H-NMR (CDCl₃) δ: 8.80 (2H, dd), 8.46 (1H, d), 7.97 (1H, d), 7.71 (1H, s), 5.99 (2H, s), 3.04 (2H, q), 1.42 (3H, t).
The Present Compound 511
¹H-NMR (CDCl₃) δ: 8.53 (1H, dd), 8.48 (1H, d), 7.98 (1H, dd), 7.93 (1H, d), 7.71 (1H, dd), 4.27 (3H, s), 3.73-3.63 (1H, m), 3.47-3.37 (1H, m), 1.35 (3H, t).
The Present Compound 512
¹H-NMR (CDCl₃) δ: 8.75 (1H, d), 8.49 (1H, d), 8.12 (1H, d), 7.94 (1H, d), 4.28 (3H, s), 3.75-3.65 (1H, m), 3.55-3.45 (1H, m), 1.38 (3H, t).
The Present Compound 513
¹H-NMR (CDCl₃) δ: 8.49 (1H, d), 7.76-7.74 (2H, m), 7.35 (1H, dd), 6.91 (1H, s), 4.05 (3H, s), 3.99 (3H, s), 2.95-2.85 (2H, m), 1.34-1.24 (3H, m).
The Present Compound 514
¹H-NMR (CDCl₃) δ: 8.51 (1H, d), 7.97 (1H, s), 7.77 (1H, d), 7.42 (1H, s), 7.37 (1H, dd), 4.18 (3H, s), 2.91 (2H, q), 2.59 (3H, s), 1.30 (3H, t).
The Present Compound 515
¹H-NMR (CDCl₃) δ: 9.08-8.97 (1H, m), 8.58-8.46 (1H, m), 8.41-8.26 (2H, m), 7.84-7.70 (1H, m), 4.12 (3H, s), 3.72-3.59 (2H, m), 3.33 (3H, s), 1.39-1.22 (3H, m).
The Present Compound 516
¹H-NMR (CDCl₃) δ: 8.49 (1H, dd), 8.18 (1H, dd), 7.75 (1H, dd), 7.71 (1H, d), 7.50-7.48 (1H, m), 7.36 (1H, dd), 7.30-7.09 (4H, m), 4.02 (3H, s), 2.90 (2H, q), 1.28 (3H, t).
The Present Compound 517
¹H-NMR (CDCl₃) δ: 8.97 (1H, dd), 8.49 (1H, dd), 8.31 (1H, d), 8.17 (1H, d), 7.89 (2H, d), 7.72 (1H, dd), 7.69-7.64 (1H, m), 7.61-7.55 (2H, m), 3.87 (3H, s), 3.67 (2H, q), 1.32 (3H, t).
The Present Compound 518
¹H-NMR (CDCl₃) δ: 9.02-8.97 (1H, m), 8.54-8.49 (1H, m), 8.33 (1H, s), 8.23 (1H, s), 7.80-7.71 (1H, m), 4.03-3.88 (3H, m), 3.75-3.63 (4H, m), 1.36-1.30 (3H, m).
The Present Compound 519
¹H-NMR (CDCl₃) δ: 8.55 (1H, dd), 8.37-8.35 (1H, m), 7.93-7.92 (1H, m), 7.81 (1H, dd), 7.43 (1H, dd), 4.19 (3H, s), 2.96 (2H, q), 1.33 (3H, t).
The Present Compound 520
¹H-NMR (CDCl₃) δ: 9.22 (1H, t), 8.77 (1H, d), 8.53 (1H, s), 3.95 (2H, q), 3.84 (3H, s), 3.33 (6H, s), 1.41 (3H, t).
The Present Compound 521
¹H-NMR (CDCl₃) δ: 9.28 (1H, d), 8.80 (1H, d), 8.62 (1H, s), 3.97 (3H, s), 3.89 (2H, q), 1.42 (3H, t). (No active proton was detected)
The Present Compound 522
¹H-NMR (CDCl₃) δ: 9.27 (1H, d), 8.79 (1H, d), 8.56 (1H, s), 7.24 (1H, brs), 5.76 (1H, brs), 4.00-3.86 (5H, m), 1.42 (3H, t).

The Present Compound 523
¹H-NMR (CDCl₃) δ: 9.27 (1H, d), 8.77 (1H, d), 8.45 (1H, s), 7.92 (1H, s), 4.34 (3H, s), 3.81 (2H, q), 1.40 (3H, t).

The Present Compound 524
¹H-NMR (CDCl₃) δ: 8.80 (1H, s), 8.46 (1H, s), 8.13 (1H, s), 7.93 (1H, s), 4.27 (3H, s), 3.76-3.66 (1H, m), 3.55-3.45 (1H, m), 1.38 (3H, t).

The Present Compound 525
¹H-NMR (DMSO-D₆) δ: 9.06 (1H, d), 8.95 (1H, s), 8.63 (1H, d), 8.31 (1H, s), 3.95 (3H, s), 3.15 (2H, q), 1.23 (3H, t). (No active proton was detected)

The Present Compound 526
¹H-NMR (CDCl₃) δ: 8.87 (1H, dd), 8.67 (1H, dd), 8.29 (1H, d), 7.96 (1H, d), 7.72 (1H, dd), 4.57 (3H, s), 3.73-3.62 (1H, m), 3.17-3.07 (1H, m), 1.48 (3H, t).

The Present Compound 527
¹H-NMR (CDCl₃) δ: 10.95 (1H, s), 8.46-8.42 (2H, m), 7.82 (1H, s), 7.76 (1H, dd), 7.38 (1H, dd), 3.07 (2H, q), 1.50 (3H, t).

The Present Compound 528
¹H-NMR (CDCl₃) δ: 9.16 (1H, d), 8.74 (1H, d), 8.70 (1H, d), 8.31 (1H, d), 3.93 (3H, s), 3.88 (2H, q), 3.28 (9H, s), 1.38 (3H, t).

The Present Compound 529
¹H-NMR (CDCl₃) δ: 8.51-8.46 (1H, m), 7.94 (1H, s), 7.86 (1H, s), 7.80-7.76 (1H, m), 7.40-7.35 (1H, m), 3.96 (3H, s), 2.96-2.90 (2H, m), 1.31-1.25 (3H, m).

The Present Compound 530
¹H-NMR (CDCl₃) δ: 8.99 (1H, dd), 8.54 (1H, dd), 7.97 (1H, s), 7.87 (1H, s), 7.72 (1H, dd), 3.95-3.88 (5H, m), 1.37 (3H, t).

The Present Compound 531
¹H-NMR (CDCl₃) δ: 8.93 (1H, dd), 8.45 (1H, dd), 8.19 (1H, s), 7.87 (1H, s), 7.66 (1H, dd), 3.77-3.75 (3H, m), 3.63 (2H, q), 1.26 (3H, t).

The Present Compound 532
¹H-NMR (CDCl₃) δ: 8.75 (1H, s), 8.72 (1H, s), 8.41 (1H, s), 7.90 (1H, s), 4.15 (3H, s), 2.54 (3H, s)

The Present Compound 533
¹H-NMR (CDCl₃) δ: 9.25 (1H, s), 8.85 (1H, s), 8.75 (1H, s), 8.32 (1H, s), 3.96 (3H, s), 3.73 (3H, s)

The Present Compound 534
¹H-NMR (CDCl₃) δ: 8.74 (1H, s), 8.71 (1H, s), 8.41 (1H, s), 7.93 (1H, s), 4.10 (3H, s), 2.97 (2H, t), 1.82-1.71 (2H, m), 1.08 (3H, t)

The Present Compound 535
¹H-NMR (CDCl₃) δ: 9.24 (1H, s), 8.79 (1H, s), 8.74 (1H, s), 8.31 (1H, s), 3.95-3.88 (5H, m), 1.92-1.81 (2H, m), 1.13 (3H, t)

The Present Compound 536
¹H-NMR (CDCl₃) δ: 8.76 (1H, s), 8.71 (1H, s), 8.41 (1H, s), 8.01 (1H, s), 4.07 (3H, s), 3.64-3.53 (1H, m), 1.38 (6H, d)

The Present Compound 537
¹H-NMR (CDCl₃) δ: 9.24 (1H, s), 8.75 (2H, d), 8.31 (1H, s), 4.71-4.60 (1H, m), 3.93 (3H, s), 1.39 (6H, d)

The Present Compound 538
¹H-NMR (CDCl₃) δ: 8.74 (1H, s), 8.71 (1H, s), 8.41 (1H, s), 7.94 (1H, s), 4.10 (3H, s), 2.98 (2H, t), 1.76-1.67 (2H, m), 1.55-1.44 (2H, m), 0.95 (3H, t)

The Present Compound 539
¹H-NMR (CDCl₃) δ: 9.24 (1H, s), 8.79 (1H, s), 8.74 (1H, s), 8.29 (1H, s), 3.97-3.91 (5H, m), 1.85-1.77 (2H, m), 1.59-1.48 (2H, m), 0.99 (3H, t)

The Present Compound 540
¹H-NMR (CDCl₃) δ: 8.76 (1H, s), 8.71 (1H, s), 8.40 (1H, s), 8.00 (1H, s), 4.05 (3H, s), 3.40-3.30 (1H, m), 1.80-1.55 (2H, m), 1.35 (3H, d), 1.02 (3H, t)

The Present Compound 541
¹H-NMR (CDCl₃) δ: 9.23 (1H, s), 8.75 (2H, s), 8.28 (1H, s), 4.54-4.44 (1H, m), 3.92 (3H, s), 2.02-1.91 (1H, m), 1.71-1.57 (1H, m), 1.37 (3H, d), 1.07 (3H, t)

The Present Compound 542
¹H-NMR (CDCl₃) δ: 8.74-8.73 (1H, m), 8.72-8.71 (1H, m), 8.41 (1H, d), 7.92 (1H, d), 4.09 (3H, s), 2.86 (2H, d), 2.03-1.91 (1H, m), 1.08 (6H, d)

The Present Compound 543
¹H-NMR (CDCl₃) δ: 9.24 (1H, s), 8.81 (1H, s), 8.75 (1H, s), 8.28 (1H, s), 3.93 (3H, s), 3.87 (2H, d), 2.42-2.30 (1H, m), 1.15 (6H, d)

The Present Compound 544
¹H-NMR (CDCl₃) δ: 8.98 (1H, dd), 8.71 (1H, d), 8.37 (1H, d), 8.35-8.32 (1H, m), 3.88 (3H, s), 1.26 (9H, s)

The Present Compound 545
¹H-NMR (CDCl₃) δ: 9.26 (1H, s), 8.71 (1H, s), 8.66 (1H, s), 8.29 (1H, s), 3.71 (3H, s), 1.41 (9H, s)

The Present Compound 546
¹H-NMR (CDCl₃) δ: 8.73 (1H, s), 8.71 (1H, s), 8.41 (1H, s), 8.02 (1H, s), 4.10 (3H, s), 3.72-3.64 (1H, m), 2.27-2.16 (2H, m), 1.85-1.62 (6H, m)

The Present Compound 547
¹H-NMR (CDCl₃) δ: 9.23 (1H, s), 8.76 (1H, s), 8.74 (1H, s), 8.31 (1H, s), 4.88-4.79 (1H, m), 3.90 (3H, s), 2.14-1.83 (6H, m), 1.80-1.69 (2H, m)

The Present Compound 548
¹H-NMR (CDCl₃) δ: 8.76-8.74 (1H, m), 8.71-8.70 (1H, m), 8.41-8.39 (1H, m), 8.01-7.99 (1H, m), 4.05 (3H, s), 3.36-3.27 (1H, m), 2.07-1.22 (10H, m)

The Present Compound 549
¹H-NMR (CDCl₃) δ: 9.23 (1H, s), 8.74 (1H, s), 8.72 (1H, s), 8.28 (1H, s), 4.43-4.34 (1H, m), 3.92 (3H, s), 2.03-1.20 (10H, m)

The Present Compound 550
¹H-NMR (CDCl₃) δ: 8.90 (1H, s), 8.74 (1H, s), 8.40 (1H, s), 8.18 (1H, s), 4.13 (3H, s), 3.68 (2H, q)

The Present Compound 551
¹H-NMR (CDCl₃) δ: 9.30-9.28 (1H, m), 8.87-8.85 (1H, m), 8.78-8.76 (1H, m), 8.36-8.34 (1H, m), 5.16 (2H, q), 4.04 (3H, s)

The Present Compound 552
¹H-NMR (CDCl₃) δ: 8.66 (1H, d), 8.63 (1H, d), 8.36 (1H, d), 7.87 (1H, d), 4.00 (3H, s), 2.95 (2H, q), 1.30 (3H, t).

The Present Compound 553
¹H-NMR (CDCl₃) δ: 8.55 (1H, dd), 8.35 (1H, s), 7.93 (1H, s), 7.81 (1H, dd), 7.43 (1H, dd), 3.95-3.93 (3H, m), 2.95 (2H, q), 1.32 (3H, t).

The Present Compound 554
¹H-NMR (CDCl₃) δ: 8.72 (2H, d), 8.41 (1H, d), 7.83 (1H, d), 6.98 (2H, d), 6.68 (2H, d), 5.81 (2H, s), 3.71 (3H, s), 2.89 (2H, q), 1.27 (3H, t).

The Present Compound 555
¹H-NMR (CDCl₃) δ: 8.83 (1H, d), 8.71 (1H, s), 7.90 (1H, s), 7.84 (1H, d), 7.05 (2H, d), 6.78 (2H, d), 5.65 (2H, s), 3.75 (3H, s), 2.97 (2H, q), 1.32 (3H, t).

A compound represented by the formula (M3):

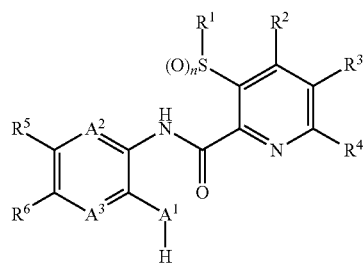

(M 3)

wherein $R^1, R^2, R^3, R^4, R^5, R^6, A^1, A^2, A^3$ and n represent any one of the combinations as listed in the following [Table 59] to [Table 61]. The intermediate compound (M3) represented by the formula (M3) can be synthesized in the same manner as in Production process 2 or Production process 7.

TABLE 59

| Intermediate compound | $R^1$ | $R^2$ | $R^3$ | $R^4$ | $R^5$ | $R^6$ | $A^1$ | $A^2$ | $A^3$ | n |
|---|---|---|---|---|---|---|---|---|---|---|
| M3-1 | Et | H | H | H | $CF_3$ | H | NMe | CH | N | 0 |
| M3-2 | Et | H | H | H | $CF_3$ | H | NMe | CH | N | 1 |
| M3-3 | Et | H | H | H | $CF_3$ | H | NMe | CH | N | 2 |
| M3-4 | Et | H | $CF_3$ | H | $CF_3$ | H | NMe | CH | N | 0 |
| M3-5 | Et | H | $CF_3$ | H | $CF_3$ | H | NMe | CH | N | 2 |
| M3-6 | Et | H | H | H | $CF_2CF_3$ | H | NMe | CH | N | 0 |
| M3-7 | Et | H | H | H | $CF_2CF_3$ | H | NMe | CH | N | 1 |
| M3-8 | Et | H | H | H | $CF_2CF_3$ | H | NMe | CH | N | 2 |
| M3-9 | Et | H | H | H | I | H | NMe | CH | N | 0 |
| M3-10 | Et | H | $CF_3$ | H | $CF_3$ | H | S | CH | N | 0 |
| M3-11 | Et | H | $CF_3$ | H | $CF_3$ | H | S | CH | N | 2 |
| M3-12 | Et | H | H | H | $CF_3$ | H | S | CH | N | 2 |
| M3-13 | Et | H | H | H | $SCF_3$ | H | NMe | CH | N | 0 |
| M3-14 | Et | H | H | H | $SCF_3$ | H | NMe | CH | N | 1 |
| M3-15 | Et | H | H | H | $SCF_3$ | H | NMe | CH | N | 2 |
| M3-16 | Et | H | H | H | $SO_2CF_3$ | H | NMe | CH | N | 2 |
| M3-17 | Et | H | $CF_3$ | H | $CF_2CF_3$ | H | NMe | CH | N | 0 |
| M3-18 | Et | H | $CF_3$ | H | $CF_2CF_3$ | H | NMe | CH | N | 1 |
| M3-19 | Et | H | $CF_3$ | H | $CF_2CF_3$ | H | NMe | CH | N | 2 |
| M3-20 | Et | H | H | H | $SOCF_3$ | H | NMe | CH | N | 2 |
| M3-21 | Et | H | H | H | I | H | NMe | CH | CH | 0 |
| M3-22 | Et | H | H | H | SF5 | H | NMe | CH | CH | 0 |
| M3-23 | Et | H | H | H | SF5 | H | NMe | CH | CH | 2 |
| M3-24 | Et | H | $CF_3$ | H | $SO_2CF_3$ | H | NMe | CH | N | 2 |

TABLE 60

| Intermediate compound | $R^1$ | $R^2$ | $R^3$ | $R^4$ | $R^5$ | $R^6$ | $A^1$ | $A^2$ | $A^3$ | n |
|---|---|---|---|---|---|---|---|---|---|---|
| M3-25 | Et | H | H | H | $CF_2CF_3$ | H | NMe | CH | CH | 0 |
| M3-26 | Et | H | H | H | $CF_2CF_3$ | H | NMe | CH | CH | 2 |
| M3-27 | Et | H | $CF_3$ | H | $SCF_3$ | H | NMe | CH | N | 0 |
| M3-28 | Et | H | $CF_3$ | H | $SCF_3$ | H | NMe | CH | N | 1 |
| M3-29 | Et | H | H | H | $CF_3$ | H | NMe | CH | CH | 0 |
| M3-30 | Et | H | H | H | $CF_3$ | H | NMe | CH | CH | 1 |
| M3-31 | Et | H | H | H | $CF_3$ | H | NMe | CH | CH | 2 |
| M3-32 | Et | H | $CF_3$ | H | $CF_3$ | H | NMe | CH | CH | 0 |
| M3-33 | Et | H | $CF_3$ | H | $CF_3$ | H | NMe | CH | CH | 1 |
| M3-34 | Et | H | $CF_3$ | H | $CF_3$ | H | NMe | CH | CH | 2 |
| M3-35 | Et | H | $CF_3$ | H | $CF_2CF_3$ | H | NMe | CH | CH | 0 |
| M3-36 | Et | H | $CF_3$ | H | $CF_2CF_3$ | H | NMe | CH | CH | 1 |
| M3-37 | Et | H | $CF_3$ | H | $CF_2CF_3$ | H | NMe | CH | CH | 2 |
| M3-38 | Et | H | H | H | CF3 | H | S | CH | N | 0 |
| M3-39 | Et | H | $CF_3$ | H | I | H | NMe | CH | N | 0 |
| M3-40 | Et | H | $CF_3$ | H | $SCF_3$ | H | NMe | CH | N | 2 |
| M3-41 | Et | H | $CF_3$ | H | I | H | NMe | CH | CH | 0 |
| M3-42 | Et | H | H | H | $CF_3$ | H | NMe | CH | CBr | 0 |
| M3-43 | Et | H | H | H | $CF_3$ | H | $N(CH_2CF_3)$ | CH | N | 0 |
| M3-44 | Et | H | $CF_3$ | H | $CF_3$ | H | $N(CH_2CF_3)$ | CH | N | 0 |
| M3-45 | Et | H | $CF_2CF_3$ | H | $CF_3$ | H | NMe | CH | N | 0 |
| M3-46 | Et | H | $CF_2CF_3$ | H | $CF_2CF_3$ | H | NMe | CH | N | 0 |
| M3-47 | Et | H | H | H | $CF_3$ | H | NH | CH | N | 0 |
| M3-48 | Et | H | $CF_3$ | H | $CF_3$ | H | NH | CH | N | 0 |
| M3-49 | Et | H | H | H | $CF_3$ | H | OH | CH | N | 0 |
| M3-50 | Et | H | $CF_3$ | H | $CF_3$ | H | OH | CH | N | 0 |

TABLE 61

| Intermediate compound | $R^1$ | $R^2$ | $R^3$ | $R^4$ | $R^5$ | $R^6$ | $A^1$ | $A^2$ | $A^3$ | n |
|---|---|---|---|---|---|---|---|---|---|---|
| M3-51 | Et | H | H | H | $CF_3$ | H | OH | CH | CH | 0 |
| M3-52 | Et | H | $CF_3$ | H | $CF_3$ | H | OH | CH | CH | 0 |
| M3-53 | Et | H | H | H | $CF_3$ | H | N-(2-Chlorothiazol-5-ylmethyl) | CH | N | 0 |
| M3-54 | Et | H | $CF_3$ | H | $CF_3$ | H | N-(2-Chloro- | CH | N | 0 |

TABLE 61-continued

| Intermediate compound | R¹ | R² | R³ | R⁴ | R⁵ | R⁶ | A¹ | A² | A³ | n |
|---|---|---|---|---|---|---|---|---|---|---|
| M3-55 | Et | H | H | H | CF₃ | H | thiazol-5-ylmethyl) NH | CH | CCF₃ | 0 |
| M3-56 | Et | H | H | H | CF₃ | H | NMe | CH | CCN | 0 |

A compound represented by the formula (M6):

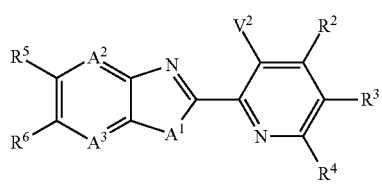

(M6)

wherein $V^2$, $R^2$, $R^3$, $R^4$, $R^5$, $R^6$, $A^1$, $A^2$ and $A^3$ represent any one of the combinations as listed in the following [Table 62] to [Table 63]. The intermediate compound (M6) represented by the formula (M6) can be synthesized in the same manner as in Production process 6.

TABLE 62

| Intermediate compound | V | R² | R³ | R⁴ | R⁵ | R⁶ | A¹ | A² | A³ |
|---|---|---|---|---|---|---|---|---|---|
| M6-1 | Cl | H | H | H | CF₃ | H | NMe | CH | N |
| M6-2 | F | H | H | H | CF₃ | H | NMe | CH | N |
| M6-3 | Cl | H | CF₃ | H | CF₃ | H | NMe | CH | N |
| M6-4 | F | H | CF₃ | H | CF₃ | H | NMe | CH | N |
| M6-5 | Cl | H | H | H | CF₂CF₃ | H | NMe | CH | N |
| M6-6 | F | H | H | H | CF₂CF₃ | H | NMe | CH | N |
| M6-7 | Cl | H | H | H | I | H | NMe | CH | N |
| M6-8 | F | H | H | H | I | H | NMe | CH | N |
| M6-9 | Cl | H | CF₃ | H | CF₃ | H | S | CH | N |
| M6-10 | F | H | CF₃ | H | CF₃ | H | S | CH | N |
| M6-11 | Cl | H | H | H | CF₃ | H | S | CH | N |
| M6-12 | F | H | H | H | CF₃ | H | S | CH | N |
| M6-13 | Cl | H | H | H | SCF₃ | H | NMe | CH | N |
| M6-14 | F | H | H | H | SCF₃ | H | NMe | CH | N |
| M6-15 | Cl | H | H | H | SO₂CF₃ | H | NMe | CH | N |
| M6-16 | F | H | H | H | SO₂CF₃ | H | NMe | CH | N |
| M6-17 | Cl | H | CF₃ | H | CF₂CF₃ | H | NMe | CH | N |
| M6-18 | F | H | CF₃ | H | CF₂CF₃ | H | NMe | CH | N |
| M6-19 | Cl | H | H | H | SOCF₃ | H | NMe | CH | N |
| M6-20 | F | H | H | H | SOCF₃ | H | NMe | CH | N |
| M6-21 | Cl | H | H | H | I | H | NMe | CH | CH |
| M6-22 | F | H | H | H | I | H | NMe | CH | CH |
| M6-23 | Cl | H | H | H | SF₅ | H | NMe | CH | CH |
| M6-24 | F | H | H | H | SF₅ | H | NMe | CH | CH |

TABLE 63

| Intermediate compound | V | R² | R³ | R⁴ | R⁵ | R⁶ | A¹ | A² | A³ |
|---|---|---|---|---|---|---|---|---|---|
| M6-25 | Cl | H | CF₃ | H | SO₂CF₃ | H | NMe | CH | N |
| M6-26 | F | H | CF₃ | H | SO₂CF₃ | H | NMe | CH | N |
| M6-27 | Cl | H | H | H | CF₂CF₃ | H | NMe | CH | CH |
| M6-28 | F | H | H | H | CF₂CF₃ | H | NMe | CH | CH |
| M6-29 | Cl | H | H | H | CF₃ | H | NMe | CH | CH |
| M6-30 | F | H | H | H | CF₃ | H | NMe | CH | CH |
| M6-31 | Cl | H | CF₃ | H | CF₃ | H | NMe | CH | CH |
| M6-32 | F | H | CF₃ | H | CF₃ | H | NMe | CH | CH |

TABLE 63-continued

| Intermediate compound | V | R² | R³ | R⁴ | R⁵ | R⁶ | A¹ | A² | A³ |
|---|---|---|---|---|---|---|---|---|---|
| M6-33 | Cl | H | CF₃ | H | CF₂CF₃ | H | NMe | CH | CH |
| M6-34 | F | H | CF₃ | H | CF₂CF₃ | H | NMe | CH | CH |
| M6-35 | Cl | H | CF₃ | H | I | H | NMe | CH | N |
| M6-36 | F | H | CF₃ | H | I | H | NMe | CH | N |
| M6-37 | Cl | H | CF₃ | H | SH | H | NMe | CH | N |
| M6-38 | F | H | CF₃ | H | SH | H | NMe | CH | N |
| M6-39 | Cl | H | CF₃ | H | SCF₃ | H | NMe | CH | N |
| M6-40 | F | H | CF₃ | H | SCF₃ | H | NMe | CH | N |
| M6-41 | Cl | H | CF₃ | H | I | H | NMe | CH | CH |
| M6-42 | F | H | CF₃ | H | I | H | NMe | CH | CH |
| M6-43 | Cl | H | H | H | CF₃ | H | NMe | CH | CBr |
| M6-44 | Cl | H | H | H | CF₃ | OCH₃ | NMe | CH | CH |
| M6-45 | Cl | H | H | H | SCF₃ | H | NMe | CH | CH |
| M6-46 | Cl | H | H | H | CF₃ | H | S | CH | CH |

A compound represented by the formula (M20):

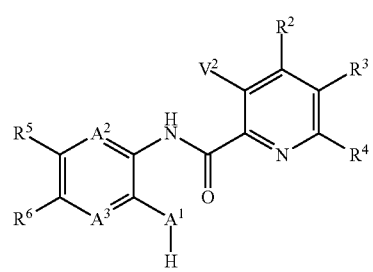

(M20)

wherein $V^2$, $R^2$, $R^3$, $R^4$, $R^5$, $R^6$, $A^1$, $A^2$ and $A^3$ represent any one of the combinations as listed in the following [Table 64] to [Table 65]. The intermediate compound (M20) represented by the formula (M20) can be synthesized in the same manner as in Production process 6.

TABLE 64

| Intermediate compound | V | R² | R³ | R⁴ | R⁵ | R⁶ | A¹ | A² | A³ |
|---|---|---|---|---|---|---|---|---|---|
| M20-1 | Cl | H | H | H | CF₃ | H | NMe | CH | N |
| M20-2 | F | H | H | H | CF₃ | H | NMe | CH | N |
| M20-3 | Cl | H | CF₃ | H | CF₃ | H | NMe | CH | N |
| M20-4 | F | H | CF₃ | H | CF₃ | H | NMe | CH | N |
| M20-5 | Cl | H | H | H | CF₂CF₃ | H | NMe | CH | N |
| M20-6 | F | H | H | H | CF₂CF₃ | H | NMe | CH | N |
| M20-7 | Cl | H | H | H | I | H | NMe | CH | N |
| M20-8 | F | H | H | H | I | H | NMe | CH | N |
| M20-9 | Cl | H | CF₃ | H | CF₃ | H | S | CH | N |
| M20-10 | F | H | CF₃ | H | CF₃ | H | S | CH | N |
| M20-11 | Cl | H | H | H | CF₃ | H | S | CH | N |
| M20-12 | F | H | H | H | CF₃ | H | S | CH | N |
| M20-13 | Cl | H | H | H | SCF₃ | H | NMe | CH | N |
| M20-14 | F | H | H | H | SCF₃ | H | NMe | CH | N |
| M20-15 | Cl | H | H | H | SO₂CF₃ | H | NMe | CH | N |
| M20-16 | F | H | H | H | SO₂CF₃ | H | NMe | CH | N |
| M20-17 | Cl | H | CF₃ | H | CF₂CF₃ | H | NMe | CH | N |
| M20-18 | F | H | CF₃ | H | CF₂CF₃ | H | NMe | CH | N |
| M20-19 | Cl | H | H | H | SOCF₃ | H | NMe | CH | N |
| M20-20 | F | H | H | H | SOCF₃ | H | NMe | CH | N |
| M20-21 | Cl | H | H | H | I | H | NMe | CH | CH |
| M20-22 | F | H | H | H | I | H | NMe | CH | CH |
| M20-23 | Cl | H | H | H | SF5 | H | NMe | CH | CH |
| M20-24 | F | H | H | H | SF5 | H | NMe | CH | CH |

TABLE 65

| Intermediate compound | V | R² | R³ | R⁴ | R⁵ | R⁶ | A¹ | A² | A³ |
|---|---|---|---|---|---|---|---|---|---|
| M20-25 | Cl | H | CF₃ | H | SO₂CF₃ | H | NMe | CH | N |
| M20-26 | F | H | CF₃ | H | SO₂CF₃ | H | NMe | CH | N |
| M20-27 | Cl | H | H | H | CF₂CF₃ | H | NMe | CH | CH |
| M20-28 | F | H | H | H | CF₂CF₃ | H | NMe | CH | CH |
| M20-29 | Cl | H | H | H | CF₃ | H | NMe | CH | CH |
| M20-30 | F | H | H | H | CF₃ | H | NMe | CH | CH |
| M20-31 | Cl | H | CF₃ | H | CF₃ | H | NMe | CH | CH |
| M20-32 | F | H | CF₃ | H | CF₃ | H | NMe | CH | CH |
| M20-33 | Cl | H | CF₃ | H | CF₂CF₃ | H | NMe | CH | CH |
| M20-34 | F | H | CF₃ | H | CF₂CF₃ | H | NMe | CH | CH |
| M20-35 | Cl | H | CF₃ | H | I | H | NMe | CH | N |
| M20-36 | F | H | CF₃ | H | I | H | NMe | CH | N |
| M20-37 | Cl | H | CF₃ | H | SH | H | NMe | CH | N |
| M20-38 | F | H | CF₃ | H | SH | H | NMe | CH | N |
| M20-39 | Cl | H | CF₃ | H | SCF₃ | H | NMe | CH | N |
| M20-40 | F | H | CF₃ | H | SCF₃ | H | NMe | CH | N |
| M20-41 | Cl | H | CF₃ | H | I | H | NMe | CH | CH |
| M20-42 | F | H | CF₃ | H | I | H | NMe | CH | CH |
| M20-43 | Cl | H | H | H | CF₃ | H | NMe | CH | CBr |
| M20-44 | Cl | H | H | H | SCF₃ | H | NMe | CH | CH |

A compound represented by the formula (P9'):

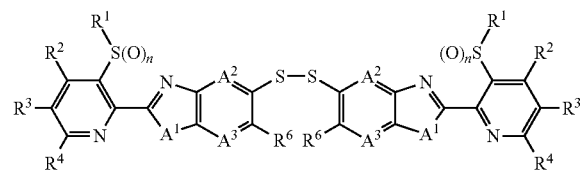

(P9')

wherein $R^1$, $R^2$, $R^3$, $R^4$, $R^6$, $A^1$, $A^2$, $A^3$ and n represent any one of the combinations as listed in the following [Table 66]. The intermediate compound (P9') represented by the formula (P9') can be synthesized in the same manner as in Production process 20.

TABLE 66

| Intermediate compound | R¹ | R² | R³ | R⁴ | R⁶ | A¹ | A² | A³ | n |
|---|---|---|---|---|---|---|---|---|---|
| P9'-1 | Et | H | H | H | H | NMe | CH | N | 0 |
| P9'-2 | Et | H | H | H | H | NMe | CH | N | 1 |
| P9'-3 | Et | H | H | H | H | NMe | CH | N | 2 |
| P9'-4 | Et | H | CF₃ | H | H | NMe | CH | N | 0 |
| P9'-5 | Et | H | CF₃ | H | H | NMe | CH | N | 1 |
| P9'-6 | Et | H | CF₃ | H | H | NMe | CH | N | 2 |

A compound represented by the formula (M2):

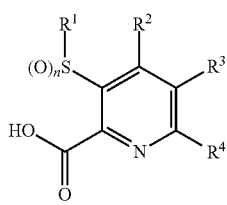

(M 2)

wherein $R^1$, $R^2$, $R^3$, $R^4$ and n represent any one of the combinations as listed in the following [Table 67]. The intermediate compound (M2) represented by the formula (M2) can be synthesized in the same manner as in Production process 12 or Production process 14.

TABLE 67

| Intermediate compound | R¹ | R² | R³ | R⁴ | n |
|---|---|---|---|---|---|
| M2-1 | Et | H | H | H | 0 |
| M2-2 | Et | H | H | H | 1 |
| M2-3 | Et | H | H | H | 2 |
| M2-4 | Et | H | CF₃ | H | 0 |
| M2-5 | Et | H | CF₃ | H | 1 |
| M2-6 | Et | H | CF₃ | H | 2 |
| M2-7 | Et | H | CF₂CF₃ | H | 2 |

A compound represented by the formula (M18):

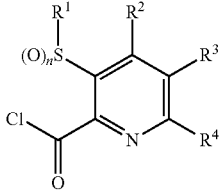

(M 18)

wherein $R^1$, $R^2$, $R^3$, $R^4$ and n represent any one of the combinations as listed in the following [Table 68]. The intermediate compound (M18) represented by the formula (M18) can be synthesized in the same manner as in Production process 13.

TABLE 68

| Intermediate compound | R¹ | R² | R³ | R⁴ | n |
|---|---|---|---|---|---|
| M18-1 | Et | H | H | H | 0 |
| M18-2 | Et | H | H | H | 1 |
| M18-3 | Et | H | H | H | 2 |
| M18-4 | Et | H | CF₃ | H | 0 |
| M18-5 | Et | H | CF₃ | H | 1 |
| M18-6 | Et | H | CF₃ | H | 2 |

A compound represented by the formula (M37):

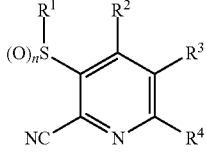

(M 37)

wherein $R^1$, $R^2$, $R^3$, $R^4$ and n represent any one of the combinations as listed in the following [Table 69]. The intermediate compound (M37) represented by the formula (M37) can synthesized in the same manner as in Production process 14.

TABLE 69

| Intermediate compound | R¹ | R² | R³ | R⁴ | n |
|---|---|---|---|---|---|
| M37-1 | Et | H | H | H | 0 |
| M37-2 | Et | H | H | H | 1 |

TABLE 69-continued

| Intermediate compound | $R^1$ | $R^2$ | $R^3$ | $R^4$ | n |
|---|---|---|---|---|---|
| M37-3 | Et | H | H | H | 2 |
| M37-4 | Et | H | $CF_3$ | H | 0 |
| M37-5 | Et | H | $CF_3$ | H | 1 |
| M37-6 | Et | H | $CF_3$ | H | 2 |

NMR data of the intermediate compounds M3-33, M3-47, M3-48, M3-49, M3-50, M3-51, M3-52, M3-53, M3-54, M3-55, M3-56, M6-1, M6-17, M6-44, M6-45, M6-46, M2-1, M2-4, M18-1, M20-44, M37-1 and M37-4 are shown in the following [Table 70] to [Table 71].

TABLE 70

| Intermediate compound | Material value |
|---|---|
| M3-33 | $^1$H-NMR (CDCl$_3$) δ: 9.61 (1H, s), 8.96 (2H, d), 7.72 (1H, s), 7.49 (1H, d), 6.83 (1H, d), 4.21 (1H, s), 3.38 (1H, brs), 2.94-2.94 (4H, brm), 1.36-1.23 (3H, m). |
| M3-47 | $^1$H-NMR (CDCl$_3$) δ: 9.87 (1H, brs), 8.33 (1H, dd), 8.25 (1H, d), 8.14 (1H, d), 7.75 (1H, dd), 7.44 (1H, dd), 5.01 (2H, brs), 2.96 (2H, q), 1.44 (3H, t). |
| M3-48 | $^1$H-NMR (CDCl$_3$) δ: 9.73 (1H, s), 8.56 (1H, dd), 8.28 (1H, dd), 8.12 (1H, d), 7.91 (1H, d), 4.99 (2H, s), 3.00 (2H, q), 1.46 (3H, t). |
| M3-49 | $^1$H-NMR (CDCl$_3$) δ: 12.34 (1H, s), 10.99 (1H, s), 8.75 (1H, d), 8.39 (1H, dd), 7.76 (1H, dd), 7.45 (1H, dd), 7.38 (1H, d), 2.98 (2H, q), 1.44 (3H, t). |
| M3-50 | $^1$H-NMR (CDCl$_3$) δ: 11.36 (1H, s), 10.93 (1H, s), 8.90 (1H, d), 8.67-8.64 (1H, m), 7.92-7.89 (1H, m), 7.54-7.50 (1H, m), 3.01 (2H, q), 1.48 (3H, t). |
| M3-51 | $^1$H-NMR (CDCl$_3$) δ: 10.45 (1H, s), 9.57 (1H, s), 8.36 (1H, dd), 7.75 (1H, dd), 7.52 (1H, d), 7.45 (1H, dd), 7.40-7.36 (1H, m), 7.11 (1H, d), 2.96 (2H, q), 1.44 (3H, t). |
| M3-52 | $^1$H-NMR (CDCl$_3$) δ: 10.34 (1H, s), 8.84 (1H, s), 8.58 (1H, d), 7.92 (1H, d), 7.67 (1H, d), 7.40 (1H, dd), 7.12 (1H, d), 3.00 (2H, q), 1.47 (3H, t). |
| M3-53 | $^1$H-NMR (CDCl$_3$) δ: 9.78 (1H, s), 8.38 (1H, dd), 8.33 (1H, dd), 7.96 (1H, d), 7.74 (1H, dd), 7.47-7.43 (2H, m), 5.66 (1H, s), 4.81 (2H, d), 2.95 (2H, q), 1.43 (3H, t). |
| M3-54 | $^1$H-NMR (CDCl$_3$) δ: 9.65 (1H, s), 8.56 (1H, s), 8.41 (1H, s), 7.95 (1H, d), 7.91 (1H, s), 7.47 (1H, s), 5.54 (1H, t), 4.81 (2H, d), 2.99 (2H, q), 1.46 (3H, t). |
| M3-55 | $^1$H-NMR (CDCl$_3$) δ: 9.88 (1H, s), 8.33 (1H, dd), 7.99 (1H, s), 7.74 (1H, dd), 7.62 (1H, s), 7.44 (1H, dd), 4.71 (2H, s), 2.95 (2H, q), 1.43 (3H, t). |
| M3-56 | $^1$H-NMR (CDCl$_3$) δ: 9.94 (1H, s), 8.35 (1H, dd), 8.14 (1H, d), 7.75 (1H, dd), 7.60 (1H, d), 7.45 (1H, dd), 4.63 (1H, d), 3.24 (3H, d), 2.96 (2H, q), 1.44 (3H, t). |

TABLE 71

| Intermediate compound | Material value |
|---|---|
| M6-1 | 1H-NMR (CDCl$_3$) δ: 8.76 (1H, d), 8.71 (1H, dd), 8.39 (1H, d), 7.97 (1H, dd), 7.48 (1H, dd), 3.97 (3H, s). |
| M6-17 | $^1$H-NMR (CDCl$_3$) δ: 8.97-8.95 (1H, m), 8.74-8.72 (1H, m), 8.41-8.39 (1H, m), 8.23-8.21 (1H, m), 4.03 (3H, s) |
| M6-44 | 1H-NMR (CDCl3) δ: 8.65 (1H, dd), 8.09 (1H, s), 7.91 (1H, dd), 7.40 (1H, dd), 6.94 (1H, s), 3.98 (3H, s), 3.81 (3H, s). |
| M6-45 | 1H-NMR (CDCl3) δ: 8.69 (1H, d), 8.21 (1H, s), 7.94 (1H, d), 7.65 (1H, d), 7.53-7.41 (2H, m), 3.85 (3H, s). |
| M6-46 | 1H-NMR (CDCl3) δ: 8.65 (1H, dd), 8.47 (1H, s), 8.08 (1H, d), 7.93 (1H, dd), 7.68 (1H, dd), 7.38 (1H, dd). |
| M2-1 | 1H-NMR (CDCl3) δ: 8.31 (1H, d), 7.75 (1H, d), 7.49 (1H, dd), 2.97 (2H, q), 1.44 (3H, t). |

TABLE 71-continued

| Intermediate compound | Material value |
|---|---|
| M2-4 | 1H-NMR (CDCl3) δ: 8.55 (1H, s), 7.92 (1H, s), 3.02 (2H, q), 1.47 (3H, t). |
| M18-1 | 1H-NMR (CDCl3) δ: 8.56 (1H, d), 7.74 (1H, d), 7.47 (1H, dd), 2.99 (2H, q), 1.42 (3H, t). |
| M20-44 | 1H-NMR (CDCl3) δ: 9.53 (1H, brs), 8.54 (1H, d), 7.90 (1H, d), 7.70-7.46 (3H, m), 6.76 (1H, d), 4.48 (1H, brs), 2.91 (3H, d). |
| M37-1 | 1H-NMR (CDCl3) δ: 8.49 (1H, dd), 7.75 (1H, dd), 7.43 (1H, dd), 3.06 (2H, q), 1.38 (3H, t). |
| M37-4 | 1H-NMR (CDCl3) δ: 8.68 (1H, s), 7.88 (1H, s), 3.13 (2H, q), 1.44 (3H, t). |

Next, Formulation Examples will be described. Herein, the term "part(s)" means "part(s) by weight".

Formulation Example 1

Any one of the present compounds 1 to 555 (10 parts) is dissolved in a mixture of xylene (35 parts) and N,N-dimethylformamide (35 parts), and to the mixture is added polyoxyethylene styryl phenyl ether (14 parts) and calcium dodecylbenzenesulfonate (6 parts), and stirred to give an emulsifiable concentrate of each compound.

Formulation Example 2

Sodium lauryl sulfate (4 parts), calcium lignin sulfonate (2 parts), a fine powder (20 parts) of synthetic hydrated silicone oxide and diatomite (54 parts) are mixed, then to the mixture is added any one of the present compounds 1 to 555 (20 parts), and mixed to give a wettable powder of each compound.

Formulation Example 3

To any one of the present compounds 1 to 555 (2 parts) is added a fine powder (1 part) of synthetic hydrated silicone oxide, calcium lignin sulfonate (2 parts), bentonite (30 parts), and kaolin clay (65 parts), and mixed. Then, to the mixture is added an appropriate amount of water, further stirred, granulated with a granulator, and draft-dried to give granules of each compound.

Formulation Example 4

Any one of the present compounds 1 to 555 (1 part) is dissolved in an appropriate amount of acetone. To the mixture is added a fine powder (5 parts) of synthetic hydrated silicone oxide, PAP (0.3 parts), and Fubasami clay (93.7 parts), and well stirred. Then, acetone is removed by evaporation to give dusts of each compound.

Formulation Example 5

A mixture (weight ratio=1:1) of polyoxyethylene alkyl ether sulfate ammonium salt and white carbon (35 parts), any one of the present compounds 1 to 555 (10 parts), and water (55 parts) are mixed, pulverized by a wet grinding method to give a suspension concentrate of each compound.

Formulation Example 6

Any one of the present compounds 1 to 555 (0.1 parts) is dissolved in xylene (5 parts) and trichloroethane (5 parts), and mixed with deodorized kerosine (89.9 parts) to give an oil solutions of each compound.

Formulation Example 7

Any one of the present compounds 1 to 555 (10 mg) is dissolved in acetone (0.5 ml). The mixture is added to animal powdered solid feed (powdered solid feed for breeding, CE-2, from CLEA Japan, Inc.) (5 g) and mixed uniformly. Then, acetone is removed by evaporation to give a poison bait of each compound.

Formulation Example 8

Any one of the present compounds 1 to 555 (0.1 parts) and Neothiosol (Chuo Kasei Co. Ltd.) (49.9 parts) are charged into an aerosol container. After an aerosol valve is attached to the container, dimethyl ether (25 parts) and LPG (25 parts) are charged into the container. The container is vibrated, and attaching an actuator to give an oily aerosol of each compound.

Formulation Example 9

Any one of the present compounds 1 to 555 (0.6 parts), BHT (2,6-di-tert-butyl-4-methylphenol) (0.01 parts), xylene (5 parts), deodorized kerosine (3.39 parts), and an emulsifier (Atmos 300, registered trade name for Atmos Chemical Ltd.) (1 part) are mixed and dissolved. The mixture and distilled water (50 parts) are charged into an aerosol container, and attaching a valve. Then, propellant (LPG) (40 parts) is pressure-charged into the container through the valve to give an aqueous aerosol of each compound.

Formulation Example 10

Any one of the present compounds 1 to 555 (0.1 g) is dissolved in propylene glycol (2 ml), and the solution is impregnated into a porous ceramic plate (4.0×4.0 cm, 1.2 cm thick) to give a heat-type smoking agent.

Formulation Example 11

Any one of the present compounds 1 to 555 (5 parts) and ethylene-methyl methacrylate copolymer (proportion of methyl methacrylate in the copolymer: 10 wt %, Acryft WD301, manufactured by Sumitomo Chemical Co., Ltd) (95 parts) are melt-mixed by a sealed, pressurized kneader (manufactured by Moriyama Co., Ltd.). The resulting mixture is extruded from a molding machine via a molding die to give a rod-shaped molded article (15 cm long, 3 mm diameter).

Formulation Example 12

Any one of the present compounds 1 to 555 (5 parts) and soft vinyl chloride resin (95 parts) are melt-mixed by a sealed, pressurized kneader (manufactured by Moriyama Co., Ltd.). The resulting mixture is extruded from a molding machine via a molding die to give a rod-shaped molded article (15 cm long, 3 mm diameter).

Formulation Example 13

Any one of the present compounds 1 to 555 (100 mg), lactose (68.75 mg), corn starch (237.5 mg), microcrystalline cellulose (43.75 mg), polyvinyl pyrrolidone (18.75 mg), sodium carboxymethyl starch (28.75 mg), and magnesium stearate (2.5 mg) are mixed, and the resulting mixture is compressed to a suitable size to give tablets.

Formulation Example 14

Any one of the present compounds 1 to 555 (25 mg), lactose (60 mg), corn starch (25 mg), carmellose calcium (6 mg), and 5% hydroxypropylmethyl cellulose (appropriate amount) are mixed, and the resulting mixture is packed into hard shell gelatin capsules or hydroxypropyl methylcellulose capsules to give capsules.

Formulation Example 15

To a mixture of any one of the present compounds 1 to 555 (1000 mg), fumaric acid (500 mg), sodium chloride (2000 mg), methylparaben (150 mg), propylparaben (50 mg), granulated sugar (25000 mg), 70% solution of sorbitol (13000 mg), VeegumK (Vanderbilt Co) (100 mg), a perfume (35 mg), and a colorant (500 mg) is added distillated water such that the final volume becomes 100 ml, and well mixed to give a suspension for oral administration.

Formulation Example 16

Any one of the present compounds 1 to 555 (5% by weight) is dissolved in Polysorbate 85 (5% by weight), benzyl alcohol (3% by weight), and propylene glycol (30% by weight), and a phosphate buffer is added thereto such that the pH becomes 6.0-6.5, and water is added thereto to be a final volume to give a liquid for oral administration.

Formulation Example 17

Aluminum distearate (5% by weight) is dispersed into a fractionated coconut oil (57% by weight) and Polysorbate (3% by weight) by heating. After cooling to room temperature, saccharine (25% by weight) is dispersed into the oily vehicle. Then, the present compounds 1 to 555 (10% by weight) is added to the mixture to give a paste for oral administration.

Formulation Example 18

Any one of the present compounds 1 to 555 (5% by weight) and a limestone powder (95% by weight) are mixed, and then the mixture is subjected to a wet granulation method to give granules for oral administration.

Formulation Example 19

Any one of the present compounds 1 to 555 (5 parts) is dissolved in diethylene glycol monoethyl ether (80 parts), and then propylene carbonate (15 parts) is mixed therewith to give a spot-on liquid.

Formulation Example 20

Any one of the present compounds 1 to 555 (10 parts) is dissolved in diethylene glycol monoethyl ether (70 parts), and then 2-octyldodecanol (20 parts) is mixed therewith to give a pour-on liquid.

Formulation Example 21

To any one of the present compounds 1 to 555 (0.5 parts) are added Nikkol TEALS-42 (Nikko Chemicals Co., Ltd., 42% aqueous solution of triethanolamine lauryl sulfate) (60 parts) and propylene glycol (20 parts). After stirring and mixing enough to form a homogeneous solution, water (19.5 parts) is added thereto and the mixture is stirred and mixed adequately to give a homogeneous shampoo formulation.

Formulation Example 22

Any one of the present compounds 1 to 555 (0.15% by weight), an animal feed (95% by weight), and a mixture (4.85% by weight) of dicalcium phosphate, diatomite, Aerosil, and carbonate (or chalk) are stirred and mixed adequately to give a premix for animal feed.

Formulation Example 23

Any one of the present compounds 1 to 555 (7.2 g) and Vosco S-55 (manufactured by Maruishi Pharmaceutical Co., Ltd.) (92.8 g) are dissolved and mixed at 100° C. Then, the mixture is poured into a suppository mold, and cooled and solidified to give a suppository.

The controlling effect on pests by the present compound will be demonstrated below with reference to Test Examples.

Test Example 1

Each test solution was prepared by diluting a formulation containing any of the present compounds 1-9, 12-16, 18-20, 22-28, 30-32, 36-37, 40, 44, 46-48, 50-51, 56, 60, 62-65, 69-70, 72, 74, 76, 79-81, 84-85, 89, 99, 138, 144, 190, 508, 511-515, 517-524, 526 and 528-529 as obtained in Formulation Example 5, with water so as to give 500 ppm of the concentration of the active ingredient.

On the other hand, on a cucumber seedling (the first true leaf stage) planted in a plastic cup was inoculated with about 30 $Aphis\ gossypii$ (whole stage), and leaving it for a day. Twenty (20) ml of each test solution was sprayed on the seedling.

Six (6) days after spraying, the number of the surviving $Aphis\ gossypii$ parasitized on the leaves of the cucumber was examined, and a control value was calculated according to the following equation:

Controlling value(%)=$\{1-(Cb \times Tai)/(Cai \times Tb)\} \times 100$ wherein the symbols represent as follows:
Cb: the number of insects in a non-treated section before treatment
Cai: the number of insects in a non-treated section on observation
Tb: the number of insects in a treated-section before treatment
Tai: the number of insects in a treated section on observation
wherein the non-treated section represents a section where the test diluted solution prepared by diluting the formulation without the present compound as in Formulation Example 5 with the same amount of water as in the treated-section was used.

As a result, in the treated-section using each test solution containing each of the present compounds 1-9, 12-16, 18-20, 22-28, 30-32, 36-37, 40, 44, 46-48, 50-51, 56, 60, 62-65, 69-70, 72, 74, 76, 79-81, 84-85, 89, 99, 138, 144, 190, 508, 511-515, 517-524, 526 and 528-529, the control value was 90% or more.

Test Example 2

Each test solution was prepared by diluting a formulation containing any of the present compounds 1-3, 5-8, 13-16, 19-20, 25, 27, 30, 32, 36-37, 44, 47-48, 50-51, 60, 62-64, 72, 81, 85, 99, 138, 144, 511-512, 515, 518, 522-524 and 528 as obtained in Formulation Example 5, with water so as to give 500 ppm of the concentration of the active ingredient.

On the other hand, a cucumber seedling (the second true leaf stage) planted in a plastic cup was drenched at its foot with 5 ml of each of the diluted solutions, and kept in a greenhouse of 25° C. for 7 days. On the cucumber leaf surface was inoculated with about 30 $Aphis\ gossypii$ (whole stage), and further kept in the greenhouse for 6 days, then the number of insect of living $Aphis\ gossypii$ parasitized on the leaves of the cucumber was examined, and a control value was calculated according to the following equation:

Controlling value(%)=$\{1-(Cb \times Tai)/(Cai \times Tb)\} \times 100$ wherein the symbols represent as follows:
Cb: the number of insects in a non-treated section before treatment
Cai: the number of insects in a non-treated section on observation
Tb: the number of insects in a treated-section before treatment
Tai: the number of insects in a treated section on observation
wherein the non-treated section represents a section where the test diluted solution prepared by diluting the formulation without the present compound as in Formulation Example 5 with the same amount of water as in the treated-section was used.

As a result, in the treated-section using each test solution containing each of the present compounds 1-3, 5-8, 13-16, 19-20, 25, 27, 30, 32, 36-37, 44, 47-48, 50-51, 60, 62-64, 72, 81, 85, 99, 138, 144, 511-512, 515, 518, 522-524 and 528, the control value was 90% or more.

Test Example 3

Each test solution was prepared by diluting formulation containing any of the present compounds 1-3, 5-9, 12-20, 22, 24-30, 32, 36-37, 44, 50, 60, 62-64, 72, 74, 81, 84-85, 89, 99, 138, 144, 511, 515, 518-519, 521, 523-524 and 529 as obtained in Formulation Example 5, with water so as to give 500 ppm of the concentration of the active ingredient.

On the other hand, a rice seedling (the second leaf stage) planted in a polyethylene cup was sprayed with 10 ml of each test solution. After air-drying, 20 third-fourth instar larvae of $Nilaparvata\ lugens$ were released, and kept in the greenhouse of 25° C. After 6 days, the number of insect of living $Nilaparvata\ lugens$ parasitized on the rice was examined, and a control value was calculated according to the following equation:

Controlling value(%)=$\{1-(Cb \times Tai)/(Cai \times Tb)\} \times 100$ wherein the symbols represent as follows:
Cb: the number of insects in a non-treated section before treatment
Cai: the number of insects in a non-treated section on observation
Tb: the number of insects in a treated-section before treatment
Tai: the number of insects in a treated section on observation
wherein the non-treated section represents a section where the test diluted solution prepared by diluting the formulation without the present compound as in Formulation Example 5 with the same amount of water as in the treated-section was used.

As a result, in the treated-section using each test solution containing each of the present compounds 1-3, 5-9, 12-20, 22, 24-30, 32, 36-37, 44, 50, 60, 62-64, 72, 74, 81, 84-85, 89, 99, 138, 144, 511, 515, 518-519, 521, 523-524 and 529, the control value was 90% or more.

Test Example 4

Each test solution was prepared by diluting a formulation containing any of the present compounds 1-3, 6, 8, 12-16, 18-19, 22, 24-27, 29, 32, 36-37, 44, 48, 50, 60, 62-64, 72, 74, 81, 85, 89, 99, 138, 144, 508, 512, 515, 518-519 and 521-524 as obtained in Formulation Example 5, with water so as to give 500 ppm of the concentration of the active ingredient.

On the other hand, a rice seedling (2 weeks after sowing, the second leaf stage) planted in a plastic cup was drenched at its foot with 5 ml of each test solution, and kept in a greenhouse of 25° C. for 7 days. Twenty (20) third-fourth instar larvae of *Nilaparvata lugens* were released, and further kept in the greenhouse for 6 days, then the number of insect of living *Nilaparvata lugens* parasitized on the rice was examined, and a control value was calculated according to the following equation:

Controlling value(%)={1-($Cb \times Tai$)/($Cai \times Tb$)}×100 wherein the symbols represent as follows:
Cb: the number of insects in a non-treated section before treatment
Cai: the number of insects in a non-treated section on observation
Tb: the number of insects in a treated-section before treatment
Tai: the number of insects in a treated section on observation
wherein the non-treated section represents a section where the test diluted solution prepared by diluting the formulation without the present compound as in Formulation Example 5 with the same amount of water as in the treated-section was used.

As a result, in the treated-section using each test solution containing each of the present compounds 1-3, 5-6, 8, 12-16, 18-19, 22, 24-27, 29, 32, 36-37, 44, 48, 50, 60, 62-64, 72, 74, 81, 85, 89, 99, 138, 144, 508, 512, 515, 518-519 and 521-524, the control value was 90% or more.

Test Example 5

Each test solution was prepared by diluting a formulation containing any of the present compounds 3, 5-6, 8, 13-16, 18-20, 24-27, 29, 36-37, 44, 47, 60, 63-64, 72, 74, 89, 99, 511, 515, 518, 521, 523-524 and 528 as obtained in Formulation Example 5, with water so as to give 500 ppm of the concentration of the active ingredient.

On the other hand, *Bemisia tabaci* adult was released on a tomato seedling (the third true leaf stage) planted in a polyethylene cup, and made to lay eggs for about 72 hours. The tomato seedling was kept in a greenhouse for 8 days. When instar larvae hatched from the eggs, the above test spray solution was sprayed in the amount of 20 ml/cup. The cup was kept in a greenhouse at 25° C. After the keeping for 7 days, the number of surviving instar larvae on the tomato leaves was examined, and a control value was calculated according to the following equation:

Controlling value(%)={1-($Cb \times Tai$)/($Cai \times Tb$)}×100 wherein the symbols represent as follows:
Cb: the number of insects in a non-treated section before treatment
Cai: the number of insects in a non-treated section on observation
Tb: the number of insects in a treated-section before treatment
Tai: the number of insects in a treated section on observation
wherein the non-treated section represents a section where the test diluted solution prepared by diluting the formulation without the present compound as in Formulation Example 5 with the same amount of water as in the treated-section was used.

As a result, in the treated-section using each test solution containing each of the present compounds 3, 5-6, 8, 13-16, 18-20, 24-27, 29, 36-37, 44, 47, 60, 63-64, 72, 74, 89, 99, 511, 515, 518, 521, 523-524 and 528, the control value was 90% or more.

Test Example 6

Each test solution was prepared by diluting a formulation containing any of the present compounds 1-5, 8-9, 11-12, 15-16, 19-20, 22-25, 27-33, 35-37, 40, 44, 46-51, 53, 58-65, 69, 71-74, 76-78, 80-85, 87, 89, 99, 138, 144, 190, 505-506, 508, 511-515, 518, 520-523 and 527-530 as obtained in Formulation Example 5, with water so as to give 500 ppm of the concentration of the active ingredient.

On the other hand, Cabbage (the third leaf stage) planted in a polyethylene cup was sprayed with 20 mL/cup of each test solution. After the test solution was dried, the aerial part was cut off, and then placed in a 50 mL volume cup. Five (5) second instar larvae of *Plutella xylostella* were released into the cup, and the cup was sealed with a lid. After the cup was kept at 25° C. for 5 days, the number of living insects was counted. A death rate was calculated according to the following equation:

Death rate(%)=(Number of dead insects/Number of tested insects)×100

As a result, in the treated-section using each test solution containing each of the present compounds 1-5, 8-9, 11-12, 15-16, 19-20, 22-25, 27-33, 35-37, 40, 44, 46-51, 53, 58-65, 69, 71-74, 76-78, 80-85, 87, 89, 99, 138, 144, 190, 505-506, 508, 511-515, 518, 520-523 and 527-530, the death rate was 80% or more.

Test Example 7

Each test solution was prepared by diluting a formulation containing any of the present compounds 1-9, 11-20, 22-35, 38-40, 44, 46-48, 50, 53, 58, 60, 62-64, 71-72, 74, 77-85, 87, 89, 99, 138, 144, 505-506, 508, 511-512, 514-515, 518-520, 523-526 and 528-530 as obtained in Formulation Example 5, with water so as to give 500 ppm of the concentration of the active ingredient.

On the other hand, an apple tree was planted in a plastic cup, and grown until the seventh-eighth leaf was spread. The apple tree was sprayed with 20 mL/cup of each test solution. After the test solution was dried, 60 first-instar *Adoxophyes orana fasciata* were released, and the cup was covered with a plastic cup upside-down which the bottom was cut off and a filter paper was put thereon. After 7 days, the number of living insects was counted, and a death rate was calculated according to the following equation:

Death rate(%)=(Number of dead insects/Number of tested insects)×100

As a result, in the treated-section using each test solution containing each of the present compounds 1-9, 11-20, 22-35, 38-40, 44, 46-48, 50, 53, 58, 60, 62-64, 71-72, 74, 77-85, 87, 89, 99, 138, 144, 505-506, 508, 511-512, 514-515, 518-520, 523-526 and 528-530, the death rate was 90% or more.

Test Example 8

Each test solution was prepared by diluting a formulation containing any of the present compounds 1, 3-5, 8, 15-16, 19-20, 23, 27, 29, 37, 40, 44, 48, 60-61, 64, 72, 74, 518, 523 and 528 as obtained in Formulation Example 5, with water so as to give 500 ppm of the concentration of the active ingredient.
A filter paper having a diameter of 5.5 cm was spread on the bottom of a polyethylene cup having a diameter of 5.5 cm and each test solution (0.7 ml) was added dropwise onto the filter paper. As a bait sucrose (30 mg) was uniformly placed on the filter paper. Into the polyethylene cup, 10 female imagoes of *Musca domestica* were released and the cup was sealed with a lid. After 24 hours, the number of surviving *Musca domestica* was examined and the death rate of the pest was calculated.
As a result, in the treatment with each test solution containing each of the present compounds 1, 3-5, 8, 15-16, 19-20, 23, 27, 29, 37, 40, 44, 48, 60-61, 64, 72, 74, 518, 523 and 528, the death rate was 100%.

Test Example 9

Each test solution was prepared by diluting a formulation containing any of the present compounds 4-5, 19-20, 28-29, 40, 44, 48, 60, 71-74, 89, 523 and 528 as obtained in Formulation Example 5, with water so as to give 500 ppm of the concentration of the active ingredient.
A filter paper having a diameter of 5.5 cm was spread on the bottom of a polyethylene cup having a diameter of 5.5 cm and each test solution (0.7 ml) was added dropwise onto the filter paper. As a bait sucrose (30 mg) was uniformly placed on the filter paper. Into the polyethylene cup, 2 male imagoes of *Blattalla germanica* were released and the cup was sealed with a lid. After 6 days, the number of surviving *Blattalla germanica* was examined and the death rate of the pest was calculated.
As a result, in the treatment with each test solution containing each of the present compounds 4-5, 19-20, 28-29, 40, 44, 48, 60, 71-74, 89, 523 and 528, the death rate was 100%.

Test Example 10

Each test solution was prepared by diluting a formulation containing any of the present compounds 1, 3-5, 8, 15-16, 19-20, 22-25, 27-28, 31-33, 35, 37, 40, 44, 48-49, 51, 59-64, 71-74, 80-81, 84-85, 89, 99, 138, 144, 505-506, 508, 514-515, 518, 520, 522-523 and 528 as obtained in Formulation Example 5, with water so as to give 500 ppm of the concentration of the active ingredient.
To ion-exchanged water (100 mL), each test solution (0.7 ml) was added (active ingredient concentration: 3.5 ppm). Into the solution, 20 last-instar larvae of *Culex pipiens pallens* were released. One day after, the number of surviving *Culex pipiens pallens* was examined and the death rate of the pest was calculated.
As a result, in the treatment with each test solution containing each of the present compounds 1, 3-5, 8, 15-16, 19-20, 22-25, 27-28, 31-33, 35, 37, 40, 44, 48-49, 51, 59-64, 71-74, 80-81, 84-85, 89, 99, 138, 144, 505-506, 508, 514-515, 518, 520, 522-523 and 528, the death rate was 95% or more.

Test Example 11

Each 2 mg of the present compounds 1, 5, 8, 15-16, 19, 23, 25-27, 30, 37, 40, 49, 61, 63, 99 and 516 was put into a screw tube (Maruemu No. 5; 27×55 mm). Acetone (0.2 ml) was added thereto and sealed with a cap. After dissolving the compound in acetone, the screw tube was rotated and inverted to uniformity coat the solution onto the whole inner wall of the tube. After removing the cap, the solution was air-dried for about 2 hours. Then, non-blood-sucking nymphal ticks, *Haemaphysalis longicornis* (5 ticks/group) were released into the tube, and the tube was sealed with the cap. After 2 days, the number of dead tick was counted, and a death rate was calculated according to the following equation:

Death rate(%)=(Number of dead tick/Number of tested tick)×100

As a result, in the treatment with each test solution containing each of the present compounds 1, 5, 8, 15-16, 19, 23, 25-27, 30, 37, 40, 49, 61, 63, 99 and 516, the death rate was 100%.

INDUSTRIAL APPLICABILITY

The present compound has a controlling effect on pests and is useful as an active ingredient of a pest control agent.

The invention claimed is:
1. A compound represented by the formula (1):

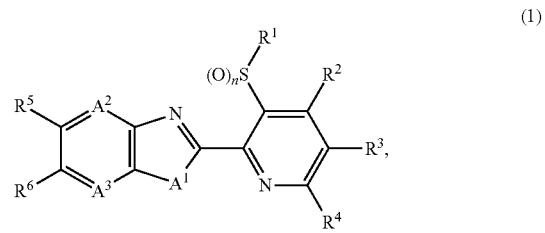

wherein
$A^1$ represents —$NR^7$—, an oxygen atom or a sulfur atom,
$A^2$ represents a nitrogen atom or =$CR^8$—,
$A^3$ represents a nitrogen atom or =$CR^9$—,
$R^1$ represents a C1-C6 chain hydrocarbon group optionally substituted by one or more atoms or groups selected from Group X or a C3-C6 alicyclic hydrocarbon group optionally substituted by one or more atoms or groups selected from Group Y,
$R^2$, $R^3$ and $R^4$ are the same or different and each represents a C1-C6 chain hydrocarbon group optionally substituted by one or more atoms or groups selected from Group X, a phenyl group optionally substituted by one or more atoms or groups selected from Group Z, a 5- or 6-membered heterocyclic group optionally substituted by one or more atoms or groups selected from Group Z, —$OR^{10}$, —$S(O)_mR^{10}$, —$S(O)_2NR^{10}R^{11}$, —$NR^{10}R^{11}$, —$NR^{10}CO_2R^{11}$, —$NR^{10}C(O)R^{11}$, —$CO_2R^{10}$, —$C(O)R^{10}$, —$C(O)NR^{10}R^{11}$, —$SF_5$, a cyano group, a nitro group, a halogen atom or a hydrogen atom,
$R^5$ and $R^6$ are the same or different and each represents a C1-C6 chain hydrocarbon group optionally substituted by one or more atoms or groups selected from Group X, a phenyl group optionally substituted by one or more atoms or groups selected from Group Z, a 5- or 6-membered heterocyclic group optionally substituted by one or more atoms or groups selected from Group Z, —$OR^{10}$, —$S(O)_mR^{10}$, —$S(O)_2NR^{10}R^{11}$, —$NR^{10}R^{11}$, —$NR^{10}CO_2R^{11}$, —$NR^{10}C(O)R^{11}$, —$CO_2R^{10}$, —$C(O)R^{10}$, —$C(O)NR^{10}R^{11}$, —$SF_5$, a cyano group, a nitro group, a halogen atom or a hydrogen atom (wherein $R^5$ and $R^6$ do not represents a hydrogen atom at the same time), $R^7$ represents a C1-C6 chain hydrocarbon group optionally substituted by one or more atoms or groups selected from Group W, a C1-C6 chain hydrocarbon group substituted by one phenyl group (wherein the phenyl group is optionally substituted by one or more atoms or groups selected from Group Z), a C1-C6 chain hydrocarbon group substituted by one 5- or 6-membered heterocyclic group (wherein the 5- or 6-membered heterocyclic group is optionally substituted by one or more atoms or groups selected from Group Z), —$CO_2R^{10}$, —$C(O)R^{10}$, a C3-C6 alicyclic hydrocarbon group optionally substituted by one or more atoms or groups selected from Group Y or a hydrogen atom, $R^8$ and $R^9$ are the same or different and each represents a C1-C6 chain hydrocarbon group optionally substituted by one or more halogen atoms, —$OR^{10}$, —$S(O)_mR^{10}$, —$NR^{10}R^{11}$, —$CO_2R^{10}$, —$C(O)R^{10}$, a cyano group, a nitro group, a halogen atom or a hydrogen atom, $R^{10}$ and $R^{11}$ are the same or different and each represents a C1-C6 chain hydrocarbon group optionally substituted by one or more atoms or groups selected from Group X, a phenyl group optionally substituted by one or more atoms or groups selected from Group Z or a hydrogen atom, each m independently represents 0, 1 or 2, and n represents 0, 1 or 2, wherein the —$S(O)_mR^{10}$, $R^{10}$ does not a hydrogen atom when m is 1 or 2, Group X: the group consisting of a C1-C6 alkoxy group optionally substituted by one or more halogen atoms, a C2-C6 alkenyloxy group optionally substituted by one or more halogen atoms, a C2-C6 alkynyloxy group optionally substituted by one or more halogen atoms, a C1-C6 alkylsulfanyl group optionally substituted by one or more halogen atoms, a C1-C6 alkylsulfinyl group optionally substituted by one or more halogen atoms, a C1-C6 alkylsulfonyl group optionally substituted by one or more halogen atoms, a C2-C6 alkylcarbonyl group optionally substituted by one or more halogen atoms, a C2-C6 alkoxycarbonyl group optionally substituted by one or more halogen atoms, a C3-C6 cycloalkyl group optionally substituted by one or more halogen atoms or one or more C1-C3 alkyl groups, a cyano group, a hydroxy group and a halogen atom, Group Y: the group consisting of a C1-C6 chain hydrocarbon group optionally substituted by one or more halogen atoms, a C1-C6 alkoxy group optionally substituted by one or more halogen atoms, a C2-C6 alkenyloxy group optionally substituted by one or more halogen atoms, a C2-C6 alkynyloxy group optionally substituted by one or more halogen atoms and a halogen atom, Group Z: the group consisting of a C1-C6 chain hydrocarbon group optionally substituted by one or more halogen atoms, a C1-C6 alkoxy group optionally substituted by one or more halogen atoms, a C1-C6 alkylsulfanyl group optionally substituted by one or more halogen atoms, a C1-C6 alkylsulfinyl group optionally substituted by one or more halogen atoms, a C1-C6 alkylsulfonyl group optionally substituted by one or more halogen atoms, a C2-C6 alkylcarbonyl group optionally substituted by one or more halogen atoms, a C2-C6 alkoxycarbonyl group optionally substituted by one or more halogen atoms, a C1-C6 alkylamino group optionally substituted by one or more halogen atoms, a C2-C8 dialkylamino group optionally substituted by one or more halogen atoms, a halogen atom, a cyano group and a nitro group, Group W: the group consisting of a C1-C6 alkoxy group optionally substituted by one or more halogen atoms, a C2-C6 alkenyloxy group optionally substituted by one or more halogen atoms, a C2-C6 alkynyloxy group optionally substituted by one or more halogen atoms, a C1-C6 alkylsulfanyl group optionally substituted by one or more halogen atoms, a C2-C6 alkylcarbonyl group optionally substituted by one or more halogen atoms, a C2-C6 alkoxycarbonyl group optionally substituted by one or more halogen atoms, a C3-C6 cycloalkyl group optionally substituted by one or more halogen atoms, a C1-C6 alkylsulfinyl group optionally substituted by one or more halogen atoms, a C1-C6 alkylsulfonyl group optionally substituted by one or more halogen atoms, hydroxy group, a halogen atom and a cyano group, or an N-oxide thereof.

2. The compound according to claim 1, wherein $A^1$ is —$NR^7$—, an oxygen atom or a sulfur atom, $A^2$ is a nitrogen atom or =$CR^8$—, $A^3$ is a nitrogen atom or =$CR^9$—, $R^1$ is a C1-C6 chain hydrocarbon group optionally substituted by one or more atoms or groups selected from Group X, $R^2$, $R^3$ and $R^4$ are the same or different and each represents a C1-C6 chain hydrocarbon group optionally substituted by one or more atoms or groups selected from Group X, a phenyl group optionally substituted by one or more atoms or groups selected from Group Z, a 5- or 6-membered heterocyclic group optionally substituted by one or more atoms or groups selected from Group Z, —$OR^{10}$, —$S(O)_mR^{10}$, —$SF_5$, a cyano group, a nitro group, a halogen atom or a hydrogen atom, $R^5$ and $R^6$ are the same or different and each represents a C1-C6 chain hydrocarbon group optionally substituted by one or more atoms or groups selected from Group X, —$OR^{10}$, —$S(O)_mR^{10}$, —$SF_5$, a halogen atom or a hydrogen atom, $R^7$ is a C1-C6 chain hydrocarbon group optionally substituted by one or more atoms or groups selected from Group W, a C1-C6 chain hydrocarbon group substituted by one phenyl group (wherein the phenyl group is optionally substituted by one or more atoms or groups selected from Group Z), a C1-C6 chain hydrocarbon group substituted by one 5- or 6-membered heterocyclic group (wherein the 5- or 6-membered heterocyclic group is optionally substituted by one or more atoms or groups selected from Group Z), or a hydrogen atom, $R^8$ is a C1-C6 chain hydrocarbon group optionally substituted by one or more halogen atoms, —$OR^{10}$, —$S(O)_mR^{10}$, a halogen atom or a hydrogen atom, and $R^9$ is a C1-C6 chain hydrocarbon group optionally substituted by one or more halogen atoms, —$OR^{10}$, —$S(O)_mR^{10}$, a halogen atom or a hydrogen atom.

3. The compound according to claim 1, wherein $A^1$ is —$NR^7$—, an oxygen atom or a sulfur atom, $A^2$ is a nitrogen atom or =$CR^8$—, $A^3$ is a nitrogen atom or =$CR^9$—, $R^1$ is a C1-C6 alkyl group optionally substituted by one or more atoms or groups selected from the group consisting of a halogen atom and cyclopropyl group (wherein the cyclopropyl group is optionally substituted by one or more halogen atoms or one or more C1-C3 alkyl group), a C2-C6 alkenyl group optionally substituted by one or more halogen atoms or a C2-C6 alkynyl group optionally substituted by one or more halogen atoms, $R^2$ and $R^4$ are the same or different each other and each represents a halogen atom or a hydrogen atom, $R^3$ is a C1-C6 alkyl group optionally substituted by one or more halogen atoms, a C2-C6 alkenyl group optionally substituted by one or more halogen atoms, a C2-C6 alkynyl group optionally substituted by one or more halogen atoms, 5- or 6-membered aromatic heterocyclic group (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), —$OR^{10}$, —$S(O)_mR^{10}$, a cyano group, a nitro group, a halogen atom or a hydrogen atom, $R^5$ is a C1-C6 alkyl group optionally substituted by one or more halogen atoms, —$OR^{10}$, —$S(O)_mR^{10}$, —$SF_5$ or a halogen atom, $R^6$ is a C1-C6 alkyl group optionally substituted by one or more halogen atoms, —$OR^{10}$, —$S(O)_mR^{10}$, a halogen atom or a hydrogen atom, $R^{10}$ is a C1-C6 alkyl group optionally substituted by one or more halogen atoms, $R^7$ is a C1-C6 alkyl group optionally substituted by one or more halogen atoms, a C3-C6 alkenyl group optionally substituted by one or more halogen atoms, a C3-C6 alkynyl group optionally substituted by one or more halogen atoms, a C1-C6 alkyl group substituted by one 5- or 6-membered aromatic heterocyclic group (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), a hydrogen atom or a C2-C6 alkoxyalkyl group optionally substituted by one or more halogen atoms, $R^8$ is a C1-C6 alkyl group optionally substituted by one or more halogen atoms, —$OR^{10}$, —$S(O)_mR^{10}$, a halogen atom or a hydrogen atom, and $R^9$ is a C1-C6 alkyl group optionally substituted by one or more halogen atoms, —$OR^{10}$, —$S(O)_mR^{10}$, a halogen atom or a hydrogen atom.

4. The compound according to claim 1, wherein $A^1$ is —$NR^7$—.

5. The compound according to claim 1, wherein $A^1$ is an oxygen atom.

6. The compound according to claim 1, wherein $A^1$ is a sulfur atom.

7. The compound according to claim 1, wherein $A^2$ is =$CR^8$—.

8. The compound according to claim 1, wherein $A^2$ is =$CR^8$—, and $A^3$ is a nitrogen atom.

9. The compound according to claim 1, wherein $A^2$ is =$CR^8$—, $A^3$ is =$CR^9$—.

10. A compound represented by the formula (1-1):

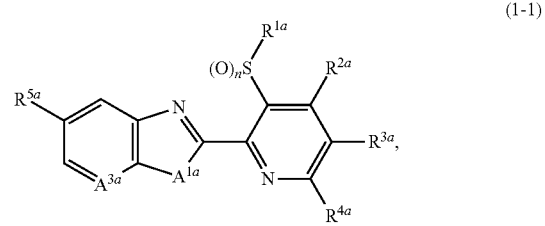

(1-1)

wherein $A^{1a}$ represents —$NR^{7a}$—, an oxygen atom or a sulfur atom, $A^{3a}$ represents a nitrogen atom or =$CR^{9a}$—, $R^{1a}$ represents a C1-C6 alkyl group optionally substituted by one or more atoms or groups selected from the group consisting of a halogen atom and a cyclopropyl group (wherein the cyclopropyl group is optionally substituted by one or more halogen atoms or one or more C1-C3 alkyl groups), a C2-C6 alkenyl group optionally substituted by one or more halogen atoms or a C2-C6 alkynyl group optionally substituted by one or more halogen atoms, $R^{2a}$ and $R^{4a}$ are the same or different and each represents a halogen atom or a hydrogen atom, $R^{3a}$ represents a C1-C6 alkyl group optionally substituted by one or more halogen atoms, a C2-C6 alkenyl group optionally substituted by one or more halogen atoms, a C2-C6 alkynyl group optionally substituted by one or more halogen atoms, 5- or 6-membered aromatic heterocyclic group (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), —$OR^{20a}$ (wherein $R^{20a}$ represents a C1-C6 alkyl group optionally substituted by one or more halogen atoms), —$S(O)_mR^{21a}$ (wherein $R^{21a}$ represents a C1-C6 alkyl group optionally substituted by one or more halogen atoms, m represents 0, 1 or 2), a cyano group, a nitro group, a halogen atom or a hydrogen atom, $R^{5a}$ represents a C1-C6 alkyl group optionally substituted by one or more halogen atoms, —$OR^{22a}$ (wherein $R^{22a}$ represents a C1-C6 alkyl group optionally substituted by one or more halogen atoms), —$S(O)_mR^{23a}$ (wherein $R^{23a}$ represents a C1-C6 alkyl group optionally substituted by one or more halogen atoms, m represents 0, 1 or 2), —$SF_5$ or a halogen atom, $R^{7a}$ represents a C1-C6 alkyl group optionally substituted by one or more halogen atoms, a C3-C6 alkenyl group optionally substituted by one or more halogen atoms, a C3-C6 alkynyl group optionally substituted by one or more halogen atoms or a C1-C6 alkyl group substituted by one 5- or 6-membered aromatic heterocyclic group, (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), $R^{9a}$ represents a C1-C6 alkyl group optionally substituted by one or more halogen atoms, —OR$^{24a}$ (wherein R$^{24a}$ represents a C1-C6 alkyl group optionally substituted by one or more halogen atoms), —S(O)$_m$R$^{25a}$ (wherein R$^{25a}$ represents a C1-C6 alkyl group optionally substituted by one or more halogen atoms, m represents 0, 1 or 2), a halogen atom or a hydrogen atom, and n represents 0, 1 or 2, or an N-oxide thereof.

11. The compound according to claim 10, wherein
A$^{1a}$ is —NR$^{7a}$—, an oxygen atom or a sulfur atom,
A$^{3a}$ is a nitrogen atom or =CR$^{9a}$—,
R$^{1a}$ is a C2-C6 alkyl group, a C1-C6 haloalkyl group or C4-C9 cyclopropylalkyl group (wherein the cyclopropyl group is optionally substituted by one or more halogen atoms or one or more C1-C3 alkyl groups),
R$^{2a}$ and R$^{4a}$ both are a hydrogen atom,
R$^{3a}$ is a C1-C6 alkyl group optionally substituted by one or more halogen atoms, a C2-C6 alkenyl group optionally substituted by one or more halogen atoms, a C2-C6 alkynyl group optionally substituted by one or more halogen atoms, pyridyl group (wherein the pyridyl group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), a pyrimidinyl group (wherein the pyrimidinyl group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), —OR$^{20a}$ (wherein R$^{20a}$ is a C1-C6 alkyl group optionally substituted by one or more halogen atoms), —S(O)$_m$R$^{21a}$ (wherein R$^{21a}$ is a C1-C6 alkyl group optionally substituted by one or more halogen atoms, and m is 0, 1 or 2), a halogen atom or a hydrogen atom,
R$^{5a}$ is a C1-C6 haloalkyl group, —OR$^{22a}$ (wherein R$^{22a}$ is a C1-C6 haloalkyl group), —S(O)$_m$R$^{23a}$ (wherein R$^{23a}$ is a C1-C6 haloalkyl group, and m is 0, 1 or 2), —SF$_5$ or a halogen atom, and
R$^{7a}$ is a C1-C6 alkyl group optionally substituted by one or more halogen atoms, a C3-C6 alkenyl group optionally substituted by one or more halogen atoms, a C3-C6 alkynyl group optionally substituted by one or more halogen atoms, a C1-C6 alkyl group substituted by one thiazolyl group (wherein the thiazolyl group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms) or a C1-C6 alkyl group substituted by one pyridyl group (wherein the pyridyl group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms).

12. The compound according to claim 10, wherein A$^{1a}$ is —NR$^{7a}$—.

13. The compound according to claim 10, wherein A$^{1a}$ is an oxygen atom.

14. The compound according to claim 10, wherein A$^{1a}$ is a sulfur atom.

15. A compound represented by the formula (1-2):

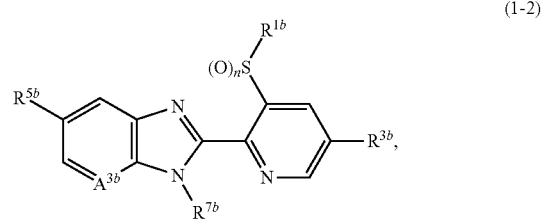

(1-2)

wherein

A$^{3b}$ represents a nitrogen atom or =CR$^{9b}$— (wherein R$^{9b}$ represents a hydrogen atom or a halogen atom), R$^{1b}$ represents an ethyl group or a cyclopropylmethyl group, R$^{7b}$ represents methyl group or a propargyl group, R$^{3b}$ represents a C1-C6 alkyl group optionally substituted by one or more halogen atoms, —OR$^{20b}$ (wherein R$^{20b}$ represents a C1-C6 alkyl group optionally substituted by one or more halogen atoms), —S(O)$_m$R$^{21b}$ (wherein R$^{21b}$ represents a C1-C6 alkyl group optionally substituted by one or more halogen atoms, m represents 0, 1 or 2), a halogen atom or a hydrogen atom, R$^{5b}$ represents a C1-C6 haloalkyl group, —OR$^{22b}$ (wherein R$^{22b}$ represents a C1-C6 haloalkyl group), —S(O)$_m$R$^{23b}$ (wherein R$^{23b}$ represents a C1-C6 haloalkyl group, m represents 0, 1 or 2), —SF$_5$ or a halogen atom, n represents 0, 1 or 2, or an N-oxide thereof.

16. A compound represented by the formula (1-3):

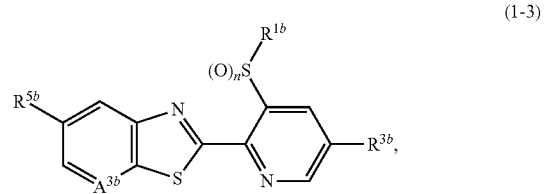

(1-3)

wherein

A$^{3b}$ represents a nitrogen atom or —CR$^{9b}$— (wherein R$^{9b}$ represents a hydrogen atom or a halogen atom), R$^{1b}$ represents an ethyl group or a cyclopropylmethyl group, R$^{3b}$ represents a C1-C6 alkyl group optionally substituted by one or more halogen atoms, —OR$^{20b}$ (wherein R$^{20b}$ represents a C1-C6 alkyl group optionally substituted by one or more halogen atoms), —S(O)$_m$R$^{21b}$ (wherein R$^{21b}$ represents a C1-C6 alkyl group optionally substituted by one or more halogen atoms, m represents 0, 1 or 2), a halogen atom or a hydrogen atom, R$^{5b}$ represents a C1-C6 haloalkyl group, —OR$^{22b}$ (wherein R$^{22b}$ represents a C1-C6 haloalkyl group), —S(O)$_m$R$^{23b}$ (wherein R$^{23b}$ represents a C1-C6 haloalkyl group, m represents 0, 1 or 2), —SF$_5$ or a halogen atom, n represents 0, 1 or 2, or an N-oxide thereof.

17. A compound represented by the formula (1-4):

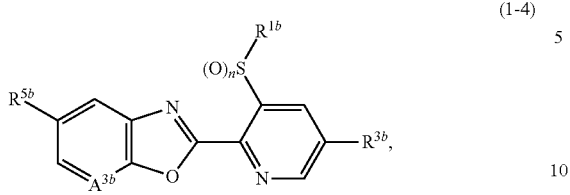

(1-4)

wherein
$A^{3b}$ represents a nitrogen atom or =$CR^{9b}$— (wherein $R^{9b}$ represents a hydrogen atom or a halogen atom),
$R^{1b}$ represents an ethyl group or a cyclopropylmethyl group,
$R^{3b}$ represents a C1-C6 alkyl group optionally substituted by one or more halogen atoms, —$OR^{20b}$ (wherein $R^{20b}$ represents a C1-C6 alkyl group optionally substituted by one or more halogen atoms), —$S(O)_mR^{21b}$ (wherein $R^{21b}$ represents a C1-C6 alkyl group optionally substituted by one or more halogen atoms, m represents 0, 1 or 2), a halogen atom or a hydrogen atom,
$R^{5b}$ represents, a C1-C6 haloalkyl group, —$OR^{22b}$ (wherein $R^{22b}$ represents a C1-C6 haloalkyl group), —$S(O)_mR^{23b}$ (wherein $R^{23b}$ represents a C1-C6 haloalkyl group, m represents 0, 1 or 2), —$SF_5$ or a halogen atom, and
n represents 0, 1 or 2,
or an N-oxide thereof.

18. A compound represented by the formula (1-5):

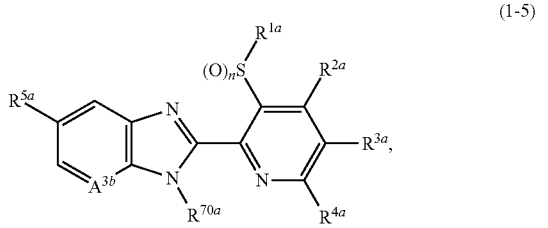

(1-5)

wherein
$R^{70a}$ represents hydrogen atom or a C2-C6 alkoxyalkyl group optionally substituted by one or more halogen atoms,
$A^{3a}$ represents a nitrogen atom or =$CR^{9a}$—,
$R^{1a}$ represents a C1-C6 alkyl group optionally substituted by one or more atoms or groups selected from the group consisting of a halogen atom and a cyclopropyl group (wherein the cyclopropyl group is optionally substituted by one or more halogen atoms or one or more C1-C3 alkyl groups), a C2-C6 alkenyl group optionally substituted by one or more halogen atoms or a C2-C6 alkynyl group optionally substituted by one or more halogen atoms,
$R^{2a}$ and $R^{4a}$ are the same or different and each represents a halogen atom or a hydrogen atom,
$R^{3a}$ represents a C1-C6 alkyl group optionally substituted by one or more halogen atoms, a C2-C6 alkenyl group optionally substituted by one or more halogen atoms, a C2-C6 alkynyl group optionally substituted by one or more halogen atoms, 5- or 6-membered aromatic heterocyclic group (wherein the 5- or 6-membered aromatic heterocyclic group is optionally substituted by one or more atoms or groups selected from the group consisting of a halogen atom, a C1-C3 alkyl group optionally substituted by one or more halogen atoms, and a C1-C3 alkoxy group optionally substituted by one or more halogen atoms), —$OR^{20a}$ (wherein $R^{20a}$ represents a C1-C6 alkyl group optionally substituted by one or more halogen atoms), —$S(O)_mR^{21a}$ (wherein $R^{21a}$ represents a C1-C6 alkyl group optionally substituted by one or more halogen atoms, m represents 0, 1 or 2), a cyano group, a nitro group, a halogen atom or a hydrogen atom,
$R^{5a}$ represents a C1-C6 alkyl group optionally substituted by one or more halogen atoms, —$OR^{22a}$ (wherein $R^{22a}$ represents a C1-C6 alkyl group optionally substituted by one or more halogen atoms), —$S(O)_mR^{23a}$ (wherein $R^{23a}$ represents a C1-C6 alkyl group optionally substituted by one or more halogen atoms, m represents 0, 1 or 2), —$SF_5$ or a halogen atom,
$R^{9a}$ represents a C1-C6 alkyl group optionally substituted by one or more halogen atoms, —$OR^{24a}$ (wherein $R^{24a}$ represents a C1-C6 alkyl group optionally substituted by one or more halogen atoms), —$S(O)_mR^{25a}$ (wherein $R^{25a}$ represents a C1-C6 alkyl group optionally substituted by one or more halogen atoms, m represents 0, 1 or 2), a halogen atom or a hydrogen atom, and
n represents 0, 1 or 2,
or an N-oxide thereof.

19. A pest control composition comprising a compound according to claim 1 and an inert carrier.

20. A method for controlling a pest, which comprises applying an effective amount of the compound according to claim 1 to the pest or a habitat of the pest.

* * * * *